(12) United States Patent
Sanz Molinero

(10) Patent No.: US 7,872,173 B2
(45) Date of Patent: Jan. 18, 2011

(54) PLANTS HAVING INCREASED YIELD AND METHOD FOR MAKING THE SAME

(75) Inventor: Ana I. Sanz Molinero, Gentbrugge (BE)

(73) Assignee: CropDesign N.V., Zwijnaarde (BE)

( * ) Notice: Subject to any disclaimer, the term of this patent is extended or adjusted under 35 U.S.C. 154(b) by 384 days.

(21) Appl. No.: 11/794,004

(22) PCT Filed: Dec. 23, 2005

(86) PCT No.: PCT/EP2005/057167

§ 371 (c)(1), (2), (4) Date: Jul. 18, 2007

(87) PCT Pub. No.: WO2006/067236

PCT Pub. Date: Jun. 29, 2006

(65) Prior Publication Data

US 2009/0126039 A1    May 14, 2009

Related U.S. Application Data

(60) Provisional application No. 60/641,688, filed on Jan. 6, 2005.

(51) Int. Cl.
  *C12N 15/82* (2006.01)
  *A01H 5/00* (2006.01)
(52) U.S. Cl. .............. 800/290; 800/287; 800/298; 800/320; 800/320.1; 800/320.2; 800/320.3
(58) Field of Classification Search ............ None
See application file for complete search history.

(56) References Cited

U.S. PATENT DOCUMENTS

| | | | |
|---|---|---|---|
| 5,922,929 | A | 7/1999 | Zimmerman et al. |
| 2003/0044972 | A1 | 3/2003 | Ristic et al. |
| 2004/0181830 | A1 | 9/2004 | Kovalic et al. |

FOREIGN PATENT DOCUMENTS

| | | | | |
|---|---|---|---|---|
| WO | WO-98/59039 | A1 | | 12/1998 |
| WO | WO-00/04761 | A1 | | 2/2000 |
| WO | WO 02/16655 | | * | 2/2002 |
| WO | WO-02/16655 | A2 | | 2/2002 |
| WO | WO-02/070647 | | | 9/2002 |
| WO | WO-03/012096 | | | 2/2003 |
| WO | WO-03/072763 | A1 | | 9/2003 |
| WO | WO-03/085115 | A1 | | 10/2003 |
| WO | WO-2004/009821 | | | 1/2004 |
| WO | WO-2004/061080 | | | 7/2004 |
| WO | WO 2004/061080 | | * | 7/2004 |

OTHER PUBLICATIONS

Wen T.N. et al. Nucleotide sequence of a rice (*Oryza sativa*) prolamin storage protein gene, RP6.Plant Physiol. Mar. 1993;101(3):1115-6.*
"Oryza sativa (japonica cultivar-group) cDNA clone: J013067J21, full insert sequence", EMBL-EBI Accession No. AK066420, Jul. 19, 2003.
"Rice stress-related protein #53", GeneSeq Database Accession No. ADQ15697, Oct. 7, 2004.
"Cotton cDNA sequence, SEQ ID 4160", GeneSeq Database Accession No. ADR63379, Dec. 2, 2004.
Kelley, L. W., "The J-domain family and the recruitment of chaperone power", TIBS Trends in Biochemical Sciences, 1998, vol. 23, No. 6, pp. 222-227.
Miernyk, J. A., "The J-domain proteins of *Arabidopsis thaliana*: an unexpectedly large and diverse family of chaperones", Cell Stress & Chaperones, 2001, vol. 6, No. 3, pp. 209-218.

* cited by examiner

*Primary Examiner*—Cynthia Collins
(74) *Attorney, Agent, or Firm*—Connolly Bove Lodge & Hutz, LLP

(57) ABSTRACT

The present invention concerns a method for increasing plant yield in plants grown under non-stress growth conditions relative to yield in corresponding wild type plants grown under comparable conditions, the method comprising preferentially increasing activity in the cytosol of a plant cell of a type I DnaJ-like polypeptide or a homologue thereof. One such method comprises introducing and/or expressing in a plant, plant part or plant cell a type I DnaJ-like nucleic acid or variant thereof. The invention also relates to transgenic plants grown under non-stress conditions having introduced and/or expressed therein a type I DnaJ-like nucleic acid or variant thereof, which plants have increased plant yield relative to corresponding wild type plants grown under comparable conditions. The present invention also concerns constructs useful in the methods of the invention.

23 Claims, 36 Drawing Sheets

seq id no 01: *Oryza sativa* CDS1877 DnaJ DNA (AK066420)

ATGTACGGACGCATGCCAAAGAAGAGTAACAATACCAAGTATTATGAGGTGCTTGGTGT
ATCTAAGACAGCAACCCAGGATGAGCTGAAGAAAGCGTACCGTAAAGCTGCCATTAAAA
ACCACCCTGATAAGGGTGGAGACCCTGAGAAGTTTAAAGAATTGGCTCAAGCTTACGAG
GTTCTTAATGATCCTGAAAAGAGGGAAATCTATGACCAATATGGCGAGGATGCACTCAA
AGAAGGAATGGGAGGAGGCAGCAGCAGTGATTCCATAGTCCCTTCGATTTATTTGAGC
AAATTTTTCAGAATCGTGGTGGCTTTGGGGGTAGAGGACACAGACAAAAGCGTGGCGAA
GATGTGGTACATACTATGAAGGTTTCTTTAGAAGACCTGTATAATGGTACTACCAAAAA
ACTGTCTTTGTCACGGAATGCTCTGTGCACAAAGTGCAAGGGTAAAGGATCCAAGAGTG
GGGCAGCAGCAACTTGCCATGGTTGTCATGGTGCAGGAATGAGAACAATAACAAGACAA
ATTGGGCTTGGCATGATCCAACAGATGAACACTGTTTGCCCTGAATGCAGAGGATCAGG
TGAGATGATAAGTGACAAGGATAAATGCCCGAGTTGTAAGGGAAACAAAGTAGTCCAGC
AGAAGAAGGTCTTGGAGGTTCATGTTGAGAAGGGAATGCAACATGGCCAAAAGATTGTA
TTCCAGGGTGAAGCTGATGAAGCTCCTGATACAGTGACAGGAGACATAGTTTTTGTCTT
GCAACTTAAAGACCACCCAAAATTTAAGAGGAAGTTTGATGACCTCTTTACTGAGCACA
CAATCTCCCTGACCGAGGCTCTGTGTGGCTTCCAGTTTGTTCTAACCCATCTTGATGGT
CGGCAACTCCTAATCAAATCTAATCCAGGGGAGGTTATAAAACCTGGTCAACACAAGGC
CATCAATGATGAAGGCATGCCCCAGCATGGCCGCCCTTTCATGAAAGGTCGTCTTTTTG
TTGAATTCAACGTGGAGTTTCCTGAGCCTGGTGCACTCACTCCTGGCCAATGCCGATCG
CTTGAGAAGATTTTGCCACCACGACCCAGGAATCAATTGTCAGACATGGAGCTAGATCA
ATGTGAGGAGACCACCATGCATGATGTCAACATAGAAGAGGAGATGAGGCGCAGGCAGC
AGCACAGGCGGCAGGAAGCATATGATGAAGACGACGACGAGGATGCTGGAGCTGGACCA
AGGGTACAGTGTGCCCAGCAGTAA seq id no 02: *Oryza sativa* CDS1877 DnaJ protein translation
SEQ ID NO: 01
MYGRMPKKSNNTKYYEVLGVSKTATQDELKKAYRKAAIKNHPDKGGDPEKFKELAQAYE
VLNDPEKREIYDQYGEDALKEGMGGGSSSDFHSPFDLFEQIFQNRGGFGGRGHRQKRGE
DVVHTMKVSLEDLYNGTTKKLSLSRNALCTKCKGKGSKSGAAATCHGCHGAGMRTITRQ
IGLGMIQQMNTVCPECRGSGEMISDKDKCPSCKGNKVVQQKKVLEVHVEKGMQHGQKIV
FQGEADEAPDTVTGDIVFVLQLKDHPKFKRKFDDLFTEHTISLTEALCGFQFVLTHLDG
RQLLIKSNPGEVIKPGQHKAINDEGMPQHGRPFMKGRLFVEFNVEFPEPGALTPGQCRS
LEKILPPRPRNQLSDMELDQCEETTMHDVNIEEEMRRRQQHRRQEAYDEDDDEDAGAGP
RVQCAQQ seq id no 03: *Oryza sativa* Orysa_DNAJ II CAAX DNA
(AK101956)
ATGTTTGGGCGTGTACCGAGGAGTAACAACACCAAGTACTATGAGGTTCTTGGAGTTCC
TAAAACTGCAAGCAAGGATGAGCTAAAGAAGGCATACCGGAAGGCTGCCATAAAAAACC
ATCCTGACAAGGGAGGGGATCCAGAAAAGTTTAAAGAATTATCACAAGCGTATGAGGTT
CTCACTGATCCTGAGAAGAGAGACATATATGACCAATATGGGGAGGATGCTCTTAAGGA
TGGAATGGGAGGAGGCAGTGACTTCCATAATCCATTTGACATATTTGAGCAGTTTTTCG
GGGTGGTGCCTTTGGGGGAGTAGCTCAAGAGTACGCAGACAGAGACGTGGTGAAGAT
GTGGCGCATACTTTGAAGGTGTCTTTAGAAGATGTGTATAATGGATCTATGAAGAAACT
ATCATTATCACGAAATATTCTGTGCCCAAAGTGCAAAGGAAAAGGGACCAAATCTGAGG

FIGURE 5

CTCCAGCAACATGCTATGGTTGTCATGGTGTAGGAATGAGGAATATAATGCGACAGATA
GGACTAGGCATGATTCAACATATGCAGACTGTCTGTCCTGAATGCAGAGGATCAGGTGA
GATCATAAGTGACAGGGATAAATGCACAAACTGCAGAGCTAGCAAAGTTATTCAGGAGA
AAAAGGTGCTTGAGGTTCATATTGAGAAGGGAATGCAACATGGCCAAAAAATTGTATTC
CAAGGTGAAGCTGATGAAGCTCCTGATACAGTGACAGGAGATATAGTATTTATCTTGCA
AGTTAAGGTACATCCAAGATTTAAGAGGAAATATGATGACCTGTTCATTGAGCGCACAA
TCTCTTTAACTGAGGCATTGTGTGGGTTCCAATTCATCCTCACTCATCTGGACAGTAGG
CAGCTCCTAATCAAGGCAAATCCTGGCGAAATTATTAAACCTGGTCAACACAAGGCCAT
AAATGATGAGGGAATGCCACACCATGGCCGGCCTTTCATGAAGGGCCGTCTCTTTGTGG
AATTCAATGTTGAGTTCCCTGAATCTGGTGTACTCTCCCGTGACCAATGCCGGGCACTT
GAGATGATCCTACCACCTAAACCTGGGCACCAATTATCAGATATGGACCTGGATCAATG
TGAGGAAACTACCATGCATGATGTGAACATAGAAGAGGAGATGAGGCGCAAGCAGTATC
AAAGGAAGCAGGAAGCGTACGACGAAGATGAGGAGGAGGATGCTCCAAGAGTACAGTGT
GCTCAACAGTAA

**seq id no 04: *Oryza sativa* Orysa_DNAJ II CAAX protein translation SEQ ID NO: 03**

MFGRVPRSNNTKYYEVLGVPKTASKDELKKAYRKAAIKNHPDKGGDPEKFKELSQAYEV
LTDPEKRDIYDQYGEDALKDGMGGGSDFHNPFDIFEQFFGGGAFGGSSSRVRRQRRGED
VAHTLKVSLEDVYNGSMKKLSLSRNILCPKCKGKGTKSEAPATCYGCHGVGMRNIMRQI
GLGMIQHMQTVCPECRGSGEIISDRDKCTNCRASKVIQEKKVLEVHIEKGMQHGQKIVF
QGEADEAPDTVTGDIVFILQVKVHPRFKRKYDDLFIERTISLTEALCGFQFILTHLDSR
QLLIKANPGEIIKPGQHKAINDEGMPHHGRPFMKGRLFVEFNVEFPESGVLSRDQCRAL
EMILPPKPGHQLSDMDLDQCEETTMHDVNIEEEMRRKQYQRKQEAYDEDEEEDAPRVQC
AQQ

**seq id no 05: *Oryza sativa* Orysa_DNAJ III CAAX DNA (AK105028)**

ATGTTCGGGCGCGCGCCGAAGAAGAGCGACAACACCAAGTACTACGAGATCCTGGGGGT
CCCCAAGACCGCCTCCCAGGACGACCTCAAGAAGGCGTACCGCAAGGCCGCCATCAAGA
ACCACCCCGACAAGGGCGGCGACCCCGAGAAGTTCAAGGAGCTTGCACAAGCTTATGAG
GTATTGAGTGACCCGGAGAAACGTGAAATCTATGACCAATATGGTGAAGATGCCCTCAA
GGAAGGAATGGGTGGAGGCGGATCCATGTTGATCCATTTGACATCTTTTCATCATTCT
TTGGACCTTCTTTTGGTGGTGGTGGCAGCAGCAGGGGCAGAAGGCAAAGGAGGGGAGAG
GATGTGATCCATCCGCTTAAGGTTTCTCTAGAAGATCTTTACAATGGTACTTCAAAGAA
GCTCTCTCTTTCCCGCAATGTCCTCTGCGCCAAGTGCAAGGGCAAGGGTTCCAAGTCTG
GTGCTTCCATGAGGTGCCCAGGTTGCCAGGGGTCTGGCATGAAAATCACCATCCGCCAG
CTGGGGCCCTCCATGATACAGCAGATGCAGCAGCCTTGCAATGAGTGTAAGGGGACTGG
AGAGAGCATTAATGAGAAGGATCGCTGCCCAGGCTGCAAGGGCGAGAAGGTTATTCAGG
AGAAGAAGGTTCTGGAGGTTCACGTTGAGAAGGGGATGCAACACAATCAGAAGATCACT
TTCCCTGGTGAAGCTGATGAGGCGCCTGATACCGTTACGGGAGACATTGTATTCGTCCT
CCAGCAGAAGGACCACTCCAAGTTCAAAAGGAAGGGCGATGATCTCTTTTATGAGCACA
CCTTATCTCTGACTGAAGCACTTTGTGGTTTCCAATTTGTCCTGACACATCTGGACAAC
AGACAGCTGCTCATTAAGTCAAACCCCGGTGAAGTTGTTAAGCCTGACCAATTCAAGGC
AATAAACGATGAGGGAATGCCAATGTACCAGAGGCCTTTCATGAAGGGGAAGCTCTACA

TTCATTTCACGGTGGAGTTCCCTGATTCCCTGGCGCCTGAACAATGCAAGGCTCTCGAG
GCTGTGCTTCCACCGAAGCCTGCATCCCAGCTGACAGAAATGGAGATAGATGAATGCGA
GGAGACCACGATGCACGATGTCAACAACATTGAGGAAGAGATGCGCAGGAAAGCCCAAG
CTGCTCAGGAGGCGTATGATGAGGACGATGAGATGCCTGGAGGTGCCCAGAGAGTTCAG
TGCGCGCAACAGTAA seq id no 06: *Oryza sativa* Orysa_DNAJ III CAAX protein translation SEQ ID NO: 05

MFGRAPKKSDNTKYYEILGVPKTASQDDLKKAYRKAAIKNHPDKGGDPEKFKELAQAYE
VLSDPEKREIYDQYGEDALKEGMGGGGSHVDPFDIFSSFFGPSFGGGGSSRGRRQRRGE
DVIHPLKVSLEDLYNGTSKKLSLSRNVLCAKCKGKGSKSGASMRCPGCQGSGMKITIRQ
LGPSMIQQMQQPCNECKGTGESINEKDRCPGCKGEKVIQEKKVLEVHVEKGMQHNQKIT
FPGEADEAPDTVTGDIVFVLQQKDHSKFKRKGDDLFYEHTLSLTEALCGFQFVLTHLDN
RQLLIKSNPGEVVKPDQFKAINDEGMPMYQRPFMKGKLYIHFTVEFPDSLAPEQCKALE
AVLPPKPASQLTEMEIDECEETTMHDVNNIEEEMRRKAQAAQEAYDEDDEMPGGAQRVQ
CAQQ seq id no 07: *Oryza sativa* Orysa_DNAJ IV CAAX DNA (AK104315)

ATGTTCGGGCGCGCGCCGAAGAAGAGCGACAACACGCGGTACTACGAGGTGCTTGGGGT
GCCCAAGGATGCGTCCCAGGATGACCTCAAGAAGGCGTACCGCAAGGCCGCCATCAAGA
ACCACCCCGACAAGGGCGGAGACCCCGAGAAGTTCAAGGAATTGGCTCAGGCTTATGAA
GTCCTGAGTGACCCTGAGAAGCGTGAAATCTATGATCAGTACGGTGAAGATGCTCTCAA
GGAGGGGATGGGTCCTGGTGGTGGGATGCATGACCCATTTGACATTTTTTCCTCATTCT
TTGGAGGTGGCTTTGGAGGTGGTAGCAGTAGGGGCAGGAGACAGCGTAGGGGAGAGGAT
GTGGTTCACCCTCTGAAGGTTTCTCTGGAGGAATTGTACAATGGCACATCAAAGAAGCT
CTCCCTTTCTCGCAATGTGCTCTGCTCCAAGTGCAATGGCAAGGGCTCGAAATCTGGTG
CTTCCATGAAGTGCTCTGGTTGTCAAGGTTCTGGTATGAAGGTCCAAATTCGCCAGTTG
GGGCCAGGAATGATTCAGCAAATGCAACATCCCTGCAATGAGTGCAAGGGAACTGGTGA
GACCATCAGCGACAAGGATAGATGCCCAGGCTGCAAGGGTGAGAAGGTGGCGCAGGAGA
AGAAGGTTCTTGAGGTGGTGGTCGAGAAGGGCATGCAGAATGGACAGAAGATCACCTTC
CCTGGTGAGGCTGATGAAGCGCCCGATACTGTCACTGGAGACATTATCTTCGTCCTCCA
GCAGAAGGAGCATCCCAAGTTCAAGAGAAAGGGAGATGACCTCTTCTACGAGCACACCC
TGAACCTCACTGAGGCCCTTGTGGCTTCCAGTTTGTTCTCACTCACTTGGACAACAGG
CAGCTGCTTATCAAGTCCAAGCCCGGTGAAGTTGTCAAGCCTGATTCATTCAAGGCTGT
CAACGACGAGGGCATGCCGATGTACCAGCGGCCATTCATGAAGGGGAAGCTCTACATCC
ACTTCTCCGTGGAATTCCCCGACTCTTTGAACCCTGACCAGTGCAAGGCCCTGGAGACC
GTCCTCCCGCCAAGGCCGGTGTCGCAGTACACCGACATGGAGCTCGACGAGTGCGAGGA
GACCATGCCGTACGACGTGAACATCGAGGAGGAGATGAGGAGGCGGCAGCAACAGCAGC
AGCAGGAGGCATACGACGAGGACGAGGACATGCACGGCGGCGGCGCCCAGCGCGTGCAG
TGCGCGCAGCAGTAA seq id no 08: *Oryza sativa* Orysa_DNAJ IV CAAX protein translation SEQ ID NO: 07

MFGRAPKKSDNTRYYEVLGVPKDASQDDLKKAYRKAAIKNHPDKGGDPEKFKELAQAYE
VLSDPEKREIYDQYGEDALKEGMGPGGGMHDPFDIFSSFFGGGFGGGSSRGRRQRRGED
VVHPLKVSLEELYNGTSKKLSLSRNVLCSKCNGKGSKSGASMKCSGCQGSGMKVQIRQL

FIGURE 5 (continued)

GPGMIQQMQHPCNECKGTGETISDKDRCPGCKGEKVAQEKKVLEVVVEKGMQNGQKITF
PGEADEAPDTVTGDIIFVLQQKEHPKFKRKGDDLFYEHTLNLTEALCGFQFVLTHLDNR
QLLIKSKPGEVVKPDSFKAVNDEGMPMYQRPFMKGKLYIHFSVEFPDSLNPDQCKALET
VLPPRPVSQYTDMELDECEETMPYDVNIEEEMRRRQQQQQQEAYDEDEDMHGGGAQRVQ
CAQQ seq id no 09: *Zea mays* ZMDJ DNA (BT016805) corrected

ATGTTCGGGCGCGCGCCGAAGAAGAGCGACAACACCAAGTACTACGAGATCCTCGGGGT
GCCCAAGTCGGCGTCCCAGGACGATCTCAAGAAGGCCTACCGCAAGGCTGCTATCAAGA
ACCACCCCGACAAGGGCGGTGACCCCGAGAAGTTCAAGGAGCTCGCACAAGCCTATGAG
GTTTTGAGTGATCCAGAGAAACGTGAGATTTATGATCAGTATGGTGAAGATGCCCTTAA
GGAAGGAATGGGCGGTGGAGGATCCCATGTTGATCCATTTGACATCTTCTCATCATTTT
TTGGACCCTCTTTTGGAGGAGGTGGTGGAAGCAGCAGGGGAAGAAGGCAAAGGAGGGGA
GAAGATGTAGTTCACCCACTTAAAGTTTCTCTGGAAGATCTTTACAATGGCACCTCAAA
GAAGCTCTCTCTTTCGCGCAATGTCATCTGCTCCAAGTGCAAGGGCAAGGGCTCGAAGT
CTGGTGCCTCAATGAGGTGCCCTGGTTGCCAGGGCTCAGGCATGAAAGTCACTATTCGT
CAGCTGGGCCCTTCCATGATACAGCAGATGCAGCAGCCTTGCAATGAGTGCAAGGGGAC
TGGAGAGAGCATCAATGAGAAGGACCGCTGTCCAGGGTGCAAGGGTGAGAAGGTCATTC
AAGAGAAGAAAGTTCTTGAGGTTCATGTTGAGAAGGGGATGCAACACAACCAGAAGATC
ACCTTCCCTGGTGAAGCTGATGAAGCGCCTGATACTGTCACTGGAGACATTGTATTCGT
CCTCCAACAGAAGGATCACTCCAAATTCAAAAGAAAGGGTGAAGATCTGTTCTATGAGC
ACACCTTGTCTCTGACCGAAGCACTATGTGGGTTCCAATTTGTTCTTACACATCTGGAC
AACAGGCAGCTTCTCATCAAATCAGACCCTGGTGAAGTTGTTAAACCTGACCAATTCAA
GGCGATTAATGATGAGGGGATGCCAATTTACCAGAGGCCTTTCATGAAGGGGAAGCTGT
ACATCCATTTCACGGTGGAGTTCCCTGACTCGTTGGCACCAGAGCAGTGCAAGGCTCTC
GAGACAGTACTTCCACCAAGGCCTTCATCCAAGCTGACAGACATGGAGATAGATGAATG
CGAGGAGACGACTATGCATGATGTGAACAACATCGAGGAAGAGATGCGCAAGAAGCAAG
CTCACGCTGCCCAGGAGGCGTACGAGGAGGACGACGAGATGCCGGGCGGAGCCCAGAGA
GTGCAGTGCGCGCAGCAGTAA seq id no 10: *Zea mays* ZMDJ protein (T01643)

MFGRAPKKSDNTKYYEILGVPKSASQDDLKKAYRKAAIKNHPDKGGDPEKFKELAQAYE
VLSDPEKREIYDQYGEDALKEGMGGGGSHVDPFDIFSSFFGPSFGGGGGSSRGRRQRRG
EDVVHPLKVSLEDLYNGTSKKLSLSRNVICSKCKGKGSKSGASMRCPGCQGSGMKVTIR
QLGPSMIQQMQPCNECKGTGESINEKDRCPGCKGEKVIQEKKVLEVHVEKGMQHNQKI
TFPGEADEAPDTVTGDIVFVLQQKDHSKFKRKGEDLFYEHTLSLTEALCGFQFVLTHLD
NRQLLIKSDPGEVVKPDQFKAINDEGMPIYQRPFMKGKLYIHFTVEFPDSLAPEQCKAL
ETVLPPRPSSKLTDMEIDECEETTMHDVNNIEEEMRRKQAHAAQEAYEEDDEMPGGAQR
VQCAQQ seq id no 11: *Zea mays* DNAJ I CAAX DNA (AY103727)

ATGTTCGGGCGCGCGCCGAAGAAGAGCGACAACACACGGTACTACGAGATCCTCGGGGT
CTCCAAGGACGCGTCCCAGGATGACCTCAAGAAAGCCTACCGCAAGGCCGCCATCAAGA
ACCACCCCGACAAGGGCGGCGATCCCGAGAAGTTCAAGGAGCTAGCTCAGGCTTATGAG
GTCCTCAGTGATCCTGAAAAGCGGGAGATTTATGATCAATATGGTGAGGATGCCCTCAA

FIGURE 5 (continued)

```
GGAGGGAATGGGAGGTGGTGGAGGGATGCACGATCCCTTTGACATATTCCAGTCATTCT
TTGGTGGTGGAAGCCCTTTTGGAGGTGGTGGCAGCAGTAGGGGCAGAAGGCAGCGAAGG
GGAGAGGATGTGGTTCATCCTCTAAAGGTTTCTCTGGAGGATTTGTACAATGGCACATC
AAAGAAGCTCTCTCTGTCCCGCAGTGTCCTCTGCTCCAAGTGCAATGGTAAGGGTTCAA
AGTCTGGAGCTTCATCGAGGTGTGCTGGTTGCCAAGGTTCTGGCTTTAAGGTCCAAATC
CGGCAGTTGGGGCCTGGAATGATCCAGCAAATGCAGCATCCTTGCAACGAGTGCAAGGG
TTCTGGAGAGACAATCAGCGACAAGGATAGATGCCCACAGTGCAAGGGTGATAAAGTTG
TGCAGGAGAAGAAGGTTCTTGAAGTGTTTGTGGAGAAAGGCATGCAGAATGGGCAGAAG
ATCACATTCCCTGGTGAAGCTGATGAAGCGCCTGACACTGTCACTGGAGATATCATTTT
TGTTCTCCAGCAGAAGGAGCATCCCAAGTTCAAGAGAAAGGGCGATGACCTCTTCTACG
AGCACACCCTGACCTTGACTGAATCTCTGTGTGGCTTCCAGTTTGTTGTGACTCACTTG
GATAACAGGCAGCTGCTGATCAAATCAAATCCGGGCGAAGTTGTGAAGCCTGATTCTTT
CAAGGCGATCAACGACGAAGGCATGCCCATGTACCAGAGGCCGTTCATGAAGGGCAAGC
TGTACATCCACTTCTCGGTGGAGTTCCCGGACTCGCTGAGCCCGGAGCAGTGCAAGGCC
CTGGAGGCTGTGCTCCCGCCCAAGCCGGTGTCGCAGTACACCGACATGGAGCTGGACGA
GTGCGAGGAGACGATGCCCTATGACGTGAACATCGAAGCGGAGATGCGGAGGCGGCAGC
AGCAGCACCAGGAGGCCTACGACGAGGATGAGGACATGCCGGGCGGCGCGCAGAGGGTG
CAGTGCGCCCAGCAGTAG
```

**seq id no 12: *Zea mays* DNAJ I CAAX protein translation SEQ ID NO: 11**

```
MFGRAPKKSDNTRYYEILGVSKDASQDDLKKAYRKAAIKNHPDKGGDPEKFKELAQAYE
VLSDPEKREIYDQYGEDALKEGMGGGGGMHDPFDIFQSFFGGGSPFGGGGSSRGRRQRR
GEDVVHPLKVSLEDLYNGTSKKLSLSRSVLCSKCNGKGSKSGASSRCAGCQGSGFKVQI
RQLGPGMIQQMQHPCNECKGSGETISDKDRCPQCKGDKVVQEKKVLEVFVEKGMQNGQK
ITFPGEADEAPDTVTGDIIFVLQQKEHPKFKRKGDDLFYEHTLTLTESLCGFQFVVTHL
DNRQLLIKSNPGEVVKPDSFKAINDEGMPMYQRPFMKGKLYIHFSVEFPDSLSPEQCKA
LEAVLPPKPVSQYTDMELDECEETMPYDVNIEAEMRRRQQQHQEAYDEDEDMPGGAQRV
QCAQQ
```

**seq id no 13: *Zea mays* DNAJ II CAAX DNA (AY108160)**

```
ATGTTTGGACGCATGCCAAGGAAGAGTAGTAACAATACCAAGTATTACGAGGTTCTTGG
TGTGTCTAAGACCGCAAGTCAGGATGAGCTTAAGAAAGCATACAGAAAAGCTGCCATAA
AAAACCATCCTGATAAGGGTGGAGACCCTGAGAAGTTTAAAGAGCTGTCTCAAGCTTAT
GATGTTCTTAGTGACCCGGAGAAGAGGGAGATCTATGACCAGTATGGAGAAGATGCCCT
TAAGGAAGGAATGGGAGGAGGCAGCAGCAGTGATTTCCATAGCCCTTTCGACATTTTTG
AGCAACTTTTTCCGGGTTCTAGCACCTTTGGGGGTGGTAGCTCAAGAGGACGCAGACAA
AAGCGTGGTGAAGATGTGGTGCATACTATGAAGGTTTCCTTAGACGATCTGTACAATGG
GACAACCAAGAAACTATCTTTATCGCGGAGTGCTTTGTGCTCCAAGTGCAAGGGGAAAG
GATCCAAGAGTGGGGCATCAGGAACATGCCATGGTTGTCGTGGTGCTGGAATGAGAACA
ATCACAAGACAGATAGGCCTTGGCATGATCCAACAGATGAACACTGTTTGCCCTGAATG
CAAAGGATCAGGTGAGATCATAAGTGACAAGGACAAATGCCCAAGCTGTAAAGGAAACA
AGGTAGTCCAGGAGAAGAAGGTGTTAGAGGTTCATGTGGAGAAAGGAATGCAACATAAC
CAAAAGATTGTATTCCAGGGTCAAGCTGATGAAGCTCCTGATACGGTTACAGGAGACAT
TGTTTTTGTCTTGCAACTTAAAGACCATCCAAAATTTAAGAGGATGTACGATGACTTAT
ATGTTGAGCACACAATCTCTCTCACCGAAGCATTGTGTGGCTTCCAGTTTGTTCTTACT
CATCTTGATGGGCGACAGCTTCTGATCAAATCTGACCCCGGGGAGGTTATTAAACCAGG
```

TCAACACAAGGCCATTAACGATGAAGGTATGCCTCAGCATGGCCGTCCTTTCATGAAGG
GCCGTCTGTTTGTTGAATTCAACGTGGTGTTTCCCGAGCCTGGTGCGCTCTCCCTGCC
CAGTGCCGATCGTTGGAGAAGATCCTTCCGCCGAAACCAGGGAGCCAACTGTCGGACAT
GGAGCTGGACCAGTGCGAGGAGACCACCCTTCACGATGTCAACATTGAAGAGGAGATGA
GGCGCAGGCAGCAGCAGAAGAAGCAGGAAGCCTACGATGAAGACGAGGAGGAGGATGCT
CAACCAAGGGTGCAATGTGCCCAGCAGTAA

**seq id no 14: *Zea mays* DNAJ II CAAX protein translation SEQ ID NO: 13**

MFGRMPRKSSNNTKYYEVLGVSKTASQDELKKAYRKAAIKNHPDKGGDPEKFKELSQAY
DVLSDPEKREIYDQYGEDALKEGMGGGSSSDFHSPFDIFEQLFPGSSTFGGGSSRGRRQ
KRGEDVVHTMKVSLDDLYNGTTKKLSLSRSALCSKCKGKGSKSGASGTCHGCRGAGMRT
ITRQIGLGMIQQMNTVCPECKGSGEIISDKDKCPSCKGNKVVQEKKVLEVHVEKGMQHN
QKIVFQGQADEAPDTVTGDIVFVLQLKDHPKFKRMYDDLYVEHTISLTEALCGFQFVLT
HLDGRQLLIKSDPGEVIKPGQHKAINDEGMPQHGRPFMKGRLFVEFNVVFPEPGALSPA
QCRSLEKILPPKPGSQLSDMELDQCEETTLHDVNIEEEMRRRQQQKKQEAYDEDEEEDA
QPRVQCAQQ

**seq id no 15: *Triticum aestivum* DnaJ DNA (BT008914)**

ATGTTCGGGCGCGGGCCGCCGAAGAAGAGCGACAGCACGCGCTACTACGAGATCCTGGG
CGTGCCCAAGGACGCGTCCCAGGACGACCTCAAGAAGGCCTACCGCAAGGCCGCCATCA
AGAACCACCCCGACAAGGGAGGCGACCCAGAGAAGTTCAAGGAGCTAGCTCAGGCTTAT
GAGGTTCTGAGTGATCCTGAGAAGCGAGAGATCTATGACCAGTATGGTGAGGATGCCCT
CAAGGAGGGAATGGGAGGTGGAGGAATGCATGATCCTTTTGACATCTTCCAGTCATTCT
TTGGTGGTGGCGGCAACCCCTTCGGAGGTGGCGGGAGCAGTAGGGGCAGGCGGCAGCGC
AGGGGTGAGGATGTGGTTCATCCTCTGAAGGTTAGCCTTGAGGAACTGTACAACGGAAC
ATCAAAGAAGCTCTCTCTTGCCCGCAATGTGCTCTGCTCGAAGTGCAATGGCAAGGGGT
CAAAGTCCGGGGCTTCGATGAAGTGTGCCGGCTGCCAAGGTGCTGGTTACAAGGTGCAG
ATAAGGCAGCTGGGACCAGGAATGATTCAGCAAATGCAGCAGCCTTGCAATGAGTGCAG
GGGAAGTGGGGAGACCATCAGCGACAAGGATCGCTGTGGGCAGTGCAAAGGCGAGAAGG
TGGTGCACGAGAAGAAAGTCCTGGAGGTGGTGGTCGAGAAGGGAATGCAGCATGGGCAG
AAGATCACCTTCCCCGGCGAGGCGGATGAAGCGCCTGATACTGTTACTGGAGACATAAT
CTTCGTCCTCCAGCAGAAGGAGCACCCCAAATTCAAGCGGAAGGGCGATGACCTCTTCT
ACGAGCACACCCTGACCCTGACCGAGGCACTGTGTGGCTTCCAGTATGTCCTGGCTCAT
TTGGACGGCAGGCAGCTGCTCATCAAGTCCAACCCTGGCGAAGTCGTCAAGCCTGATTC
GTTCAAGGCGATCAACGACGAGGGCATGCCCATGTACCAGAGGCCGTTCATGAAGGGCA
AGCTGTACATCCACTTCACGGTTGATTTCCCGACTCGCTGAGCCTGGACCAGTGCAAG
GCGCTCGAGACTGTCCTGCCGCCCAAGCCGGCGTCGCAGTACACGGACATGGAGCTGGA
CGAGTGCGAGGAGACGATGGCCTACGACATTGACATCGAGGAGGAGATGCGGAGGCGAC
AGCAGCAGCAGGCACAGGAGGCCTACGACGAGGACGAGGACATGCCCGGTGGCGGCGGC
CAGCGGGTGCAGTGCGCCCAGCAGTAG seq id no 16: *Triticum aestivum* DnaJ protein translation
SEQ ID NO: 15

MFGRGPPKKSDSTRYYEILGVPKDASQDDLKKAYRKAAIKNHPDKGGDPEKFKELAQAY
EVLSDPEKREIYDQYGEDALKEGMGGGGMHDPFDIFQSFFGGGGNPFGGGGSSRGRRQR
RGEDVVHPLKVSLEELYNGTSKKLSLARNVLCSKCNGKGSKSGASMKCAGCQGAGYKVQ
IRQLGPGMIQQMQQPCNECRGSGETISDKDRCGQCKGEKVVHEKKVLEVVVEKGMQHGQ
KITFPGEADEAPDTVTGDIIFVLQQKEHPKFKRKGDDLFYEHTLTLTEALCGFQYVLAH
LDGRQLLIKSNPGEVVKPDSFKAINDEGMPMYQRPFMKGKLYIHFTVDFPDSLSLDQCK
ALETVLPPKPASQYTDMELDECEETMAYDIDIEEEMRRRQQQQAQEAYDEDEDMPGGGG
QRVQCAQQ seq id no 17: *Arabidopsis thaliana* AtJ2 DNA (L36113)

ATGTTTGGAAGAGGACCTTCAAGGAAGAGCGATAACACAAAGTTCTACGAGATCCTTGG
TGTTCCTAAGACCGCAGCACCAGAAGATCTCAAGAAAGCTTATAAGAAAGCCGCTATCA
AAAACCATCCTGATAAGGGTGGTGATCCCGAAAAGTTTAAAGAGTTAGCACAGGCTTAT
GAAGTTTTAAGTGATCCTGAGAAGCGTGAGATCTATGATCAATATGGGGAAGATGCACT
CAAGGAAGGAATGGGTGGTGGAGGTGGTGGACACGATCCATTTGATATCTTCTCTTCCT
TCTTTGGTAGTGGTGGACACCCATTCGGAAGTCATAGCCGGGGAAGGAGGCAGAGGCGT
GGTGAAGATGTTGTTCATCCCTTGAAGGTTTCCTTAGAGGATGTTTATCTCGGAACAAC
AAAGAAGCTCTCACTTTCTAGGAAGGCTTTGTGCTCAAAGTGTAACGGCAAGGGTTCAA
AGTCTGGAGCTTCACTGAAATGTGGTGGCTGTCAAGGCTCGGGAATGAAGATCTCGATC
AGGCAGTTTGGACCTGGAATGATGCAGCAGGTGCAGCATGCTTGTAATGATTCCAAAGG
CACAGGAGAGACCATCAATGATCGGGACAGGTGTCCACAATGCAAAGGAGAGAAGGTTG
TCTCTGAGAAGAAGGTGCTTGAAGTAAATGTGGAGAAGGGAATGCAACACAATCAGAAG
ATCACATTCAGTGGACAAGCCGATGAAGCGCCTGATACTGTCACCGGAGATATAGTGTT
TGTCATTCAGCAGAAGGAGCACCCAAAGTTCAAAAGAAAGGGTGAGGATCTCTTTGTGG
AGCACACCATCTCTCTAACCGAGGCCTTGTGTGGCTTCCAGTTTGTCTTGACCCATTTG
GACAAAAGACAGCTTCTCATCAAATCCAAGCCCGGAGAGGTCGTCAAACCTGATTCATA
CAAGGCGATAAGTGATGAGGGAATGCCAATATACCAAAGTCCGTTCATGAAGGGTAAGC
TATACATTCACTTCACGGTTGAATTCCCGGAATCGCTGAGCCCGGATCAGACAAAGGCC
ATTGAAGCAGTTTTGCCAAAGCCAACCAAGGCAGCTATAAGCGATATGGAAATAGACGA
CTGCGAAGAGACGACTCTGCATGATGTGAACATTGAGGATGAGATGAAAAGGAAGGCGC
AAGCTCAAAGAGAGGCTTATGATGTCGATGAGGAAGATCACCCAGGCGGTGCTCACCGT
GTGCAATGTGCCCAGCAGTGA seq id no 18: *Arabidopsis thaliana* AtJ2 protein (AAB86799)

MFGRGPSRKSDNTKFYEILGVPKTAAPEDLKKAYKKAAIKNHPDKGGDPEKFKELAQAY
EVLSDPEKREIYDQYGEDALKEGMGGGGGHDPFDIFSSFFGSGGHPFGSHSRGRRQRR
GEDVVHPLKVSLEDVYLGTTKKLSLSRKALCSKCNGKGSKSGASMKCGGCQGSGMKISI
RQFGPGMMQQVQHACNDCKGTGETINDRDRCPQCKGEKVVSEKKVLEVNVEKGMQHNQK
ITFSGQADEAPDTVTGDIVFVIQQKEHPKFKRKGEDLFVEHTISLTEALCGFQFVLTHL
DKRQLLIKSKPGEVVKPDSYKAISDEGMPIYQRPFMKGKLYIHFTVEFPESLSPDQTKA
IEAVLPKPTKAAISDMEIDDCEETTLHDVNIEDEMKRKAQAQREAYDDDEEDHPGGAQR
VQCAQQ

FIGURE 5 (continued)

seq id no 19: *Arabidopsis thaliana* AtJ3 DNA (NM_114279)

ATGTTCGGTAGAGGACCCTCGAAGAAGAGCGACAACACTAAGTTCTACGAGATCTTAGG
TGTTCCTAAGAGCGCTTCACCAGAAGATCTCAAGAAAGCTTACAAAAAAGCCGCTATCA
AGAATCATCCTGATAAGGGTGGAGATCCCGAGAAGGTGAATAATTTCTTAGATCCGTAT
GAAGTGCTTAGTGACCCGGAGAAGCGTGAGATTTATGACCAGTATGGAGAGGATGCACT
CAAGGAAGGAATGGGTGGTGGAGGAGGTGGACATGATCCATTTGATATTTCTCATCCT
TCTTTGGTGGAGGCCCCTTTGGAGGTGAGTCTCCTTGGACACTGTGGCAGAGGCGTGGT
GAGGATGTTGTTCATCCCTTGAAGGTATCTCTTGAGGATGTGTACCTTGGTACAATGAA
GAAGCTTTCACTTTCTAGGAATGCTCTCTGCTCTAAGTGTAACGGGTTAGTACATTCGA
CTCGATCCTCCTTGAAATGTGGAGGGTGTCAGGGATCTGGTATGAAGGTGTCTATTAGG
CAGCTTGGACCTGGAATGATCCAGCAGATGCAGCATGCATGTAATGAATGCAAAGGGAC
AGGTGAGACCATCAATGATCGGGACAGGTGTCCACAATGCAAGGAGACAAGGTCATTC
CTGAAGAAGGTGCTTGAAGTGAATGTGGAGAAGGGAATGCAACACAGTCAGAAGATC
ACATTTGAAGGACAAGCAGATGAAGCGGTATCTACTCTCATACATTTAATAGTGTTTGT
CCTTCAGCAGAAAGAGCACCCAAAGTTCAAGAGAAAGGGAGAAGACCTCTTTGTGGAGC
ACACACTTTCTCTAACCGAAGCTTTGTGTGGCTTCCAATTTGTTCTGACTCACTTGGAT
GGCAGAAGTCTTCTCATTAAATCTAATCCTGGGGAGGTCGTGAAACCTGGTACGTATTC
AGATGCATCGTATGAAGGAATGCCGATATACCAGAGGCCATTCATGAAGGGTAAGCTCT
ACATCCACTTCACAGTGGAGTTCCCGGACTCGTTGAGCCCAGATCAGACCAAAGCACTG
GAAGCTGTTCTACCTAAGCCGTCAACAGCTCAGTTGAGTGACATGGAGATAGATGAATG
CGAGGAGACCACGCTCCACGATGTCAACATTGAGGATGAGATGAGGAGGAAGGCACAAG
CTCAAAGAGAGGCTTATGATGATGACGATGAAGATGATGACCATCCGGGTGGTGCTCAA
AGGGTGCAATGTGCCCAGCAGTAA seq id no 20: *Arabidopsis thaliana* AtJ3 protein (S71199)

MFGRGPSKKSDNTKFYEILGVPKSASPEDLKKAYKKAAIKNHPDKGGDPEKFKELAQAY
EVLSDPEKREIYDQYGEDALKEGMGGGGGGHDPFDIFSSFFGGGPFGGNTSRQRRQRRG
EDVVHPLKVSLEDVYLGTMKKLSLSRNALCSKCNGKGSKSGASLKCGGCQGSGMKVSIR
QLGPGMIQQMQHACNECKGTGETINDRDRCPQCKGDKVIPEKKVLEVNVEKGMQHSQKI
TFEGQADEAPDTVTGDIVFVLQQKEHPKFKRKGEDLFVEHTLSLTEALCGFQFVLTHLD
GRSLLIKSNPGEVVKPDSYKAISDEGMPIYQRPFMKGKLYIHFTVEFPDSLSPDQTKAL
EAVLPKPSTAQLSDMEIDECEETTLHDVNIEDEMRRKAQAQREAYDDDDEDDDHPGGAQ
RVQCAQQ seq id no 21: *Atriplex nummularia* ANJ1 DNA (L09124)

ATGTTTGGAAGAGCACCAAAGAAGAGTGATAGCACCAGATATTACGAGATCTTAGGCGT
ACCAAAAGATGCATCTCCTGAAGATTTGAAGAAGGCTTATAAAAAAGCTGCCATTAAAA
ATCATCCTGACAAGGGAGGTGATCCCGAGAAGTTTAAAGAGCTAGCTCATGCTTATGAG
GTCCTCAGTGATCCCGAAAAGCGTGAGATCTATGATCAATATGGTGAGGATGCACTTAA
GGAAGGAATGGGTGGAGGTGGCGGTATGCATGATCCATTCGACATCTTCCAATCCTTCT
TTGGAGGAAGTCCATTTGGTGGTGTTGGTTCTAGCCGAGGAAGAAGGCAAAGGCGGGGA
GAAGATGTAGTTCATCCTCTTAAGGTTTCACTCGAGGATCTCTTTACCGGTACAACAAA
GAAGCTCTCACTCTCTCGCAATGTAATTTGTTCAAAGTGTACTGGCAAAGGATCAAAAT
CGGGAGCTTCTATGAAGTGTTCTGGATGTCAAGGTACTGGTATGAAGGTTTCTATCAGA
CATCTGGGACCCTCAATGATCCAGCAGATGCAGCACCCTTGTAATGAATGCAAAGGAAC
TGGAGAGACGATTAATGACAAAGATCGTTGCCCTCAGTGCAAAGGTGAGAAGGTTGTGC
AGGAGAAGAAGGTCTTAGAGGTTGTTGTGGAGAAGGGCATGCAACATGGACAGAAAATT

```
ACTTTCCCTGGAGAGGCTGATGAAGCTCCTGATACTGTCACTGGAGATATAGTCTTTGT
CCTGCAGCAGAAAGAGCACCCTAAGTTCAAGAGAAAGGGTGAAGATCTCTTCTACGAGC
ACACTCTAAGCCTGACTGAAGCTCTTTGCGGCTTTAGATTTGTGCTGACTCACCTTGAT
GGAAGGCAACTTCTTATCAAATCAAACCTGGGAGAAGTTGTCAAGCCTGATCAATTCAA
GGCAATTGAGGATGAGGGTATGCCTATATACCAAAGGCCGTTCATGAAGGGCAAGATGT
ACATCCATTTCACAGTGGAGTTCCCCGATTCGTTAAACCCTGATCAAGTTAAATCCTTG
GAAGCGATCCTTCCTCCTAAGCCATCAATGTCTCTCACATACATGGAGTTAGATGAATG
TGAAGAGACAACACTGCATAATGTCAACATTGAAGAAGAGATGAAAAGGAAGCAGACAC
AAGCACAGCAGGAGGCATACGATGAAGATGACGAACCTGCCGGTGGTCAGAGGGTCCAA
TGTGCTCAACAGTGA
``` seq id no 22: *Atriplex nummularia* ANJ1 protein translation
SEQ ID NO: 21

```
MFGRAPKKSDSTRYYEILGVPKDASPEDLKKAYKKAAIKNHPDKGGDPEKFKELAHAYE
VLSDPEKREIYDQYGEDALKEGMGGGGGMHDPFDIFQSFFGGSPFGGVGSSRGRRQRRG
EDVVHPLKVSLEDLFTGTTKKLSLSRNVICSKCTGKGSKSGASMKCSGCQGTGMKVSIR
HLGPSMIQQMQHPCNECKGTGETINDKDRCPQCKGEKVVQEKKVLEVVVEKGMQHGQKI
TFPGEADEAPDTVTGDIVFVLQQKEHPKFKRKGEDLFYEHTLSLTEALCGFRFVLTHLD
GRQLLIKSNLGEVVKPDQFKAIEDEGMPIYQRPFMKGKMYIHFTVEFPDSLNPDQVKSL
EAILPPKPSMSLTYMELDECEETTLHNVNIEEEMKRKQTQAQQEAYDEDDEPAGGQRVQ
CAQQ
``` seq id no 23: *Cucumis sativus* DnaJ DNA (X67695)

```
ATGTTTGGAAGGCCGAAGAAGAGCGATAATACCAAATATTATGAGATTCTTGGAGTCTC
GAAGAATGCGTCGCAAGACGATCTAAAGAAGGCTTATAGAAAGGCCGCCATCAAGAACC
ATCCTGATAAAGGTGGCGACCCTGAAAAATTCAAGGAGTTAGCACAAGCCTACGAGGTG
CTGAGTGATCCAGAGAAACGTGAGATATATGATCAATATGGCGAGGATGCCCTCAAGGA
AGGAATGGGAGGTGGCGGTGGTCATGATCCATTTGACATATTCCAGTCTTTCTTTGGTG
GAAGCCCGTTTGGTGGTGGTGGAAGCAGCAGAGGCCGAAGGCAGAGAAGGGGAGAGGAT
GTTATCCATCCTCTCAAGGTCTCGTTGGAAGATCTCTACAACGGTACTTCAAAGAAGCT
CTCTCTTTCACGTAATGTAATTTGCTCAAAGTGCAAGGGTAAGGGTTCTAAATCTGGTG
CTTCAATGAAGTGTCCTGGCTGTCAAGGTTCTGGTATGAAAGTTTCCATCAGACACCTT
GGCCCCTCTATGATTCAGCAAATGCAGCATCCTTGCAATGAATGTAAAGGAACTGGTGA
GACCATCAATGATAAAGATCGCTGCTCACAATGCAAGGGTGAAAAGGTTGTTCAGGAGA
AAAAAGTTTTGGAAGTTATTGTGGAGAAGGGTATGCAAAATGCACAAAAGATTACATTC
CCTGGTGAAGCAGATGAAGCGCCCGACACTGTTACTGGGGACATTGTCTTTGTCCTACA
ACAAAAAGAGCACCCCAAGTTTAAGAGAAAGGGCGATGACCTCTTTGTAGAGCATACCT
TGTCTCTCGTCGAGTCTCTGTGTGGTTTCCAATTTATTCTGACTCATTTGGATGGCCGA
CAGCTACTCATCAAATCACTTCCCGGTGAAGTAGTGAAGCCTGACCAATTCAAGGCCAT
AAACGATGAGGGTATGCCTATGTACCAGAGGCCATTCATGAAGGGCAAACTTTACATCC
ACTTCAGTGTTGAGTTCCCAGACTCCTTGAACCCCGAACAGTGCAAGGCGCTGGAGGGC
GTTCTGCCTCCCAGGACCTCAGTGCAGCTCTCAGATATGGAATTGGATGAATGTGAAGA
GACCACTCTCCACGATGTCAACATTGAAGAGGAGATGCGCAGGAAGCAAGCACAAGAGG
CATACGATGAAGATGAGGATATGCACGGTGGTGCACAGAGAGTGCAGTGTGCTCAACAA
TGA
```

FIGURE 5 (continued)

seq id no 24: *Cucumis sativus* DnaJ protein (X67695) translation SEQ ID NO: 23

MFGRPKKSDNTKYYEILGVSKNASQDDLKKAYRKAAIKNHPDKGGDPEKFKELAQAYEV
LSDPEKREIYDQYGEDALKEGMGGGGGHDPFDIFQSFFGGSPFGGGGSSRGRRQRRGED
VIHPLKVSLEDLYNGTSKKLSLSRNVICSKCKGKGSKSGASMKCPGCQGSGMKVSIRHL
GPSMIQQMQHPCNECKGTGETINDKDRCSQCKGEKVVQEKKVLEVIVEKGMQNAQKITF
PGEADEAPDTVTGDIVFVLQQKEHPKFKRKGDDLFVEHTLSLVESLCGFQFILTHLDGR
QLLIKSLPGEVVKPDQFKAINDEGMPMYQRPFMKGKLYIHFSVEFPDSLNPEQCKALEG
VLPPRTSVQLSDMELDECEETTLHDVNIEEEMRRKQAQEAYDEDEDMHGGAQRVQCAQQ seq id no 25: *Daucus carota* DnaJ DNA (AF308737)

ATGTTTGGGAGAGCACCAAAGAAGAGTGACAATACAAAGTACTATGAAATTCTTGGTGT
CCCAAAAACAGCATCACCTGATGATCTGAAGAAAGCTTACAGGAAGGCTGCTATCAAGA
ATCATCCTGATAAGGGTGGCGATCCTGAAAAGTTTAAAGAGCTTGCGCAAGCATATGAG
GTTCTGAGTGACCCAGAGAAGCGTGAAATCTATGATCAGTATGGAGAGGATGCTCTCAA
GGAGGGAATGGGTGGTGGTGGAGGTGGTGGCCATGACCCATTTGACATTTTCCAATCCT
TCTTTGGTGGCAGCCCGTTTGGTGGAGGTGGCAGCAGCAGAGGACGAAGGCAAAGAAGG
GGGGAGGATGTCATTCATCCCCTTAAGGTTTCACTGGAAGATCTTTGCAATGGGACTTC
CAAGAAGCTTTCCCTTTCACGTAATGTAATTTGTTCTAAATGCAAGGGAAAGGGGTCCA
AGTCGGGTGCTTCAATGACATGTCCTGGCTGCCAGGGTTCTGGAATGAAGGTTTCTATC
AGGCACTTGGGCCCATCTATGATCCAGCAGATGCAGCATCCCTGCAATGACTGCAAGGG
TACTGGAGAAACAATCAACGACAAGGATCGCTGCCCTCAATGCAAAGGTCAAAAGGTTG
TGCAGGAGAAGAAAGCAATAGAAGTTATTGTGGAGAAGGGTATGCAAAACGGACAGAAG
ATTACATTCCCTGGAGAAGCTGATGAAGCGCCTGACACGGTTACTGGGGACATAGTGTT
TGTGTTGCAACAAAAGGAGCACCCCAAGTTTAAGAGGAAGGGTGATGATCTTTTTGTTG
AACATTCATTAACTCTCAGTGAAGCACTTTGTGGCTTCCAATTTACTTTGACTCACCTG
GACGGCAGGCAGCTTCTTATTAAATCCCAGCCAGGAGAAGTTATCAAGCCAGATCAATT
TAAGGGGATAAATGATGAAGGAATGCCAATGTATCAGAGGCCATTTATGCGAGGAAAGC
TTTACATTCACTTTAGTGTAGATTTCCCAGAGTCCTTGACCCCTGAGCAGTGCAAAGCT
CTTGAAGCTGTGTTACCTCCGAGGCCTTCAATTCAGATGACAGACATGGAACTGGATGA
ATGTGAAGAAACAACACTGCATGATGTGAATATTGAAGAGGAGATGCGTCGGAAACAGC
AAGCTGCCCAAGAGGCATATGACGAAGACGAAGATATGCATGGCGGTGCTCAGAGGGTG
CAGTGTGCTCAACAATGA seq id no 26: *Daucus carota* DnaJ protein translation SEQ ID NO: 25

MFGRAPKKSDNTKYYEILGVPKTASPDDLKKAYRKAAIKNHPDKGGDPEKFKELAQAYE
VLSDPEKREIYDQYGEDALKEGMGGGGGGHDPFDIFQSFFGGSPFGGGGSSRGRRQRR
GEDVIHPLKVSLEDLCNGTSKKLSLSRNVICSKCKGKGSKSGASMTCPGCQGSGMKVSI
RHLGPSMIQQMQHPCNDCKGTGETINDKDRCPQCKGQKVVQEKKAIEVIVEKGMQNGQK
ITFPGEADEAPDTVTGDIVFVLQQKEHPKFKRKGDDLFVEHSLTLSEALCGFQFTLTHL
DGRQLLIKSQPGEVIKPDQFKGINDEGMPMYQRPFMRGKLYIHFSVDFPESLTPEQCKA
LEAVLPPRPSIQMTDMELDECEETTLHDVNIEEEMRRKQQAAQEAYDEDEDMHGGAQRV
QCAQQ

FIGURE 5 (continued)

seq id no 27: *Glycine max* DnaJ DNA (AF169022)

```
ATGTTTGGGAGGGCACCGAAGAAGAGCGATAATACGAGGTACTACGAAATCCTCGGCGT
CTCCAAGAACGCTTCGCAGGATGATCTGAAGAAGGCTTACAAGAAAGCCGCCATTAAGA
ATCACCCCGACAAGGGCGGTGATCCCGAGAAGTTTAAAGAGCTGGCGCAAGCTTATGAG
GTTCTGAGTGACCCTGAGAAGCGTGAGATATATGATCAGTATGGTGAAGATGCGCTTAA
GGAAGGAATGGGTGGTGGCGGTGGCCATGATCCATTTGATATCTTTTCATCTTTCTTTG
GCGGTGGGAGTCCCTTTGGATCAGGTGGAAGTAGTCGAGGTAGGAGGCAGAGGCGCGGA
GAAGACGTGGTTCACCCTCTCAAGGTCTCTTTGGAGGACCTTTATCTTGGAACTTCCAA
GAAGCTCTCCCTCTCCAGAAATGTTATATGCTCCAAGTGCAGTGGCAAGGGTTCTAAGT
CTGGTGCTTCGATGAAGTGTGCTGGTTGTCAAGGAACTGGTATGAAGGTTTCTATAAGA
CATCTTGGCCCATCCATGATTCAGCAGATGCAGCATGCCTGCAATGAATGTAAGGGTAC
TGGAGAAACTATCAATGACAGAGATCGCTGCCCACAGTGCAAGGGAGAGAAGGTTGTGC
AGGAGAAGAAAGTCCTTGAAGTTATTGTAGAAAAGGGGATGCAGAATGGGCAGAAGATA
ACATTCCCTGGCGAAGCTGATGAAGCGCCGGACACAATTACTGGGGATATCGTCTTTGT
CCTTCAGCAGAAGGAACATCCCAAATTCAAAAGAAAGGCTGAAGATCTTTTGTAGAGC
ACACTTTGTCCCTTACCGAGGCCTTGTGTGGCTTCCAATTTGTGCTGACTCACTTGGAT
AGCCGTCAGCTTCTTATTAAATCAAATCCCGGGGAAGTTGTGAAGCCTGATTCATACAA
GGCTATAAATGATGAGGGAATGCCCATGTATCAGAGGCCATTCATGAAGGGGAAACTTT
ACATTCACTTCACTGTGGAGTTTCCAGATTCTCTAAACCCTGATCAAGTTAAGGCCTTG
GAGGCTGTTCTGCCACCAAAGCCTTCTTCACAATTGACAGACATGGAGCTGGATGAATG
TGAGGAAACTACACTCCATGATGTCAACATGGAGGAGGAGACTAGGAGGAAGCAGCAAC
AAGCTCAGGAGGCATATGATGAGGATGATGACATGCCTGGTGGTGCACAGAGGGTACAG
TGCGCCCAGCAGTAA
``` seq id no 28: *Glycine max* DnaJ protein translation SEQ ID NO: 27

```
MFGRAPKKSDNTRYYEILGVSKNASQDDLKKAYKKAAIKNHPDKGGDPEKFKELAQAYE
VLSDPEKREIYDQYGEDALKEGMGGGGHDPFDIFSSFFGGGSPFGSGGSSRGRRQRRG
EDVVHPLKVSLEDLYLGTSKKLSLSRNVICSKCSGKGSKSGASMKCAGCQGTGMKVSIR
HLGPSMIQQMQHACNECKGTGETINDRDRCPQCKGEKVVQEKKVLEVIVEKGMQNGQKI
TFPGEADEAPDTITGDIVFVLQQKEHPKFKRKAEDLFVEHTLSLTEALCGFQFVLTHLD
SRQLLIKSNPGEVVKPDSYKAINDEGMPMYQRPFMKGKLYIHFTVEFPDSLNPDQVKAL
EAVLPPKPSSQLTDMELDECEETTLHDVNMEEETRRKQQQAQEAYDEDDDMPGGAQRVQ
CAQQ
``` seq id no 29: *Hevea brasiliensis* DnaJ DNA (AF085275)

```
ATGTTTGGAAGAGCACCCAAAAAAAGCGATAACACCAAGTACTATGAGATTCTTGGGGT
CTCAAAGAACGCTTCACAGGATGATCTAAAGAAGGCTTATAGAAAAGCTGCCATCAAGA
ACCATCCTGACAAGGGTGGTGATCCTGAAAAGTTTAAAGAGTTGGCCCAAGCTTATGAG
GTTTTGAGTGATCCAGAGAAACGTGAGATATATGATCAATATGGAGAGGACGCCCTCAA
GGAGGGAATGGGCAGTGGAGGTGGTGCTCATGACCCATTTGACATTTTCCAATCCTTCT
TTGGTGGCAACCCATTTGGTGGTGGTGGTAGCAGCAGAGGCCGTAGGAAGGAGGGAGAG
GATGTTATCCATCCTCTCAAGGTTTCTTTGGAAGATCTCTACAATGGCACCTCAAAGAA
GCTGTCTCTTTCCCGTAATGTTATCTGCTCAAAGTGCAAAGGTAAAGGGTCCAAATCAG
GTGCATCAATGAAATGTTCGGGTTGCCAAGGTTCTGGAATGAAGGTCTCCATAAGACAA
CTTGGTCCCTCTATGATCCAGCAAATGCAGCATCCTTGTAATGAATGTAAGGGTACTGG
TGAGACCATTAATGATAAGGATCGTTGCCCTCAATGTAAAGGTGAAAAGGTTGTTCAGG
```

FIGURE 5 (continued)

AGAAGAAAGTGCTGGAAGTTATTGTTGAGAAGGGTATGCAAAATGGACAGAGGATTACT
TTCCCTGGAGAAGCTGATGAAGCTCCTGATACTATTACAGGGGACATTGTTTTTGTCCT
TCAGCAAAAGGAGCATCCTAAGTTCAAGCGAAAGGGTGATGACCTAATTGTTGATCACA
CTTTATCTCTTACAGAGGCACTTTGTGCCTCCCAGTTTATATTAACCCATCTAGATGGA
GACCTCCTCATAAAATCCCAACCTGGGGAGGTAGTGAAGCCTGATCAATTCAAGGCCAT
AAATGATGAAGGGATGCCAATGTATCAGAGGCCATTCATGAGGGGGAAACTGTACATTC
ATTTCAGTGTTGATTTCCCAGACTCTCTGCCCCCTGATCAGTGCAAAGCCCTAGAGGCA
GTTCTTCCCTCAAGAACATCAGTCCAGCTGTCTGACATGGAGCTGGATGAATGTGAGGA
GACAACTTTACACGATGTGAACTTTGACGAGGAGATGCGAAGGAAGCAACAACAGGCCC
AAGAGGCATATGATGAAGATGATGATATGCATGGTGGTGGCCAGAGGGTGCAATGTGCT
CAGCAATAA seq id no 30: Hevea brasiliensis DnaJ protein (AAD12055)

MFGRAPKKSDNTKYYEILGVSKNASQDDLKKAYRKAAIKNHPDKGGDPEKFKELAQAYE
VLSDPEKREIYDQYGEDALKEGMGSGGGAHDPFDIFQSFFGGNPFGGGGSSRGRRKEGE
DVIHPLKVSLEDLYNGTSKKLSLSRNVICSKCKGKGSKSGASMKCSGCQGSGMKVSIRQ
LGPSMIQQMQHPCNECKGTGETINDKDRCPQCKGEKVVQEKKVLEVIVEKGMQNGQRIT
FPGEADEAPDTITGDIVFVLQQKEHPKFKRKGDDLIVDHTLSLTEALCASQFILTHLDG
DLLIKSQPGEVVKPDQFKAINDEGMPMYQRPFMRGKLYIHFSVDFPDSLPPDQCKALEA
VLPSRTSVQLSDMELDECEETTLHDVNFDEEMRRKQQQAQEAYDEDDDMHGGGQRVQCA
QQ seq id no 31: Lycopersicum esculentum DnaJ DNA (AF124139)

ATGTTTGGAAGAGCACCGAAGAAGAGCGATAATACAAAGTATTATGAGATCTTAGGAGT
TCCTAAGGCTGCTTCTCAGGAAGATCTCAAAAAGGCTTATCGTAAAGCTGCTATCAAAA
ATCACCCTGATAAGGGAGGCGATCCTGAGAAGTTTAAAGAGCTTGCTCAAGCTTATGAG
GTTCTGAGTGACCCGGAGAAGCGTGAGATATATGATCAGTATGGAGAGGATGCTCTAAA
GGAAGGAATGGGTGGTGGAGGTGGTGGACATGAACCATTTGATATATTTCAATCATTCT
TCGGTGGTGGTGGAAACCCCTTTGGTGGTGGTGGAAGCAGCAGAGTCCGAAGACAGAGA
AGAGGAGAGGATGTTATCCACCCGCTCAAGGTTTCTTTAGAGGATCTTTACAATGGGAC
ATCAAAGAAGCTTTCACTATCTCGCAATGTGTTGTGCTCAAAGTGCAAGGGCAAAGGTT
CCAAGTCAGGTGCTTCAATGAAATGTTCTGGCTGTCAAGGGTCTGGAATGAAAGTTTCT
ATCAGACAGCTCGGTCCATCCATGATCCAGCAGATGCAGCACCCTTGCAATGAGTGCAA
GGGTACTGGAGAGACGATCAGTGACAAAGATAGGTGCCCTCAGTGCAAGGGTGAGAAGG
TTGTGCAGGAGAAGAAGGTGTTGGAAGTTCACGTGGAGAAGGGTATGCAGAATGGGCAA
AAGATAACATTTCCAGGCGAGGCAGATGAAGCGCCAGATACCATCACTGGAGACATTGT
TTTTGTCTTGCAACAAAAGGAACATCCTAAGTTCAAGCGAAAGGGAGATGATCTTTTTG
TTGAGCACACATTGAGCCTTGACGAGTCTCTATGTGGTTTCCAGTTTGTTCTGACTCAC
CTAGACAACAGACAGCTGCTCATTAAGTCCCAACCTGGCGAAGTTGTCAAGCCTGATCA
GTTTAAGGCTATCAACGATGAAGGAATGCCGATGTACCAAAGGCCGTTCATGAAGGGCA
AAATGTACATTCACTTCACTGTTGATTTCCCCGAGTCATTACACGCAGAGCAGTGCAAG
AACCTTGAGGCTGTGCTGCCTCCCAAAACCAAATTGCAGATATCAGATATGGAATTGGA
CGAGTGGGAGGAGACTACTTTGCACGATGTCAACATTGAGGAGGAGATGCGAAGGAAGC
AGCAAGCTGCCCAAGAGGCACAGGACGAAGATGACGATATGCCTGGTGGTGCACAGAGA
GTCCAATGTGCACAGCAGTAA

FIGURE 5 (continued)

seq id no 32: Lycopersicum esculentum DnaJ protein (AAF28382)

MFGRAPKKSDNTKYYEILGVPKAASQEDLKKAYRKAAIKNHPDKGGDPEKFKELAQAYE
VLSDPEKREIYDQYGEDALKEGMGGGGGGHEPFDIFQSFFGGGGNPFGGGGSSRVRRQR
RGEDVIHPLKVSLEDLYNGTSKKLSLSRNVLCSKCKGKGSKSGASMKCSGCQGSGMKVS
IRQLGPSMIQQMQHPCNECKGTGETISDKDRCPQCKGEKVVQEKKVLEVHVEKGMQNGQ
KITFPGEADEAPDTITGDIVFVLQQKEHPKFKRKGDDLFVEHTLSLDESLCGFQFVLTH
LDNRQLLIKSQPGEVVKPDQFKAINDEGMPMYQRPFMKGKMYIHFTVDFPESLHAEQCK
NLEAVLPPKTKLQISDMELDEWEETTLHDVNIEEEMRRKQQAAQEAQDEDDDMPGGAQR
VQCAQQ seq id no 33: Medicago sativa DnaJ DNA (AJ000995)

ATGTTTGGGCGCGGACCAACAAGGAAGAGTGATAACACCAAATATTACGATATTCTTGG
TGTTTCAAAAAGTGCTAGTGAAGATGAAATCAAGAAAGCCTATAGAAAGGCAGCGATGA
AGAACCATCCAGATAAGGGTGGGGATCCTGAGAAGTTCAAGGAGTTGGGCCAAGCATAT
GAAGTGTTGAGCGATCCTGAAAAGAAAGAACTGTATGATCAATATGGTGAAGATGCCCT
TAAAGAAGGAATGGGGGGAGGCGCAGGAAGCTCATTTCATAATCCGTTTGATATTTTCG
AATCATTTTTTGGTGCAGGCTTTGGTGGTGGTGGTCCTTCACGCGCAAGAAGACAGAAG
CAAGGAGAAGATGTGGTGCATTCTATAAAGGTTTCCTTGGAGGATGTGTATAACGGCAC
TACAAAGAAGCTATCACTTTCTAGGAATGCACTGTGCTCAAAATGTAAAGGGAAAGGTT
CAAAAAGTGGAACTGCTGGAAGGTGTTTTGGATGCCAGGGCACAGGTATGAAGATTACC
AGAAGGCAAATTGGACTGGGCATGATTCAACAAATGCAACACGTCTGTCCTGACTGCAA
AGGAACAGGCGAGGTCATTAGTGAGAGAGATAGATGCCCTCAATGCAAGGGAAACAAGA
TTACTCAAGAAAGAAGGTGCTGGAGGTGCATGTGGAAAAGGGGATGCAGCAGGGTCAC
AAGATTGTATTCGAAGGACAAGCTGATGAACTCCCTGATACAATCACAGGAGACATAGT
TTTTGTCTTGCAAGTAAAGGGACATCCGAAGTTTCGGAGGGAGCGTGATGACCTTCACA
TTGAACACAATTTGAGCTTAACTGATGCTCTCTGTGGCTTCCAGTTTAATGTCACACAT
CTTGATGGAAGGCAACTATTGGTCAAATCGAACCCCGGCGAAGTCATCAAGCCAGGTCA
ACATAAAGCTATAAATGATGAGGGAATGCCACAACATGGTAGGCCGTTCATGAAGGGAC
GCCTATACATCAAGTTTAGTGTTGATTTCCCGGATTCGGGTTTTCTTTCCCCAAGCCAA
AGCCTGGAATTAGAAAAGATATTACCTCAAAAGACAAGCAAGAACTTGTCCCAAAAGGA
GGTAGATGATTGTGAGGAGACCACCCTGCATGATGTCAATATTGCAGAGGAGATGAGTC
GAAAGAAGCAACAATACCGTGAGGCATATGATGACGATGATGATGAAGATGATGAGCAC
TCGCAGCCTCGGGTGCAATGCGCTCAACAGTAG seq id no 34: Medicago sativa DnaJ protein (CAA04447)

MFGRGPTRKSDNTKYYDILGVSKSASEDEIKKAYRKAAMKNHPDKGGDPEKFKELGQAY
EVLSDPEKKELYDQYGEDALKEGMGGGAGSSFHNPFDIFESFFGAGFGGGGPSRARRQK
QGEDVVHSIKVSLEDVYNGTTKKLSLSRNALCSKCKGKGSKSGTAGRCFGCQGTGMKIT
RRQIGLGMIQQMQHVCPDCKGTGEVISERDRCPQCKGNKITQEKKVLEVHVEKGMQQGH
KIVFEGQADELPDTITGDIVFVLQVKGHPKFRRERDDLHIEHNLSLTDALCGFQFNVTH
LDGRQLLVKSNPGEVIKPGQHKAINDEGMPQHGRPFMKGRLYIKFSVDFPDSGFLSPSQ
SLELEKILPQKTSKNLSQKEVDDCEETTLHDVNIAEEMSRKKQQYREAYDDDDDEDDEH
SQPRVQCAQQ

FIGURE 5 (continued)

**seq id no 35: *Nicotiana tabacum* DnaJ DNA (AJ299254)**

ATGTTTGGGAGAGGACCAAAGAAGAGTGATAATACGAGGTACTATGAAATATTGGGTGT
GTCAAAGAATGCATCAGATGATGAAATCAAGAAAGCTTATAGAAAAGCTGCTATGAAGA
ATCACCCTGATAAGGGTGGTGACCCTGAAAAGTTTAAGGAGCTTGCTCAAGCTTATGAG
GTGTTGAGTGACTCACAGAAGCGTGAGATTTATGATCAGTATGGAGAAGATGCATTAAA
AGAAGGAATGGGTGGCGGCGGCGGAATGCATGATCCATTTGACATCTTTGAATCTTTCT
TTGGTGGCAATCCATTTGGAGGTGGTGGTAGCAGCAGAGGAAGAAGACAGAGAAGGGGT
GAGGATGTAGTGCATCCACTGAAGGTCTCTCTCGAGGACCTTTACAGTGGGATAACCAA
AAAACTCTCCCTTTCGCGCAATGTCATTTGCTCCAAGTGCAGTGGGAAAGGATCGAAGT
CTGGTGCTTCAATGAAGTGTTCTGGTTGTAAAGGTAGTGGTATGAAGGTTTCAATTAGA
CAACTTGGCCCTTCAATGATCCAGCAAATGCAGCACGCTTGTAATGAATGCAAGGGTAC
TGGAGAGACTATTGACGATAAGGATCGGTGCCCTCGGTGCAAAGGTGAAAAAGTGGTTC
AGGAGAAGAAAGTCCTTGAAGTTCATGTTGAGAAAGGCATGCAAAATGGACAGAAAATT
ACATTCCCTGGAAAGGCTGATGAAACCCCTGATGCAATTACTGGAGATATAGTTTTTGT
GCTCCAGCAGAAAGACACCCGAGGTTCCAAGAGAAAGGGCGACGATCTGTTTGTAGATC
ACACATTGAGTCTAACTGAGGCTTTATGTGGCTTCCAGTTCATAATGACACACTTGGAT
GGCAGACAACTCCTCATAAAATCAAATCTCGGGGAAGTTGTTAAACCTGATCAATTCAA
GGCAATCAATGATGAGGGAACGCCAATGTATCAGAGGCCATTTATGAGGGGCAAATTGT
ACATTCGTTTCGTCGTTGAATTCCCAGATTCATTGAACACAGAACAGGTGAAGGCTCTG
GAGGCAATCTTACCACCAAGACCTCAGTCACAGTACACAGACATGGAATTGGATGAGTG
TGAGGAGACTTCTTTACATGATGTGAATATTGAGGAGGAAATGAGAAGGAAACAGGCAG
CTCAACAAGAGGCATATGATGAGGATGATGAGATGCATGGTGGTGGAGGACAGAGAGTA
CAATGTGCACAGCAGTAA

**seq id no 36: *Nicotiana tabacum* DnaJ protein (CAC12824)**

MFGRGPKKSDNTRYYEILGVSKNASDDEIKKAYRKAAMKNHPDKGGDPEKFKELAQAYE
VLSDSQKREIYDQYGEDALKEGMGGGGGMHDPFDIFESFFGGNPFGGGGSSRGRRQRRG
EDVVHPLKVSLEDLYSGITKKLSLSRNVICSKCSGKGSKSGASMKCSGCKGSGMKVSIR
QLGPSMIQQMQHACNECKGTGETIDDKDRCPRCKGEKVVQEKKVLEVHVEKGMQNGQKI
TFPGKADETPDAITGDIVFVLQQKDTRGSKRKGDDLFVDHTLSLTEALCGFQFIMTHLD
GRQLLIKSNLGEVVKPDQFKAINDEGTPMYQRPFMRGKLYIRFVVEFPDSLNTEQVKAL
EAILPPRPQSQYTDMELDECEETSLHDVNIEEEMRRKQAAQQEAYDEDDEMHGGGGQRV
QCAQQ

**seq id no 37: *Salix gilgiana* DnaJ2 DNA (AB003137)**

ATGTTTGGGCGTGCTCCGAGGAGGAGTGACAACACCAAGTATTATGAGGTTTTGGCTGT
GTCAAAAGGTGCAAGTCAAGATGAACTGAAGAAGGCTTATAAGAAAGCTGCCATAAAGA
ATCATCCTGATAAAGGTGGAGATCCTGAAAAGTTCAAGGAGTTGTCTCAAGCTTATGAA
GTCCTTAGTGATCCAGATAAAAGAGAAATTTATGATCAATATGGGGAAGATGCACTTAA
GGAGGGGATGGGACCTGGTGGTGGTGGGGGTGGTCACAATCCATTTGATATATTCGAAT
CATTTTTTGGTGGAGGTGGTTTTGGTGGTGGTAGCAGCTCAAGAGGAAGAAGGCAGAAG
CAAGGTGAAGATGTAGCGCACCCTCTGAAGGTTTCCTTAGAGGATTTGTACAATGGAAC
TTCAAAGAAACTCTCTCTTTCCAGAAACATTTTGTGTGCCAAATGTAAAGGGAAAGGTT
CAAAGAGTGGAGCCTTTGGGAATGTCGTGGCTGCCAAGGTACTGGAATGAAAGTTTCA
ATCCGACAAATTGGATTGGGCATGATGCAACAAATGCAACATGTGTGTCCTGAATGCAG
GGGCTCAGGTGAGCTAATTAGTGAGAAGGATAAATGCCCTCATTGCAGAGGGAACAAGG
TAACGCAGGAAAAGAGGGTGCTGGAAGTGCATGTTGAAGGGGAATGCAGCATGGCCAG

FIGURE 5 (continued)

```
AAGATAGTTTTCGAAGGTCAAGCTGATGAAGCTCCTGACACAATTACAGGGGATGTTGT
TTTTGTATTGCAACTGAAAAAGCACTCCAAGTTTGAACGGAAAATGGATGATCTCTTTG
TGGAACACTCTCTCAGTTTAACAGAGGCTCTTTGCGGGTATCAGTTTGCCCTTACCCAT
CTTGATGGTCGGCAGCTTCTTATCAAATCAAATCCTTACGAGATTGTAAAACCTGGTCA
ATACAAAGCAATTAACGATGAAGGAATGCCACATCATCACAGGCCCTTCATGAGGGGCA
AGCTCTATATCCATTTTAATGTGGTGTTCCCTGACTCGGGCACTCTATCCCCTGAGCAG
TGCCGTACTTTAGAGACTATACTACCCCCAAGGCAAAGCAAAAACTTGTCAGAGATGGA
GATTGATAACTGCGAAGAGACAATTATGCATGATGTCAATATGGAGGAGGAGAAAAGGC
GGAAACAGCAGCAGCGCCACCAGCATGAAGCATATGATGAGGATGAGGAGGAGGAATCA
TCCATGCCCCGGGTGCAGTGTGCCCAGCAGTAA
```

**seq id no 38: *Salix gilgiana* DnaJ2 protein (BAA76883)**

```
MFGRAPRRSDNTKYYEVLAVSKGASQDELKKAYKKAAIKNHPDKGGDPEKFKELSQAYE
VLSDPDKREIYDQYGEDALKEGMGPGGGGGGHNPFDIFESFFGGGGFGGGSSSRGRRQK
QGEDVAHPLKVSLEDLYNGTSKKLSLSRNILCAKCKGKGSKSGAFGKCRGCQGTGMKVS
IRQIGLGMMQQMQHVCPECRGSGELISEKDKCPHCRGNKVTQEKRVLEVHVERGMQHGQ
KIVFEGQADEAPDTITGDVVFVLQLKKHSKFERKMDDLFVEHSLSLTEALCGYQFALTH
LDGRQLLIKSNPYEIVKPGQYKAINDEGMPHHHRPFMRGKLYIHFNVVFPDSGTLSPEQ
CRTLETILPPRQSKNLSEMEIDNCEETIMHDVNMEEEKRRKQQQRHQHEAYDEDEEEES
SMPRVQCAQQ
```

**seq id no 39: *Salix gilgiana* DnaJ DNA (AB015601)**

```
ATGTTTGGGAGAGCACCAAAGAAAAGCGACAACACCAAGTACTATGAGGTTCTTGGAGT
CTCAAAGAGTGCTTCACAGGATGATCTAAAGAAGGCTTATAGGAAAGCAGCTATCAAGA
ACCATCCTGATAAGGGCGGTGATCCTGAAAAGTTCAAGGAGTTGGCGCAAGCATATGAG
GTTCTGAGTGACCCTGAGAAGCGTGAGATATATGATCAGTATGGAGAGGATGCCCTCAA
GGAAGGAATGGGTAGCGGCGGCAGCGGCGCTCACGATCCATTCGATATCTTCCAATCCT
TCTTTGGTGGTGGCAATCCATTCGGTGGTGGAGGTAGCAGCAGGGGCCGAAGGCAAAGA
AGGGGCGAGGATGTGATCCACCCTCTGAAAGTTTCTTTTGAAGACCTTTATAATGGCAC
ATCCAAGAAGCTTTCTCTTTCACGAAATGTAATCTGCTCCAAGTGCAAGGGCAAAGGTT
CCAAATCCGGAGCATCATCAAAATGTGCTGGTTGCCAAGGTTCTGGAATGAAGGTCTCC
ATAAGACACCTCGGTCCTTCTATGATCCAGCAAATGCAGCATGCCTGCAATGAATGCAA
GGGCACTGGCGAGACAATTAACGATAAGGACCGATGCCCTCAATGCAAGGGTGAGAAGG
TTGTCCAGGAGAAGAAAGTGTTGGAAGTAGTTGTTGAGAAGGGCATGCAAAATGGGCAG
AAGGTAACATTCCTGGAGAAGCTGATGAGGCGCCTGACACTGTTACAGGGGACATAGT
CTTCGTCCTGCAGCAAAAGGATCACCCTAAGTTTAAGAGAAAGGGTGATGACCTATTTG
TTGAGCACACACTATCTCTTACTGAGGCACTATGTGGCTTCCAATTCGTCTTGACCCAT
TTGGATGGAAGGCAGCTCCTGATAAAATCTCAACCCGGGGAAGTAGTCAAGCCTGATCA
ATTCAAGGCTATAAATGATGAAGGAATGCCGATGTACCAAAGGCCATTTATGAGAGGGA
AACTCTACATTCATTTCAGTGTTGAATTCCCAGACTCCCTGTCCCTGATATGTGCAAG
GCGTTGGAGGCCGTGCTTCCTCCGCGAGCCTCTGTTCAGCTGACTGACATGGAGCTTGA
TGAATGCGAGGAAACTACTTTACATGATGTGAACATCGATGAGGAGATGAGGAGGAAAC
AGCAACAGCAGGCCCAAGAAGCGTATGATGAAGATGATGAGATGCCTGGTGGTGCCCAG
AGGGTGCAGTGTGCTCAGCAATAA
```

FIGURE 5 (continued)

seq id no 40: *Salix gilgiana* DnaJ2 protein (BAA35121)

MFGRAPKKSDNTKYYEVLGVSKSASQDDLKKAYRKAAIKNHPDKGGDPEKFKELAQAYE
VLSDPEKREIYDQYGEDALKEGMGSGGSGAHDPFDIFQSFFGGGNPFGGGGSSRGRRQR
RGEDVIHPLKVSFEDLYNGTSKKLSLSRNVICSKCKGKGSKSGASSKCAGCQGSGMKVS
IRHLGPSMIQQMQHACNECKGTGETINDKDRCPQCKGEKVVQEKKVLEVVVEKGMQNGQ
KVTFPGEADEAPDTVTGDIVFVLQQKDHPKFKRKGDDLFVEHTLSLTEALCGFQFVLTH
LDGRQLLIKSQPGEVVKPDQFKAINDEGMPMYQRPFMRGKLYIHFSVEFPDSLSPDMCK
ALEAVLPPRASVQLTDMELDECEETTLHDVNIDEEMRRKQQQQAQEAYDEDDEMPGGAQ
RVQCAQQ seq id no 41: *Solanum tuberosum* DnaJ DNA (X94301)

ATGTTTGGGAGGGCACCAGAGAAGAGCGACAACACGAAGTACTATGAGATCTTAGGTGT
CCCTAAGACTGCTGCACAGGAAGATCTCAAGAAAGCTTACCGTAAAGCTGCTATTAAGA
ATCATCCTGATAAGGGAGGTGATCCTGAAAAGTTTAAAGAGCTTGCACAAGCTTATGAG
GTTCTGAGTGATCCCGAGAAGCGTGAGATATATGATCAGTATGGAGAAGATGCTCTCAA
GGAAGGAATGGGTGGTGGAGGTGGTGGACACGACCCATTTGATATTTTCTCATCTTTCT
TTGGTGGCAGCCCATTTGGTGGAGGTGGTGGAAGCAGCAGAGGAAGAAGACAAAGAAGA
GGAGAGGATGTTGTCCATCCTCTCAAAGTTTCTCTGGAGGATCTGTACAATGGAACATC
AAAGAAGCTGTCACTATCTCGCAATGTATTGTGCTCGAAGTGCAAGGGGAAAGGATCTA
AATCAGGTGCTTCAATGAAGTGTTCTGGCTGTCAAGGGTCTGGGATGAAAGTCACTATT
AGACAACTTGGCCCATCCATGATCCAGCAGATGCAGCACCCTTGCAACGAGTGTAAGGG
TACTGGTGAGATGATCAATGATAAAGATAGGTGTGGGCAGTGTAAGGTGAGAAAGTTG
TGCAGGAGAAGAAGGTGTTGGAAGTTGTTGTCGAGAAGGGTATGCAGAACGGACAGAAG
ATAACATTCCCGGGCGAAGCTGATGAAGCACCTGATACCGTCACTGGGGACATAGTTTT
TGTCTTGCAACAGAAGGAACATCCCAAGTTTAAGCGAAAGGGAGATGATCTCTTTGTAG
AGCACACCTTGAGCTTAACCGAGGCCCTGTGTGGTTTCCAGTTCATCTTGACTCACCTA
GATAATAGGCAGCTGATCATCAAGCCCCAAGCCGGAGAAGTTGTCAAGCCTGATCAATT
TAAAGCCATAAATGATGAAGGAATGCCTATGTACCAAAGGCCATTTATGAGAGGAAAAC
TATACATTCACTTTACTGTAGAATTCCCCGACACATTATCCCCCGAGCAATGCAAGAAC
CTTGAAGCAGTATTGCCACCAAAACCGAAAACACAAATGACTGATATGGAATTGGACGA
GTGCGAGGAGACCACCTTACATGATGTTAACATCGAAGAGGAGATGCGGAGGAAGCAGC
AACAGGCCCAAGAGGCATATGACGAAGATGATGAAGACATGCATGGAGGTGCACAGAGA
GTTCAGTGTGCACAACAGTAA seq id no 42: *Solanum tuberosum* DnaJ protein (CAA63965)

MFGRAPEKSDNTKYYEILGVPKTAAQEDLKKAYRKAAIKNHPDKGGDPEKFKELAQAYE
VLSDPEKREIYDQYGEDALKEGMGGGGGHDPFDIFSSFFGGSPFGGGGGSSRGRRQRR
GEDVVHPLKVSLEDLYNGTSKKLSLSRNVLCSKCKGKGSKSGASMKCSGCQGSGMKVTI
RQLGPSMIQQMQHPCNECKGTGEMINDKDRCGQCKGEKVVQEKKVLEVVVEKGMQNGQK
ITFPGEADEAPDTVTGDIVFVLQQKEHPKFKRKGDDLFVEHTLSLTEALCGFQFILTHL
DNRQLIIKPQAGEVVKPDQFKAINDEGMPMYQRPFMRGKLYIHFTVEFPDTLSPEQCKN
LEAVLPPKPKTQMTDMELDECEETTLHDVNIEEEMRRKQQQAQEAYDEDDEDMHGGAQR
VQCAQQ

FIGURE 5 (continued)

seq id no 43: *Oryza sativa* DnaJ DNA (AK110691)

ATGGTCAAGGACACCAAATTCTACGACACCCTCGGCTGCGCGCCCGACGCTACCGAGTC
TCAGCTCAAGACCGCATACCGCAAGGGCGCCCTCAAGCACCACCCCGACAAGAACGCAC
ACTCGCCCGAATCCGAGGAGAAGTTCAAGGAGATCTCACACGCATACGAAGTCCTCTCA
GACCCCCAAAAGCGCCAAATCTACGACCAGTATGGTGAGGAGGGTCTCGAGCAGGGTGG
TGGAATGGGCGGCGGCGGAGGCATGGCTGCCGAGGACTTGTTCGCACAGTTCTTCGGCG
GCGGCGGTGGAGGCGGAGGCTTCGGTGGCATGGGCGGCATGTTCGGCGGTCGCGAGCCC
GGCCCCAAGAAGGCTCGCACCATCCACCACGTTCACAAGGTCTCTCTCGAGGACATCTA
CCGCGGCAAGGTTTCCAAGCTTGCCCTGCAGAAGAGCGTCATCTGCTCCAAGTGTGATG
GCCGCGGTGGTAAGGAGGGTGCTGTGAAGACTTGCCAGGGCTGCCAGGGCCAGGGTATG
AAGACCATGATGCGCCAGATGGGTCCCATGATCCAGCGATTCCAGACCGTCTGCCCCGA
CTGCAACGGTGAGGGGGAGCAGGTCCGCGAGAAGGACAAGTGCAAGCAGTGCTCCGGAA
AGAAGACCATCATCGAGCGCAAGGTGCTCCACGTCCACGTCGACAAGGGTGTGCAAAGC
GGCACCAAGATCGACTTCAGAGGCGAGGGTGACCAGATGCCTGGCGTTGAGCCCGGTGA
TGTGCAGTTCGAGATCGAGCAGAAGCCTCACCCTCGCTTCCAGCGCAAGGGTGACGACC
TCTACTACCACGCCGAGATCGACCTTCTTACTGCGCTCGCCGGCGGTGCCATCTACGTT
GAGCACCTTGACGAGCGCTGGTTGACCGTCGAGATCCTGCCCGGCGAGGTTATCGCACC
AGGCGAGGTCAAGGTCATCCGCGGCCAGGGTATGCCCTCATACCGCCACCACGACCACG
GCAACCTTTACATCCAGTTCGACGTCAAGTTCCCCACATCCATCCAAGGCCCTGCCGAC
AAGGACGGCCAGTCCACCTCCATGTCCGCACAACAGATCAAGGCCCTCGAATCCGTCCT
TCCTCCTCGCAAGCCCCAATCGATCCCTCCTCCCGATGCTATGACCGAGGACTTCCAGC
TCGAGCGCGTAGACCCCATGGAGGGCTCCCGCTCCAAGGGCGCCCACAGCATGGACGAG
GACGATGACGAGATGGGCGGCGGTGGCGAGCGCGTGCAGTGCGCGTCGCAGTAA seq id no 44: *Oryza sativa* DnaJ protein translation SEQ ID NO: 43

MVKDTKFYDTLGCAPDATESQLKTAYRKGALKHHPDKNAHSPESEEKFKEISHAYEVLS
DPQKRQIYDQYGEEGLEQGGGMGGGGMAAEDLFAQFFGGGGGGGFGGMGGMFGGREP
GPKKARTIHHVHKVSLEDIYRGKVSKLALQKSVICSKCDGRGGKEGAVKTCQGCQGQGM
KTMMRQMGPMIQRFQTVCPDCNGEGEQVREKDKCKQCSGKKTIIERKVLHVHVDKGVQS
GTKIDFRGEGDQMPGVEPGDVQFEIEQKPHPRFQRKGDDLYYHAEIDLLTALAGGAIYV
EHLDERWLTVEILPGEVIAPGEVKVIRGQGMPSYRHHDHGNLYIQFDVKFPTSIQGPAD
KDGQSTSMSAQQIKALESVLPPRKPQSIPPPDAMTEDFQLERVDPMEGSRSKGAHSMDE
DDDEMGGGGERVQCASQ seq id no 45: *Triticum aestivum* DnaJ DNA (BT009366)

ATGGTAAAAGATACCAAACTATATGATACTCTGGGTATTTCCCCGACCTGTACTGAAGC
CGAGTTAAAAAAAGCATACAAAATCGGAGCACTTAAACACCATCCTGATAAAAACGCCT
CAAATCCAGCCGCCGCAGAAAAATTTAAAGAAATATCGCACGCATATGAAGTACTATCT
GACCCTCAAAAAAGACACATATACGACCAATATGGCGAAGAGGGCCTTGAGGGAGGTGG
TGGTGCTGCGGGAGGGATGAACGCAGAAGATTTATTCTCTCAATTCTTCAGCGGTGGCT
CTGCCTTCGGAGGTGGAGGATTGGGTGGCATGTTCGGGGGAGGGCCACAGCAACGTGGC
CCCCCAAAAGCCCGCACCATTCATCACGTTCACAAGGTATCTCTAGAAGATATCTACCG
CGGTAAAATCTCAAAACTGGCACTACAAAAGTCAGTCATATGCCACAAGTGTGAGGGAC
GGGGTGGCAAAGATGGTGCAGTAAAAAAATGTGCCGGCTGTGATGGACATGGAATGAAA
ACAATGATGCGTCAAATGGGTCCTATGATTCAGCGGTTTCAAACTCACTGCCCCGACTG

FIGURE 5 (continued)

```
CAATGGTGAGGGAGAAGTCATCCGAGAGAAAGATAAATGTAAGACGTGTAACGGTAAAA
AGACCAACGTGGAACGCAAAGTACTCCACGTTCATGTGGACAGAGGTGTTCGATCGGGG
CACCGGATTGAATTTAAAGGTGAAGGAGACCAAACCCCCGGAGTTCAACCTGGAGATGT
TATCTTTGAAATTGAGCAGAAACCACATCCAAGATTCCAACGAAAAGACGATGACCTTA
TTTACCACGCAGAGATCGACCTTGTTACTGCCTTAGCGGGCGGGTCAATCTTCATTGAG
CACTTAGACGAAAGATGGCTGAGTGTGGAGATACTTCCTGGAGAGGTTATCTCACCTGG
ATCCGTTAAGATGATACGCGGTCAGGGTATGCCATCCCATCGTCACCACGACTATGGAA
ATATGTTTGTACAGTTTGATGTCAAATTCCCCGAAAGTAACTTTGCTGCAAATTCCGAG
GCATACGCAGCTCTGAAGAGTATTATTCCGCCGACTGTGGTACCTATCACTCCACCCAC
TGATACCATGACTGAAACTGTATACTTCGAAGACATTGACCCTACTCAACAAGCTCGTG
CACAGGGTGCGACAGCAATGGATGAAGACGATGAAGATGGCCATCCAGCCGGCGCCGAA
CGGGTTCAATGTGCGTCACAGTAA
``` seq id no 46: *Triticum aestivum* DnaJ protein translation
SEQ ID NO: 45

```
MVKDTKLYDTLGISPTCTEAELKKAYKIGALKHHPDKNASNPAAAEKFKEISHAYEVLS
DPQKRHIYDQYGEEGLEGGGGAAGGMNAEDLFSQFFSGGGSAFGGGGLGGMFGGGPQQRG
PPKARTIHHVHKVSLEDIYRGKISKLALQKSVICHKCEGRGGKDGAVKKCAGCDGHGMK
TMMRQMGPMIQRFQTHCPDCNGEGEVIREKDKCKTCNGKKTNVERKVLHVHVDRGVRSG
HRIEFKGEGDQTPGVQPGDVIFEIEQKPHPRFQRKDDDLIYHAEIDLVTALAGGSIFIE
HLDERWLSVEILPGEVISPGSVKMIRGQGMPSHRHHDYGNMFVQFDVKFPESNFAANSE
AYAALKSIIPPTVVPITPPTDTMTETVYFEDIDPTQQARAQGATAMDEDDEDGHPAGAE
RVQCASQ
``` seq id no 47: *Caenorhabditis elegans* DnaJ DNA (NM_072051)

```
ATGTTTGGAGGTGGAAGTAGTGGTCCCGTGGACACCACTTTATACACAACACTCAATGT
GAGACCAGACGCTTCGCAGGCCGACATTAAGAAATCTTACTTCAAACTTGCTAAAGAAT
ACCATCCAGATAAAAACCCGGACCATGGAGATAAATTCAAAGAGATCAGTTTTGCCTAT
GAAGTTCTTTCGAGCCCTGAAAAACGACGCTTGTATGACGCCAGAGGTTTGGAAGGAGT
TCAAGGAGGAGGAGCTGGTGGTGGTGGAGGAGGCTTTCCTGGAGGTCTGTTCTCTCACT
TCTTCGGCGGTGCTGGCGGTGATGACGATGACGACGATGATGATATGGGTGGTCATCCA
TTTGGTGGCTTGTTCGGTGGAATGGGTGGAATGGGACGAGGTGGCCCACGTCGGCGGAA
ATTCCAAGATACTGTTCATCCCCTCAATGTTACACTCGAAGAGCTTTACGTCGGAAAAA
CATCAAAGCTGAAGCTTTCCAAAAAGGCACTCTGTAAAACTTGCGAAGGGTCAGGTGGA
AAGAAGGGAGAAAAATATAAGTGTGATGCATGCCGTGGTCGTGGAGTGAAGACGATCGT
TCAGCAAATTGGCCCCGGAATGCTCCAACAAATGCAGGTTCACTGTGATGCTTGTAAGG
GTTCTGGAGGCAAAGTTCCAGCAGGTGATAAGTGCAAAGGATGCCATGGAGAAAAGTAC
GAAAACGTTTCGAAAATATTGGAGGTTCACGTTCTTCCTGGCATGAAACATAACGATAA
AATTACATTCAAAGGAGATGGAGACCAATCTGACCCAGATGGTGAGCCAGGAGATGTTG
TCATTGTTATTCAACAGAAAGATCATGATATTTTCAAGAGAGATGGAGATGATCTTCAC
ATGACCAAGAAACTATCACTGAATGAGGCACTTTGCGGCTATAATTTCCTTATCAAACA
TCTTGATGGCCATCCTTTGGTTCTTTCTAGTAAACAAGGAGATGTTATCAAGCCAGGAG
TCATCAGAGGAGTTCTTGGAAAAGGAATGCCAAATAAGAAATACCCAGAACTCAAAGGA
AACTTGTTCGTTGAATTTGAAGTCGAATTTCCAAAGGAGCATTTCCTCGATGATGAAAA
AGCTTATGCCGTTCTGAAAAGCTGCTTCCCTACCTCAAAAGTTGTCAATGTCACCCCAG
CTGCCGCAGAAGTTTCTCTTATGGAATATGACGAGAAGAAGTACAGCCGAGGACGTGGC
GGAGACGCTTACAATGAAGATTCGGACGAAGAACAACACGGAGGACATCACGGACAAGG
CGTCAGATGCCAACACCAATAG
``` seq id no 48: *Caenorhabditis elegans* DnaJ protein
(NP_504452)

MFGGGSSGPVDTTLYTTLNVRPDASQADIKKSYFKLAKEYHPDKNPDHGDKFKEISFAY
EVLSSPEKRRLYDARGLEGVQGGGAGGGGGGFPGGLFSHFFGGAGGDDDDDDDMGGHP
FGGLFGGMGGMGRGGPRRRKFQDTVHPLNVTLEELYVGKTSKLKLSKKALCKTCEGSGG
KKGEKYKCDACRGRGVKTIVQQIGPGMLQQMQVHCDACKGSGGKVPAGDKCKGCHGEKY
ENVSKILEVHVLPGMKHNDKITFKGDGDQSDPDGEPGDVVIVIQQKDHDIFKRDGDDLH
MTKKLSLNEALCGYNFLIKHLDGHPLVLSSKQGDVIKPGVIRGVLGKGMPNKKYPELKG
NLFVEFEVEFPKEHFLDDEKAYAVLKSCFPTSKVVNVTPAAAEVSLMEYDEKKYSRGRG
GDAYNEDSDEEQHGGHHGQGVRCQHQ seq id no 49: *Homo sapiens* HsJ2 DNA (D13388)

ATGGTGAAAGAAACAACTTACTACGATGTTTTGGGGGTCAAACCCAATGCTACTCAGGA
AGAATTGAAAAAGGCTTATAGGAAACTGGCCTTGAAGTACCATCCTGATAAGAACCCAA
ATGAAGGAGAGAAGTTTAAACAGATTTCTCAAGCTTACGAAGTTCTCTCTGATGCAAAG
AAAAGGGAATTATATGACAAAGGAGGAGAACAGGCAATTAAAGAGGGTGGAGCAGGTGG
CGGTTTTGGCTCCCCCATGGACATCTTTGATATGTTTTTGGAGGAGGAGGAAGGATGC
AGAGAGAAAGGAGAGGTAAAAATGTTGTACATCAGCTCTCAGTAACCCTAGAAGACTTA
TATAATGGTGCAACAAGAAAACTGGCTCTGCAAAAGAATGTGATTTGTGACAAATGTGA
AGGTAGAGGAGGTAAGAAGGAGCAGTAGAGTGCTGTCCCAATTGCCGAGGTACTGGAA
TGCAAATAAGAATTCATCAGATAGGACCTGGAATGGTTCAGCAAATTCAGTCTGTGTGC
ATGGAGTGCCAGGGCCATGGGGAGCGGATCAGTCCTAAAGATAGATGTAAAAGCTGCAA
CGGAAGGAAGATAGTTCGAGAGAAAAAATTTAGAAGTTCATATTGACAAAGGCATGA
AAGATGGCCAGAAGATAACATTCCATGGTGAAGGAGACCAAGAACCAGGACTGGAGCCA
GGCGATATTATCATTGTGTTAGATCAGAAGGACCATGCTGTTTTACTCGACGAGGAGA
AGACCTTTCATGTGTATGGACATACAGCTCGTTGAAGCACTGTGTGGCTTCCACAAGC
CAATATCTACTCTTGACAACCGAACCATCGTCATCACCTCTCATCCAGGTCAGATTGTC
AAGCATGGAGATATCAAGTGTGTACTAAATGAAGGCATGCCAATTTATCGTAGACCATA
TGAAAAGGGTCGCCTAATCATCGAATTTAAGGTAAACTTTCCTGAGAATGGCTTTCTCT
CTCCTGATAAACTGTCTTTGCTGGAAAAACTCCTACCCGAGAGGAAGGAAGTGGAAGAG
ACTGATGAGATGGACCAAGTAGAACTGGTGGACTTTGATCCAAATCAGGAAAGACGGCG
CCACTACAATGGAGAAGCATATGAGGATGATGAACATCATCCCAGAGGTGGTGTTCAGT
GTCAGACCTCTTAA seq id no 50: *Homo sapiens* HsJ2 protein (P31689)

MVKETTYYDVLGVKPNATQEELKKAYRKLALKYHPDKNPNEGEKFKQISQAYEVLSDAK
KRELYDKGGEQAIKEGGAGGGFGSPMDIFDMFFGGGGRMQRERRGKNVVHQLSVTLEDL
YNGATRKLALQKNVICDKCEGRGGKKGAVECCPNCRGTGMQIRIHQIGPGMVQQIQSVC
MECQGHGERISPKDRCKSCNGRKIVREKKILEVHIDKGMKDGQKITFHGEGDQEPGLEP
GDIIIVLDQKDHAVFTRRGEDLFMCMDIQLVEALCGFQKPISTLDNRTIVITSHPGQIV
KHGDIKCVLNEGMPIYRRPYEKGRLIIEFKVNFPENGFLSPDKLSLLEKLLPERKEVEE
TDEMDQVELVDFDPNQERRRHYNGEAYEDDEHHPRGGVQCQTS

FIGURE 5 (continued)

seq id no 51: *Sacharomyces cereviseae* YDJ1 DNA (NC_001146)

ATGGTTAAAGAAACTAAGTTTTACGATATTCTAGGTGTTCCAGTAACTGCCACTGATGT
CGAAATTAAGAAAGCTTATAGAAAATGCGCCTTAAAATACCATCCAGATAAGAATCCAA
GTGAGGAAGCTGCAGAAAAGTTCAAAGAAGCTTCAGCAGCCTATGAAATTTATCAGAT
CCTGAAAAGAGAGATATATATGACCAATTTGGTGAAGATGGTCTAAGTGGTGCTGGTGG
CGCTGGCGGATTCCCAGGTGGTGGATTCGGTTTTGGTGACGATATCTTTTCCCAATTCT
TTGGTGCTGGTGGCGCACAAGACCAAGAGGTCCCCAAAGAGGTAAAGATATCAAGCAT
GAAATTTCTGCCTCACTTGAAGAATTATATAAGGGTAGGACAGCTAAGTTAGCCCTTAA
CAAACAGATCCTATGTAAAGAATGTGAAGGTCGTGGTGGTAAGAAAGGCGCCGTCAAGA
AGTGTACCAGCTGTAATGGTCAAGGTATTAAATTTGTAACAAGACAAATGGGTCCAATG
ATCCAAAGATTCCAAACAGAGTGTGATGTCTGTCACGGTACTGGTGATATCATTGATCC
TAAGGATCGTTGTAAATCTTGTAACGGTAAGAAAGTTGAAAACGAAAGGAAGATCCTAG
AAGTCCATGTCGAACCAGGTATGAAAGATGGTCAAAGAATCGTTTTCAAAGGTGAAGCT
GACCAAGCCCCAGATGTCATTCCAGGTGATGTTGTCTTCATAGTTTCTGAGAGACCACA
CAAGAGCTTCAAGAGAGATGGTGATGATTAGTATATGAGGCTGAAATTGATCTATTGA
CTGCTATCGCTGGTGGTGAATTTGCATTGGAACATGTTCTGGTGATTGGTTAAAGGTC
GGTATTGTTCCAGGTGAAGTTATTGCCCCAGGTATGCGTAAGGTCATCGAAGGTAAAGG
TATGCCAATTCCAAAATACGGTGGCTATGGTAATTTAATCATCAAATTTACTATCAAGT
TCCCAGAAAACCATTTCACATCAGAAGAAAACTTGAAGAAGTTAGAAGAAATTTTGCCT
CCAAGAATTGTCCCAGCCATTCCAAAGAAAGCTACTGTGGACGAATGTGTACTCGCAGA
CTTTGACCCAGCCAAATACAACAGAACACGGGCCTCCAGGGGTGGTGCAAACTATGATT
CCGATGAAGAAGAACAAGGTGGCGAAGGTGTTCAATGTGCATCTCAATGA seq id no 52: *Saccharomyces cereviseae* YDJ1 DNA (NP_014335)

MVKETKFYDILGVPVTATDVEIKKAYRKCALKYHPDKNPSEEAAEKFKEASAAYEILSD
PEKRDIYDQFGEDGLSGAGGAGGFPGGGFGFGDDIFSQFFGAGGAQRPRGPQRGKDIKH
EISASLEELYKGRTAKLALNKQILCKECEGRGGKKGAVKKCTSCNGQGIKFVTRQMGPM
IQRFQTECDVCHGTGDIIDPKDRCKSCNGKKVENERKILEVHVEPGMKDGQRIVFKGEA
DQAPDVIPGDVVFIVSERPHKSFKRDGDDLVYEAEIDLLTAIAGGEFALEHVSGDWLKV
GIVPGEVIAPGMRKVIEGKGMPIPKYGGYGNLIIKFTIKFPENHFTSEENLKKLEEILP
PRIVPAIPKKATVDECVLADFDPAKYNRTRASRGGANYDSDEEEQGGEGVQCASQ seq id no 53: *Homo sapiens* DNAJA2 DNA (NM_005880)

ATGGCTAACGTGGCTGACACGAAGCTGTACGACATCCTGGGCGTCCCGCCCGGCGCCAG
CGAGAACGAGCTGAAGAAGGCATACAGAAAGTTAGCCAAGGAATATCATCCTGATAAGA
ATCCAAATGCAGGAGACAAATTTAAAGAAATAAGTTTTGCATATGAAGTACTATCAAAT
CCTGAGAAGCGTGAGTTATATGACAGATACGGAGAGCAAGGTCTTCGGGAAGGCAGCGG
CGGAGGTGGTGGCATGGATGATATTTCTCTCACATTTTGGTGGGGGATTGTTCGGCT
TCATGGGCAATCAGAGTAGAAGTCGAAATGGCAGAAGAAGAGGAGAGGACATGATGCAT
CCACTCAAAGTATCTTTAGAAGATCTGTATAATGGCAAGACAACCAAACTACAACTTAG
CAAGAATGTGCTCTGTAGTGCATGCAGTGGCCAAGGCGGAAAGTCTGGAGCTGTCCAAA
AGTGTAGTGCTTGTCGAGGTCGAGGTGTGCGCATCATGATCAGACAGCTGGCTCCAGGG
ATGGTACAACAGATGCAGTCTGTGTGCTCTGATTGTAATGGAGAAGGAGAGGTAATTAA
TGAAAAAGACCGCTGTAAAAAATGTGAAGGGAAGAAGGTGATTAAAGAAGTCAAGATTC
TTGAAGTCCACGTAGACAAAGGCATGAAACATGGACAGAGAATTACATTCACTGGGGAA
GCAGACCAGGCCCCAGGAGTGGAACCCGGAGACATTGTTCTTTTGCTACAGGAGAAAGA
ACATGAGGTATTTCAGAGAGATGGGAATGATTTGCACATGACATATAAAATAGGACTTG

FIGURE 5 (continued)

```
TTGAAGCTCTATGTGGATTTCAGTTCACATTTAAGCACCTTGATGGACGTCAGATTGTG
GTGAAATACCCCCCTGGCAAAGTAATTGAACCAGGGTGTGTTCGTGTAGTTCGAGGTGA
AGGGATGCCGCAGTATCGTAATCCCTTTGAAAAAGGTGATCTTTACATAAAGTTTGATG
TGCAGTTTCCTGAAAACAACTGGATCAACCCAGACAAGCTTTCTGAACTAGAAGATCTT
CTGCCATCTAGACCGGAAGTTCCTAACATAATTGGAGAAACAGAGGAGGTAGAGCTTCA
GGAATTTGATAGCACTCGAGGCTCAGGAGGTGGTCAGAGGCGTGAAGCCTATAATGATA
GCTCTGATGAAGAAAGCAGCAGCCATCATGGACCTGGAGTGCAGTGTGCCCATCAGTAA
``` seq id no 54: *Homo sapiens* DNAJA2 protein (NP_005871)

```
MANVADTKLYDILGVPPGASENELKKAYRKLAKEYHPDKNPNAGDKFKEISFAYEVLSN
PEKRELYDRYGEQGLREGSGGGGMDDIFSHIFGGGLFGFMGNQSRSRNGRRRGEDMMH
PLKVSLEDLYNGKTTKLQLSKNVLCSACSGQGGKSGAVQKCSACRGRGVRIMIRQLAPG
MVQQMQSVCSDCNGEGEVINEKDRCKKCEGKKVIKEVKILEVHVDKGMKHGQRITFTGE
ADQAPGVEPGDIVLLLQEKEHEVFQRDGNDLHMTYKIGLVEALCGFQFTFKHLDGRQIV
VKYPPGKVIEPGCVRVVRGEGMPQYRNPFEKGDLYIKFDVQFPENNWINPDKLSELEDL
LPSRPEVPNIIGETEEVELQEFDSTRGSGGGQRREAYNDSSDEESSSHHGPGVQCAHQ
``` seq id no 55: *Mus musculus* mDj3 DNA (NM_019794.1)

```
ATGGCGAACGTGGCCGACACGAAGCTGTACGACATCCTGGGCGTCCCTCCCGGCGCTAG
CGAGAACGAGCTGAAGAAGGCATACCGAAAGTTAGCCAAAGAATACCACCCTGATAAGA
ATCCAAATGCTGGAGACAAATTTAAAGAAATAAGTTTTGCATATGAAGTATTGTCAAAT
CCAGAGAAGCGAGAGCTGTATGACAGATATGGAGAACAAGGCCTACGGGAAGGCAGCGG
CGGAGGCGGTGGCATGGATGATATCTTCTCACATATTTTGGTGGAGGATTGTTTGGCT
TTATGGGCAATCAGAGTAGAAGTCGAAATGGCAGAAGAAGAGGCGAGGACATGATGCAT
CCACTAAAAGTATCTTTAGAAGACCTGTACAATGGCAAGACAACCAAACTACAACTTAG
CAAGAATGTGCTCTGTAGTGCATGCAGTGGCCAAGGTGGGAAGTCTGGAGCTGTTCAGA
AATGCAGCGCTTGTCGGGTCGAGGTGTGCGCATTATGATCAGACAGCTGGCTCCAGGA
ATGGTGCAGCAGATGCAGTCCGTGTGCTCCGACTGTAATGGAGAAGGGGAGGTCATCAA
TGAAAAAGACCGCTGTAAAAAATGTGAAGGGAAGAAGGTAATCAAAGAAGTCAAGATTC
TGGAAGTCCATGTAGACAAAGGCATGAAACATGGACAGAGGATTACGTTCACTGGGGAA
GCAGACCAGGCTCCAGGAGTGGAACCTGGAGATATTGTTCTTTTGCTACAGGAAAAAGA
ACATGAGGTGTTCCAGAGAGATGGGAATGATTTGCATATGACATATAAGATAGGACTCG
TTGAAGCTTTATGTGGATTTCAGTTCACATTTAAACATCTTGATGCTCGTCAGATTGTG
GTGAAATACCCCCCTGGCAAAGTAATTGAACCAGGATGTGTTCGTGTTGTTCGAGGTGA
AGGAATGCCACAGTATCGTAATCCCTTTGAAAAGGGTGATCTCTACATAAAGTTTGATG
TACAGTTTCCTGAGAATAACTGGATCAACCCAGACAAACTTTCTGAATTAGAAGATCTC
CTGCCATCTAGACCAGAAGTTCCTAATGTTATTGGAGAGACAGAAGAAGTGGAGCTTCA
GGAATTTGATAGCACTCGAGGCTCTGGCGGTGGTCAGAGACGTGAAGCCTATAATGATA
GCTCTGATGAAGAAAGTAGCAGCCATCATGGACCTGGAGTGCAGTGTGCCCATCAGTAA
``` seq id no 56: *Mus musculus* mDj3 protein (Q9QYJ0)

```
MANVADTKLYDILGVPPGASENELKKAYRKLAKEYHPDKNPNAGDKFKEISFAYEVLSN
PEKRELYDRYGEQGLREGSGGGGMDDIFSHIFGGGLFGFMGNQSRSRNGRRRGEDMMH
PLKVSLEDLYNGKTTKLQLSKNVLCSACSGQGGKSGAVQKCSACRGRGVRIMIRQLAPG
```

FIGURE 5 (continued)

MVQQMQSVCSDCNGEGEVINEKDRCKKCEGKKVIKEVKILEVHVDKGMKHGQRITFTGE
ADQAPGVEPGDIVLLLQEKEHEVFQRDGNDLHMTYKIGLVEALCGFQFTFKHLDARQIV
VKYPPGKVIEPGCVRVVRGEGMPQYRNPFEKGDLYIKFDVQFPENNWINPDKLSELEDL
LPSRPEVPNVIGETEEVELQEFDSTRGSGGGQRREAYNDSSDEESSSHHGPGVQCAHQ seq id no 57: Oryza sativa PRO RP prolamine promoter

CTTCTACATCGGCTTAGGTGTAGCAACACGACTTTATTATTATTATTATTATTATT
ATTATTTTACAAAAATATAAAATAGATCAGTCCCTCACCACAAGTAGAGCAAGTTGGTG
AGTTATTGTAAAGTTCTACAAAGCTAATTTAAAAGTTATTGCATTAACTTATTTCATAT
TACAAACAAGAGTGTCAATGGAACAATGAAAACCATATGACATACTATAATTTTGTTTT
TATTATTGAAATTATATAATTCAAAGAGAATAAATCCACATAGCCGTAAAGTTCTACAT
GTGGTGCATTACCAAAATATATATAGCTTACAAAACATGACAAGCTTAGTTTGAAAAAT
TGCAATCCTTATCACATTGACACATAAAGTGAGTGATGAGTCATAATATTATTTTCTTT
GCTACCCATCATGTATATATGATAGCCACAAGTTACTTTGATGATGATATCAAAGAAC
ATTTTAGGTGCACCTAACAGAATATCCAAATAATATGACTCACTTAGATCATAATAGA
GCATCAAGTAAAACTAACACTCTAAAGCAACCGATGGGAAAGCATCTATAAATAGACAA
GCACAATGAAAATCCTCATCATCCTTCACCACAATTCAAATATTATAGTTGAAGCATAG
TAGTA seq id no 58: Primer prm04266

GGGGACAAGTTTGTACAAAAAAGCAGGCTTCACAATGTACGGACGCATGCC seq id no 59: Primer prm04267

GGGGACCACTTTGTACAAGAAAGCTGGGTGCATCGAATTGTTCTTACTGC

PLANTS HAVING INCREASED YIELD AND METHOD FOR MAKING THE SAME

RELATED APPLICATIONS

This application is a national stage application (under 35 U.S.C. 371) of PCT/EP2005/057167 filed Dec. 23, 2005, which claims benefit of European application 04106985.7 filed Dec. 24, 2004 and U.S. Provisional Application 60/641,688 filed Jan. 6, 2005.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_14546_00019. The size of the text file is 172 KB, and the text file was created on Jan. 4, 2010.

DnaJ domain proteins (or DnaJ proteins) of type I (to date there being at least 8 in Arabidopsis; Miernyk (2001) Cell Stress & Chaperone 6(3): 209-218), comprise (from amino terminus to carboxy terminus) the domains identified within the archetypal DnaJ protein as first characterized in Escherichia coli:

1) a G/F domain region of about 30 amino acid residues, rich in glycine (G) and phenylalanine (F), which is proposed to regulate target polypeptide specificity;
2) a Cys-rich zinc finger domain containing four repeats of the CXXCXGXG (SEQ ID NO: 66), where X represents a charged or polar residue; these four repeats function in pairs to form zinc binding domain I and II (InterPro reference IPR001305; Linke et al. (2003) J Biol Chem 278(45): 44457-44466); the zinc finger domain is thought to mediate direct protein:protein interactions and more specifically to bind non-native polypeptides to be delivered to Hsp70;
3) a carboxy-terminal domain (CTD; InterPro reference IPR002939).

The present invention relates generally to the field of molecular biology and concerns a method for increasing plant yield, in plants grown under non-stress conditions, relative to yield in corresponding wild type plants grown under comparable conditions. More specifically, the present invention concerns a method for increasing plant yield in plants grown under non-stress conditions, comprising preferentially increasing activity in the cytosol of a plant cell of a type I DnaJ-like polypeptide or a homologue thereof. The present invention also concerns plants having preferentially increased activity in the cytosol of a type I DnaJ-like polypeptide or a homologue thereof, which plants have increased yield when grown under non-stressed conditions relative to yield in corresponding wild type plants grown under comparable conditions. The invention also provides constructs useful in the methods of the invention.

The ever-increasing world population and the dwindling supply of arable land available for agriculture fuel agricultural research towards improving the efficiency of agriculture. Conventional means for crop and horticultural improvements utilise selective breeding techniques to identify plants having desirable characteristics. However, such selective breeding techniques have several drawbacks, namely that these techniques are typically labour intensive and result in plants that often contain heterogeneous genetic components that may not always result in the desirable trait being passed on from parent plants. Advances in molecular biology have allowed mankind to modify the germplasm of animals and plants. Genetic engineering of plants entails the isolation and manipulation of genetic material (typically in the form of DNA or RNA) and the subsequent introduction of that genetic material into a plant. Such technology has the capacity to deliver crops or plants having various improved economic, agronomic or horticultural traits. A trait of particular economic interest is yield. Yield is normally defined as the measurable produce of economic value from a crop. This may be defined in terms of quantity and/or quality. Yield is directly dependent on several factors, for example, the number and size of the organs, plant architecture (for example, the number of branches), seed production and more. Root development, nutrient uptake and stress tolerance may also be important factors in determining yield. Optimizing one of the above-mentioned factors may therefore increase crop yield. Furthermore, plant seeds are an important source of human and animal nutrition. Crops such as, corn, rice, wheat, canola and soybean account for over half of total human caloric intake, whether through direct consumption of the seeds themselves or through consumption of meat products raised on processed seeds. They are also a source of sugars, oils and many kinds of metabolites used in industrial processes. Seeds contain an embryo, the source of new shoots and roots after germination, and an endosperm, the source of nutrients for embryo growth, during germination and early growth of seedlings. The development of a seed involves many genes, and requires the transfer of metabolites from roots, leaves and stems into the growing seed. The endosperm, in particular, assimilates the metabolic precursors of carbohydrate polymers, oil and proteins and synthesizes them into storage macromolecules to fill out the grain. The ability to increase plant seed yield, whether through increased harvest index, increased thousand kernel weight, seed number, seed biomass, seed development, seed filling or any other seed-related trait would have many applications in agriculture, and even many non-agricultural uses such as in the biotechnological production of substances such as pharmaceuticals, antibodies or vaccines.

It has now been found that preferentially increasing activity in the cytosol of a plant cell of a type I DnaJ-like polypeptide gives plants grown under non-stress conditions increased yield relative to corresponding wild type plants grown under comparable conditions.

DnaJ is a molecular co-chaperone of the Hsp40 (Heat shock protein 40) family. Hsp40 cooperates with chaperone heat shock protein 70 (Hsp70, also called DnaK) and co-chaperone nucleotide exchange factor GrpE to facilitate different aspects of cellular protein metabolism that include ribosome assembly, protein translocation, protein folding and unfolding, suppression of polypeptide aggregation and cell signalling (Walid (2001) Curr Protein Peptide Sci 2: 227-244). DnaJ stimulates Hsp70 to hydrolyze ATP, a key step in the stable binding of a substrate to Hsp70. In addition, DnaJ itself also possesses molecular chaperone functions since it has been shown to bind to nascent chains in in vitro translation systems and to prevent the aggregation of denatured polypeptides (Laufen et al. (2001) Proc Natl Acad Sci USA 96: 5452-5457). Members of the DnaJ family have been identified in a variety of organisms (both in prokaryotes and eucaryotes) and in a variety of cellular compartments, such as cytosol, mitochondria, peroxisome, glyoxysome, endoplasmic reticulum and chloroplast stroma. Within one organism, multiple Hsp40s can interact with a single Hsp70 to generate Hsp70::Hsp40 pairs that facilitate numerous reactions in cellular protein metabolism.

All DnaJ proteins are defined by the presence of a so-called "J" domain, consisting of approximately 70 amino acids, usually located at the amino terminus of the protein, and by the presence of the highly conserved HPD tri-peptide in the middle of the J-domain (InterPro reference IPR001623; Zdobnov et al., (2002) 18(8): 1149-50); The "J" domain, consisting of four alpha helices, interacts with Hsp70 proteins. In the genome of *Arabidopsis thaliana*, at least 89 proteins comprising the J-domain have been identified (Miernyk (2001) Cell Stress & Chaperones). 18 Hsp70 proteins have been identified to date.

DnaJ proteins have been further classified into Type I, Type II and Type III.

DnaJ domain proteins (or DnaJ proteins) of type I (to date there being at least 8 in Arabidopsis; Miernyk (2001) Cell Stress & Chaperone 6(3): 209-218), comprise (from amino terminus to carboxy terminus) the domains identified within the archetypal DnaJ protein as first characterized in *Escherichia coli*:

1) a G/F domain region of about 30 amino acid residues, rich in glycine (G) and phenylalanine (F), which is proposed to regulate target polypeptide specificity;
2) a Cys-rich zinc finger domain containing four repeats of the CXXCXGXG, where X represents a charged or polar residue; these four repeats function in pairs to form zinc binding domain I and II (InterPro reference IPR001305; Linke et al. (2003) J Biol Chem 278(45): 44457-44466); the zinc finger domain is thought to mediate direct protein:protein interactions and more specifically to bind non-native polypeptides to be delivered to Hsp70;
3) a carboxy-terminal domain (CTD; InterPro reference IPR002939).

Type II DnaJ domain proteins (to date there being at least 35 in Arabidopsis) comprise the J domain located at the amino terminus of the protein, either the G/F domain or the zinc finger domain and a CTD. Type III DnaJ domain proteins (to date there being at least 45 in Arabidopsis) comprise only the J domain, which may be located anywhere within the protein.

In their native form, DnaJ proteins may be targeted to a variety of subcellular compartments, in either a soluble or a membrane-bound form. Examples of such subcellular compartments in plants include mitochondria, chloroplasts, peroxisomes, nucleus, cytoplasm and secretory pathway. Signal sequences and transit peptides, usually located at the amino terminus of the nuclear-encoded DnaJ proteins, are responsible for the targeting of these proteins to specific subcellular compartments.

Examples of cellular membranes to which DnaJ proteins may be targeted under specific circumstances include the mitochondrial outer membrane, the chloroplastic outer membrane, the peroxisomal membrane, the nuclear envelope, the endoplasmic reticulum (ER) and the cell membrane itself (Miernyk (2001) Cell Stress & Chaperone 6(3): 209-218). One type of membrane association of a DnaJ protein happens after posttranslational modification of the protein, i.e., after isoprenylation. An isoprenoid group is attached to the cysteine of the farnesylation CaaX motif (where C is Cys, a an aliphatic amino acid residue and X any amino acid) located at the carboxy terminus end of the protein. This farnesylation has been shown to result in higher biological activity and membrane association of the DnaJ protein, especially at elevated temperatures (Zhu J-K et al., (1993) The Plant Cell 5:341-9).

It has been suggested that DnaJ proteins play a role (together with HSP70) in conferring tolerance to heat stress in plants. Whilst DnaJ may have a protective role to play in heat-stressed plants, it is not apparent whether there might be any added advantage to increasing levels and/or activity of DnaJ in nonheat-stressed plants.

It was therefore surprising to find that a type I DnaJ-like polypeptide could be used under non-stress growth conditions to give plants having increased yield relative to yield in corresponding wild type plants grown under comparable conditions.

Therefore, according to one embodiment of the present invention, there is provided a method for increasing plant yield in plants grown under non-stress conditions, comprising preferentially increasing activity in the cytosol of a plant cell of a type I DnaJ-like polypeptide or a homologue thereof, which type I DnaJ-like polypeptide or homologue thereof comprises a CaaX motif in its carboxy terminus.

The term "cytosol" refers to the subcellular location of the DnaJ protein useful in the methods of the invention. A transient or prolonged association of the DnaJ protein with the outer surface of mitochondria, chloroplasts, peroxisome, nucleus, ER or with the cellular membrane, is encompassed by the term cytosol.

The "carboxy terminus" of a protein may readily be identified by a person skilled in the art.

Reference herein to "corresponding wild type plants" is taken to mean any suitable control plant or plants, the choice of which would be within the capabilities of a person skilled in the art and may include, for example, corresponding wild type plants or corresponding plants without the gene of interest. A "control plant" as used herein refers not only to whole plants, but also to plant parts, including seeds and seed parts.

Reference herein to "non-stressed (growth) conditions" is taken to mean growth/cultivation of a plant at any stage in its life cycle (from seed to mature plant and back to seed again) under normal growth conditions, which include the everyday mild stresses that every plant encounters, but which do not include severe stress. An example of a severe stress is heat stress, the occurrence of which would be well known in the art, and which would depend upon various factors, such as the region in which the plant is grown and which would depend upon the plant itself.

Advantageously, performance of the methods according to the present invention results in plants having increased plant yield, particularly increased seed yield.

The term "increased yield" as defined herein is taken to mean an increase in any one or more of the following, each relative to corresponding wild type plants: (i) increased biomass (weight) of one or more parts of a plant, particularly aboveground (harvestable) parts, increased root biomass or increased biomass of any other harvestable part; (ii) increased seed yield, which includes an increase in seed biomass (seed weight) and which may be an increase in the seed weight per plant or on an individual seed basis; (iii) increased number of (filled) seeds; (iv) increased fill rate (which is the number of filled seeds divided by the total number of seeds and multiplied by 100); (v) increased seed size, which may also influence the composition of seeds; (vi) increased seed volume, which may also influence the composition of seeds; (vii) increased harvest index, which is expressed as a ratio of the yield of harvestable parts, such as seeds, over the total biomass; and (viii) increased thousand kernel weight (TKW), which is extrapolated from the number of filled seeds counted and their total weight. An increased TKW may result from an increased seed size and/or seed weight.

Taking corn as an example, a yield increase may be manifested as one or more of the following: increase in the number of plants per hectare or acre, an increase in the number of ears per plant, an increase in the number of rows, number of kernels per row, kernel weight, thousand kernel weight, ear length/diameter, among others. Taking rice as an example, a yield increase may be manifested as an increase in one or more of the following: number of plants per hectare or acre, number of panicles per plant, number of spikelets per panicle, number of flowers per panicle, increase in the seed filling rate, increase in thousand kernel weight, among others. An increase in yield may also result in modified architecture, or may occur because of modified architecture.

According to a preferred feature, performance of the methods of the invention result in plants having increased seed yield. Therefore, according to the present invention, there is provided a method for increasing plant seed yield in plants grown under non-stress conditions, which method comprises preferentially increasing activity in the cytosol of a plant cell of a type I DnaJ-like polypeptide or a homologue thereof, which type I DnaJ-like polypeptide comprises a CaaX motif at its carboxy terminus.

Further preferably, the increased seed yield is manifested as an increase in harvest index relative to corresponding wild type plants. Therefore, according to the present invention, there is provided a method for increasing harvest index in plants grown under non-stress conditions, which method comprises preferentially increasing activity in the cytosol of a plant cell of a type I DnaJ-like polypeptide or a homologue thereof, which type I DnaJ-like polypeptide comprises a CaaX motif at its carboxy terminus.

Since the transgenic plants according to the present invention have increased yield, it is likely that these plants exhibit an increased growth rate (during at least part of their life cycle), relative to the growth rate of corresponding wild type plants at a corresponding stage in their life cycle. The increased growth rate may be specific to one or more parts of a plant (including seeds), or may be throughout substantially the whole plant. A plant having an increased growth rate may even exhibit early flowering. The increase in growth rate may take place at one or more stages in the life cycle of a plant or during substantially the whole plant life cycle. Increased growth rate during the early stages in the life cycle of a plant may reflect enhanced vigour. The increase in growth rate may alter the harvest cycle of a plant allowing plants to be sown later and/or harvested sooner than world otherwise be possible. If the growth rate is sufficiently increased, it may allow for the further sowing of seeds of the same plant species (for example sowing and harvesting of rice plants followed by sowing and harvesting of further rice plants all within one conventional growing period). Similarly, if the growth rate is sufficiently increased, it may allow for the further sowing of seeds of different plants species (for example the sowing and harvesting of rice plants followed by, for example, the sowing and optional harvesting of soybean, potato or any other suitable plant crop). Harvesting additional times from the same rootstock in the case of some plants may also be possible. Altering the harvest cycle of a plant may lead to an increase in annual biomass production per acre (due to an increase in the number of times (say in a year) that any particular plant may be grown and harvested). An increase in growth rate may also allow for the cultivation of transgenic plants in a wider geographical area than their wild-type counterparts, since the territorial limitations for growing a crop are often determined by adverse environmental conditions either at the time of planting (early season) or at the time of harvesting (late season). Such adverse conditions may be avoided if the harvest cycle is shortened. The growth rate may be determined by deriving various parameters from growth curves, such parameters may be: T-Mid (the time taken for plants to reach 50% of their maximal size) and T-90 (time taken for plants to reach 90% of their maximal size), amongst others.

Performance of the methods of the invention gives plants having an increased growth rate. Therefore, according to the present invention, there is provided a method for increasing the growth rate of plants grown under non-stress conditions relative to the growth rate of wild type plants grown under comparable conditions, which method comprises preferentially increasing activity in the cytosol of a plant cell of a type I DnaJ-like polypeptide or a homologue thereof, which type I DnaJ-like polypeptide or homologue thereof comprises a CaaX motif at its carboxy terminus.

The abovementioned growth characteristics may advantageously be modified in any plant.

The term "plant" as used herein encompasses whole plants, ancestors and progeny of the plants and plant parts, including seeds, shoots, stems, leaves, roots (including tubers), flowers, and tissues and organs, wherein each of the aforementioned comprise the gene/nucleic acid of interest. The term "plant" also encompasses plant cells, suspension cultures, callus tissue, embryos, meristematic regions, gametophytes, sporophytes, pollen, and microspores, again wherein each of the aforementioned comprise the gene/nucleic acid of interest.

Plants that are particularly useful in the methods of the invention include all plants which belong to the superfamily Viridiplantae, in particular monocotyledonous and dicotyledonous plants including fodder or forage legumes, ornamental plants, food crops, trees or shrubs selected from the list comprising *Acacia* spp., *Acer* spp., *Actinidia* spp., *Aesculus* spp., *Agathis australis*, *Albizia amara*, *Alsophila tricolor*, *Andropogon* spp., *Arachis spp*, *Areca catechu*, *Astelia fragrans*, *Astragalus cicer*, *Baikiaea plunjuga*, *Betula* spp., *Brassica* spp., *Bruguiera gymnorrhiza*, *Burkea africana*, *Butea frondosa*, *Cadaba farinosa*, *Calliandra* spp, *Camellia sinensis*, *Canna indica*, *Capsicum* spp., *Cassia* spp., *Centroema pubescens*, *Chaenomeles* spp., *Cinnamomum cassia*, *Coffea arabica*, *Colophospermum mopane*, *Coronillia varia*, *Cotoneaster serotina*, *Crataegus* spp., *Cucumis* spp., *Cupressus* spp., *Cyathea dealbata*, *Cydonia oblonga*, *Cryptomeria japonica*, *Cymbopogon* spp., *Cynthea dealbata*, *Cydonia oblonga*, *Dalbergia monetaria*, *Davallia divaricata*, *Desmodium* spp., *Dicksonia squarosa*, *Diheteropogon amplectens*, *Dioclea* spp, *Dolichos* spp., *Dorycnium rectum*, *Echinochloa pyramidalis*, *Ehrartia* spp., *Eleusine coracana*, *Eragrestis* spp., *Erythrina* spp., *Eucalyptus* spp., *Euclea schimperi*, *Eulalia villosa*, *Fagopyrum* spp., *Feijoa sellowiana*, *Fragaria* spp., *Flemingia* spp, *Freycinetia banksii*, *Geranium thunbergii*, *Ginkgo biloba*, *Glycine javanica*, *Gliricidia* spp, *Gossypium hirsutum*, *Grevillea* spp., *Guibourtia coleosperma*, *Hedysarum* spp., *Hemarthia altissima*, *Heteropogon contortus*, *Hordeum vulgare*, *Hyparrhenia rufa*, *Hypericum erectum*, *Hyperthelia dissoluta*, *Indigo incamata*, *Iris* spp., *Leptarrhena pyrolifolia*, *Lespediza* spp., *Leffuca* spp., *Leucaena leucocephala*, *Loudetia simplex*, *Lotonus bainesii*, *Lotus* spp., *Macrotyloma axillare*, *Malus* spp., *Manihot esculenta*, *Medicago sauva*, *Metasequoia glyptostroboides*, *Musa sapientum*, *Nicotianum* spp., *Onobrychis* spp., *Ornithopus* spp., *Oryza* spp., *Peltophorum africanum*, *Pennisetum* spp., *Persea gratissima*, *Petunia* spp., *Phaseolus* spp., *Phoenix canariensis*, *Phonnium cookianum*, *Photinia* spp., *Picea glauca*, *Pinus* spp., *Pisum sativum*, *Podocarpus totara*, *Pogonarthria fleckii*, *Pogonarthria squarrosa*, *Populus* spp., *Prosopis cineraria*, *Pseudotsuga menziesii*, *Pterolobium stellatum*, *Pyrus communis*, *Quercus* spp., *Rhaphiolepis umbellata*, *Rhopalostylis sapida*, *Rhus natalensis*, *Ribes grossularia*, *Ribes* spp., *Robinia pseudoacacia*, *Rosa* spp., *Rubus* spp., *Salix* spp., *Schyzachyrium sanguineum*, *Sciadopitys verticillata*, *Sequoia sempervirens*, *Sequoiadendron giganteum*, *Sorghum bicolor*, *Spinacia* spp., *Sporobolus fimbriatus*, *Stiburus alopecuroides*, *Stylosanthos humilis*, *Tadehagi* spp, *Taxodium distichum*, *Themeda triandra*, *Trifolium* spp., *Triticum* spp.,

*Tsuga heterophylla, Vaccinium* spp., *Vicia* spp., *Vitis vinifera, Watsonia pyramidata, Zantedeschia aethiopica, Zea mays,* amaranth, artichoke, asparagus, broccoli, Brussels sprouts, cabbage, canola, carrot, cauliflower, celery, collard greens, flax, kale, lentil, oilseed rape, okra, onion, potato, rice, soybean, strawberry, sugar beet, sugarcane, sunflower, tomato, squash, tea and algae, amongst others.

Preferably, the plant is a crop plant such as soybean, sunflower, canola, alfalfa, rapeseed, cotton, tomato, potato or tobacco. Further preferably, the plant is a monocotyledonous plant, such as sugarcane. More preferably the plant is a cereal, such as rice, maize, wheat, barley, millet, rye, sorghum or oats.

The activity of a type I DnaJ-like polypeptide may be increased by raising levels of the polypeptide. Alternatively, activity may also be increased when there is no change in levels of a type I DnaJ-like polypeptide, or even when there is a reduction in levels of a type I DnaJ-like polypeptide. This may occur when the intrinsic properties of the polypeptide are altered, for example, by making mutant versions that are more active that the wild type polypeptide. Reference herein to "preferentially" increasing activity is taken to mean a targeted increase in activity of a type I DnaJ-like polypeptide or a homologue thereof in the cytosol of a plant grown under non-stressed conditions, which increase in activity is above that found in the cytosol of cells of wild type plants grown under comparable conditions.

The term "type I DnaJ-like polypeptide or a homologue thereof" as defined herein refers to a type I DnaJ polypeptide comprising a CaaX motif at its carboxy terminus.

Common to all DnaJ proteins is the presence of a J-domain, which consists of approximately 70 amino acids (usually located at the amino terminus of the protein) and which comprises the highly conserved HPD tri-peptide in its middle (InterPro reference IPR001623; Zdobnov et al., (2002) 18(8): 1149-50); The "J" domain, consisting of four alpha helices, interacts with Hsp70 proteins. In the genome of *Arabidopsis thaliana*, at least 89 proteins comprising the J-domain have been identified (Miernyk (2001) Cell Stress & Chaperones). To date, 18 Hsp70 proteins have been identified.

Type I DnaJ domain proteins (or DnaJ proteins) are further characterised by the presence of the following from amino terminus to carboxy terminus:

1. a G/F domain region of about 30 amino acid residues, rich in glycine (G) and phenylalanine (F), which is proposed to regulate target polypeptide specificity; and 2. a Cys-rich zinc finger domain containing four repeats of the CXXCXGXG(SEQ ID NO: 66), where X represents a charged or polar residue; these four repeats function in pairs to form zinc binding domain I and II (InterPro reference IPR001305; Linke et al. (2003) J Biol Chem 278(45): 44457-44466); the zinc finger domain is thought to mediate direct protein:protein interactions and more specifically to bind non-native polypeptides to be delivered to Hsp70; and 3. a carboxy-terminal domain (CTD; InterPro reference IPR002939).

In their native form, DnaJ proteins may be targeted to a variety of subcellular compartments, in either a soluble or a membrane-bound form. DnaJ proteins useful in methods of the invention are those without a signal sequence or a transit peptide, and are therefore principally located in the cytosol of a plant cell.

DnaJ proteins useful in methods of the invention are those comprising a CaaX motif at their carboxy terminus. This polypeptide is thus present in either a soluble or a membrane-bound form, with existence in either form being reversible.

A "type I DnaJ-like polypeptide or a homologue thereof" may readily be identified using routine techniques well known in the art. For example, stimulation of the ATPase activity of DnaK by DnaJ may readily be determined in vitro as in Zhou et al., (2000), Protein Expression & Purification 19: 253-258. The ability of DnaJ to promote complex formation between DnaK and non-native polypeptides, such as denatured luciferase, may be determined by ELISA (Fan et al., (2004) Molec. Biol. Cell 15: 761-773).

A "type I DnaJ-like polypeptide or a homologue thereof" may readily be identified using sequence alignment. Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the alignment of two complete sequences that maximizes the number of matches and minimizes the number of gaps. The BLAST algorithm (Altschul et al., (1990) J Mol Biol 215: 403-10) calculates percent sequence identity and performs a statistical analysis of the similarity between the two sequences. The software for performing BLAST analysis is publicly available through the National Centre for Biotechnology Information. Homologues of type I DnaJ-like polypeptides and their percentage of identity to the type I DnaJ-like amino acid sequence useful in methods of the invention, as represented by SEQ ID NO: 2, may readily be identified using, for example, the VNTI AlignX multiple alignment program, based on a modified ClustalW algorithm (InforMax, Bethesda, Md., with default settings for gap opening penalty and gap extension. Preferably, type I DnaJ-like polypeptides or homologues thereof comprising a CaaX motif at their carboxy terminus, and which are useful in methods of the invention, are those having in increasing order of preference at least 35%, 40%, 45%, 50%, 55%, 60%, 65%, 70%, 75%, 80%, 85%, 90% or 95% identity to SEQ ID NO: 2.

Examples of polypeptides covered by the term "type I DnaJ-like polypeptide or a homologue thereof" are listed in Table 1 as SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54 and SEQ ID NO: 56. Type I DnaJ-like polypeptide sequence used to exemplify the invention is as represented by SEQ ID NO: 2.

TABLE 1

Examples of nucleic acids (DNA SEQ ID) from different organisms encoding type I DnaJ-like polypeptides (Protein SEQ ID)

| Gene Name | Accession number DNA | DNA SEQ ID | Accession number protein | Protein SEQ ID | Source |
|---|---|---|---|---|---|
| CDS1877 DnaJ | AK066420.1 | SEQ ID NO: 1 | VT | SEQ ID NO: 2 | Oryza sativa |
| Orysa_DNAJ II CAAX | AK10195 | SEQ ID NO: 3 | VT | SEQ ID NO: 4 | Oryza sativa |
| Orysa_DNAJ III CAAX | AK105028 | SEQ ID NO: 5 | VT | SEQ ID NO: 6 | Oryza sativa |
| Orysa_DNAJ IV CAAX | AK104315 | SEQ ID NO: 7 | VT | SEQ ID NO: 8 | Oryza sativa |
| Zeama_ZMDJ 1 | BT016805 * | SEQ ID NO: 9 | T01643 | SEQ ID NO: 10 | Zea mays |
| Zeama_DNAJ I CAAX | AY103727.1 | SEQ ID NO: 11 | VT | SEQ ID NO: 12 | Zea mays |
| Zeama_DNAJ II CAAX | AY108160.1 | SEQ ID NO: 13 | VT | SEQ ID NO: 14 | Zea mays |
| Triae_DNAJ | BT008914.1 | SEQ ID NO: 15 | VT | SEQ ID NO: 16 | Triticum aestivum |
| At5g22060 AtJ2 CAAX | L36113 | SEQ ID NO: 17 | AAB8679 | SEQ ID NO: 18 | Arabidopsis thaliana |
| At3g44110 AtJ3 CAAX | NM_114279 | SEQ ID NO: 19 | S71199 | SEQ ID NO: 20 | Arabidopsis thaliana |
| Atrnu_DNAJ | L09124 | SEQ ID NO: 21 | VT | SEQ ID NO: 22 | Atriplex nummularia |
| Cucsa_DNAJ-1 | X67695 | SEQ ID NO: 23 | VT | SEQ ID NO: 24 | Cucumis sativus |
| Dauca_J1P | AF308737 | SEQ ID NO: 25 | VT | SEQ ID NO: 26 | Daucus carota |
| Glyma_pm37 DNAJ | AF169022 | SEQ ID NO: 27 | VT | SEQ ID NO: 28 | Glycine max |
| Hevbr_DNAJ | AF085275 | SEQ ID NO: 29 | AAD1205 | SEQ ID NO: 30 | Hevea brasiliensis |
| Lyces_DNAJ | AF124139 | SEQ ID NO: 31 | AAF28382 | SEQ ID NO: 32 | Lycopersicum esculentum |
| Medsa_DNAJ | AJ000995 | SEQ ID NO: 33 | CAA0444 | SEQ ID NO: 34 | Medicago sativa |
| Nicta_DNAJ | AJ299254 | SEQ ID NO: 35 | CAC1282 | SEQ ID NO: 36 | Nicotiana tabacum |
| Salgi_DNAJ2 | AB003137 | SEQ ID NO: 37 | BAA7688 | SEQ ID NO: 38 | Salix gilgiana |
| Salgi_DNAJ | AB015601 | SEQ ID NO: 39 | BAA3512 | SEQ ID NO: 40 | Salix gilgiana |
| Solto_DNAJ | X94301 | SEQ ID NO: 41 | CAA6396 | SEQ ID NO: 42 | Solanum tuberosum |
| Orysa_DNAJ CASQ | AK110691 | SEQ ID NO: 43 | VT | SEQ ID NO: 44 | Oryza sativa |
| Triae_DNAJ II CASQ | BT009366 | SEQ ID NO: 45 | VT | SEQ ID NO: 46 | Triticum aestivum |
| Ceael_DNaJ | NM_072051 | SEQ ID NO: 47 | NP_50445 | SEQ ID NO: 48 | Caenorhabditis elegans |
| Homsa_HsJ2 | D13388 | SEQ ID NO: 49 | P31689 | SEQ ID NO: 50 | Homo sapiens |
| Sacce_YDJ1 | NC_001146 | SEQ ID NO: 51 | NP_01433 | SEQ ID NO: 52 | Saccharomyces cereviseae |
| Homsa_DNAJ A2 | NM_005880 | SEQ ID NO: 53 | NP_00587 | SEQ ID NO: 54 | Homo sapiens |
| Musmu_mDj3 | NM_019794 | SEQ ID NO: 55 | Q9QYJ0 | SEQ ID NO: 56 | Mus musculus |

VT = virtual translation;
* with minor corrections

It is to be understood that sequences falling under the definition of type I DnaJ-like polypeptide or homologue thereof are not to be limited to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54 and SEQ ID NO: 56 listed in Table 1, but that any type I DnaJ-like polypeptide comprising a CaaX motif at its carboxy terminus may be suitable for use in the methods of the invention.

The nucleic acid encoding a type I DnaJ-like polypeptide or a homologue thereof may be any natural or synthetic nucleic acid. Therefore the term "type I DnaJ-like nucleic acid/gene" as defined herein is any nucleic acid/gene encoding a type I DnaJ-like polypeptide or a homologue thereof as defined hereinabove. Examples of type I DnaJ-like nucleic acids include those listed in Table 1 as SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51 SEQ ID NO: 53 and SEQ ID NO: 55. Type I DnaJ-like nucleic acids/ genes and variants thereof may be suitable in practising the methods of the invention. Variant type I DnaJ-like nucleic acid/genes include portions of a type I DnaJ-like nucleic acid/gene and/or nucleic acids capable of hybridising with a type I DnaJ-like nucleic acid/gene.

The term portion as defined herein refers to a piece of DNA comprising at least 600 nucleotides, which portion encodes a polypeptide of at least 200 amino acids, comprising from the amino terminus to the carboxy terminus, a DnaJ domain, a G/F rich domain and a Cys-rich zinc finger domain, a CTD domain and a CaaX motif. Preferably, the portion comprises at least 1050 nucleotides, which portion encodes a polypeptide of at least 350 amino acids comprising from the amino terminus to the carboxy terminus, a DnaJ domain, a G/F rich domain, a Cys-rich zinc finger domain, a CTD domain and a CaaX motif. Further preferably, a portion as defined above is a portion of a nucleic acid as represented by any one of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51 SEQ ID NO: 53 or SEQ ID NO: 55 of Table 1.

A portion may be prepared, for example, by making one or more deletions to a type I DnaJ-like nucleic acid. One example consists in removing polynucleotide sequences encoding specific subcellular targeting sequences, such as mitochondrial or plastidic targeting sequences. The portions may be used in isolated form or they may be fused to other coding (or non coding) sequences in order to, for example, produce a protein that combines several activities. When fused to other coding sequences, the resulting polypeptide produced upon translation could be bigger than that predicted for the type I DnaJ-like fragment. For example, an oligonucleotide coding for the farnesylation motif could be fused to a type I DnaJ-like polynucleotide sequence encoding a type I DnaJ-like polypeptide originally lacking this motif. The portion may be fused to another portion of a coding sequence of another member of the type I DnaJ family thereby replacing domains between the two original type I DnaJ-like polypeptides. For example the CTD domain of one type I DnaJ-like polypeptide may be exchanged for the CTD domain of another type I DnaJ-like polypeptide.

Another variant of a type I DnaJ-like nucleic acid/gene is a nucleic acid capable of hybridising under reduced stringency conditions, preferably under stringent conditions, with a type I DnaJ-like nucleic acid/gene as hereinbefore defined, which hybridising sequence encodes at least the J-domain and the Cys-rich zinc finger domain of a type I DnaJ-like polypeptide. Preferably such variant comprises all of the domains characterizing type I DnaJ-like polypeptides, from the amino terminus to the carboxy terminus, a DnaJ domain, a G/F rich domain, a Cys-rich zinc finger domain and a CTD domain, and additionally a CaaX motif.

Preferably, the hybridising sequence is one that is capable of hybridising to a nucleic acid as represented by any one of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51 SEQ ID NO: 53 or SEQ ID NO: 55 of Table 1 or to a portion of any of the aforementioned sequences as defined hereinabove.

The term "hybridisation" as defined herein is a process wherein substantially homologous complementary nucleotide sequences anneal to each other. The hybridisation process can occur entirely in solution, i.e. both complementary nucleic acids are in solution. The hybridisation process can also occur with one of the complementary nucleic acids immobilised to a matrix such as magnetic beads, Sepharose beads or any other resin. The hybridisation process can furthermore occur with one of the complementary nucleic acids immobilised to a solid support such as a nitrocellulose or nylon membrane or immobilised by e.g. photolithography to, for example, a siliceous glass support (the latter known as nucleic acid arrays or microarrays or as nucleic acid chips). In order to allow hybridisation to occur, the nucleic acid molecules are generally thermally or chemically denatured to melt a double strand into two single strands and/or to remove hairpins or other secondary structures from single stranded nucleic acids. The stringency of hybridisation is influenced by conditions such as temperature, salt concentration, ionic strength and hybridisation buffer composition.

"Stringent hybridisation conditions" and "stringent hybridisation wash conditions" in the context of nucleic acid hybridisation experiments such as Southern and Northern hybridisations are sequence dependent and are different under different environmental parameters. The skilled artisan is aware of various parameters which may be altered during hybridisation and washing and which will either maintain or change the stringency conditions.

The $T_m$ is the temperature under defined ionic strength and pH, at which 50% of the target sequence hybridises to a perfectly matched probe. The $T_m$ is dependent upon the solution conditions and the base composition and length of the probe. For example, longer sequences hybridise specifically at higher temperatures. The maximum rate of hybridisation is obtained from about 16° C. up to 32° C. below $T_m$. The presence of monovalent cations in the hybridisation solution reduce the electrostatic repulsion between the two nucleic acid strands thereby promoting hybrid formation; this effect is visible for sodium concentrations of up to 0.4M. Formamide reduces the melting temperature of DNA-DNA and DNA-RNA duplexes with 0.6 to 0.7° C. for each percent formamide, and addition of 50% formamide allows hybridisation to be performed at 30 to 45° C., though the rate of hybridisation will be lowered. Base pair mismatches reduce the hybridisation rate and the thermal stability of the duplexes. On average and for large probes, the $T_m$ decreases about 1° C. per % base mismatch. The $T_m$ may be calculated using the following equations, depending on the types of hybrids:

1. DNA-DNA hybrids (Meinkoth and Wahl, Anal. Biochem., 138: 267-284, 1984):

$T_m$=81.5° C.+16.6×log [Na$^+$]$^a$+0.41×%[G/C$^b$]−500× [L$^c$]$^{-1}$−0.61×% formamide 2. DNA-RNA or RNA-RNA hybrids:
$T_m = 79.8 + 18.5 \,(\log_{10}[Na^+]^a) + 0.58 \,(\% \, G/C^b) + 11.8 \,(\% \, G/C^b)^2 - 820/L^c$ 3. oligo-DNA or oligo-RNA$^d$ hybrids:
For <20 nucleotides: $T_m = 2 \,(I_n)$
For 20-35 nucleotides: $T_m = 22 + 1.46 \,(I_n)$ $^a$ or for other monovalent cation, but only accurate in the 0.01-0.4 M range.

$^b$ only accurate for % GC in the 30% to 75% range.

$^c$ L=length of duplex in base pairs.

$^d$ Oligo, oligonucleotide; $I_n$, effective length of primer=2×(no. of G/C)+(no. of A/T).

Note: for each 1% formamide, the $T_m$ is reduced by about 0.6 to 0.7° C., while the presence of 6 M urea reduces the $T_m$ by about 30° C.

defined ionic strength and pH. Medium stringency conditions are when the temperature is 20° C. below $T_m$, and high stringency conditions are when the temperature is 10° C. below $T_m$. For example, stringent conditions are those that are at least as stringent as, for example, conditions A-L; and reduced stringency conditions are at least as stringent as, for example, conditions M-R. Non-specific binding may be controlled using any one of a number of known techniques such as, for example, blocking the membrane with protein containing solutions, additions of heterologous RNA, DNA, and SDS to the hybridisation buffer, and treatment with RNase. Examples of hybridisation and wash conditions are listed in Table 2 below.

TABLE 2

Examples of hybridisation and wash conditions

| Stringency Condition | Polynucleotide Hybrid± | Hybrid Length (bp)‡ | Hybridization Temperature and Buffer† | Wash Temperature and Buffer† |
| --- | --- | --- | --- | --- |
| A | DNA:DNA | > or equal to 50 | 65° C. 1 × SSC; or 42° C., 1 × SSC and 50% formamide | 65° C.; 0.3 × SSC |
| B | DNA:DNA | <50 | Tb*; 1 × SSC | Tb*; 1 × SSC |
| C | DNA:RNA | > or equal to 50 | 67° C. 1 × SSC; or 45° C., 1 × SSC and 50% formamide | 67° C.; 0.3 × SSC |
| D | DNA:RNA | <50 | Td*; 1 × SSC | Td*; 1 × SSC |
| E | RNA:RNA | > or equal to 50 | 70° C. 1 × SSC; or 50° C., 1 × SSC and 50% formamide | 70° C.; 0.3 × SSC |
| F | RNA:RNA | <50 | Tf*; 1 × SSC | Tf*; 1 × SSC |
| G | DNA:DNA | > or equal to 50 | 65° C. 4 × SSC; or 45° C., 4 × SSC and 50% formamide | 65° C.; 1 × SSC |
| H | DNA:DNA | <50 | Th*; 4 × SSC | Th*; 4 × SSC |
| I | DNA:RNA | > or equal to 50 | 67° C. 4 × SSC; or 45° C., 4 × SSC and 50% formamide | 67° C.; 1 × SSC |
| J | DNA:RNA | <50 | Tj*; 4 × SSC | Tj*; 4 × SSC |
| K | RNA:RNA | > or equal to 50 | 70° C. 4 × SSC; or 40° C., 6 × SSC and 50% formamide | 67° C.; 1 × SSC |
| L | RNA:RNA | <50 | Tl*; 2 × SSC | Tl*; 2 × SSC |
| M | DNA:DNA | > or equal to 50 | 50° C. 4 × SSC; or 40° C., 6 × SSC and 50% formamide | 50° C.; 2 × SSC |
| N | DNA:DNA | <50 | Tn*; 6 × SSC | Tn*; 6 × SSC |
| O | DNA:RNA | > or equal to 50 | 55° C. 4 × SSC; or 42° C., 6 × SSC and 50% formamide | 55° C.; 2 × SSC |
| P | DNA:RNA | <50 | Tp*; 6 × SSC | Tp*; 6 × SSC |
| Q | RNA:RNA | > or equal to 50 | 60° C. 4 × SSC; or 45° C., 6 × SSC and 50% formamide | 60° C.; 2 × SSC |
| R | RNA:RNA | <50 | Tr*; 4 × SSC | Tr*; 4 × SSC |

‡The "hybrid length" is the anticipated length for the hybridising nucleic acid. When nucleic acids of known sequence are hybridised, the hybrid length may be determined by aligning the sequences and identifying the conserved regions described herein.
†SSPE (1 × SSPE is 0.15M NaCl, 10 mM NaH$_2$PO$_4$, and 1.25 mM EDTA, pH 7.4) may be substituted for SSC (1 × SSC is 0.15M NaCl and 15 mM sodium citrate) in the hybridisation and wash buffers; washes are performed for 15 minutes after hybridisation is complete. The hybridisations and washes may additionally include 5x Denhardt's reagent, 0.5-1.0% SDS, 100 µg/ml denatured, fragmented salmon sperm DNA, 0.5% sodium pyrophosphate, and up to 50% formamide.
*Tb-Tr: The hybridisation temperature for hybrids anticipated to be less than 50 base pairs in length should be 5-10° C. less than the melting temperature $T_m$ of the hybrids; the $T_m$ is determined according to the above-mentioned equations.
±The present invention also encompasses the substitution of any one, or more DNA or RNA hybrid partners with either a PNA, or a modified nucleic acid.

Specificity of hybridisation is typically the function of post-hybridisation washes. To remove background resulting from non-specific hybridisation, samples are washed with dilute salt solutions. Critical factors of such washes include the ionic strength and temperature of the final wash solution: the lower the salt concentration and the higher the wash temperature, the higher the stringency of the wash. Wash conditions are typically performed at or below hybridisation stringency. Generally, suitable stringent conditions for nucleic acid hybridisation assays or gene amplification detection procedures are as set forth above. Conditions of greater or less stringency may also be selected. Generally, low stringency conditions are selected to be about 50° C. lower than the thermal melting point ($T_m$) for the specific sequence at a defined ionic strength and pH.

For the purposes of defining the level of stringency, reference can be made to Sambrook et al., (2001) Molecular Cloning: a laboratory manual, $3^{rd}$ Edition Cold Spring Harbor Laboratory Press, CSH, New York or to Current Protocols in Molecular Biology, John Wiley & Sons, N.Y. (1989).

A type I DnaJ-like nucleic acid or variant thereof may be derived from any natural or artificial source. This nucleic acid may be modified from its native form in composition and/or genomic environment through deliberate human manipulation. The nucleic acid is either of prokaryotic or eukaryotic origin, from a microbial source, such as yeast or fungi, or from a plant, algae or animal (including human) source. Preferably the nucleic acid is of eukaryotic origin. The nucleic acid is further preferably of plant origin, whether from the same plant species (for example to the one in which it is to be introduced) or whether from a different plant species. The nucleic acid may be isolated from a monocotyledonous species, preferably from the family Poaceae, further preferably from *Oryza sativa*. More preferably, the type I DnaJ-like nucleic acid isolated from *Oryza sativa* is represented by SEQ ID NO: 1 and the type I DnaJ-like amino acid sequence is as represented by SEQ ID NO: 2.

The activity of a type I DnaJ-like polypeptide or a homologue thereof may be increased by introducing a genetic modification (preferably in the locus of a type I DnaJ-like gene). The locus of a gene as defined herein is taken to mean a genomic region, which includes the gene of interest and 10 KB up- or downstream of the coding region.

The genetic modification may be introduced, for example, by any one (or more) of the following methods: T-DNA activation, TILLING, site-directed mutagenesis, directed evolution and homologous recombination or by introducing and/or expressing in the cytosol of a plant cell a nucleic acid encoding a type DnaJ-like polypeptide or a homologue thereof, which type I DnaJ-like polypeptide comprises a CaaX motif at its carboxy terminus. Following introduction of the genetic modification, there follows an optional step of selecting for increased activity in the cytosol of a plant cell of a type I DnaJ-like polypeptide, which increase in activity in the gives plants having increased plant yield under non-stress conditions.

T-DNA activation tagging (Hayashi et al. Science (1992) 1350-1353) involves insertion of T-DNA usually containing a promoter (may also be a translation enhancer or an intron), in the genomic region of the gene of interest or 10 KB up- or downstream of the coding region of a gene in a configuration such that the promoter directs expression of the targeted gene. Typically, regulation of expression of the targeted gene by its natural promoter is disrupted and the gene falls under the control of the newly introduced promoter. The promoter is typically embedded in a T-DNA. This T-DNA is randomly inserted into the plant genome, for example, through *Agrobacterium* infection and leads to overexpression of genes near the inserted T-DNA. The resulting transgenic plants show dominant phenotypes due to overexpression of genes close to the introduced promoter. The promoter to be introduced may be any promoter capable of directing expression of a gene in the desired organism, in this case a plant. For example, constitutive, tissue-specific, cell type-specific and inducible promoters are all suitable for use in T-DNA activation. Preferably, the promoter is one capable driving expression of the gene in plant seed tissue.

A genetic modification may also be introduced in the locus of a type I DnaJ-like gene using the technique of TILLING (Targeted Induced Local Lesions In Genomes). This is a mutagenesis technology useful to generate and/or identify, and to eventually isolate mutagenised variants of a type I DnaJ-like nucleic acid capable of exhibiting DnaJ-like activity. TILLING also allows selection of plants carrying such mutant variants. These mutant variants may even exhibit higher DnaJ-like activity than that exhibited by the gene in its natural form. TILLING combines high-density mutagenesis with high-throughput screening methods. The steps typically followed in TILLING are: (a) EMS mutagenesis (Redei G P and Koncz C (1992) In Methods in Arabidopsis Research, Koncz C, Chua N H, Schell J, eds. Singapore, World Scientific Publishing Co, pp. 16-82; Feldmann et al. (1994) In Meyerowitz E M, Somerville C R, eds, Arabidopsis. Cold Spring Harbor Laboratory Press, Cold Spring Harbor, N.Y., pp 137-172; Lightner J and Caspar T (1998) In J Martinez-Zapater, J Salinas, eds, Methods on Molecular Biology, Vol. 82. Humana Press, Totowa, N.J., pp 91-104); (b) DNA preparation and pooling of individuals; (c) PCR amplification of a region of interest; (d) denaturation and annealing to allow formation of heteroduplexes; (e) DHPLC, where the presence of a heteroduplex in a pool is detected as an extra peak in the chromatogram; (f) identification of the mutant individual; and (g) sequencing of the mutant PCR product. Methods for TILLING are well known in the art (McCallum et al., (2000) Nat Biotechnol 18: 455-457; reviewed by Stemple (2004) Nat Rev Genet 5(2): 145-50).

Site-directed mutagenesis may be used to generate variants of type I DnaJ-like nucleic acids or portions thereof. Several methods are available to achieve site-directed mutagenesis, the most common being PCR based methods (Current Protocols in Molecular Biology. Wiley Eds.

Directed evolution may be used which consists of iterations of DNA shuffling followed by appropriate screening and/or selection to generate variants of type I DnaJ-like nucleic acids or portions thereof encoding type I DnaJ-like polypeptides or homologues or portions thereof having an increased biological activity (Castle et al., (2004) Science 304(5674): 1151-4; U.S. Pat. Nos. 5,811,238 and 6,395,547).

T-DNA activation, TILLING, site-directed mutagenesis and directed evolution are examples of technologies that enable the generation of novel alleles and type I DnaJ-like variants.

Homologous recombination allows introduction in a genome of a selected nucleic acid at a defined selected position. Homologous recombination is a standard technology used routinely in biological sciences for lower organisms such as yeast or the moss *Physcomitrella*. Methods for performing homologous recombination in plants have been described not only for model plants (Offring a et al., (1990) EMBO J 9(10): 3077-84) but also for crop plants, for example rice (Terada et al., (2002) Nat Biotech 20(10): 1030-4; Iida and Terada (2004) Curr Opin Biotech 15(2):132-8). The nucleic acid to be targeted (which may be a type I DnaJ-like nucleic acid or variant thereof as hereinbefore defined) is targeted to the locus of a type I DnaJ-like gene. The nucleic acid to be targeted may be an improved allele used to replace the endogenous gene or may be introduced in addition to the endogenous gene.

According to a preferred embodiment of the invention, plant yield may be increased by introducing and/or expressing in the cytosol of a plant cell a nucleic acid encoding a type I DnaJ-like polypeptide or a homologue thereof, which type I DnaJ-like polypeptide or homologue thereof comprises a CaaX motif at its carboxy terminus.

A preferred method for introducing a genetic modification (which in this case need not be in the locus of a type I DnaJ-like gene) is to introduce and/or express in the cytosol of a plant cell an exogenous nucleic acid encoding a type I DnaJ-like polypeptide or a homologue thereof, which exogenous type I DnaJ-like polypeptide or a homologue thereof comprises a CaaX motif at its carboxy terminus. The nucleic acid to be introduced into a plant may be a full-length nucleic acid or may be a portion or a hybridizing sequence as hereinbefore defined.

The term "exogenous" as defined herein refers to an isolated gene/nucleic acid, which may be from the same or different plant species, for example an isolated rice gene/ nucleic acid introduced and/or expressed in a rice plant is "exogenous" according to the definition above.

"Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived. To produce such homologues, amino acids of the protein may be replaced by other amino acids having similar properties (such as similar hydrophobicity, hydrophilicity, antigenicity, propensity to form or break α-helical structures or β-sheet structures). Conservative substitution tables are well known in the art (see for example Creighton (1984) Proteins. W.H. Freeman and Company). Table 3 below gives examples of conserved amino acid substitutions.

TABLE 2

Examples of conserved amino acid substitutions

| Residue | Conservative Substitutions |
|---------|----------------------------|
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

Homologues include orthologues and paralogoues, which encompass evolutionary concepts used to describe ancestral relationships of genes. Paralogues are genes within the same species that have originated through duplication of an ancestral gene and orthologues are genes from different organisms that have originated through speciation.

Orthologues in, for example, monocot plant species may easily be found by performing a so-called reciprocal blast search. This may be done by a first blast involving blasting a query sequence (for example, SEQ ID NO: 1 or SEQ ID NO: 2) against any sequence database, such as the publicly available NCBI database which may be found at the NCBI web site. BLASTN or TBLASTX (using standard default values) may be used when starting from a nucleotide sequence and BLASTP or TBLASTN (using standard default values) may be used when starting from a protein sequence. The BLAST results may optionally be filtered. The full-length sequences of either the filtered results or non-filtered results are then BLASTed back (second BLAST) against sequences from the organism from which the query sequence is derived (where the query sequence is SEQ ID NO: 1 or SEQ ID NO: 2 the second blast would therefore be against rice sequences). The results of the first and second BLASTs are then compared. A paralogue is identified if a high-ranking hit from the second blast is from the same species as from which the query sequence is derived; an orthologue is identified if a high-ranking hit is not from the same species as from which the query sequence is derived. High-ranking hits are those having a low E-value. The lower the E-value, the more significant the score (or in other words the lower the chance that the hit was found by chance). Computation of the E-value is well known in the art. In the case of large families, ClustalW may be used, followed by a neighbour joining tree, to help visualize clustering of related genes and to identify orthologues and paralogues.

A homologue may be in the form of a "substitutional variant" of a protein, i.e. where at least one residue in an amino acid sequence has been removed and a different residue inserted in its place. Amino acid substitutions are typically of single residues, but may be clustered depending upon functional constraints placed upon the polypeptide; insertions will usually be of the order of about 1 to 10 amino acid residues. Preferably, amino acid substitutions comprise conservative amino acid substitutions (see Table 3 above).

A homologue may also be in the form of an "insertional variant" of a protein, i.e. where one or more amino acid residues are introduced into a predetermined site in a protein. Insertions may comprise amino-terminal and/or carboxy-terminal fusions as well as intra-sequence insertions of single or multiple amino acids. Generally, insertions within the amino acid sequence will be smaller than amino- or carboxy-terminal fusions, of the order of about 1 to 10 residues. Examples of amino- or carboxy-terminal fusion proteins or peptides include the binding domain or activation domain of a transcriptional activator as used in the yeast two-hybrid system, phage coat proteins, (histidine)6-tag, glutathione S-transferase-tag, protein A, maltose-binding protein, dihydrofolate reductase, Tag-100 epitope, c-myc epitope, FLAG-epitope, lacZ, CMP (calmodulin-binding peptide), HA epitope, protein C epitope and VSV epitope.

Homologues in the form of "deletion variants" of a protein are characterised by the removal of one or more amino acids from a protein. One example of such a deletion variant is to remove the mitochondrial or plastidic targeting sequences from type I DnaJ-like proteins otherwise targeted to these organelles.

Amino acid variants of a protein may readily be made using peptide synthetic techniques well known in the art, such as solid phase peptide synthesis and the like, or by recombinant DNA manipulation. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

The type I DnaJ-like polypeptide or homologue thereof may be a derivative. "Derivatives" include peptides, oligopeptides, polypeptides, proteins and enzymes which may comprise substitutions, deletions or additions of naturally and non-naturally occurring amino acid residues compared to the amino acid sequence of a naturally-occurring form of the protein, for example, as presented in SEQ ID NO: 2. "Derivatives" of a protein encompass peptides, oligopeptides, polypeptides, proteins and enzymes which may comprise naturally occurring altered, glycosylated, acylated, prenylated or non-naturally occurring amino acid residues compared to the amino acid sequence of a naturally-occurring form of the polypeptide. A derivative may also comprise one or more non-amino acid substituents compared to the amino acid sequence from which it is derived, for example a reporter molecule or other ligand, covalently or non-covalently bound to the amino acid sequence, such as a reporter molecule which is bound to facilitate its detection, and non-naturally occurring amino acid residues relative to the amino acid sequence of a naturally-occurring protein.

The type I DnaJ-like polypeptide or homologue thereof may be encoded by an alternative splice variant of a type I DnaJ-like nucleic acid/gene. The term "alternative splice variant" as used herein encompasses variants of a nucleic acid sequence in which selected introns and/or exons have been excised, replaced or added, or in which introns have been shortened or lengthened. Such variants will be ones in which the biological activity of the protein is retained, which may be achieved by selectively retaining functional segments of the protein. Such splice variants may be found in nature or may be manmade. Methods for making such splice variants are well known in the art. Preferred are splice variants encoding a polypeptide being a type I DnaJ-like polypeptide or a homologue thereof, which type I DnaJ-like polypeptide or homologue thereof comprises a CaaX motif at its carboxy terminus, particularly splice variants of SEQ ID NO: 1.

The homologue may also be encoded by an allelic variant of a nucleic acid encoding a type I DnaJ-like polypeptide or a homologue thereof, preferably an allelic variant of the nucleic acid represented by SEQ ID NO: 1. Further preferably, the polypeptide encoded by the allelic variant is a type I DnaJ-like polypeptide or a homologue thereof, which type I DnaJ-like polypeptide or homologue thereof comprises a CaaX motif at its carboxy terminus.

Allelic variants exist in nature, and encompassed within the methods of the present invention is the use of these natural alleles. Allelic variants encompass Single Nucleotide Polymorphisms (SNPs), as well as Small Insertion/Deletion Polymorphisms (INDELs). The size of INDELs is usually less than 100 bp. SNPs and INDELs form the largest set of sequence variants in naturally occurring polymorphic strains of most organisms.

According to a preferred aspect of the present invention, enhanced or increased expression of the type I DnaJ-like nucleic acid or variant thereof is envisaged. Methods for obtaining enhanced or increased expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a type I DnaJ-like nucleic acid or variant thereof. For example, endogenous promoters may be altered in vivo by mutation, deletion, and/or substitution (see, Kmiec, U.S. Pat. No. 5,565,350; Zarling et al., PCT/US93/03868), or isolated promoters may be introduced into a plant cell in the proper orientation and distance from a gene of the present invention so as to control the expression of the gene.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold, Buchman and Berg, Mol. Cell biol. 8:4395-4405 (1988); Callis et al., Genes Dev. 1:1183-1200 (1987). Such intron enhancement of gene expression is typically greatest when placed near the 5' end of the transcription unit. Use of the maize introns Adh1-S intron 1, 2, and 6, the Bronze-1 intron are known in the art. See generally, The Maize Handbook, Chapter 116, Freeling and Walbot, Eds., Springer, N.Y. (1994).

The invention also provides genetic constructs and vectors to facilitate introduction and/or expression of the nucleotide sequences useful in the methods according to the invention.

Therefore, there is provided a gene construct comprising:
(i) a nucleic acid or variant thereof encoding a type I DnaJ-like polypeptide or a homologue thereof, which type I DnaJ-like polypeptide or homologue thereof comprises a CaaX motif at its carboxy terminus; and
(ii) one or more control sequences capable of driving expression of the nucleic acid sequence of (i); and optionally
(iii) a transcription termination sequence.

Also provided by the present invention is the use of a construct, as defined herein, in methods for increasing plant yield in plants grown under non-stress conditions.

Constructs useful in the methods according to the present invention may be constructed using recombinant DNA technology well known to persons skilled in the art. The gene constructs may be inserted into vectors, which may be commercially available, suitable for transforming into plants and suitable for expression of the gene of interest in the transformed cells.

Plants are transformed with a vector comprising the sequence of interest (i.e., nucleic acid or variant thereof encoding a type I DnaJ-like polypeptide or homologue thereof that comprises a CaaX motif at its carboxy terminus). The sequence of interest is operably linked to one or more control sequences (at least to a promoter). The terms "regulatory element", "control sequence" and "promoter" are all used interchangeably herein and are to be taken in a broad context to refer to regulatory nucleic acid sequences capable of effecting expression of the sequences to which they are ligated. Encompassed by the aforementioned terms are transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences. The term "regulatory element" also encompasses a synthetic fusion molecule or derivative that confers, activates or enhances expression of a nucleic acid molecule in a cell, tissue or organ. The term "operably linked" as used herein refers to a functional linkage between the promoter sequence and the gene of interest, such that the promoter sequence is able to initiate transcription of the gene of interest.

Advantageously, any type of promoter, whether natural or synthetic, may be used to drive expression of the nucleic acid sequence. Preferably, the promoter is a tissue-specific promoter, i.e. one that is capable of preferentially initiating transcription in certain tissues, such as the leaves, roots, seed tissue etc. Plant-derived promoters are particularly preferred, especially plant-derived tissue-specific promoters. The term "tissue-specific" as defined herein refers to a promoter that is expressed predominantly in at least one plant tissue or organ, but which may have residual expression elsewhere in the plant due to leaky promoter expression. Further preferably, the tissue-specific promoter is a seed-specific promoter, more particularly a promoter isolated from a gene encoding a seed-storage protein, especially an endosperm-specific promoter.

Most preferably the endosperm-specific promoter is isolated from a prolamin gene, such as a rice prolamin RP6 (Wen et al. (1993) Plant Physiol 101(3): 1115-6) promoter as represented by SEQ ID NO: 57, or a promoter of similar strength and/or a promoter with a similar expression pattern as the rice prolamin promoter. Similar strength and/or similar expression pattern may be analysed, for example, by coupling the promoters to a reporter gene and checking the function of the reporter gene in tissues of the plant. One well-known reporter gene is beta-glucuronidase and the calorimetric GUS stain used to visualize beta-glucuronidase activity in plant tissue. It should be clear that the applicability of the present invention is not restricted to the type I DnaJ-like nucleic acid represented by SEQ ID NO: 1, nor is the applicability of the invention restricted to expression of a type I DnaJ-like nucleic acid when driven by a prolamin promoter.

Examples of seed-specific promoters are presented in Table 4, which promoters or derivatives thereof are useful in performing the methods of the present invention. It should be understood that the list below is not exhaustive.

Optionally, one or more terminator sequences may also be used in the construct introduced into a plant. The term "terminator" encompasses a control sequence which is a DNA sequence at the end of a transcriptional unit which signals 3' processing and polyadenylation of a primary transcript and termination of transcription. Additional regulatory elements may include transcriptional as well as translational enhancers. Those skilled in the art will be aware of terminator and enhancer sequences that may be suitable for use in performing the invention. Such sequences would be known or may readily be obtained by a person skilled in the art.

The genetic constructs of the invention may further include an origin of replication sequence that is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the f1-ori and colE1.

The genetic construct may optionally comprise a selectable marker gene. As used herein, the term "selectable marker

TABLE 4

Examples of seed-specific promoters for use in the present invention

| GENE SOURCE | EXPRESSION PATTERN | REFERENCE |
| --- | --- | --- |
| seed-specific genes | seed | Simon, et al., Plant Mol. Biol. 5: 191, 1985; Scofield, et al., J. Biol. Chem. 262: 12202, 1987; Baszczynski, et al., Plant Mol. Biol. 14: 633, 1990. |
| Brazil Nut albumin | seed | Pearson, et al., Plant Mol. Biol. 18: 235-245, 1992. |
| legumin | seed | Ellis, et al., Plant Mol. Biol. 10: 203-214, 1988. |
| glutelin (rice) | seed | Takaiwa, et al., Mol. Gen. Genet. 208: 15-22, 1986; Takaiwa, et al., FEBS Letts. 221: 43-47, 1987. |
| zein | seed | Matzke et al Plant Mol Biol, 14(3): 323-32 1990. |
| napA | seed | Stalberg, et al., Planta 199: 515-519, 1996. |
| wheat LMW and HMW glutenin-1 | endosperm | Mol Gen Genet 216: 81-90, 1989; NAR 17: 461-2, 1989. |
| wheat SPA | seed | Albani et al., Plant Cell, 9: 171-184, 1997. |
| wheat α, β, γ-gliadins | endosperm | EMBO 3: 1409-15, 1984. |
| barley ltr1 promoter | endosperm | |
| barley B1, C, D, hordein | endosperm | Theor Appl Gen 98: 1253-62, 1999; Plant J 4: 343-55, 1993; Mol Gen Genet 250: 750-60, 1996. |
| barley DOF | endosperm | Mena et al., The Plant Journal, 116(1): 53-62, 1998. |
| blz2 | endosperm | EP99106056.7 |
| synthetic promoter | endosperm | Vicente-Carbajosa et al., Plant J. 13: 629-640, 1998. |
| rice prolamin NRP33 | endosperm | Wu et al., Plant Cell Physiology 39(8) 885-889, 1998. |
| rice α-globulin Glb-1 | endosperm | Wu et al., Plant Cell Physiology 39(8) 885-889, 1998. |
| rice OSH1 | embryo | Sato et al., Proc. Natl. Acad. Sci. USA, 93: 8117-8122, 1996. |
| rice α-globulin REB/OHP-1 | endosperm | Nakase et al., Plant Mol. Biol. 33: 513-522, 1997. |
| rice ADP-glucose PP | endosperm | Trans Res 6: 157-68, 1997. |
| maize ESR gene family | endosperm | Plant J 12: 235-46, 1997. |
| sorgum γ-kafirin | endosperm | PMB 32: 1029-35, 1996. |
| KNOX | embryo | Postma-Haarsma et al., Plant Mol. Biol. 39: 257-71, 1999. |
| rice oleosin | embryo and aleurone | Wu et al., J. Biochem., 123: 386, 1998. |
| sunflower oleosin | seed (embryo and dry seed) | Cummins, et al., Plant Mol. Biol. 19: 873-876, 1992. | gene" includes any gene that confers a phenotype on a cell in which it is expressed to facilitate the identification and/or selection of cells that are transfected or transformed with a nucleic acid construct of the invention. Suitable markers may be selected from markers that confer antibiotic or herbicide resistance, that introduce a new metabolic trait or that allow visual selection. Examples of selectable marker genes include genes conferring resistance to antibiotics (such as nptII that phosphorylates neomycin and kanamycin, or hptII, phosphorylating hygromycin), to herbicides (for example bar which provides resistance to Basta; aroA or gox providing resistance against glyphosate), or genes that provide a metabolic trait (such as manA that allows plants to use mannose as sole carbon source). Visual marker genes result in the formation of colour (for example β-glucuronidase, GUS), luminescence (such as luciferase) or fluorescence (Green Fluorescent Protein, GFP, and derivatives thereof).

The present invention also encompasses plants and plant parts obtainable by the methods according to the present invention. The present invention therefore provides plants and parts thereof obtainable by the methods according to the present invention, which plants have introduced therein a nucleic acid or variant thereof encoding a type I DnaJ-like polypeptide or a homologue thereof, which type I DnaJ-like polypeptide or homologue thereof comprises a CaaX motif at its carboxy terminus.

The invention also provides a method for the production of transgenic plants having increased plant yield when grown under non-stress conditions, comprising introduction and/or expression in the cytosol of a plant cell of a nucleic acid or a variant thereof encoding a type I DnaJ-like polypeptide or a homologue thereof, which type I DnaJ-like polypeptide or homologue thereof comprises a CaaX motif at its carboxy terminus.

More specifically, the present invention provides a method for the production of transgenic plants with increased yield which method comprises:
 (i) introducing and/or expressing in the cytosol of plant, plants part or plant cell a nucleic acid or variant thereof encoding a type I DnaJ-like polypeptide or a homologue thereof, which type I DnaJ-like polypeptide or homologue thereof comprises a CaaX motif at its carboxy terminus; and
 (ii) cultivating the plant, plant part or plant cell under non-stress conditions promoting plant growth and development.

The nucleic acid may be introduced directly into a plant cell or into the plant itself (including introduction into a tissue, organ or any other part of a plant). According to a preferred feature of the present invention, the nucleic acid is preferably introduced into a plant by transformation.

The term "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

Transformation of plant species is now a fairly routine technique. Advantageously, any of several transformation methods may be used to introduce the gene of interest into a suitable ancestor cell. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens F A et al., (1982) Nature 296, 72-74; Negrutiu I et al. (1987) Plant Mol Biol 8: 363-373); electroporation of protoplasts (Shillito R D et al. 1985 Bio/Technol 3, 1099-1102); microinjection into plant material (Crossway A et al. (1986) Mol. Gen Genet 202: 179-185); DNA or RNA-coated particle bombardment (Klein T M et al. (1987) Nature 327: 70) infection with (non-integrative) viruses and the like. Transgenic rice plants expressing a type I DnaJ-like nucleic acid/gene are preferably produced via Agrobacterium-mediated transformation using any of the well known methods for rice transformation, such as described in any of the following: published European patent application EP 1198985 A1, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al, (Nat. Biotechnol 14(6): 745-50, 1996) or Frame et al, (Plant Physiol 129(1): 13-22, 2002), which disclosures are incorporated by reference herein as if fully set forth.

Generally after transformation, plant cells or cell groupings are selected for the presence of one or more markers which are encoded by plant-expressible genes co-transferred with the gene of interest, following which the transformed material is regenerated into a whole plant.

Following DNA transfer and regeneration, putatively transformed plants may be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed to give homozygous second generation (or T2) transformants, and the T2 plants further propagated through classical breeding techniques.

The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention clearly extends to any plant cell or plant produced by any of the methods described herein, and to all plant parts and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced in the parent by the methods according to the invention. The invention also includes host cells containing an isolated type I DnaJ-like nucleic acid or variant thereof. Preferred host cells according to the invention are plant cells. The invention also extends to harvestable parts of a plant such as but not limited to seeds, leaves, fruits, flowers, stem cultures, rhizomes, tubers and bulbs. The invention furthermore relates to products derived, preferably directly derived from a harvestable part of such a plant, such products may be dry pellets or powders, oils, fats and fatty acids, starch or proteins.

The present invention also encompasses the use of type I DnaJ-like nucleic acids or variants thereof and the use of type I DnaJ-like polypeptides or homologues thereof, which type I DnaJ-like polypeptide or homologue thereof comprises a CaaX motif at its carboxy terminus. One such use relates to improving plant yield, especially in increasing yield as defined hereinabove.

Type I DnaJ-like nucleic acids or variants thereof, or type I DnaJ-like polypeptides or homologues thereof, may find use in breeding programmes in which a DNA marker is identified which may be genetically linked to a type I DnaJ-like gene or variant thereof. The type I DnaJ-like nucleic acids/genes or variants thereof, or type I DnaJ-like polypeptides or homologues thereof may be used to define a molecular marker. This DNA or protein marker may then be used in breeding programmes to select plants having increased plant yield. The type I DnaJ-like gene or variant thereof may, for example, be a nucleic acid as represented by any one of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51 SEQ ID NO: 53 or SEQ ID NO: 55 of Table 1.

Allelic variants of a type I DnaJ-like nucleic acid/gene may also find use in marker-assisted breeding programmes. Such breeding programmes sometimes require introduction of allelic variation by mutagenic treatment of the plants, using for example EMS mutagenesis; alternatively, the programme may start with a collection of allelic variants of so called "natural" origin caused unintentionally. Identification of allelic variants then takes place, for example, by PCR. This is followed by a step for selection of superior allelic variants of the sequence in question and which give increased yield in a plant. Selection is typically carried out by monitoring yield performance of plants containing different allelic variants of the sequence in question, for example, different allelic variants of any one of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51 SEQ ID NO: 53 or SEQ ID NO: 55 of Table 1. Yield performance may be monitored in a greenhouse or in the field. Further optional steps include crossing plants, in which the superior allelic variant was identified, with another plant. This could be used, for example, to make a combination of interesting phenotypic features. A type I DnaJ-like nucleic acid or variant thereof may also be used as probes for genetically and physically mapping the genes that they are a part of, and as markers for traits linked to those genes. Such information may be useful in plant breeding in order to develop lines with desired phenotypes. Such use of type I DnaJ-like nucleic acids or variants thereof requires only a nucleic acid sequence of at least 15 nucleotides in length. The type I DnaJ-like nucleic acids or variants thereof may be used as restriction fragment length polymorphism (RFLP) markers. Southern blots (Sambrook J, Fritsch E F and Maniatis T (1989) Molecular Cloning, A Laboratory Manual) of restriction-digested plant genomic DNA may be probed with the type I DnaJ-like nucleic acids or variants thereof. The resulting banding patterns may then be subjected to genetic analyses using computer programs such as MapMaker (Lander et al., (1987) Genomics 1: 174-181) in order to construct a genetic map. In addition, the nucleic acids may be used to probe Southern blots containing restriction endonuclease-treated genomic DNAs of a set of individuals representing parent and progeny of a defined genetic cross. Segregation of the DNA polymorphisms is noted and used to calculate the position of the type I DnaJ-like nucleic acid or variant thereof in the genetic map previously obtained using this population (Botstein et al. (1980) Am. J. Hum. Genet. 32:314-331).

The production and use of plant gene-derived probes for use in genetic mapping is described in Bematzky and Tanksley (1986) Plant Mol. Biol. Reporter 4: 37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

The nucleic acid probes may also be used for physical mapping (i.e., placement of sequences on physical maps; see Hoheisel et al. in: Non-mammalian Genomic Analysis: A Practical Guide, Academic press 1996, pp. 319-346, and references cited therein).

In another embodiment, the nucleic acid probes may be used in direct fluorescence in situ hybridization (FISH) mapping (Trask (1991) Trends Genet. 7:149-154). Although current methods of FISH mapping favour use of large clones (several kb to several hundred kb; see Laan et al. (1995) Genome Res. 5:13-20), improvements in sensitivity may allow performance of FISH mapping using shorter probes.

A variety of nucleic acid amplification-based methods for genetic and physical mapping may be carried out using the nucleic acids. Examples include allele-specific amplification (Kazazian (1989) J. Lab. Clin. Med 11:95-96), polymorphism of PCR-amplified fragments (CAPS; Sheffield et al. (1993) Genomics 16:325-332), allele-specific ligation (Landegren et al., (1988) Science 241:1077-1080), nucleotide extension reactions (Sokolov (1990) Nucleic Acid Res. 18:3671), Radiation Hybrid Mapping (Walter et al., (1997) Nat. Genet. 7:22-28) and Happy Mapping (Dear and Cook (1989) Nucleic Acid Res. 17:6795-6807). For these methods, the sequence of a nucleic acid is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Performance of the methods according to the present invention result in plants having increased plant yield in plants grown under non-stress conditions, as described hereinbefore. This increased plant yield may also be combined with other economically advantageous traits, such as further yield-enhancing traits, tolerance to various stresses, traits modifying various architectural features and/or biochemical and/or physiological features.

DESCRIPTION OF FIGURES

The present invention will now be described with reference to the following figures in which:

Figure 2:
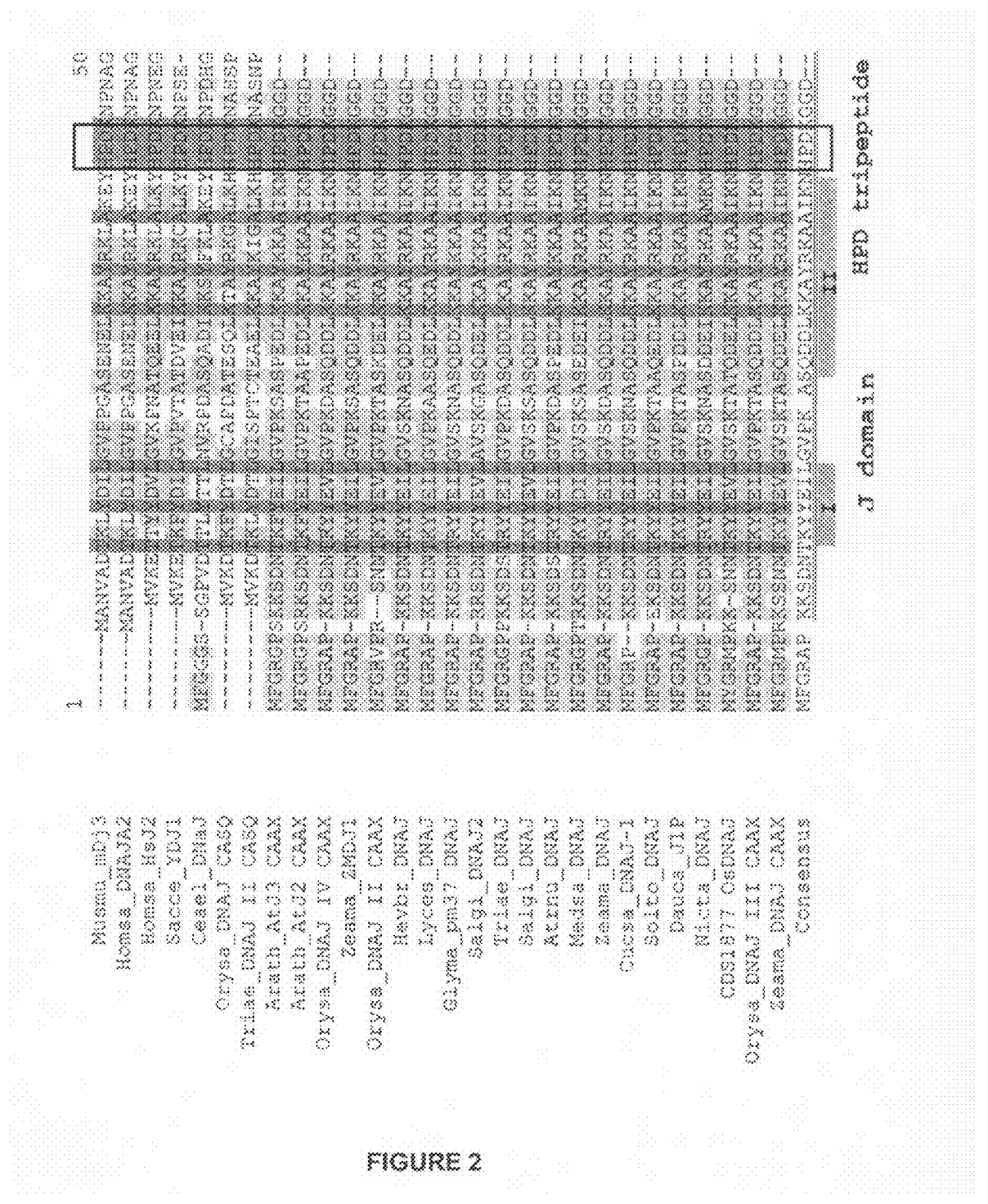
Figure 2:
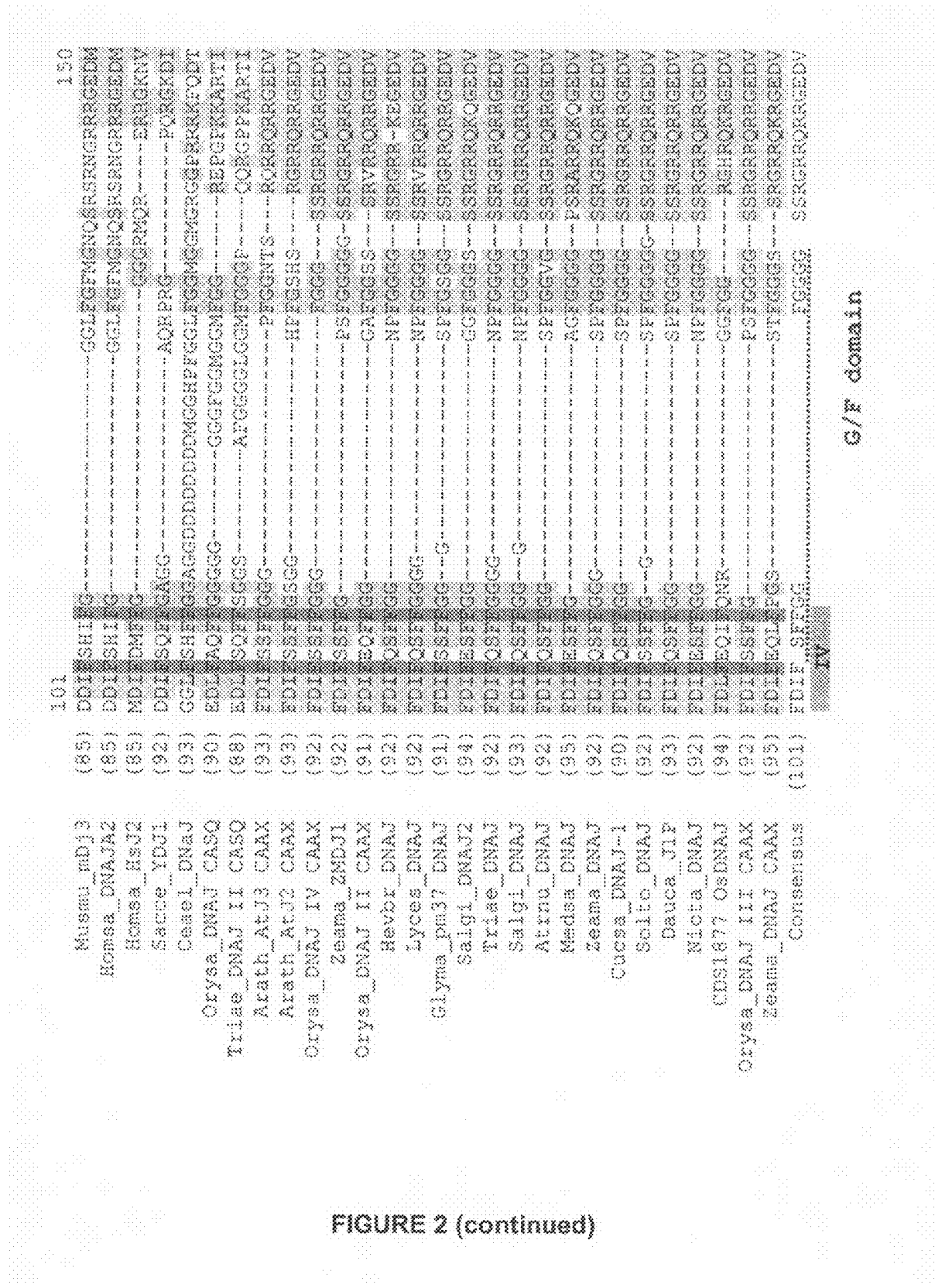
Figure 2:
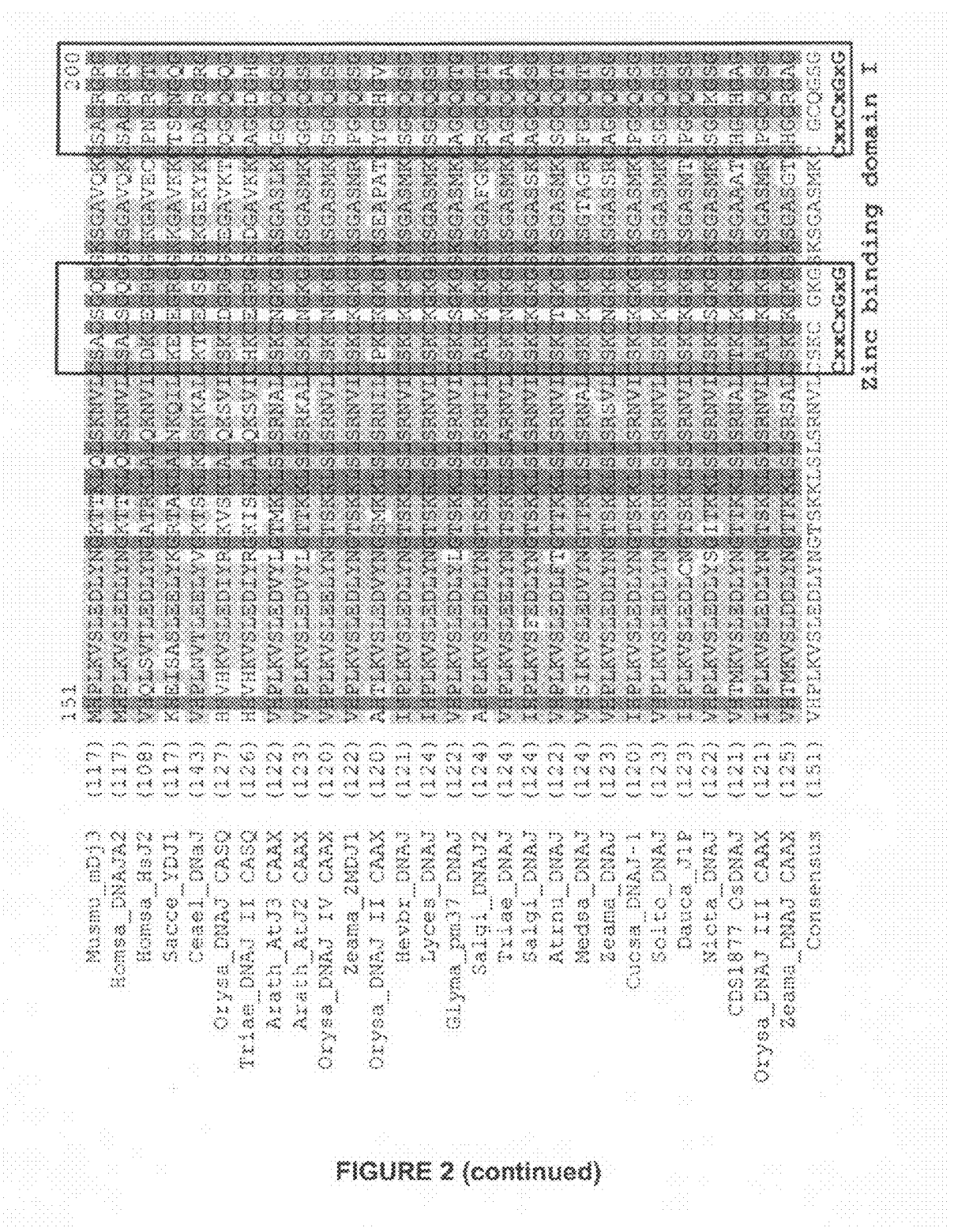
Figure 2:
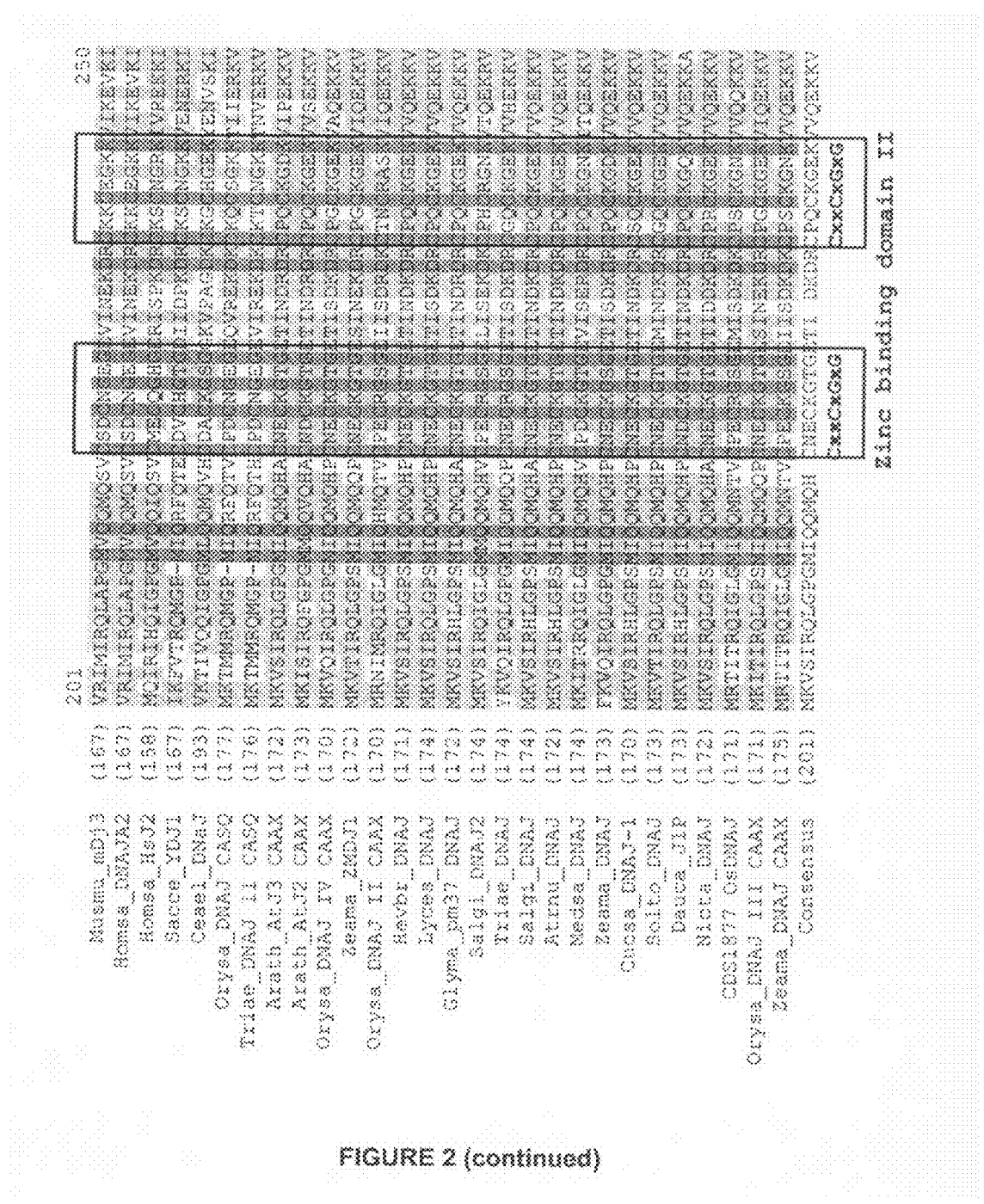
Figure 2:
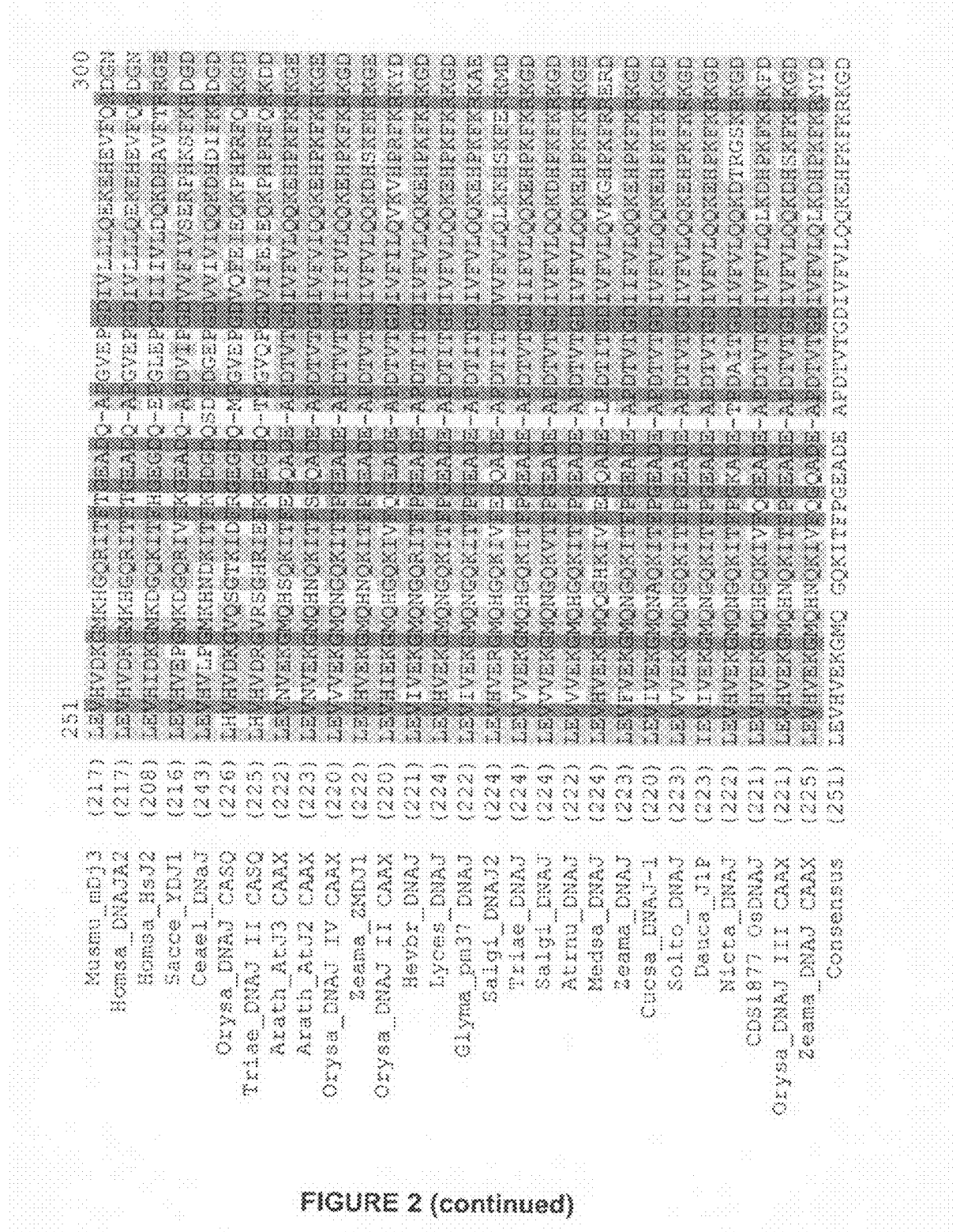
Figure 2:
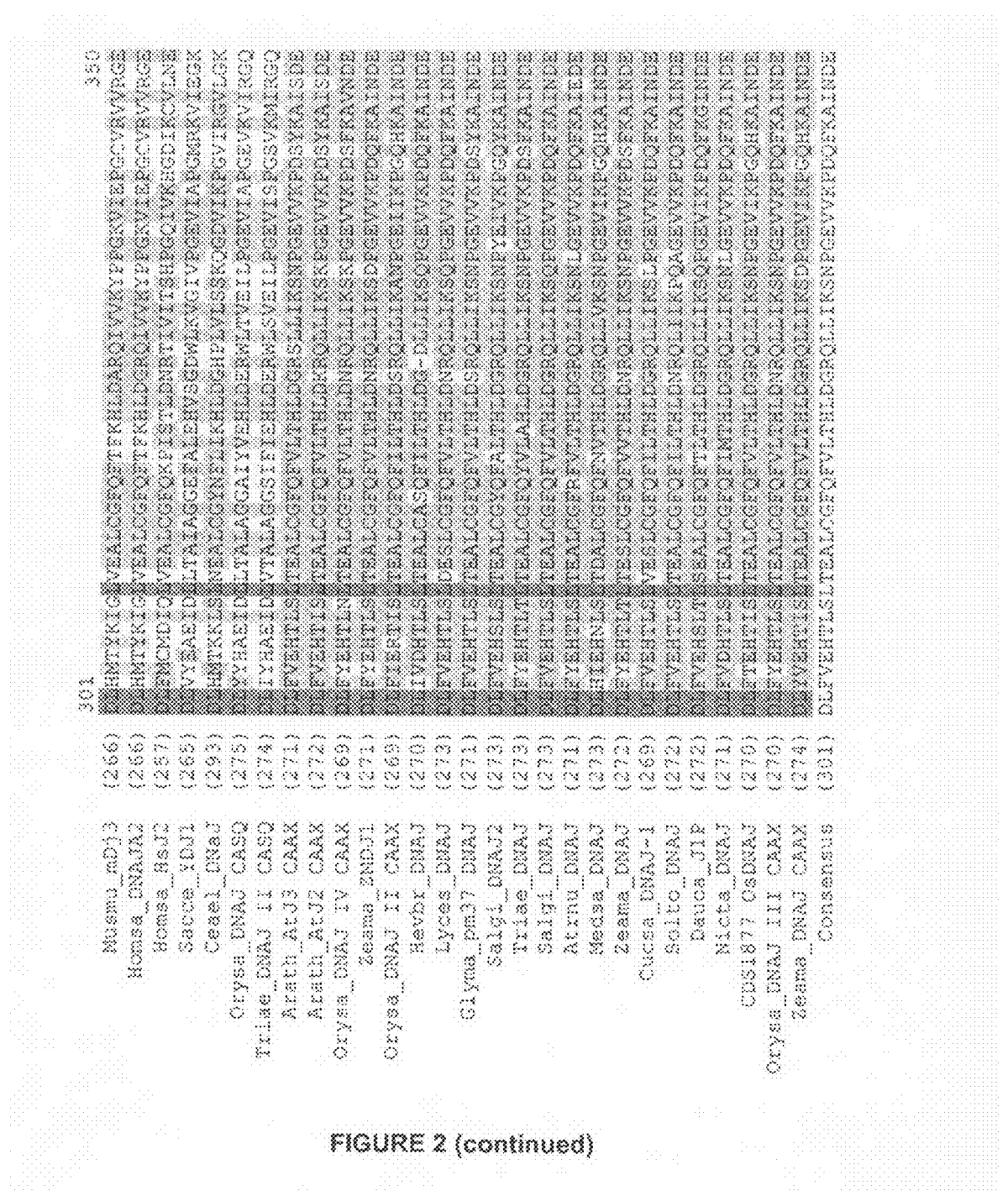
Figure 2:
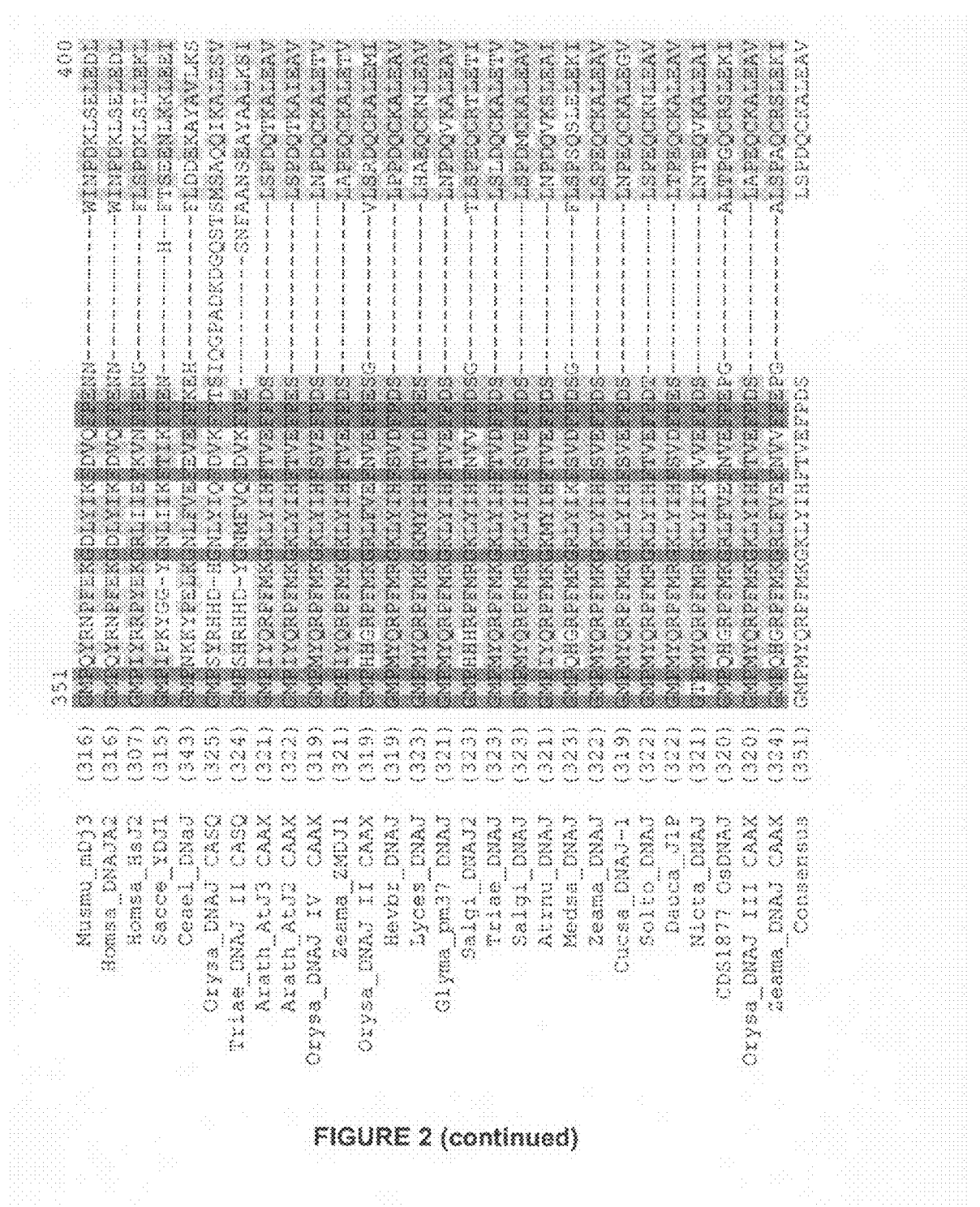
Figure 2:
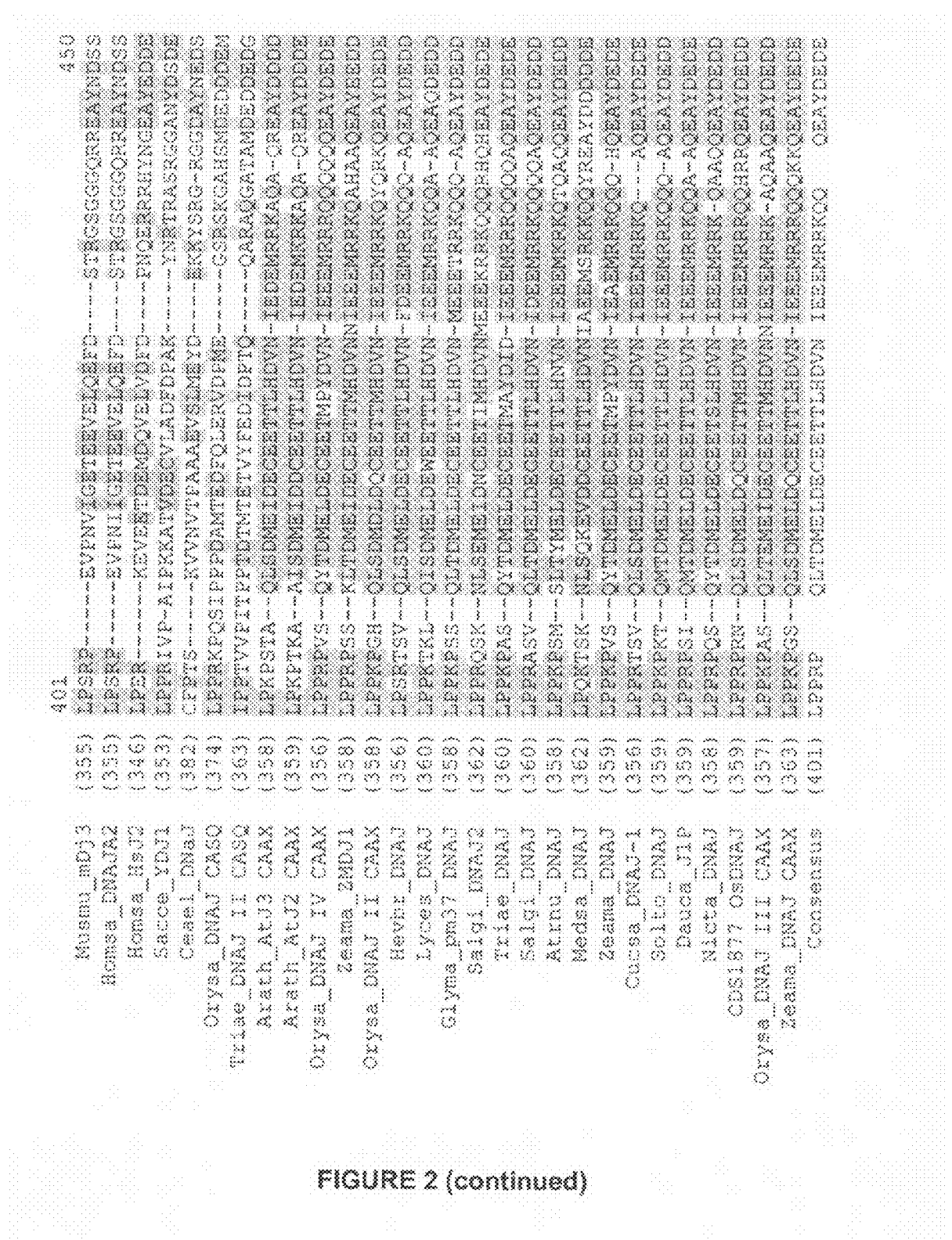
Figure 2:
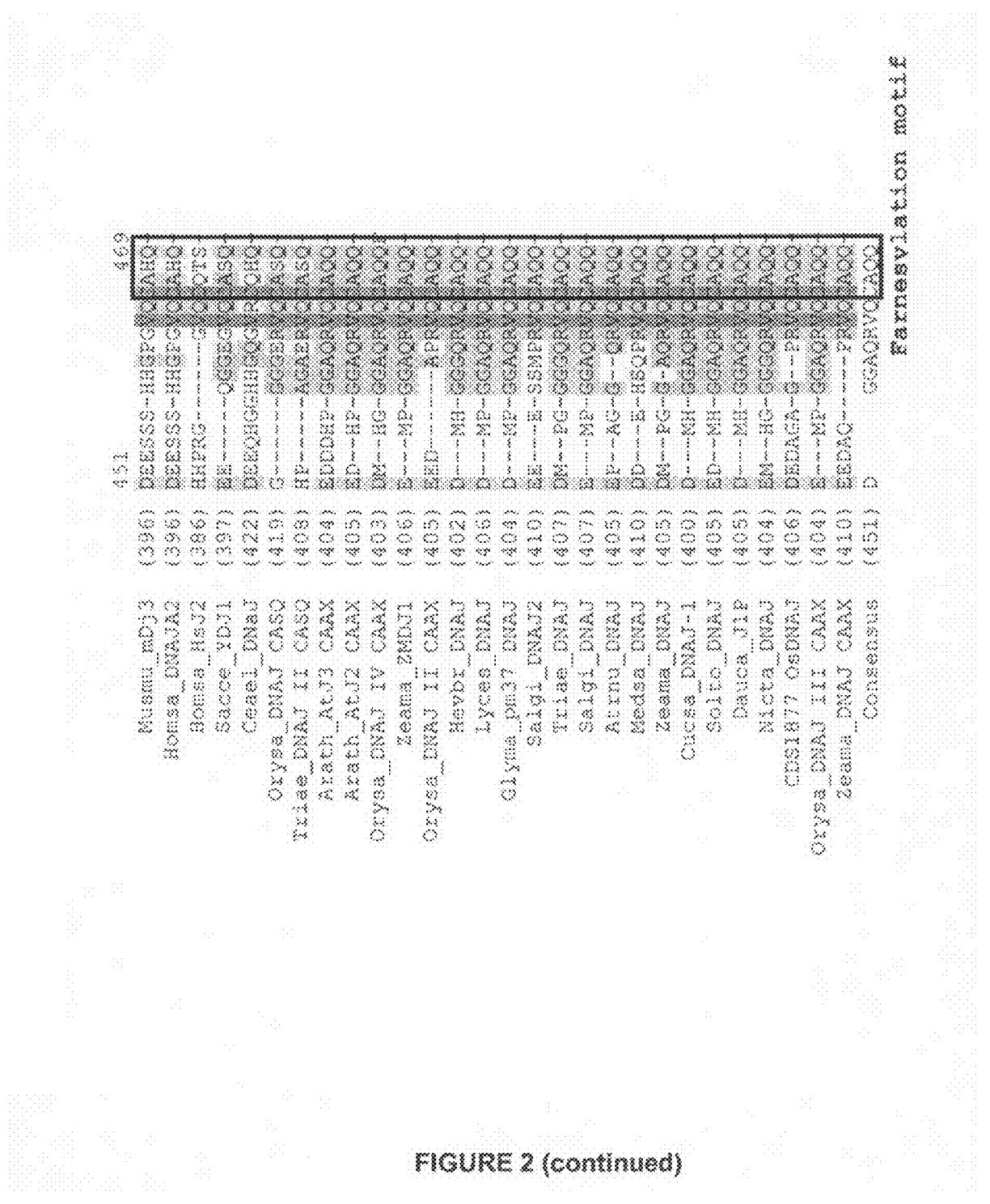

FIG. 2 shows a multiple alignment of several type I DnaJ-like proteins from the Table 1, using VNTI AlignX multiple alignment program, based on a modified ClustalW algorithm (InforMax, Bethesda, Md. ), with default settings for gap opening penalty of 10 and a gap extension of 0.05). The J domain is double-underlined, its four helices represented as grey boxes and its conserved HPD tripeptide boxed. The G/F domain is dotted-underlined. The two zinc binding domains I and II and their conserved CxxCxGxG (SEQ ID NO: 66) are boxed. In the CTD domain, the farnesylation motif is boxed. The sequences aligned are: Musmu_mDj3 (SEQ ID NO: 5), Homsa_DNAJA2 (SEQ ID NO: 54), Homsa_HsJ2 (SEQ ID NO: 50), Sacce_YDJ1 (SEQ ID NO: 52), Ceael_DNaJ (SEQ ID NO: 48), Orysa_DNAJ CASQ SEQ ID NO: 44), Triae_D-NAJ II CASQ (SEQ ID NO: 46), Arath_AtJ3 CAAX (SEQ ID NO: 20), Arath_AtJ2 CAAX (SEQ ID NO: 18), Orysa_DNAJ IV CAAX (SEQ ID NO: 8), Zeama_ZMDJ1 (SEQ ID NO: 10), Orysa_DNAJ II CAAX (SEQ ID NO: 4), Hevbr_DNAJ (SEQ ID NO: 30), Lyces_DNAJ (SEQ ID NO: 32), Glyma_pm37 DNAJ (SEQ ID NO: 28), Salgi_DNAJ2 (SEQ ID NO: 38), Triae_DNAJ (SEQ ID NO: 16), Salgi_DNAJ (SEQ ID NO: 40), Atrnu_DNAJ (SEQ ID NO:22), Medsa_DNAJ (SEQ ID NO:34), Zeama_DNAJ (SEQ ID NO: 12), Cucsa_DNAJ-1 (SEQ ID NO: 24), Solto_DNAJ (SEQ ID NO: 42), Dauca_J1P (SEQ ID NO:26), Nicta_DNAJ (SEQ ID NO: 36), CDS 1877 OsDNAJ (SEQ ID NO:2), Orysa_DNAJ III CAAX (SEQ ID NO:6), and Zeama_DNAJ CAAX (SEQ ID NO: 14).

| MIPS accession number | NCBI protein accession number |
|---|---|
| At3g44110 | S71199 |
| At5g22060 | AAB86799.1 |
| At1g28210 | NP849719 |
| At1g80030 | AAK60328 |
| At2g22360 | AAD22362 |
| At3g17830 | NM112664 |
| At4g39960 | AAL36077 |
| At5g48030 | BAB11067 |

Figure 1:
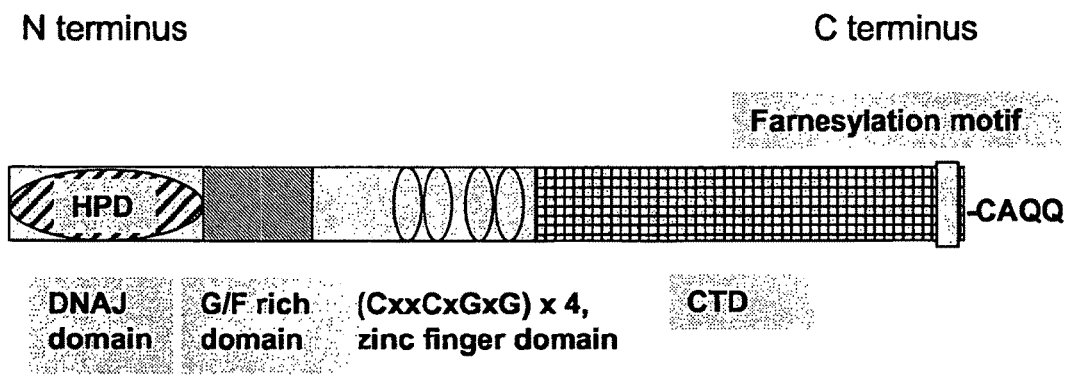
FIG. 1 shows the typical domain structure of type I DnaJ-like polypeptide. The J domain is located at the amino terminal end of the protein and encodes an HSP70-binding domain comprising the highly conserved HPD tripeptide. The G/F domain rich in glycine and phenylalanine is specifying target proteins for Hsp70 chaperone activity. The four cysteine-rich domains are involved in the coordination of zinc, with two zinc ions per type I DnaJ monomer. The CTD domain is the less conserved of the four domains defined, and may comprise a farnesylation motif CaaX.
Figure 3:
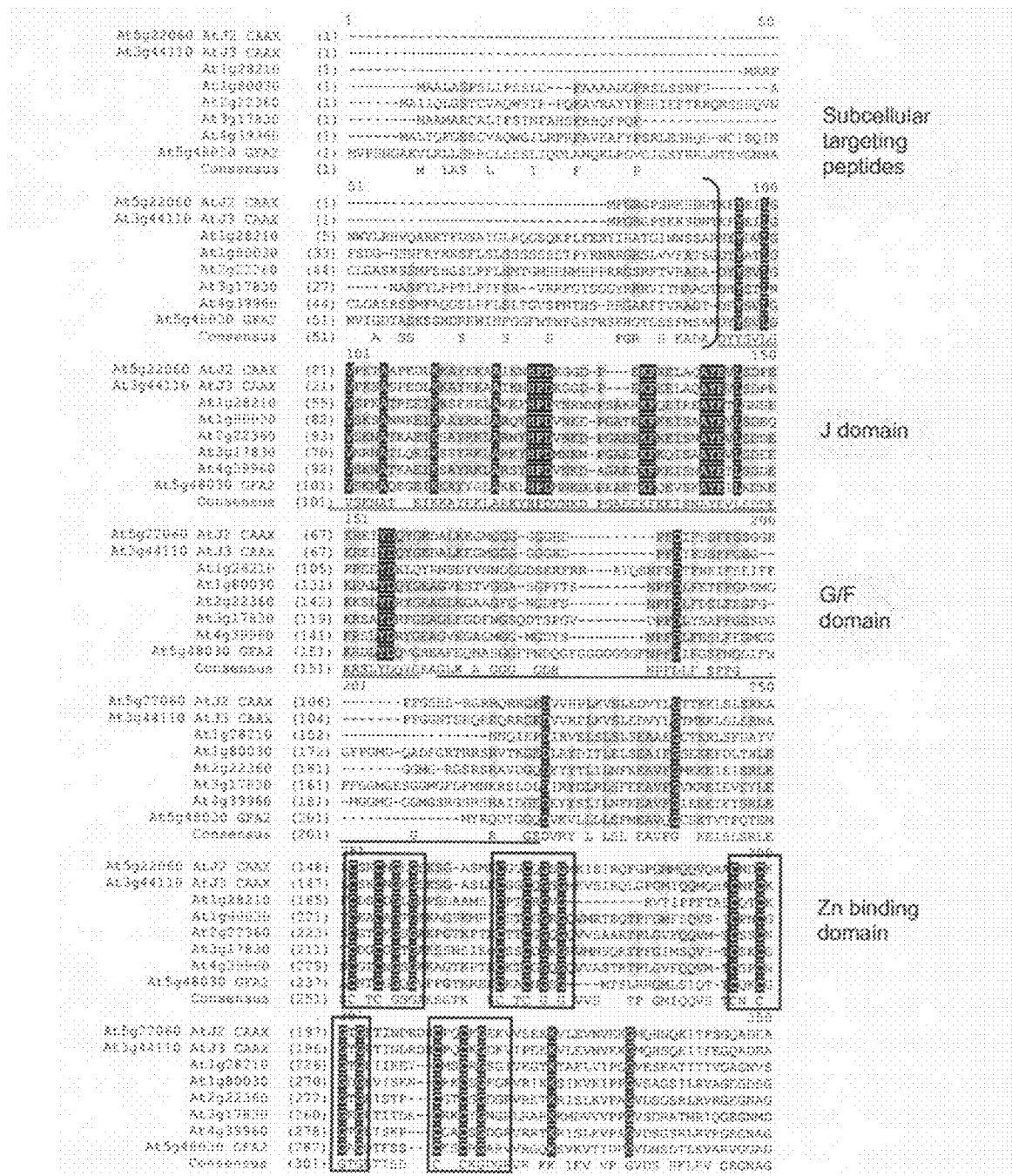
FIG. 3 shows an alignment of type I DnaJ-like polypeptides from *Arabidopsis thaliana* as disclosed in the table below. The J domain is double underlined, the G/F domain is underlined in bold, the two zinc binding domains I and II and their conserved CxxCxGxG (SEQ ID NO: 66) are boxed, and the CTD is single underlined. The farnesylation motif CaaX at the carboxy terminus of the proteins is represented in bold when present. The amino acid sequences preceding the J domain (separated by a parenthesis; approximate location) represent subcellular targeting sequences. The sequences are: At5g22060 AtJ2 CAAX (SEQ ID NO: 18), At3g44110 AtJ3 CAAX (SEQ ID NO: 20), At1g28210 (SEQ ID NO: 60), At1g80030 (SEQ ID NO: 61), At2g22360 (SEQ ID NO: 62), At3g17830 (SEQ ID NO: 63), At4g39960 (SEQ ID NO: 64), and At5b48030 GFA2 (SEQ ID NO: 65).
Figure 4:
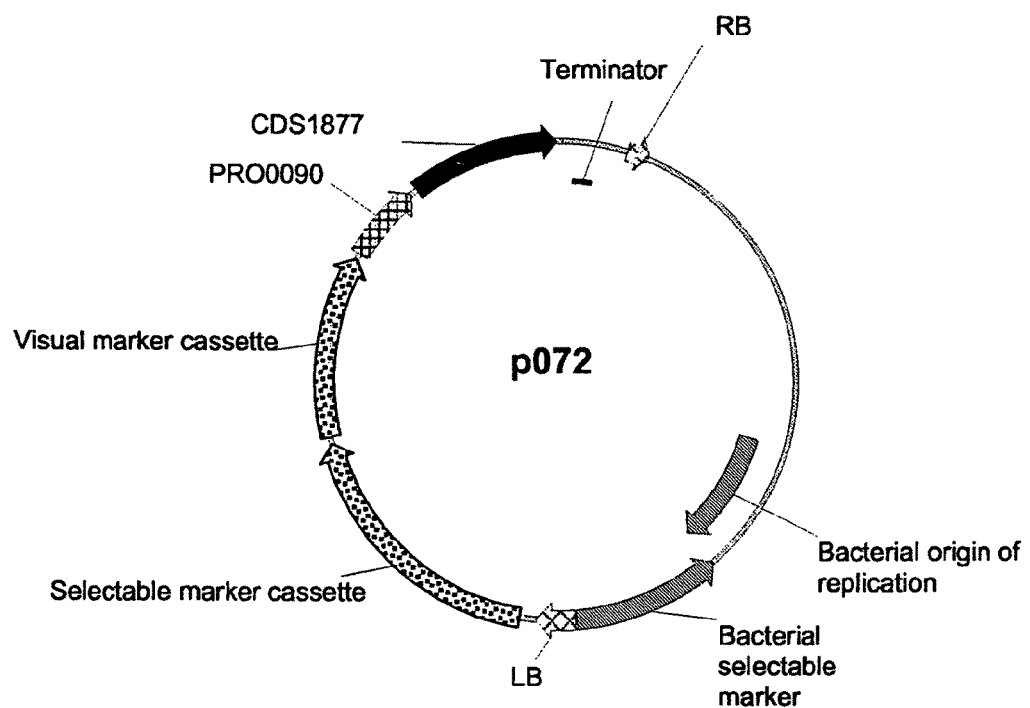

FIG. 4 shows a binary vector for expression in *Oryza sativa* of an *Oryza sativa* type I DnaJ-like (internal reference CDS1877) under the control of a prolamin promoter (internal reference PRO0090).

FIG. 5 details examples of polynucleotide (from start to stop) and polypeptide sequences useful in performing the methods according to the present invention.

EXAMPLES

The present invention will now be described with reference to the following examples, which are by way of illustration alone.

DNA manipulation: unless otherwise stated, recombinant DNA techniques are performed according to standard protocols described in (Sambrook (2001) Molecular Cloning: a laboratory manual, 3rd Edition Cold Spring Harbor Laboratory Press, CSH, New York) or in Volumes 1 and 2 of Ausubel et al., (1994), Current Protocols in Molecular Biology, Current Protocols. Standard materials and methods for plant molecular work are described in Plant Molecular Biology Labfase (1993) by R. D. D. Croy, published by BIOS Scientific Publications Ltd (UK) and Blackwell Scientific Publications (UK).

Example 1

Gene Cloning

The *Oryza sativa* type I DnaJ-like gene (CDS1877) was amplified by PCR using as template an *Oryza sativa* seedling cDNA library (Invitrogen, Paisley, UK). After reverse transcription of RNA extracted from seedlings, the cDNAs were cloned into pCMV Sport 6.0. Average insert size of the bank was 1.6 kb and the original number of clones was of the order of $1.67 \times 10^7$ cfu. Original titer was determined to be $3.34 \times 10^6$ cfu/ml after first amplification of $6 \times 10^{10}$ cfu/ml. After plasmid extraction, 200 ng of template was used in a 50 µl PCR mix. Primers prmO4266 (SEQ ID NO: 58; sense, start codon in bold, AttB1 site in italic: 5' *GGGGACAAG TTTGTA-CAAAAAAGCAGGCTT*CACAATGTACG-GACGCATGCC 3') and prm04267 (SEQ ID NO: 59; reverse, complementary, stop in bold, AttB2 site in italic: 5' *GGG-GACCACTTTGTACAAGAAAGCTGGGTG*-CATCGAATTGTTCTTACTGC 3'), which include the AttB sites for Gateway recombination, were used for PCR amplification. PCR was performed using Hifi Taq DNA polymerase in standard conditions. A PCR fragment of 1340 bp (including attB sites) was amplified and purified also using standard methods. The first step of the Gateway procedure, the BP reaction, was then performed, during which the PCR fragment recombines in vivo with the pDONR201 plasmid to produce, according to the Gateway terminology, an "entry clone", p04452. Plasmid pDONR201 was purchased from Invitrogen, as part of the Gateway® technology.

Example 2

Vector Construction

The entry clone p04452 was subsequently used in an LR reaction with p00830, a destination vector used for *Oryza sativa* transformation. This vector contains as functional elements within the T-DNA borders: a plant selectable marker; a screenable marker expression cassette; and a Gateway cassette intended for LR in vivo recombination with the sequence of interest already cloned in the entry clone. A rice RP6 prolamin promoter (SEQ ID NO: 57; Wen et al. (1993) Plant Physiol 101(3): 11156) for endosperm-specific expression (PRO0090) was located upstream of this Gateway cassette.

After the LR recombination step, the resulting expression vector p072 (FIG. 4) was transformed into *Agrobacterium* strain LBA4044 and subsequently to *Oryza sativa* plants. Transformed rice plants were allowed to grow and were then examined for the parameters described in Example 3.

Example 3

Evaluation and Results of Type I DnaJ-Like Under the Control of the Rice RP6 Promoter Approximately 15 to 20 independent TO rice transformants were generated. The primary transformants were transferred from a tissue culture chamber to a greenhouse for growing and harvest of T1 seed. 5 events, of which the T1 progeny segregated 3:1 for presence/absence of the transgene, were retained. For each of these events, approximately 10 T1 seedlings containing the transgene (hetero- and homozygotes) and approximately 10 T1 seedlings lacking the transgene (nullizygotes) were selected by monitoring visual marker expression. 4 T1 events were further evaluated in the T2 generation following the same evaluation procedure as for the T1 generation but with more individuals per event.

Statistical Analysis: F-Test

A two factor ANOVA (analysis of variants) was used as a statistical model for the overall evaluation of plant phenotypic characteristics. An F-test was carried out on all the parameters measured of all the plants of all the events transformed with the gene of the present invention. The F-test was carried out to check for an effect of the gene over all the transformation events and to verify for an overall effect of the gene, also known as a global gene effect. The threshold for significance for a true global gene effect was set at a 5% probability level for the F-test. A significant F-test value points to a gene effect, meaning that it is not only the presence or position of the gene that is causing the differences in phenotype.

Since two experiments with overlapping events were carried out, a combined analysis was performed in addition to the analysis described above. This is useful to check consistency of the effects over the two experiments, and if this is the case, to accumulate evidence from both experiments in order to increase confidence in the conclusion. The method used was a mixed-model approach that takes into account the multi-level structure of the data (i.e. experiment-event-segregants). P-values were obtained by comparing likelihood ratio test to chi square distributions.

3.1 Seed-Related Parameter Measurements

The mature primary panicles were harvested, bagged, barcode-labeled and then dried for three days in an oven at 37° C. The panicles were then threshed and all the seeds were collected and counted. The filled husks were separated from the empty ones using an air-blowing device. The empty husks were discarded and the remaining fraction was counted again. The filled husks were weighed on an analytical balance. The number of filled seeds was determined by counting the number of filled husks that remained after the separation step. The total seed yield was measured by weighing all filled husks harvested from a plant. Total seed number per plant was measured by counting the number of husks harvested from a plant. The harvest index in the present invention is defined as the ratio of total seed yield and the aboveground area ($mm^2$) multiplied by a factor $10^6$.

3.2 Aboveground Area

Plant aboveground area was determined by counting the total number of pixels from the pictures from the aboveground plant parts discriminated from the background. This value was averaged for the pictures taken on the same time point from the different angles and was converted to a physical surface value expressed in square mm by calibration. Experiments show that the aboveground plant area measured this way correlates with the biomass of plant The table of results (Table 5) below shows percentage difference between the transgenics and the corresponding nullizygotes, for harvest index.

The combined analysis performed confirms the consistency of the effects over the two experiments, and thus increases confidence in the conclusion.

TABLE 5

| | Harvest index Harvest Index | | |
|---|---|---|---|
| | T1% increase | T2% increase | P value combined |
| Event 1 | 55 | 24 | 0.0024 |
| Event 2 | 35 | 11 | 0.0585 |
| Overall | 9 (5 events) | 8 (4 events) | 0.0063 |

The invention claimed is:

1. A method for increasing plant yield in plants grown under non-stress conditions relative to yield in corresponding wild type plants grown under comparable conditions, comprising
   i) introducing and/or expressing in the cytosol of a plant cell a construct comprising an endosperm-specific promoter and an exogenous type I DnaJ-like nucleic acid encoding a type I DnaJ-like polypeptide or a homologue thereof comprising a CaaX motif at its carboxy terminus, and
   ii) selecting a plant with increased plant yield compared to a corresponding wild type plant.

2. The method according to claim 1, wherein said type I DnaJ-like nucleic acid is of prokaryotic or eukaryotic origin.

3. The method according to claim 1, wherein said endosperm-specific promoter is a rice prolamin RP6 promoter.

4. The method according to claim 1, wherein said increased plant yield is increased seed yield or increased harvest index.

5. A plant obtained by the method according to claim 1.

6. A method for the production of a transgenic plant having increased yield, which method comprises:
   (i) introducing and/or expressing in the cytosol of a plant, plant part or plant cell a construct comprising an endosperm-specific promoter and a nucleic acid encoding a type I DnaJ-like polypeptide or a homologue thereof comprising a CaaX motif at its carboxy terminus;
   (ii) selecting a plant with increased plant yield compared to a corresponding wild type plant, and
   (iii) cultivating the plant, plant part or plant cell under non-stress growth conditions promoting plant growth and development.

7. A transgenic plant having increased yield under non-stress growth conditions resulting from a type I DnaJ-like nucleic acid introduced and/or expressed in said plant, wherein said type I DnaJ-like nucleic acid encodes a type I DnaJ-like polypeptide or a homologue thereof comprising a CaaX motif at its carboxy terminus, and wherein said type I DnaJ-like nucleic acid is operably linked to an endosperm-specific promoter.

8. The transgenic plant according to claim 7, wherein said plant is a monocotyledonous plant.

9. Harvestable parts of the transgenic plant according to claim 7, wherein the harvestable parts comprise said type I DnaJ-like nucleic acid operably linked to the endosperm-specific promoter.

10. Harvestable parts according to claim 9, wherein said harvestable parts are seeds.

11. The method according to claim 1, wherein said type I DnaJ-like nucleic acid is of plant origin.

12. The method according to claim 1, wherein said type I DnaJ-like nucleic acid is derived from a monocotyledonous plant.

13. The method according to claim 12, wherein the monocotyledonous plant is from the family Poaceae.

14. The method according to claim 12, wherein the monocotyledonous plant is *Oryza sativa*.

15. The transgenic plant according to claim 7, wherein said plant is selected from the group consisting of sugarcane, rice, maize, wheat, barley, millet, rye, oats and sorghum.

16. The transgenic plant according to claim 7, wherein said type I DnaJ-like nucleic acid is of prokaryotic or eukaryotic origin.

17. The transgenic plant according to claim 7, wherein said type I DnaJ-like nucleic acid is of plant origin.

18. The transgenic plant according to claim 7, wherein said type I DnaJ-like nucleic acid is derived from a monocotyledonous plant.

19. The transgenic plant according to claim 18, wherein the monocotyledonous plant is from the family Poaceae.

20. The transgenic plant according to claim 18, wherein the monocotyledonous plant is *Oryza sativa*.

21. The transgenic plant according to claim 7, wherein said endosperm-specific promoter is a rice prolamin RP6 promoter.

22. The transgenic plant according to claim 7, wherein said increased plant yield is increased seed yield or increased harvest index.

23. A plant obtained by the method according to claim 6.

* * * * *

SEQUENCE LISTING

<160> NUMBER OF SEQ ID NOS: 66

<210> SEQ ID NO 1
<211> LENGTH: 1263
<212> TYPE: DNA
<213> ORGANISM: Oryza sativa

<400> SEQUENCE: 1

```
atgtacggac gcatgccaaa gaagagtaac aataccaagt attatgaggt gcttggtgta      60
tctaagacag caacccagga tgagctgaag aaagcgtacc gtaaagctgc cattaaaaac     120
caccctgata agggtggaga ccctgagaag tttaaagaat tggctcaagc ttacgaggtt     180
cttaatgatc ctgaaaagag ggaaatctat gaccaatatg gcgaggatgc actcaaagaa     240
ggaatgggag gaggcagcag cagtgatttc catagtccct tcgatttatt tgagcaaatt     300
tttcagaatc gtggtggctt tgggggtaga ggacacagac aaaagcgtgg cgaagatgtg     360
gtacatacta tgaaggtttc tttagaagac ctgtataatg gtactaccaa aaaactgtct     420
ttgtcacgga atgctctgtg cacaaagtgc aagggtaaag gatccaagag tggggcagca     480
gcaacttgcc atggttgtca tggtgcagga tgagaacaa taacaagaca aattgggctt     540
ggcatgatcc aacagatgaa cactgtttgc cctgaatgca gaggatcagg tgagatgata     600
agtgacaagg ataaatgccc gagttgtaag ggaaacaaag tagtccagca gaagaaggtc     660
ttggaggttc atgttgagaa gggaatgcaa catggccaaa agattgtatt ccagggtgaa     720
gctgatgaag ctcctgatac agtgacagga gacatagttt ttgtcttgca acttaaagac     780
cacccaaaat ttaagaggaa gtttgatgac ctctttactg agcacacaat ctccctgacc     840
gaggctctgt gtggcttcca gtttgttcta acccatcttg atggtcggca actcctaatc     900
aaatctaatc caggggaggt tataaaacct ggtcaacaca aggccatcaa tgatgaaggc     960
atgcccagc atgccgcc tttcatgaaa ggtcgtcttt tgttgaatt caacgtggag    1020
tttcctgagc ctggtgcact cactcctggc caatgccgat cgcttgagaa gattttgcca    1080
ccacgaccca ggaatcaatt gtcagacatg gagctagatc aatgtgagga gaccaccatg    1140
catgatgtca acatagaaga ggagatgagg cgcaggcagc agcacaggcg gcaggaagca    1200
tatgatgaag acgacgacga ggatgctgga gctggaccaa gggtacagtg tgcccagcag    1260
taa                                                                  1263
```

<210> SEQ ID NO 2
<211> LENGTH: 420
<212> TYPE: PRT
<213> ORGANISM: Oryza sativa

<400> SEQUENCE: 2

```
Met Tyr Gly Arg Met Pro Lys Lys Ser Asn Asn Thr Lys Tyr Tyr Glu
1               5                   10                  15
Val Leu Gly Val Ser Lys Thr Ala Thr Gln Asp Glu Leu Lys Lys Ala
            20                  25                  30
Tyr Arg Lys Ala Ala Ile Lys Asn His Pro Asp Lys Gly Gly Asp Pro
        35                  40                  45
Glu Lys Phe Lys Glu Leu Ala Gln Ala Tyr Glu Val Leu Asn Asp Pro
    50                  55                  60
Glu Lys Arg Glu Ile Tyr Asp Gln Tyr Gly Glu Asp Ala Leu Lys Glu
65                  70                  75                  80
Gly Met Gly Gly Gly Ser Ser Ser Asp Phe His Ser Pro Phe Asp Leu
                85                  90                  95
Phe Glu Gln Ile Phe Gln Asn Arg Gly Gly Phe Gly Gly Arg Gly His
            100                 105                 110
Arg Gln Lys Arg Gly Glu Asp Val Val His Thr Met Lys Val Ser Leu
        115                 120                 125
Glu Asp Leu Tyr Asn Gly Thr Thr Lys Lys Leu Ser Leu Ser Arg Asn
```

-continued

```
            130                 135                 140
Ala Leu Cys Thr Lys Cys Lys Gly Lys Gly Ser Lys Ser Gly Ala Ala
145                 150                 155                 160

Ala Thr Cys His Gly Cys His Gly Ala Gly Met Arg Thr Ile Thr Arg
                165                 170                 175

Gln Ile Gly Leu Gly Met Ile Gln Gln Met Asn Thr Val Cys Pro Glu
            180                 185                 190

Cys Arg Gly Ser Gly Glu Met Ile Ser Asp Lys Asp Lys Cys Pro Ser
        195                 200                 205

Cys Lys Gly Asn Lys Val Val Gln Gln Lys Lys Val Leu Glu Val His
210                 215                 220

Val Glu Lys Gly Met Gln His Gly Gln Lys Ile Val Phe Gln Gly Glu
225                 230                 235                 240

Ala Asp Glu Ala Pro Asp Thr Val Thr Gly Asp Ile Val Phe Val Leu
                245                 250                 255

Gln Leu Lys Asp His Pro Lys Phe Lys Arg Lys Phe Asp Asp Leu Phe
            260                 265                 270

Thr Glu His Thr Ile Ser Leu Thr Glu Ala Leu Cys Gly Phe Gln Phe
        275                 280                 285

Val Leu Thr His Leu Asp Gly Arg Gln Leu Leu Ile Lys Ser Asn Pro
290                 295                 300

Gly Glu Val Ile Lys Pro Gln His Lys Ala Ile Asn Asp Glu Gly
305                 310                 315                 320

Met Pro Gln His Gly Arg Pro Phe Met Lys Gly Arg Leu Phe Val Glu
                325                 330                 335

Phe Asn Val Glu Phe Pro Glu Pro Gly Ala Leu Thr Pro Gly Gln Cys
            340                 345                 350

Arg Ser Leu Glu Lys Ile Leu Pro Pro Arg Pro Arg Asn Gln Leu Ser
        355                 360                 365

Asp Met Glu Leu Asp Gln Cys Glu Glu Thr Thr Met His Asp Val Asn
370                 375                 380

Ile Glu Glu Glu Met Arg Arg Arg Gln Gln His Arg Arg Gln Glu Ala
385                 390                 395                 400

Tyr Asp Glu Asp Asp Glu Asp Ala Gly Ala Gly Pro Arg Val Gln
                405                 410                 415

Cys Ala Gln Gln
            420

<210> SEQ ID NO 3
<211> LENGTH: 1251
<212> TYPE: DNA
<213> ORGANISM: Oryza sativa

<400> SEQUENCE: 3
atgtttgggc gtgtaccgag gagtaacaac accaagtact atgaggttct tggagttcct      60
aaaactgcaa gcaaggatga gctaaagaag cataccggaa ggctgccat aaaaaaccat      120 cctgacaagg gagggatcc agaaaagttt aagaattat cacaagcgta tgaggttctc       180
actgatcctg agaagagaga catatatgac caatatgggg aggatgctct taaggatgga    240
atgggaggag gcagtgactt ccataatcca tttgacatat ttgagcagtt tttcgggggt    300
ggtgcctttg ggggagtag ctcaagagta cgcagacaga gacgtggtga agatgtggcg    360
catactttga aggtgtcttt agaagatgtg tataatggat ctatgaagaa actatcatta   420
tcacgaaata ttctgtgccc aaagtgcaaa ggaaaaggga ccaaatctga ggctccagca    480
```

-continued

```
acatgctatg gttgtcatgg tgtaggaatg aggaatataa tgcgacagat aggactaggc      540
atgattcaac atatgcagac tgtctgtcct gaatgcagag gatcaggtga gatcataagt      600
gacagggata aatgcacaaa ctgcagagct agcaaagtta ttcaggagaa aaaggtgctt      660
gaggttcata ttgagaaggg aatgcaacat ggccaaaaaa ttgtattcca aggtgaagct      720
gatgaagctc ctgatacagt gacaggagat atagtattta tcttgcaagt taaggtacat      780
ccaagattta agaggaaata tgatgacctg ttcattgagc gcacaatctc tttaactgag      840
gcattgtgtg ggttccaatt catcctcact catctggaca gtaggcagct cctaatcaag      900
gcaaatcctg gcgaaattat taaacctggt caacacaagg ccataaatga tgagggaatg      960
ccacaccatg gccggccttt catgaagggc cgtctctttg tggaattcaa tgttgagttc     1020
cctgaatctg gtgtactctc ccgtgaccaa tgccgggcac ttgagatgat cctaccacct     1080
aaacctgggc accaattatc agatatggac ctggatcaat gtgaggaaac taccatgcat     1140
gatgtgaaca tagaagagga gatgaggcgc aagcagtatc aaaggaagca ggaagcgtac     1200
gacgaagatg aggaggagga tgctccaaga gtacagtgtg ctcaacagta a              1251
```

<210> SEQ ID NO 4
<211> LENGTH: 416
<212> TYPE: PRT
<213> ORGANISM: Oryza sativa

<400> SEQUENCE: 4

```
Met Phe Gly Arg Val Pro Arg Ser Asn Asn Thr Lys Tyr Tyr Glu Val
1               5                   10                  15

Leu Gly Val Pro Lys Thr Ala Ser Lys Asp Glu Leu Lys Lys Ala Tyr
            20                  25                  30

Arg Lys Ala Ala Ile Lys Asn His Pro Asp Lys Gly Gly Asp Pro Glu
        35                  40                  45

Lys Phe Lys Glu Leu Ser Gln Ala Tyr Glu Val Leu Thr Asp Pro Glu
    50                  55                  60

Lys Arg Asp Ile Tyr Asp Gln Tyr Gly Glu Asp Ala Leu Lys Asp Gly
65                  70                  75                  80

Met Gly Gly Gly Ser Asp Phe His Asn Pro Phe Asp Ile Phe Glu Gln
                85                  90                  95

Phe Phe Gly Gly Gly Ala Phe Gly Gly Ser Ser Ser Arg Val Arg Arg
            100                 105                 110

Gln Arg Arg Gly Glu Asp Val Ala His Thr Leu Lys Val Ser Leu Glu
        115                 120                 125

Asp Val Tyr Asn Gly Ser Met Lys Lys Leu Ser Leu Ser Arg Asn Ile
    130                 135                 140

Leu Cys Pro Lys Cys Lys Gly Lys Gly Thr Lys Ser Glu Ala Pro Ala
145                 150                 155                 160

Thr Cys Tyr Gly Cys His Gly Val Gly Met Arg Asn Ile Met Arg Gln
                165                 170                 175

Ile Gly Leu Gly Met Ile Gln His Met Gln Thr Val Cys Pro Glu Cys
            180                 185                 190

Arg Gly Ser Gly Glu Ile Ile Ser Asp Arg Asp Lys Cys Thr Asn Cys
        195                 200                 205

Arg Ala Ser Lys Val Ile Gln Glu Lys Lys Val Leu Glu Val His Ile
    210                 215                 220

Glu Lys Gly Met Gln His Gly Gln Lys Ile Val Phe Gln Gly Glu Ala
225                 230                 235                 240
```

```
Asp Glu Ala Pro Asp Thr Val Thr Gly Asp Ile Val Phe Ile Leu Gln
                245                 250                 255
Val Lys Val His Pro Arg Phe Lys Arg Lys Tyr Asp Asp Leu Phe Ile
            260                 265                 270
Glu Arg Thr Ile Ser Leu Thr Glu Ala Leu Cys Gly Phe Gln Phe Ile
        275                 280                 285
Leu Thr His Leu Asp Ser Arg Gln Leu Leu Ile Lys Ala Asn Pro Gly
    290                 295                 300
Glu Ile Ile Lys Pro Gly Gln His Lys Ala Ile Asn Asp Glu Gly Met
305                 310                 315                 320
Pro His His Gly Arg Pro Phe Met Lys Gly Arg Leu Phe Val Glu Phe
                325                 330                 335
Asn Val Glu Phe Pro Glu Ser Gly Val Leu Ser Arg Asp Gln Cys Arg
            340                 345                 350
Ala Leu Glu Met Ile Leu Pro Pro Lys Pro Gly His Gln Leu Ser Asp
        355                 360                 365
Met Asp Leu Asp Gln Cys Glu Glu Thr Thr Met His Asp Val Asn Ile
    370                 375                 380
Glu Glu Glu Met Arg Arg Lys Gln Tyr Gln Arg Lys Gln Glu Ala Tyr
385                 390                 395                 400
Asp Glu Asp Glu Glu Asp Ala Pro Arg Val Gln Cys Ala Gln Gln
                405                 410                 415

<210> SEQ ID NO 5
<211> LENGTH: 1254
<212> TYPE: DNA
<213> ORGANISM: Oryza sativa

<400> SEQUENCE: 5
atgttcgggc gcgcgccgaa gaagagcgac aacaccaagt actacgagat cctgggggtc      60
cccaagaccg cctcccagga cgacctcaag aaggcgtacc gcaaggccgc catcaagaac     120
caccccgaca gggcggcga ccccgagaag ttcaaggagc ttgcacaagc ttatgaggta     180
ttgagtgacc cggagaaacg tgaaatctat gaccaatatg gtgaagatgc cctcaaggaa     240
ggaatgggtg gaggcggatc ccatgttgat ccatttgaca tcttttcatc attctttgga     300
ccttcttttg gtggtggtgg cagcagcagg ggcagaaggc aaaggagggg agaggatgtg     360
atccatccgc ttaaggtttc tctagaagat ctttacaatg gtacttcaaa gaagctctct     420 cttttcccgca atgtcctctg cgccaagtgc aagggcaagg gttccaagtc tggtgcttcc     480
atgaggtgcc caggttgcca ggggtctggc atgaaaatca ccatccgcca gctgggccc     540 tccatgatac agcagatgca gcagccttgc aatgagtgta aggggactgg agagagcatt     600
aatgagaagg atcgctgccc aggctgcaag ggcgagaagg ttattcagga gaagaaggtt     660
ctggaggttc acgttgagaa ggggatgcaa cacaatcaga gatcactttt ccctggtgaa     720
gctgatgagg cgcctgatac cgttacggga cattgtat tcgtcctcca gcagaaggac     780
cactccaagt tcaaaaggaa gggcgatgat ctcttttatg agcacacctt atctctgact     840
gaagcacttt gtggtttcca atttgtcctg acacatctgg acaacagaca gctgctcatt     900
aagtcaaacc ccggtgaagt tgttaagcct gaccaattca aggcaataaa cgatgaggga     960
atgccaatgt accagaggcc tttcatgaag gggaagctct acattcattt cacggtggag    1020
ttccctgatt ccctggcgcc tgaacaatgc aaggctctcg aggctgtgct tccaccgaag    1080
cctgcatccc agctgacaga aatggagata gatgaatgcg aggagaccac gatgcacgat    1140
```

-continued

```
gtcaacaaca ttgaggaaga gatgcgcagg aaagcccaag ctgctcagga ggcgtatgat      1200
gaggacgatg agatgcctgg aggtgcccag agagttcagt gcgcgcaaca gtaa            1254
```

<210> SEQ ID NO 6
<211> LENGTH: 417
<212> TYPE: PRT
<213> ORGANISM: Oryza sativa

<400> SEQUENCE: 6

```
Met Phe Gly Arg Ala Pro Lys Lys Ser Asp Asn Thr Lys Tyr Tyr Glu
 1               5                  10                  15

Ile Leu Gly Val Pro Lys Thr Ala Ser Gln Asp Asp Leu Lys Lys Ala
            20                  25                  30

Tyr Arg Lys Ala Ala Ile Lys Asn His Pro Asp Lys Gly Gly Asp Pro
        35                  40                  45

Glu Lys Phe Lys Glu Leu Ala Gln Ala Tyr Glu Val Leu Ser Asp Pro
    50                  55                  60

Glu Lys Arg Glu Ile Tyr Asp Gln Tyr Gly Glu Asp Ala Leu Lys Glu
65                  70                  75                  80

Gly Met Gly Gly Gly Ser His Val Asp Pro Phe Asp Ile Phe Ser
                85                  90                  95

Ser Phe Phe Gly Pro Ser Phe Gly Gly Gly Ser Ser Arg Gly Arg
            100                 105                 110

Arg Gln Arg Arg Gly Glu Asp Val Ile His Pro Leu Lys Val Ser Leu
        115                 120                 125

Glu Asp Leu Tyr Asn Gly Thr Ser Lys Lys Leu Ser Leu Ser Arg Asn
    130                 135                 140

Val Leu Cys Ala Lys Cys Lys Gly Lys Gly Ser Lys Ser Gly Ala Ser
145                 150                 155                 160

Met Arg Cys Pro Gly Cys Gln Gly Ser Gly Met Lys Ile Thr Ile Arg
                165                 170                 175

Gln Leu Gly Pro Ser Met Ile Gln Gln Met Gln Gln Pro Cys Asn Glu
            180                 185                 190

Cys Lys Gly Thr Gly Glu Ser Ile Asn Glu Lys Asp Arg Cys Pro Gly
        195                 200                 205

Cys Lys Gly Glu Lys Val Ile Gln Glu Lys Lys Val Leu Glu Val His
    210                 215                 220

Val Glu Lys Gly Met Gln His Asn Gln Lys Ile Thr Phe Pro Gly Glu
225                 230                 235                 240

Ala Asp Glu Ala Pro Asp Thr Val Thr Gly Asp Ile Val Phe Val Leu
                245                 250                 255

Gln Gln Lys Asp His Ser Lys Phe Lys Arg Lys Gly Asp Asp Leu Phe
            260                 265                 270

Tyr Glu His Thr Leu Ser Leu Thr Glu Ala Leu Cys Gly Phe Gln Phe
        275                 280                 285

Val Leu Thr His Leu Asp Asn Arg Gln Leu Leu Ile Lys Ser Asn Pro
    290                 295                 300

Gly Glu Val Val Lys Pro Asp Gln Phe Lys Ala Ile Asn Asp Glu Gly
305                 310                 315                 320

Met Pro Met Tyr Gln Arg Pro Phe Met Lys Gly Lys Leu Tyr Ile His
                325                 330                 335

Phe Thr Val Glu Phe Pro Asp Ser Leu Ala Pro Glu Gln Cys Lys Ala
            340                 345                 350
```

-continued

```
Leu Glu Ala Val Leu Pro Pro Lys Pro Ala Ser Gln Leu Thr Glu Met
        355                 360                 365

Glu Ile Asp Glu Cys Glu Glu Thr Thr Met His Asp Val Asn Asn Ile
    370                 375                 380

Glu Glu Glu Met Arg Arg Lys Ala Gln Ala Ala Gln Glu Ala Tyr Asp
385                 390                 395                 400

Glu Asp Asp Glu Met Pro Gly Gly Ala Gln Arg Val Gln Cys Ala Gln
                405                 410                 415

Gln
```

<210> SEQ ID NO 7
<211> LENGTH: 1254
<212> TYPE: DNA
<213> ORGANISM: Oryza sativa

<400> SEQUENCE: 7

```
atgttcgggc gcgcgccgaa gaagagcgac aacacgcggt actacgaggt gcttggggtg     60
cccaaggatg cgtcccagga tgacctcaag aaggcgtacc gcaaggccgc catcaagaac    120
caccccgaca gggcggagac ccccgagaag ttcaaggaat ggctcaggc ttatgaagtc     180
ctgagtgacc ctgagaagcg tgaaatctat gatcagtacg gtgaagatgc tctcaaggag    240
gggatgggtc ctggtggtgg gatgcatgac ccatttgaca tttttcctc attctttgga     300
ggtggctttg gaggtggtag cagtagggc aggagacagc gtaggggaga ggatgtggtt     360
caccctctga aggtttctct ggaggaattg tacaatggca catcaaagaa gctctccctt    420
tctcgcaatg tgctctgctc caagtgcaat ggcaagggct cgaaatctgg tgcttccatg    480
aagtgctctg ttgtcaagg ttctggtatg aaggtccaaa ttcgccagtt ggggccagga    540
atgattcagc aaatgcaaca tccctgcaat gagtgcaagg gaactggtga gaccatcagc    600
gacaaggata tgcccagg ctgcaagggt gagaaggtgg cgcaggagaa gaaggttctt     660
gaggtggtgg tcgagaaggg catgcagaat ggacagaaga tcaccttccc tggtgaggct    720
gatgaagcgc ccgatactgt cactggagac attatcttcg tcctccagca gaaggagcat    780
cccaagttca gagaaagggg agatgacctc ttctacgagc acaccctgaa cctcactgag    840
gccctttgtg gcttccagtt tgttctcact cacttggaca caggcagct gcttatcaag    900
tccaagcccg gtgaagttgt caagcctgat tcattcaagg ctgtcaacga cgagggcatg    960
ccgatgtacc agcggccatt catgaagggg aagctctaca tccacttctc cgtggaattc   1020
cccgactctt tgaaccctga ccagtgcaag gccctggaga ccgtcctccc gccaaggccg   1080
gtgtcgcagt acaccgacat ggagctcgac gagtgcgagg agaccatgcc gtacgacgtg   1140
aacatcgagg aggagatgag gaggcggcag caacagcagc agcaggaggc atacgacgag   1200
gacgaggaca tgcacggcgg cggcgcccag cgcgtgcagt gcgcgcagca gtaa          1254
```

<210> SEQ ID NO 8
<211> LENGTH: 417
<212> TYPE: PRT
<213> ORGANISM: Oryza sativa

<400> SEQUENCE: 8

```
Met Phe Gly Arg Ala Pro Lys Lys Ser Asp Asn Thr Arg Tyr Tyr Glu
1               5                   10                  15

Val Leu Gly Val Pro Lys Asp Ala Ser Gln Asp Asp Leu Lys Lys Ala
            20                  25                  30

Tyr Arg Lys Ala Ala Ile Lys Asn His Pro Asp Lys Gly Gly Asp Pro
```

```
            35                  40                  45
Glu Lys Phe Lys Glu Leu Ala Gln Ala Tyr Glu Val Leu Ser Asp Pro
    50                  55                  60
Glu Lys Arg Glu Ile Tyr Asp Gln Tyr Gly Glu Asp Ala Leu Lys Glu
65                  70                  75                  80
Gly Met Gly Pro Gly Gly Met His Asp Pro Phe Asp Ile Phe Ser
                85                  90                  95
Ser Phe Phe Gly Gly Phe Gly Gly Ser Ser Arg Gly Arg Arg
                100                 105                 110
Gln Arg Arg Gly Glu Asp Val Val His Pro Leu Lys Val Ser Leu Glu
            115                 120                 125
Glu Leu Tyr Asn Gly Thr Ser Lys Lys Leu Ser Leu Ser Arg Asn Val
        130                 135                 140
Leu Cys Ser Lys Cys Asn Gly Lys Gly Ser Lys Ser Gly Ala Ser Met
145                 150                 155                 160
Lys Cys Ser Gly Cys Gln Gly Ser Gly Met Lys Val Gln Ile Arg Gln
                165                 170                 175
Leu Gly Pro Gly Met Ile Gln Gln Met Gln His Pro Cys Asn Glu Cys
                180                 185                 190
Lys Gly Thr Gly Glu Thr Ile Ser Asp Lys Asp Arg Cys Pro Gly Cys
            195                 200                 205
Lys Gly Glu Lys Val Ala Gln Glu Lys Lys Val Leu Glu Val Val Val
        210                 215                 220
Glu Lys Gly Met Gln Asn Gly Gln Lys Ile Thr Phe Pro Gly Glu Ala
225                 230                 235                 240
Asp Glu Ala Pro Asp Thr Val Thr Gly Asp Ile Ile Phe Val Leu Gln
                245                 250                 255
Gln Lys Glu His Pro Lys Phe Lys Arg Lys Gly Asp Asp Leu Phe Tyr
                260                 265                 270
Glu His Thr Leu Asn Leu Thr Glu Ala Leu Cys Gly Phe Gln Phe Val
            275                 280                 285
Leu Thr His Leu Asp Asn Arg Gln Leu Leu Ile Lys Ser Lys Pro Gly
        290                 295                 300
Glu Val Val Lys Pro Asp Ser Phe Lys Ala Val Asn Asp Glu Gly Met
305                 310                 315                 320
Pro Met Tyr Gln Arg Pro Phe Met Lys Gly Lys Leu Tyr Ile His Phe
                325                 330                 335
Ser Val Glu Phe Pro Asp Ser Leu Asn Pro Asp Gln Cys Lys Ala Leu
                340                 345                 350
Glu Thr Val Leu Pro Pro Arg Pro Val Ser Gln Tyr Thr Asp Met Glu
            355                 360                 365
Leu Asp Glu Cys Glu Glu Thr Met Pro Tyr Asp Val Asn Ile Glu Glu
        370                 375                 380
Glu Met Arg Arg Arg Gln Gln Gln Gln Gln Glu Ala Tyr Asp Glu
385                 390                 395                 400
Asp Glu Asp Met His Gly Gly Gly Ala Gln Arg Val Gln Cys Ala Gln
                405                 410                 415
Gln

<210> SEQ ID NO 9
<211> LENGTH: 1260
<212> TYPE: DNA
<213> ORGANISM: Zea mays
```

-continued

```
<400> SEQUENCE: 9
atgttcgggc gcgcgccgaa gaagagcgac aacaccaagt actacgagat cctcggggtg      60
cccaagtcgg cgtcccagga cgatctcaag aaggcctacc gcaaggctgc tatcaagaac     120
caccccgaca agggcggtga ccccgagaag ttcaaggagc tcgcacaagc ctatgaggtt     180
ttgagtgatc cagagaaacg tgagatttat gatcagtatg gtgaagatgc ccttaaggaa     240
ggaatgggcg gtggaggatc ccatgttgat ccatttgaca tcttctcatc attttttgga     300
ccctcttttg gaggaggtgg tggaagcagc aggggaagaa ggcaaaggag gggagaagat     360
gtagttcacc cacttaaagt ttctctggaa gatctttaca atggcacctc aaagaagctc     420
tctctttcgc gcaatgtcat ctgctccaag tgcaagggca agggctcgaa gtctggtgcc     480
tcaatgaggt gccctggttg ccagggctca ggcatgaaag tcactattcg tcagctgggc     540
ccttccatga tacagcagat gcagcagcct tgcaatgagt gcaaggggac tggagagagc     600
atcaatgaga aggaccgctg tccagggtgc aagggtgaga aggtcattca agagaagaaa     660
gttcttgagg ttcatgttga aggggatg caacacaacc agaagatcac cttccctggt     720
gaagctgatg aagcgcctga tactgtcact ggagacattg tattcgtcct caacagaaag     780
gatcactcca aattcaaaag aaagggtgaa gatctgttct atgagcacac cttgtctctg     840
accgaagcac tatgtggggtt ccaatttgtt cttacacatc tggacaacag gcagcttctc     900
atcaaatcag accctggtga agttgttaaa cctgaccaat tcaaggcgat taatgatgag     960
gggatgccaa tttaccagag gcctttcatg aaggggaagc tgtacatcca tttcacggtg    1020
gagttccctg actcgttggc accagagcag tgcaaggctc tcgagacagt acttccacca    1080
aggccttcat ccaagctgac agacatggag atagatgaat gcgaggagac gactatgcat    1140
gatgtgaaca acatcgagga agagatgcgc aagaagcaag ctcacgctgc ccaggaggcg    1200
tacgaggagg acgacgagat gccgggcgga gcccagagag tgcagtgcgc gcagcagtaa    1260

<210> SEQ ID NO 10
<211> LENGTH: 419
<212> TYPE: PRT
<213> ORGANISM: Zea mays

<400> SEQUENCE: 10

Met Phe Gly Arg Ala Pro Lys Lys Ser Asp Asn Thr Lys Tyr Tyr Glu
1               5                  10                  15

Ile Leu Gly Val Pro Lys Ser Ala Ser Gln Asp Asp Leu Lys Lys Ala
            20                  25                  30

Tyr Arg Lys Ala Ala Ile Lys Asn His Pro Asp Lys Gly Gly Asp Pro
        35                  40                  45

Glu Lys Phe Lys Glu Leu Ala Gln Ala Tyr Glu Val Leu Ser Asp Pro
    50                  55                  60

Glu Lys Arg Glu Ile Tyr Asp Gln Tyr Gly Glu Asp Ala Leu Lys Glu
65                  70                  75                  80

Gly Met Gly Gly Gly Gly Ser His Val Asp Pro Phe Asp Ile Phe Ser
                85                  90                  95

Ser Phe Phe Gly Pro Ser Phe Gly Gly Gly Gly Ser Ser Arg Gly
            100                 105                 110

Arg Arg Gln Arg Arg Gly Glu Asp Val Val His Pro Leu Lys Val Ser
        115                 120                 125

Leu Glu Asp Leu Tyr Asn Gly Thr Ser Lys Lys Leu Ser Leu Ser Arg
    130                 135                 140
```

Asn Val Ile Cys Ser Lys Cys Lys Gly Lys Gly Ser Lys Ser Gly Ala
145                 150                 155                 160

Ser Met Arg Cys Pro Gly Cys Gln Gly Ser Gly Met Lys Val Thr Ile
            165                 170                 175

Arg Gln Leu Gly Pro Ser Met Ile Gln Met Gln Gln Pro Cys Asn
        180                 185                 190

Glu Cys Lys Gly Thr Gly Glu Ser Ile Asn Glu Lys Asp Arg Cys Pro
        195                 200                 205

Gly Cys Lys Gly Glu Lys Val Ile Gln Glu Lys Lys Val Leu Glu Val
        210                 215                 220

His Val Glu Lys Gly Met Gln His Asn Gln Lys Ile Thr Phe Pro Gly
225                 230                 235                 240

Glu Ala Asp Glu Ala Pro Asp Thr Val Thr Gly Asp Ile Val Phe Val
                245                 250                 255

Leu Gln Gln Lys Asp His Ser Lys Phe Lys Arg Lys Gly Glu Asp Leu
                260                 265                 270

Phe Tyr Glu His Thr Leu Ser Leu Thr Glu Ala Leu Cys Gly Phe Gln
            275                 280                 285

Phe Val Leu Thr His Leu Asp Asn Arg Gln Leu Leu Ile Lys Ser Asp
        290                 295                 300

Pro Gly Glu Val Val Lys Pro Asp Gln Phe Lys Ala Ile Asn Asp Glu
305                 310                 315                 320

Gly Met Pro Ile Tyr Gln Arg Pro Phe Met Lys Gly Lys Leu Tyr Ile
                325                 330                 335

His Phe Thr Val Glu Phe Pro Asp Ser Leu Ala Pro Glu Gln Cys Lys
            340                 345                 350

Ala Leu Glu Thr Val Leu Pro Pro Arg Pro Ser Ser Lys Leu Thr Asp
        355                 360                 365

Met Glu Ile Asp Glu Cys Glu Glu Thr Thr Met His Asp Val Asn Asn
    370                 375                 380

Ile Glu Glu Glu Met Arg Arg Lys Gln Ala His Ala Ala Gln Glu Ala
385                 390                 395                 400

Tyr Glu Glu Asp Asp Glu Met Pro Gly Gly Ala Gln Arg Val Gln Cys
                405                 410                 415

Ala Gln Gln

<210> SEQ ID NO 11
<211> LENGTH: 1257
<212> TYPE: DNA
<213> ORGANISM: Zea mays

<400> SEQUENCE: 11
atgttcgggc gcgcgccgaa gaagagcgac aacacacggt actacgagat cctcggggtc      60
tccaaggacg cgtcccagga tgacctcaag aaagcctacc gcaaggccgc catcaagaac     120
caccccgaca agggcggcga tcccgagaag ttcaaggagc tagctcaggc ttatgaggtc     180
ctcagtgatc ctgaaaagcg ggagatttat gatcaatatg gtgaggatgc cctcaaggag     240
ggaatgggag gtggtggagg gatgcacgat ccctttgaca tattccagtc attctttggt     300
ggtggaagcc ttttggagg tggtggcagc agtaggggca aaggcagcg aaggggagag       360 gatgtggttc atcctctaaa ggtttctctg gaggatttgt acaatggcac atcaaagaag     420
ctctctctgt cccgcagtgt cctctgctcc aagtgcaatg gtaagggttc aaagtctgga    480
gcttcatcga ggtgtgctgg ttgccaaggt tctggcttta aggtccaaat ccggcagttg     540

```
gggcctggaa tgatccagca aatgcagcat ccttgcaacg agtgcaaggg ttctggagag    600
acaatcagcg acaaggatag atgcccacag tgcaagggtg ataaagttgt gcaggagaag    660
aaggttcttg aagtgtttgt ggagaaaggc atgcagaatg gcagaagat cacattccct    720 ggtgaagctg atgaagcgcc tgacactgtc actggagata tcattttgt tctccagcag    780 aaggagcatc ccaagttcaa agaaagggc gatgacctct tctacgagca caccctgacc    840
ttgactgaat ctctgtgtgg cttccagttt gttgtgactc acttggataa caggcagctg    900
ctgatcaaat caaatccggg cgaagttgtg aagcctgatt ctttcaaggc gatcaacgac    960
gaaggcatgc ccatgtacca gaggccgttc atgaagggca agctgtacat ccacttctcg   1020
gtggagttcc cggactcgct gagcccggag cagtgcaagg ccctggaggc tgtgctcccg   1080
cccaagccgg tgtcgcagta caccgacatg gagctggacg agtgcgagga gacgatgccc   1140
tatgacgtga acatcgaagc ggagatgcgg aggcggcagc agcagcacca ggaggcctac   1200
gacgaggatg aggacatgcc gggcggcgcg cagagggtgc agtgcgccca gcagtag      1257
```

<210> SEQ ID NO 12
<211> LENGTH: 418
<212> TYPE: PRT
<213> ORGANISM: Zea mays

<400> SEQUENCE: 12

```
Met Phe Gly Arg Ala Pro Lys Lys Ser Asp Asn Thr Arg Tyr Tyr Glu
1               5                   10                  15

Ile Leu Gly Val Ser Lys Asp Ala Ser Gln Asp Leu Lys Lys Ala
            20                  25                  30

Tyr Arg Lys Ala Ala Ile Lys Asn His Pro Asp Lys Gly Gly Asp Pro
        35                  40                  45

Glu Lys Phe Lys Glu Leu Ala Gln Ala Tyr Glu Val Leu Ser Asp Pro
    50                  55                  60

Glu Lys Arg Glu Ile Tyr Asp Gln Tyr Gly Glu Asp Ala Leu Lys Glu
65                  70                  75                  80

Gly Met Gly Gly Gly Gly Met His Asp Pro Phe Asp Ile Phe Gln
                85                  90                  95

Ser Phe Phe Gly Gly Gly Ser Pro Phe Gly Gly Gly Ser Ser Arg
            100                 105                 110

Gly Arg Arg Gln Arg Arg Gly Glu Asp Val Val His Pro Leu Lys Val
        115                 120                 125

Ser Leu Glu Asp Leu Tyr Asn Gly Thr Ser Lys Lys Leu Ser Leu Ser
    130                 135                 140

Arg Ser Val Leu Cys Ser Lys Cys Asn Gly Lys Gly Ser Lys Ser Gly
145                 150                 155                 160

Ala Ser Ser Arg Cys Ala Gly Cys Gln Gly Ser Gly Phe Lys Val Gln
                165                 170                 175

Ile Arg Gln Leu Gly Pro Gly Met Ile Gln Met Gln His Pro Cys
            180                 185                 190

Asn Glu Cys Lys Gly Ser Gly Glu Thr Ile Ser Asp Lys Asp Arg Cys
        195                 200                 205

Pro Gln Cys Lys Gly Asp Lys Val Val Gln Glu Lys Val Leu Glu
    210                 215                 220

Val Phe Val Glu Lys Gly Met Gln Asn Gly Gln Lys Ile Thr Phe Pro
225                 230                 235                 240

Gly Glu Ala Asp Glu Ala Pro Asp Thr Val Thr Gly Asp Ile Ile Phe
                245                 250                 255
```

```
Val Leu Gln Gln Lys Glu His Pro Lys Phe Lys Arg Lys Gly Asp Asp
            260                 265                 270

Leu Phe Tyr Glu His Thr Leu Thr Leu Thr Glu Ser Leu Cys Gly Phe
            275                 280                 285

Gln Phe Val Thr His Leu Asp Asn Arg Gln Leu Leu Ile Lys Ser
            290                 295                 300

Asn Pro Gly Glu Val Val Lys Pro Asp Ser Phe Lys Ala Ile Asn Asp
305                 310                 315                 320

Glu Gly Met Pro Met Tyr Gln Arg Pro Phe Met Lys Gly Lys Leu Tyr
                325                 330                 335

Ile His Phe Ser Val Glu Phe Pro Asp Ser Leu Ser Pro Glu Gln Cys
            340                 345                 350

Lys Ala Leu Glu Ala Val Leu Pro Lys Pro Val Ser Gln Tyr Thr
            355                 360                 365

Asp Met Glu Leu Asp Glu Cys Glu Thr Met Pro Tyr Asp Val Asn
370                 375                 380

Ile Glu Ala Glu Met Arg Arg Gln Gln Gln His Gln Glu Ala Tyr
385                 390                 395                 400

Asp Glu Asp Glu Asp Met Pro Gly Gly Ala Gln Arg Val Gln Cys Ala
                405                 410                 415

Gln Gln

<210> SEQ ID NO 13
<211> LENGTH: 1269
<212> TYPE: DNA
<213> ORGANISM: Zea mays

<400> SEQUENCE: 13
atgtttggac gcatgccaag gaagagtagt aacaatacca agtattacga ggttcttggt      60
gtgtctaaga ccgcaagtca ggatgagctt aagaaagcat acagaaaagc tgccataaaa     120
aaccatcctg ataagggtgg agaccctgag aagtttaaag agctgtctca agcttatgat     180
gttcttagtg acccggagaa gagggagatc tatgaccagt atggagaaga tgcccttaag     240
gaaggaatgg gaggaggcag cagcagtgat ttccatagcc ctttcgacat ttttgagcaa     300 cttttttccgg gttctagcac ctttgggggt ggtagctcaa gaggacgcag acaaaagcgt     360
ggtgaagatg tggtgcatac tatgaaggtt tccttagacg atctgtacaa tgggacaacc     420
aagaaactat cttatcgcg gagtgctttg tgctccaagt gcaaggggaa aggatccaag     480 agtgggcat caggaacatg ccatggttgt cgtggtgctg aatgagaac aatcacaaga     540 cagataggcc ttggcatgat ccaacagatg aacactgttt gccctgaatg caaaggatca     600
ggtgagatca taagtgacaa ggacaaatgc ccaagctgta aaggaaacaa ggtagtccag     660
gagaagaagg tgttagaggt tcatgtggag aaaggaatgc aacataacca aaagattgta     720
ttccagggtc aagctgatga agctcctgat acggttacag agacattgt ttttgtcttg     780 caacttaaag accatccaaa atttaagagg atgtacgatg acttatatgt tgagcacaca     840
atctctctca ccgaagcatt gtgtggcttc agtttgttc ttactcatct tgatgggcga     900
cagcttctga tcaaatctga ccccggggag gttattaaac aggtcaaca caaggccatt     960 aacgatgaag gtatgcctca gcatggccgt cctttcatga agggccgtct gtttgttgaa    1020
ttcaacgtgg tgtttcccga gcctggtgcg ctctccctg cccagtgccg atcgttggag    1080
aagatccttc cgccgaaacc agggagccaa ctgtcggaca tggagctgga ccagtgcgag    1140
```

-continued

```
gagaccaccc ttcacgatgt caacattgaa gaggagatga ggcgcaggca gcagcagaag   1200
aagcaggaag cctacgatga agacgaggag gaggatgctc aaccaagggt gcaatgtgcc   1260
cagcagtaa                                                          1269
```

<210> SEQ ID NO 14
<211> LENGTH: 422
<212> TYPE: PRT
<213> ORGANISM: Zea mays

<400> SEQUENCE: 14

```
Met Phe Gly Arg Met Pro Arg Lys Ser Ser Asn Asn Thr Lys Tyr Tyr
1               5                   10                  15

Glu Val Leu Gly Val Ser Lys Thr Ala Ser Gln Asp Glu Leu Lys Lys
            20                  25                  30

Ala Tyr Arg Lys Ala Ala Ile Lys Asn His Pro Asp Lys Gly Gly Asp
        35                  40                  45

Pro Glu Lys Phe Lys Glu Leu Ser Gln Ala Tyr Asp Val Leu Ser Asp
    50                  55                  60

Pro Glu Lys Arg Glu Ile Tyr Asp Gln Tyr Gly Glu Asp Ala Leu Lys
65                  70                  75                  80

Glu Gly Met Gly Gly Ser Ser Asp Phe His Ser Pro Phe Asp
                85                  90                  95

Ile Phe Glu Gln Leu Phe Pro Gly Ser Ser Thr Phe Gly Gly Gly Ser
            100                 105                 110

Ser Arg Gly Arg Arg Gln Lys Arg Gly Glu Asp Val Val His Thr Met
        115                 120                 125

Lys Val Ser Leu Asp Asp Leu Tyr Asn Gly Thr Thr Lys Lys Leu Ser
    130                 135                 140

Leu Ser Arg Ser Ala Leu Cys Ser Lys Cys Lys Gly Lys Gly Ser Lys
145                 150                 155                 160

Ser Gly Ala Ser Gly Thr Cys His Gly Cys Arg Gly Ala Gly Met Arg
                165                 170                 175

Thr Ile Thr Arg Gln Ile Gly Leu Gly Met Ile Gln Gln Met Asn Thr
            180                 185                 190

Val Cys Pro Glu Cys Lys Gly Ser Gly Glu Ile Ile Ser Asp Lys Asp
        195                 200                 205

Lys Cys Pro Ser Cys Lys Gly Asn Lys Val Val Gln Glu Lys Lys Val
    210                 215                 220

Leu Glu Val His Val Glu Lys Gly Met Gln His Asn Gln Lys Ile Val
225                 230                 235                 240

Phe Gln Gly Gln Ala Asp Glu Ala Pro Asp Thr Val Thr Gly Asp Ile
                245                 250                 255

Val Phe Val Leu Gln Leu Lys Asp His Pro Lys Phe Lys Arg Met Tyr
            260                 265                 270

Asp Asp Leu Tyr Val Glu His Thr Ile Ser Leu Thr Glu Ala Leu Cys
        275                 280                 285

Gly Phe Gln Phe Val Leu Thr His Leu Asp Gly Arg Gln Leu Leu Ile
    290                 295                 300

Lys Ser Asp Pro Gly Glu Val Ile Lys Pro Gly Gln His Lys Ala Ile
305                 310                 315                 320

Asn Asp Glu Gly Met Pro Gln His Gly Arg Pro Phe Met Lys Gly Arg
                325                 330                 335

Leu Phe Val Glu Phe Asn Val Val Phe Pro Glu Pro Gly Ala Leu Ser
            340                 345                 350
```

```
Pro Ala Gln Cys Arg Ser Leu Glu Lys Ile Leu Pro Pro Lys Pro Gly
        355                 360                 365

Ser Gln Leu Ser Asp Met Glu Leu Asp Gln Cys Glu Glu Thr Thr Leu
    370                 375                 380

His Asp Val Asn Ile Glu Glu Met Arg Arg Gln Gln Gln Lys
385                 390                 395                 400

Lys Gln Glu Ala Tyr Asp Glu Asp Glu Glu Asp Ala Gln Pro Arg
                405                 410                 415

Val Gln Cys Ala Gln Gln
            420

<210> SEQ ID NO 15
<211> LENGTH: 1266
<212> TYPE: DNA
<213> ORGANISM: Triticum aestivum

<400> SEQUENCE: 15
atgttcgggc gcgggccgcc gaagaagagc gacagcacgc gctactacga gatcctgggc    60
gtgcccaagg acgcgtccca ggacgacctc aagaaggcct accgcaaggc cgccatcaag   120
aaccaccccg acaagggagg cgacccagag aagttcaagg agctagctca ggcttatgag   180
gttctgagtg atcctgagaa gcgagagatc tatgaccagt atggtgagga tgccctcaag   240
gagggaatgg gaggtggagg aatgcatgat cctttgaca tcttccagtc attctttggt    300
ggtggcggca acccccttcgg aggtggcggg agcagtaggg gcaggcggca gcgcaggggt   360
gaggatgtgg ttcatcctct gaaggttagc cttgaggaac tgtacaacgg aacatcaaag   420
aagctctctc ttgcccgcaa tgtgctctgc tcgaagtgca atggcaaggg gtcaaagtcc   480
ggggcttcga tgaagtgtgc cggctgccaa ggtgctggtt acaaggtgca gataaggcag   540
ctgggaccag gaatgattca gcaaatgcag cagccttgca atgagtgcag gggaagtggg   600
gagaccatca gcgacaagga tcgctgtggg cagtgcaaag gcgagaaggt ggtgcacgag   660
aagaaagtcc tggaggtggt ggtcgagaag ggaatgcagc atgggcagaa gatcaccttc   720
cccggcgagg cggatgaagc gcctgatact gttactggag acataatctt cgtcctccag   780
cagaaggagc accccaaatt caagcggaag ggcgatgacc tcttctacga gcacaccctg   840
accctgaccg aggcactgtg tggcttccag tatgtcctgg ctcatttgga cggcaggcag   900
ctgctcatca gtccaacccc tggcgaagtc gtcaagcctg attcgttcaa ggcgatcaac   960
gacgagggca tgcccatgta ccagaggccg ttcatgaagg gcaagctgta catccacttc  1020
acggttgatt ttcccgactc gctgagcctg gaccagtgca aggcgctcga gactgtcctg  1080
ccgcccaagc cggcgtcgca gtacacggac atggagctgg acgagtgcga ggagacgatg  1140
gcctacgaca ttgacatcga ggaggagatg cggaggcgac agcagcagca ggcacaggag  1200
gcctacgacg aggacgagga catgcccggt ggcggcggcc agcgggtgca gtgcgcccag  1260
cagtag                                                             1266

<210> SEQ ID NO 16
<211> LENGTH: 421
<212> TYPE: PRT
<213> ORGANISM: Triticum aestivum

<400> SEQUENCE: 16

Met Phe Gly Arg Gly Pro Pro Lys Lys Ser Asp Ser Thr Arg Tyr Tyr
1               5                   10                  15
```

```
Glu Ile Leu Gly Val Pro Lys Asp Ala Ser Gln Asp Leu Lys Lys
         20                  25                  30

Ala Tyr Arg Lys Ala Ala Ile Lys Asn His Pro Asp Lys Gly Gly Asp
         35                  40                  45

Pro Glu Lys Phe Lys Glu Leu Ala Gln Ala Tyr Glu Val Leu Ser Asp
 50                  55                  60

Pro Glu Lys Arg Glu Ile Tyr Asp Gln Tyr Gly Glu Asp Ala Leu Lys
65                   70                  75                  80

Glu Gly Met Gly Gly Gly Met His Asp Pro Phe Asp Ile Phe Gln
             85                  90                  95

Ser Phe Phe Gly Gly Gly Asn Pro Phe Gly Gly Gly Ser Ser
             100                 105                 110

Arg Gly Arg Arg Gln Arg Gly Glu Asp Val Val His Pro Leu Lys
         115                 120                 125

Val Ser Leu Glu Glu Leu Tyr Asn Gly Thr Ser Lys Lys Leu Ser Leu
    130                 135                 140

Ala Arg Asn Val Leu Cys Ser Lys Cys Asn Gly Lys Gly Ser Lys Ser
145                 150                 155                 160

Gly Ala Ser Met Lys Cys Ala Gly Cys Gln Gly Ala Gly Tyr Lys Val
             165                 170                 175

Gln Ile Arg Gln Leu Gly Pro Gly Met Ile Gln Gln Met Gln Gln Pro
         180                 185                 190

Cys Asn Glu Cys Arg Gly Ser Gly Glu Thr Ile Ser Asp Lys Asp Arg
         195                 200                 205

Cys Gly Gln Cys Lys Gly Glu Lys Val Val His Glu Lys Lys Val Leu
    210                 215                 220

Glu Val Val Glu Lys Gly Met Gln His Gly Gln Lys Ile Thr Phe
225                 230                 235                 240

Pro Gly Glu Ala Asp Glu Ala Pro Asp Thr Val Thr Gly Asp Ile Ile
             245                 250                 255

Phe Val Leu Gln Gln Lys Glu His Pro Lys Phe Lys Arg Lys Gly Asp
         260                 265                 270

Asp Leu Phe Tyr Glu His Thr Leu Thr Leu Thr Glu Ala Leu Cys Gly
         275                 280                 285

Phe Gln Tyr Val Leu Ala His Leu Asp Gly Arg Gln Leu Leu Ile Lys
         290                 295                 300

Ser Asn Pro Gly Glu Val Val Lys Pro Asp Ser Phe Lys Ala Ile Asn
305                 310                 315                 320

Asp Glu Gly Met Pro Met Tyr Gln Arg Pro Phe Met Lys Gly Lys Leu
             325                 330                 335

Tyr Ile His Phe Thr Val Asp Phe Pro Asp Ser Leu Ser Leu Asp Gln
             340                 345                 350

Cys Lys Ala Leu Glu Thr Val Leu Pro Pro Lys Pro Ala Ser Gln Tyr
         355                 360                 365

Thr Asp Met Glu Leu Asp Glu Cys Glu Glu Thr Met Ala Tyr Asp Ile
    370                 375                 380

Asp Ile Glu Glu Glu Met Arg Arg Arg Gln Gln Gln Ala Gln Glu
385                 390                 395                 400

Ala Tyr Asp Glu Asp Glu Asp Met Pro Gly Gly Gly Gln Arg Val
             405                 410                 415

Gln Cys Ala Gln Gln
             420
```

<210> SEQ ID NO 17
<211> LENGTH: 1260
<212> TYPE: DNA
<213> ORGANISM: Arabidopsis thaliana

<400> SEQUENCE: 17

```
atgtttggaa gaggaccttc aaggaagagc gataacacaa agttctacga gatccttggt      60
gttcctaaga ccgcagcacc agaagatctc aagaaagctt ataagaaagc cgctatcaaa     120
aaccatcctg ataagggtgg tgatcccgaa aagtttaaag agttagcaca ggcttatgaa     180
gttttaagtg atcctgagaa gcgtgagatc tatgatcaat atggggaaga tgcactcaag     240
gaaggaatgg gtggtggagg tggtggacac gatccatttg atatcttctc ttccttcttt     300
ggtagtggtg gacacccatt cggaagtcat agccggggaa ggaggcagag gcgtggtgaa     360
gatgttgttc atcccttgaa ggtttcctta gaggatgttt atctcggaac aacaaagaag     420
ctctcacttt ctaggaaggc tttgtgctca agtgtaacg gcaagggttc aaagtctgga     480
gcttcactga atgtggtgg ctgtcaaggc tcgggaatga agatctcgat caggcagttt     540
ggacctggaa tgatgcagca ggtgcagcat gcttgtaatg attccaaagg cacaggagag     600
accatcaatg atcgggacag gtgtccacaa tgcaaaggag agaaggttgt ctctgagaag     660
aaggtgcttg aagtaaatgt ggagaaggga atgcaacaca tcagaagat cacattcagt     720
ggacaagccg atgaagcgcc tgatactgtc accggagata tagtgtttgt cattcagcag     780
aaggagcacc caaagttcaa agaaaggg gaggatctct tgtggagca caccatctct     840
ctaaccgagg ccttgtgtgg cttccagttt gtcttgaccc atttggacaa agacagctt     900
ctcatcaaat ccaagcccgg agaggtcgtc aaacctgatt catacaaggc gataagtgat     960
gagggaatgc caatatacca agtccgttc atgaagggta gctatacat tcacttcacg    1020
gttgaattcc cggaatcgct gagcccggat cagacaaagg ccattgaagc agttttgcca    1080
aagccaacca aggcagctat aagcgatatg gaaatagacg actgcgaaga gacgactctg    1140
catgatgtga acattgagga tgagatgaaa aggaaggcgc aagctcaaag agaggcttat    1200
gatgtcgatg aggaagatca cccaggcggt gctcaccgtg tgcaatgtgc ccagcagtga    1260
```

<210> SEQ ID NO 18
<211> LENGTH: 419
<212> TYPE: PRT
<213> ORGANISM: Arabidopsis thaliana

<400> SEQUENCE: 18

Met Phe Gly Arg Gly Pro Ser Arg Lys Ser Asp Asn Thr Lys Phe Tyr
1               5                   10                  15

Glu Ile Leu Gly Val Pro Lys Thr Ala Ala Pro Glu Asp Leu Lys Lys
            20                  25                  30

Ala Tyr Lys Lys Ala Ala Ile Lys Asn His Pro Asp Lys Gly Gly Asp
        35                  40                  45

Pro Glu Lys Phe Lys Glu Leu Ala Gln Ala Tyr Glu Val Leu Ser Asp
    50                  55                  60

Pro Glu Lys Arg Glu Ile Tyr Asp Gln Tyr Gly Glu Asp Ala Leu Lys
65                  70                  75                  80

Glu Gly Met Gly Gly Gly Gly Gly His Asp Pro Phe Asp Ile Phe
            85                  90                  95

Ser Ser Phe Phe Gly Ser Gly Gly His Pro Phe Gly Ser His Ser Arg
            100                 105                 110

Gly Arg Arg Gln Arg Arg Gly Glu Asp Val Val His Pro Leu Lys Val

-continued

```
            115                 120                 125
Ser Leu Glu Asp Val Tyr Leu Gly Thr Thr Lys Lys Leu Ser Leu Ser
    130                 135                 140

Arg Lys Ala Leu Cys Ser Lys Cys Asn Gly Lys Gly Ser Lys Ser Gly
145                 150                 155                 160

Ala Ser Met Lys Cys Gly Gly Cys Gln Gly Ser Gly Met Lys Ile Ser
                165                 170                 175

Ile Arg Gln Phe Gly Pro Gly Met Met Gln Gln Val Gln His Ala Cys
            180                 185                 190

Asn Asp Cys Lys Gly Thr Gly Glu Thr Ile Asn Asp Arg Asp Arg Cys
        195                 200                 205

Pro Gln Cys Lys Gly Glu Lys Val Val Ser Glu Lys Val Leu Glu
    210                 215                 220

Val Asn Val Glu Lys Gly Met Gln His Asn Gln Lys Ile Thr Phe Ser
225                 230                 235                 240

Gly Gln Ala Asp Glu Ala Pro Asp Thr Val Thr Gly Asp Ile Val Phe
                245                 250                 255

Val Ile Gln Gln Lys Glu His Pro Lys Phe Lys Arg Lys Gly Glu Asp
            260                 265                 270

Leu Phe Val Glu His Thr Ile Ser Leu Thr Glu Ala Leu Cys Gly Phe
        275                 280                 285

Gln Phe Val Leu Thr His Leu Asp Lys Arg Gln Leu Leu Ile Lys Ser
    290                 295                 300

Lys Pro Gly Glu Val Val Lys Pro Asp Ser Tyr Lys Ala Ile Ser Asp
305                 310                 315                 320

Glu Gly Met Pro Ile Tyr Gln Arg Pro Phe Met Lys Gly Lys Leu Tyr
                325                 330                 335

Ile His Phe Thr Val Glu Phe Pro Glu Ser Leu Ser Pro Asp Gln Thr
            340                 345                 350

Lys Ala Ile Glu Ala Val Leu Pro Lys Pro Thr Lys Ala Ala Ile Ser
        355                 360                 365

Asp Met Glu Ile Asp Asp Cys Glu Glu Thr Thr Leu His Asp Val Asn
    370                 375                 380

Ile Glu Asp Glu Met Lys Arg Lys Ala Gln Ala Gln Arg Glu Ala Tyr
385                 390                 395                 400

Asp Asp Asp Glu Glu Asp His Pro Gly Gly Ala Gln Arg Val Gln Cys
                405                 410                 415

Ala Gln Gln

<210> SEQ ID NO 19
<211> LENGTH: 1263
<212> TYPE: DNA
<213> ORGANISM: Arabidopsis thaliana

<400> SEQUENCE: 19
atgttcggta gaggaccctc gaagaagagc gacaacacta agttctacga gatcttaggt      60
gttcctaaga gcgcttcacc agaagatctc aagaaagctt acaaaaaagc cgctatcaag     120
aatcatcctg ataagggtgg agatcccgag aaggtgaata atttcttaga tccgtatgaa     180
gtgcttagtg acccggagaa gcgtgagatt tatgaccagt atggagagga tgcactcaag     240
gaaggaatgg gtggtggagg aggtggacat gatccatttg atatttttctc atccttcttt     300 ggtggaggcc ccttttggagg tgagtctcct tggacactgt ggcagaggcg tggtgaggat     360
gttgttcatc ccttgaaggt atctcttgag gatgtgtacc ttggtacaat gaagaagctt     420
```

```
tcactttcta ggaatgctct ctgctctaag tgtaacgggt tagtacattc gactcgatcc      480
tccttgaaat gtggagggtg tcagggatct ggtatgaagg tgtctattag gcagcttgga      540
cctggaatga tccagcagat gcagcatgca tgtaatgaat gcaaagggac aggtgagacc      600
atcaatgatc gggacaggtg tccacaatgc aaaggagaca aggtcattcc tgagaagaag      660
gtgcttgaag tgaatgtgga aagggaatg caacacagtc agaagatcac atttgaagga       720
caagcagatg aagcggtatc tactctcata catttaatag tgtttgtcct tcagcagaaa      780
gagcacccaa agttcaagag aaaggggaaa gacctctttg tggagcacac actttctcta      840
accgaagctt tgtgtggctt ccaatttgtt ctgactcact tggatggcag aagtcttctc      900
attaaatcta atcctgggga ggtcgtgaaa cctggtacgt attcagatgc atcgtatgaa      960
ggaatgccga tataccagag gccattcatg aagggtaagc tctacatcca cttcacagtg     1020
gagttcccgg actcgttgag cccagatcag accaaagcac tggaagctgt tctacctaag     1080
ccgtcaacag ctcagttgag tgacatggag atagatgaat gcgaggagac cacgctccac     1140
gatgtcaaca ttgaggatga gatgaggagg aaggcacaag ctcaaagaga ggcttatgat     1200
gatgacgatg aagatgatga ccatccgggt ggtgctcaaa gggtgcaatg tgcccagcag     1260
taa                                                                   1263
```

```
<210> SEQ ID NO 20
<211> LENGTH: 420
<212> TYPE: PRT
<213> ORGANISM: Arabidopsis thaliana

<400> SEQUENCE: 20
```

Met Phe Gly Arg Gly Pro Ser Lys Lys Ser Asp Asn Thr Lys Phe Tyr
1               5                   10                  15

Glu Ile Leu Gly Val Pro Lys Ser Ala Ser Pro Glu Asp Leu Lys Lys
            20                  25                  30

Ala Tyr Lys Lys Ala Ala Ile Lys Asn His Pro Asp Lys Gly Gly Asp
        35                  40                  45

Pro Glu Lys Phe Lys Glu Leu Ala Gln Ala Tyr Glu Val Leu Ser Asp
    50                  55                  60

Pro Glu Lys Arg Glu Ile Tyr Asp Gln Tyr Gly Glu Asp Ala Leu Lys
65                  70                  75                  80

Glu Gly Met Gly Gly Gly Gly Gly His Asp Pro Phe Asp Ile Phe
                85                  90                  95

Ser Ser Phe Phe Gly Gly Gly Pro Phe Gly Gly Asn Thr Ser Arg Gln
            100                 105                 110

Arg Arg Gln Arg Arg Gly Glu Asp Val Val His Pro Leu Lys Val Ser
        115                 120                 125

Leu Glu Asp Val Tyr Leu Gly Thr Met Lys Lys Leu Ser Leu Ser Arg
    130                 135                 140

Asn Ala Leu Cys Ser Lys Cys Asn Gly Lys Gly Ser Lys Ser Gly Ala
145                 150                 155                 160

Ser Leu Lys Cys Gly Gly Cys Gln Gly Ser Gly Met Lys Val Ser Ile
                165                 170                 175

Arg Gln Leu Gly Pro Gly Met Ile Gln Gln Met Gln His Ala Cys Asn
            180                 185                 190

Glu Cys Lys Gly Thr Gly Glu Thr Ile Asn Asp Arg Asp Arg Cys Pro
        195                 200                 205

Gln Cys Lys Gly Asp Lys Val Ile Pro Glu Lys Lys Val Leu Glu Val

-continued

```
        210                 215                 220
Asn Val Glu Lys Gly Met Gln His Ser Gln Lys Ile Thr Phe Glu Gly
225                 230                 235                 240

Gln Ala Asp Glu Ala Pro Asp Thr Val Thr Gly Asp Ile Val Phe Val
                245                 250                 255

Leu Gln Gln Lys Glu His Pro Lys Phe Lys Arg Lys Gly Glu Asp Leu
            260                 265                 270

Phe Val Glu His Thr Leu Ser Leu Thr Glu Ala Leu Cys Gly Phe Gln
        275                 280                 285

Phe Val Leu Thr His Leu Asp Gly Arg Ser Leu Leu Ile Lys Ser Asn
    290                 295                 300

Pro Gly Glu Val Val Lys Pro Asp Ser Tyr Lys Ala Ile Ser Asp Glu
305                 310                 315                 320

Gly Met Pro Ile Tyr Gln Arg Pro Phe Met Lys Gly Lys Leu Tyr Ile
                325                 330                 335

His Phe Thr Val Glu Phe Pro Asp Ser Leu Ser Pro Asp Gln Thr Lys
            340                 345                 350

Ala Leu Glu Ala Val Leu Pro Lys Pro Ser Thr Ala Gln Leu Ser Asp
        355                 360                 365

Met Glu Ile Asp Glu Cys Glu Glu Thr Thr Leu His Asp Val Asn Ile
    370                 375                 380

Glu Asp Glu Met Arg Arg Lys Ala Gln Ala Gln Arg Glu Ala Tyr Asp
385                 390                 395                 400

Asp Asp Asp Glu Asp Asp Asp His Pro Gly Gly Ala Gln Arg Val Gln
                405                 410                 415

Cys Ala Gln Gln
            420
```

<210> SEQ ID NO 21
<211> LENGTH: 1254
<212> TYPE: DNA
<213> ORGANISM: Atriplex nummularia

<400> SEQUENCE: 21

```
atgtttggaa gagcaccaaa gaagagtgat agcaccagat attacgagat cttaggcgta      60
ccaaaagatg catctcctga agatttgaag aaggcttata aaaaagctgc cattaaaaat     120
catcctgaca agggaggtga tcccgagaag tttaaagagc tagctcatgc ttatgaggtc     180
ctcagtgatc ccgaaaagcg tgagatctat gatcaatatg gtgaggatgc acttaaggaa     240
ggaatgggtg gaggtggcgg tatgcatgat ccattcgaca tcttccaatc cttctttgga     300
ggaagtccat tggtggtgt tggttctagc cgaggaagaa ggcaaaggcg gggagaagat     360
gtagttcatc ctcttaaggt ttcactcgag gatctcttta ccggtacaac aaagaagctc     420
tcactctctc gcaatgtaat tgttcaaag tgtactggca aggatcaaa atcgggagct     480
tctatgaagt gttctggatg tcaaggtact ggtatgaagg tttctatcag acatctggga     540
ccctcaatga tccagcagat gcagcaccct tgtaatgaat gcaaaggaac tggagagacg     600
attaatgaca agatcgttg ccctcagtgc aaaggtgaga aggttgtgca ggagaagaag     660
gtcttagagg ttgttgtgga agggcatg caacatggac agaaaattac tttccctgga     720
gaggctgatg aagctcctga tactgtcact ggagatatag tctttgtcct gcagcagaaa     780
gagcaccta agttcaagag aaagggtgaa gatctcttct acgagcacac tctaagcctg     840
actgaagctc tttgcggctt tagatttgtg ctgactcacc ttgatggaag gcaacttctt     900
```

-continued

```
atcaaatcaa acctgggaga agttgtcaag cctgatcaat tcaaggcaat tgaggatgag    960
ggtatgccta taccaaaag gccgttcatg aagggcaaga tgtacatcca tttcacagtg   1020
gagttccccg attcgttaaa ccctgatcaa gttaaatcct tggaagcgat ccttcctcct   1080
aagccatcaa tgtctctcac atacatggag ttagatgaat gtgaagagac aacactgcat   1140
aatgtcaaca ttgaagaaga gatgaaaagg aagcagacac aagcacagca ggaggcatac   1200
gatgaagatg acgaacctgc cggtggtcag agggtccaat gtgctcaaca gtga         1254
```

<210> SEQ ID NO 22
<211> LENGTH: 417
<212> TYPE: PRT
<213> ORGANISM: Atriplex nummularia

<400> SEQUENCE: 22

```
Met Phe Gly Arg Ala Pro Lys Lys Ser Asp Ser Thr Arg Tyr Tyr Glu
1               5                   10                  15

Ile Leu Gly Val Pro Lys Asp Ala Ser Pro Glu Asp Leu Lys Lys Ala
            20                  25                  30

Tyr Lys Lys Ala Ala Ile Lys Asn His Pro Asp Lys Gly Gly Asp Pro
        35                  40                  45

Glu Lys Phe Lys Glu Leu Ala His Ala Tyr Glu Val Leu Ser Asp Pro
    50                  55                  60

Glu Lys Arg Glu Ile Tyr Asp Gln Tyr Gly Glu Asp Ala Leu Lys Glu
65                  70                  75                  80

Gly Met Gly Gly Gly Gly Met His Asp Pro Phe Asp Ile Phe Gln
                85                  90                  95

Ser Phe Phe Gly Gly Ser Pro Phe Gly Gly Val Gly Ser Ser Arg Gly
            100                 105                 110

Arg Arg Gln Arg Arg Gly Glu Asp Val Val His Pro Leu Lys Val Ser
        115                 120                 125

Leu Glu Asp Leu Phe Thr Gly Thr Thr Lys Lys Leu Ser Leu Ser Arg
    130                 135                 140

Asn Val Ile Cys Ser Lys Cys Thr Gly Lys Gly Ser Lys Ser Gly Ala
145                 150                 155                 160

Ser Met Lys Cys Ser Gly Cys Gln Gly Thr Gly Met Lys Val Ser Ile
                165                 170                 175

Arg His Leu Gly Pro Ser Met Ile Gln Gln Met Gln His Pro Cys Asn
            180                 185                 190

Glu Cys Lys Gly Thr Gly Glu Thr Ile Asn Asp Lys Asp Arg Cys Pro
        195                 200                 205

Gln Cys Lys Gly Glu Lys Val Val Gln Glu Lys Val Leu Glu Val
    210                 215                 220

Val Val Glu Lys Gly Met Gln His Gly Gln Lys Ile Thr Phe Pro Gly
225                 230                 235                 240

Glu Ala Asp Glu Ala Pro Asp Thr Val Thr Gly Asp Ile Val Phe Val
                245                 250                 255

Leu Gln Gln Lys Glu His Pro Lys Phe Lys Arg Lys Gly Glu Asp Leu
            260                 265                 270

Phe Tyr Glu His Thr Leu Ser Leu Thr Glu Ala Leu Cys Gly Phe Arg
        275                 280                 285

Phe Val Leu Thr His Leu Asp Gly Arg Gln Leu Leu Ile Lys Ser Asn
    290                 295                 300

Leu Gly Glu Val Val Lys Pro Asp Gln Phe Lys Ala Ile Glu Asp Glu
305                 310                 315                 320
```

Gly Met Pro Ile Tyr Gln Arg Pro Phe Met Lys Gly Lys Met Tyr Ile
            325                 330                 335

His Phe Thr Val Glu Phe Pro Asp Ser Leu Asn Pro Asp Gln Val Lys
            340                 345                 350

Ser Leu Glu Ala Ile Leu Pro Pro Lys Pro Ser Met Ser Leu Thr Tyr
            355                 360                 365

Met Glu Leu Asp Glu Cys Glu Glu Thr Thr Leu His Asn Val Asn Ile
        370                 375                 380

Glu Glu Glu Met Lys Arg Lys Gln Thr Gln Ala Gln Gln Glu Ala Tyr
385                 390                 395                 400

Asp Glu Asp Asp Glu Pro Ala Gly Gly Gln Arg Val Gln Cys Ala Gln
                405                 410                 415

Gln

<210> SEQ ID NO 23
<211> LENGTH: 1242
<212> TYPE: DNA
<213> ORGANISM: Cucumis sativus

<400> SEQUENCE: 23

```
atgtttggaa ggccgaagaa gagcgataat accaaatatt atgagattct tggagtctcg      60
aagaatgcgt cgcaagacga tctaaagaag gcttatagaa aggccgccat caagaaccat     120
cctgataaag gtggcgaccc tgaaaaattc aaggagttag cacaagccta cgaggtgctg     180
agtgatccag agaaacgtga gatatatgat caatatggcg aggatgccct caaggaagga     240
atgggaggtg gcggtggtca tgatccattt gacatattcc agtctttctt tggtggaagc     300
ccgtttggtg gtggtggaag cagcagaggc cgaaggcaga aaggggaga ggatgttatc      360
catcctctca aggtctcgtt ggaagatctc tacaacggta cttcaagaa gctctctctt      420
tcacgtaatg taatttgctc aaagtgcaag ggtaagggtt ctaaatctgg tgcttcaatg     480
aagtgtcctg gctgtcaagg ttctggtatg aaagtttcca tcagacacct tggcccctct     540
atgattcagc aaatgcagca tccttgcaat gaatgtaaag aactggtga caccatcaat     600
gataaagatc gctgctcaca atgcaagggt gaaaaggttg ttcaggagaa aaagttttg      660
gaagttattg tggagaaggg tatgcaaaat gcacaaaaga ttacattccc tggtgaagca     720
gatgaagcgc ccgacactgt tactggggac attgtctttg tcctacaaca aaaagagcac     780
cccaagttta agagaaaggg cgatgacctc tttgtagagc ataccttgtc tctcgtcgag     840
tctctgtgtg gtttccaatt tattctgact catttggatg ccgacagct actcatcaaa      900
tcacttcccg gtgaagtagt gaagcctgac caattcaagg ccataaacga tgagggtatg     960
cctatgtacc agaggccatt catgaagggc aaactttaca tccacttcag tgttgagttc    1020
ccagactcct tgaaccccga acagtgcaag gcgctggagg gcgttctgcc tccaggacc     1080
tcagtgcagc tctcagatat ggaattggat gaatgtgaag agaccactct ccacgatgtc    1140
aacattgaag aggagatgcg caggaagcaa gcacaagagg catacgatga agatgaggat    1200
atgcacggtg gtgcacagag agtgcagtgt gctcaacaat ga                       1242
```

<210> SEQ ID NO 24
<211> LENGTH: 413
<212> TYPE: PRT
<213> ORGANISM: Cucumis sativus

<400> SEQUENCE: 24

-continued

```
Met Phe Gly Arg Pro Lys Lys Ser Asp Asn Thr Lys Tyr Tyr Glu Ile
1               5                   10                  15

Leu Gly Val Ser Lys Asn Ala Ser Gln Asp Asp Leu Lys Lys Ala Tyr
            20                  25                  30

Arg Lys Ala Ala Ile Lys Asn His Pro Asp Lys Gly Gly Asp Pro Glu
        35                  40                  45

Lys Phe Lys Glu Leu Ala Gln Ala Tyr Glu Val Leu Ser Asp Pro Glu
    50                  55                  60

Lys Arg Glu Ile Tyr Asp Gln Tyr Gly Glu Asp Ala Leu Lys Glu Gly
65                  70                  75                  80

Met Gly Gly Gly Gly His Asp Pro Phe Asp Ile Phe Gln Ser Phe
                85                  90                  95

Phe Gly Gly Ser Pro Phe Gly Gly Gly Ser Ser Arg Gly Arg Arg
            100                 105                 110

Gln Arg Arg Gly Glu Asp Val Ile His Pro Leu Lys Val Ser Leu Glu
        115                 120                 125

Asp Leu Tyr Asn Gly Thr Ser Lys Lys Leu Ser Leu Ser Arg Asn Val
    130                 135                 140

Ile Cys Ser Lys Cys Lys Gly Lys Gly Ser Lys Ser Gly Ala Ser Met
145                 150                 155                 160

Lys Cys Pro Gly Cys Gln Gly Ser Gly Met Lys Val Ser Ile Arg His
            165                 170                 175

Leu Gly Pro Ser Met Ile Gln Gln Met Gln His Pro Cys Asn Glu Cys
        180                 185                 190

Lys Gly Thr Gly Glu Thr Ile Asn Asp Lys Asp Arg Cys Ser Gln Cys
    195                 200                 205

Lys Gly Glu Lys Val Val Gln Glu Lys Lys Val Leu Glu Val Ile Val
210                 215                 220

Glu Lys Gly Met Gln Asn Ala Gln Lys Ile Thr Phe Pro Gly Glu Ala
225                 230                 235                 240

Asp Glu Ala Pro Asp Thr Val Thr Gly Asp Ile Val Phe Val Leu Gln
            245                 250                 255

Gln Lys Glu His Pro Lys Phe Lys Arg Lys Gly Asp Asp Leu Phe Val
        260                 265                 270

Glu His Thr Leu Ser Leu Val Glu Ser Leu Cys Gly Phe Gln Phe Ile
    275                 280                 285

Leu Thr His Leu Asp Gly Arg Gln Leu Leu Ile Lys Ser Leu Pro Gly
290                 295                 300

Glu Val Val Lys Pro Asp Gln Phe Lys Ala Ile Asn Asp Glu Gly Met
305                 310                 315                 320

Pro Met Tyr Gln Arg Pro Phe Met Lys Gly Lys Leu Tyr Ile His Phe
            325                 330                 335

Ser Val Glu Phe Pro Asp Ser Leu Asn Pro Glu Gln Cys Lys Ala Leu
        340                 345                 350

Glu Gly Val Leu Pro Pro Arg Thr Ser Val Gln Leu Ser Asp Met Glu
    355                 360                 365

Leu Asp Glu Cys Glu Glu Thr Thr Leu His Asp Val Asn Ile Glu Glu
370                 375                 380

Glu Met Arg Arg Lys Gln Ala Gln Glu Ala Tyr Asp Glu Asp Glu Asp
385                 390                 395                 400

Met His Gly Gly Ala Gln Arg Val Gln Cys Ala Gln Gln
            405                 410
```

<210> SEQ ID NO 25
<211> LENGTH: 1257
<212> TYPE: DNA
<213> ORGANISM: Daucus carota

<400> SEQUENCE: 25

```
atgtttggga gcaccaaa gaagagtgac aatacaaagt actatgaaat tcttggtgtc        60
ccaaaaacag catcacctga tgatctgaag aaagcttaca ggaaggctgc tatcaagaat     120
catcctgata agggtggcga tcctgaaaag tttaagagc ttgcgcaagc atatgaggtt      180
ctgagtgacc cagagaagcg tgaaatctat gatcagtatg gagaggatgc tctcaaggag     240
ggaatgggtg gtggtggagg tggtggccat gacccatttg acattttcca atccttcttt     300
ggtggcagcc cgtttggtgg aggtggcagc agcagaggac gaaggcaaag aagggggggag   360
gatgtcattc atccccttaa ggtttcactg gaagatcttt gcaatgggac ttccaagaag    420
ctttccctt cacgtaatgt aatttgttct aaatgcaagg gaaaggggtc caagtcgggt    480
gcttcaatga catgtcctgg ctgccagggt tctggaatga aggtttctat caggcacttg    540
ggcccatcta tgatccagca gatgcagcat ccctgcaatg actgcaaggg tactggagaa    600
acaatcaacg acaaggatcg ctgccctcaa tgcaaaggtc aaaaggttgt gcaggagaag    660
aaagcaatag aagttattgt ggagaagggt atgcaaaacg gacagaagat tacattccct    720
ggagaagctg atgaagcgcc tgacacggtt actggggaca tagtgtttgt gttgcaacaa    780
aaggagcacc ccaagtttaa gaggaagggt gatgatcttt tgttgaaca ttcattaact     840
ctcagtgaag cactttgtgg cttccaattt actttgactc acctggacgg caggcagctt    900
cttattaaat cccagccagg agaagttatc aagccagatc aatttaaggg gataaatgat    960
gaaggaatgc caatgtatca gaggccattt atgcgaggaa agctttacat tcactttagt   1020
gtagatttcc cagagtcctt gaccctgag cagtgcaaag ctcttgaagc tgtgttacct     1080
ccgaggcctt caattcagat gacagacatg gaactggatg aatgtgaaga aacaacactg   1140
catgatgtga atattgaaga ggagatgcgt cggaaacagc aagctgccca gaggcatat    1200
gacgaagacg aagatatgca tggcggtgct cagagggtgc agtgtgctca acaatga      1257
```

<210> SEQ ID NO 26
<211> LENGTH: 418
<212> TYPE: PRT
<213> ORGANISM: Daucus carota

<400> SEQUENCE: 26

```
Met Phe Gly Arg Ala Pro Lys Lys Ser Asp Asn Thr Lys Tyr Tyr Glu
1               5                   10                  15

Ile Leu Gly Val Pro Lys Thr Ala Ser Pro Asp Asp Leu Lys Lys Ala
            20                  25                  30

Tyr Arg Lys Ala Ala Ile Lys Asn His Pro Asp Lys Gly Gly Asp Pro
        35                  40                  45

Glu Lys Phe Lys Glu Leu Ala Gln Ala Tyr Glu Val Leu Ser Asp Pro
    50                  55                  60

Glu Lys Arg Glu Ile Tyr Asp Gln Tyr Gly Glu Asp Ala Leu Lys Glu
65                  70                  75                  80

Gly Met Gly Gly Gly Gly Gly Gly His Asp Pro Phe Asp Ile Phe
                85                  90                  95

Gln Ser Phe Phe Gly Gly Ser Pro Phe Gly Gly Gly Ser Ser Arg
            100                 105                 110

Gly Arg Arg Gln Arg Arg Gly Glu Asp Val Ile His Pro Leu Lys Val
```

-continued

```
                  115                 120                 125
Ser Leu Glu Asp Leu Cys Asn Gly Thr Ser Lys Lys Leu Ser Leu Ser
    130                 135                 140

Arg Asn Val Ile Cys Ser Lys Cys Lys Gly Lys Gly Ser Lys Ser Gly
145                 150                 155                 160

Ala Ser Met Thr Cys Pro Gly Cys Gln Gly Ser Gly Met Lys Val Ser
                165                 170                 175

Ile Arg His Leu Gly Pro Ser Met Ile Gln Gln Met Gln His Pro Cys
            180                 185                 190

Asn Asp Cys Lys Gly Thr Gly Glu Thr Ile Asn Asp Lys Asp Arg Cys
        195                 200                 205

Pro Gln Cys Lys Gly Gln Lys Val Val Gln Glu Lys Lys Ala Ile Glu
    210                 215                 220

Val Ile Val Glu Lys Gly Met Gln Asn Gly Gln Lys Ile Thr Phe Pro
225                 230                 235                 240

Gly Glu Ala Asp Glu Ala Pro Asp Thr Val Thr Gly Asp Ile Val Phe
                245                 250                 255

Val Leu Gln Gln Lys Glu His Pro Lys Phe Lys Arg Lys Gly Asp Asp
            260                 265                 270

Leu Phe Val Glu His Ser Leu Thr Leu Ser Glu Ala Leu Cys Gly Phe
        275                 280                 285

Gln Phe Thr Leu Thr His Leu Asp Gly Arg Gln Leu Leu Ile Lys Ser
    290                 295                 300

Gln Pro Gly Glu Val Ile Lys Pro Asp Gln Phe Lys Gly Ile Asn Asp
305                 310                 315                 320

Glu Gly Met Pro Met Tyr Gln Arg Pro Phe Met Arg Gly Lys Leu Tyr
                325                 330                 335

Ile His Phe Ser Val Asp Phe Pro Glu Ser Leu Thr Pro Glu Gln Cys
            340                 345                 350

Lys Ala Leu Glu Ala Val Leu Pro Pro Arg Pro Ser Ile Gln Met Thr
        355                 360                 365

Asp Met Glu Leu Asp Glu Cys Glu Glu Thr Thr Leu His Asp Val Asn
    370                 375                 380

Ile Glu Glu Glu Met Arg Arg Lys Gln Gln Ala Ala Gln Glu Ala Tyr
385                 390                 395                 400

Asp Glu Asp Glu Asp Met His Gly Gly Ala Gln Arg Val Gln Cys Ala
                405                 410                 415

Gln Gln

<210> SEQ ID NO 27
<211> LENGTH: 1254
<212> TYPE: DNA
<213> ORGANISM: Glycine max

<400> SEQUENCE: 27
atgtttggga gggcaccgaa gaagagcgat aatacgaggt actacgaaat cctcggcgtc    60
tccaagaacg cttcgcagga tgatctgaag aaggcttaca agaaagccgc cattaagaat   120
caccccgaca agggcggtga tcccgagaag tttaagagc tggcgcaagc ttatgaggtt    180
ctgagtgacc ctgagaagcg tgagatatat gatcagtatg gtgaagatgc gcttaaggaa   240
ggaatgggtg gtggcggtgg ccatgatcca tttgatatct tttcatcttt ctttggcggt   300
gggagtccct ttgatcagg tgaagtagt cgaggtagga ggcagaggcg cggagaagac    360
gtggttcacc ctctcaaggt ctctttggag gacctttatc ttggaacttc caagaagctc   420
```

```
tccctctcca gaaatgttat atgctccaag tgcagtggca agggttctaa gtctggtgct    480
tcgatgaagt gtgctggttg tcaaggaact ggtatgaagg tttctataag acatcttggc    540
ccatccatga ttcagcagat gcagcatgcc tgcaatgaat gtaagggtac tggagaaact    600
atcaatgaca gagatcgctg cccacagtgc aagggagaga aggttgtgca ggagaagaaa    660
gtccttgaag ttattgtaga aaaggggatg cagaatgggc agaagataac attccctggc    720
gaagctgatg aagcgccgga cacaattact ggggatatcg tctttgtcct tcagcagaag    780
gaacatccca aattcaaaag aaaggctgaa gatcttttg tagagcacac tttgtccctt    840
accgaggcct tgtgtggctt ccaatttgtg ctgactcact tggatagccg tcagcttctt    900
attaaatcaa atcccgggga agttgtgaag cctgattcat acaaggctat aaatgatgag    960
ggaatgccca tgtatcagag gccattcatg aaggggaaac tttacattca cttcactgtg   1020
gagtttccag attctctaaa ccctgatcaa gttaaggcct tggaggctgt tctgccacca   1080
aagccttctt cacaattgac agacatggag ctggatgaat gtgaggaaac tacactccat   1140
gatgtcaaca tggaggagga gactaggagg aagcagcaac aagctcagga ggcatatgat   1200
gaggatgatg acatgcctgg tggtgcacag agggtacagt gcgcccagca gtaa         1254

<210> SEQ ID NO 28
<211> LENGTH: 417
<212> TYPE: PRT
<213> ORGANISM: Glycine max

<400> SEQUENCE: 28

Met Phe Gly Arg Ala Pro Lys Lys Ser Asp Asn Thr Arg Tyr Tyr Glu
1               5                   10                  15

Ile Leu Gly Val Ser Lys Asn Ala Ser Gln Asp Asp Leu Lys Lys Ala
            20                  25                  30

Tyr Lys Lys Ala Ala Ile Lys Asn His Pro Asp Lys Gly Gly Asp Pro
        35                  40                  45

Glu Lys Phe Lys Glu Leu Ala Gln Ala Tyr Glu Val Leu Ser Asp Pro
    50                  55                  60

Glu Lys Arg Glu Ile Tyr Asp Gln Tyr Gly Glu Asp Ala Leu Lys Glu
65                  70                  75                  80

Gly Met Gly Gly Gly Gly His Asp Pro Phe Asp Ile Phe Ser Ser
                85                  90                  95

Phe Phe Gly Gly Gly Ser Pro Phe Gly Ser Gly Gly Ser Ser Arg Gly
            100                 105                 110

Arg Arg Gln Arg Arg Gly Glu Asp Val Val His Pro Leu Lys Val Ser
        115                 120                 125

Leu Glu Asp Leu Tyr Leu Gly Thr Ser Lys Lys Leu Ser Leu Ser Arg
    130                 135                 140

Asn Val Ile Cys Ser Lys Cys Ser Gly Lys Gly Ser Lys Ser Gly Ala
145                 150                 155                 160

Ser Met Lys Cys Ala Gly Cys Gln Gly Thr Gly Met Lys Val Ser Ile
                165                 170                 175

Arg His Leu Gly Pro Ser Met Ile Gln Gln Met Gln His Ala Cys Asn
            180                 185                 190

Glu Cys Lys Gly Thr Gly Glu Thr Ile Asn Asp Arg Asp Arg Cys Pro
        195                 200                 205

Gln Cys Lys Gly Glu Lys Val Val Gln Glu Lys Lys Val Leu Glu Val
    210                 215                 220
```

-continued

```
Ile Val Glu Lys Gly Met Gln Asn Gly Gln Lys Ile Thr Phe Pro Gly
225                 230                 235                 240
Glu Ala Asp Glu Ala Pro Asp Thr Ile Thr Gly Asp Ile Val Phe Val
                245                 250                 255
Leu Gln Gln Lys Glu His Pro Lys Phe Lys Arg Lys Ala Glu Asp Leu
            260                 265                 270
Phe Val Glu His Thr Leu Ser Leu Thr Glu Ala Leu Cys Gly Phe Gln
        275                 280                 285
Phe Val Leu Thr His Leu Asp Ser Arg Gln Leu Leu Ile Lys Ser Asn
    290                 295                 300
Pro Gly Glu Val Val Lys Pro Asp Ser Tyr Lys Ala Ile Asn Asp Glu
305                 310                 315                 320
Gly Met Pro Met Tyr Gln Arg Pro Phe Met Lys Gly Lys Leu Tyr Ile
                325                 330                 335
His Phe Thr Val Glu Phe Pro Asp Ser Leu Asn Pro Asp Gln Val Lys
                340                 345                 350
Ala Leu Glu Ala Val Leu Pro Pro Lys Pro Ser Ser Gln Leu Thr Asp
            355                 360                 365
Met Glu Leu Asp Glu Cys Glu Glu Thr Thr Leu His Asp Val Asn Met
370                 375                 380
Glu Glu Glu Thr Arg Arg Lys Gln Gln Gln Ala Gln Glu Ala Tyr Asp
385                 390                 395                 400
Glu Asp Asp Asp Met Pro Gly Gly Ala Gln Arg Val Gln Cys Ala Gln
                405                 410                 415
Gln

<210> SEQ ID NO 29
<211> LENGTH: 1248
<212> TYPE: DNA
<213> ORGANISM: Hevea brasiliensis

<400> SEQUENCE: 29
atgtttggaa gagcacccaa aaaaagcgat aacaccaagt actatgagat tcttggggtc      60
tcaaagaacg cttcacagga tgatctaaag aaggcttata gaaaagctgc catcaagaac     120
catcctgaca aggtggtgga tcctgaaaag tttaaagagt tggcccaagc ttatgaggtt     180
ttgagtgatc cagagaaacg tgagatatat gatcaatatg gagaggacgc cctcaaggag     240
ggaatgggca gtggaggtgg tgctcatgac ccatttgaca ttttccaatc cttctttggt     300
ggcaacccat tggtggtgg tggtagcagc agaggccgta ggaaggaggg agaggatgtt     360
atccatcctc tcaaggtttc tttggaagat ctctacaatg cacctcaaa gaagctgtct     420
cttttcccgta atgttatctg ctcaaagtgc aaaggtaaag ggtccaaatc aggtgcatca     480
atgaaatgtt cgggttgcca aggttctgga atgaaggtct ccataagaca acttggtccc     540
tctatgatcc agcaaatgca gcatccttgt aatgaatgta aggtactgg tgagaccatt     600
aatgataagg atcgttgccc tcaatgtaaa ggtgaaaagg ttgttcagga agaaagtg      660
ctggaagtta tgttgagaa gggtatgcaa atggacaga ggattacttt ccctggagaa     720
gctgatgaag ctcctgatac tattacaggg acattgttt ttgtccttca gcaaaggag     780
catcctaagt tcaagcgaaa gggtgatgac ctaattgttg atcacacttt atctcttaca     840
gaggcacttt gtgcctccca gtttatatta acccatctag atggagacct cctcataaaa     900
tcccaacctg gggaggtagt gaagcctgat caattcaagg ccataaatga tgaagggatg     960
ccaatgtatc agaggccatt catgaggggg aaactgtaca ttcatttcag tgttgatttc    1020
```

```
ccagactctc tgcccctga tcagtgcaaa gccctagagg cagttcttcc ctcaagaaca   1080
tcagtccagc tgtctgacat ggagctggat gaatgtgagg agacaacttt acacgatgtg   1140
aactttgacg aggagatgcg aaggaagcaa caacaggccc aagaggcata tgatgaagat   1200
gatgatatgc atggtggtgg ccagagggtg caatgtgctc agcaataa              1248
```

<210> SEQ ID NO 30
<211> LENGTH: 415
<212> TYPE: PRT
<213> ORGANISM: Hevea brasiliensis

<400> SEQUENCE: 30

```
Met Phe Gly Arg Ala Pro Lys Lys Ser Asp Asn Thr Lys Tyr Tyr Glu
1               5                   10                  15

Ile Leu Gly Val Ser Lys Asn Ala Ser Gln Asp Asp Leu Lys Lys Ala
            20                  25                  30

Tyr Arg Lys Ala Ala Ile Lys Asn His Pro Asp Lys Gly Gly Asp Pro
        35                  40                  45

Glu Lys Phe Lys Glu Leu Ala Gln Ala Tyr Glu Val Leu Ser Asp Pro
    50                  55                  60

Glu Lys Arg Glu Ile Tyr Asp Gln Tyr Gly Glu Asp Ala Leu Lys Glu
65                  70                  75                  80

Gly Met Gly Ser Gly Gly Ala His Asp Pro Phe Asp Ile Phe Gln
                85                  90                  95

Ser Phe Phe Gly Gly Asn Pro Phe Gly Gly Gly Ser Ser Arg Gly
            100                 105                 110

Arg Arg Lys Glu Gly Glu Asp Val Ile His Pro Leu Lys Val Ser Leu
        115                 120                 125

Glu Asp Leu Tyr Asn Gly Thr Ser Lys Lys Leu Ser Leu Ser Arg Asn
    130                 135                 140

Val Ile Cys Ser Lys Cys Lys Gly Lys Gly Ser Lys Ser Gly Ala Ser
145                 150                 155                 160

Met Lys Cys Ser Gly Cys Gln Gly Ser Gly Met Lys Val Ser Ile Arg
                165                 170                 175

Gln Leu Gly Pro Ser Met Ile Gln Gln Met Gln His Pro Cys Asn Glu
            180                 185                 190

Cys Lys Gly Thr Gly Glu Thr Ile Asn Asp Lys Asp Arg Cys Pro Gln
        195                 200                 205

Cys Lys Gly Glu Lys Val Val Gln Glu Lys Lys Val Leu Glu Val Ile
    210                 215                 220

Val Glu Lys Gly Met Gln Asn Gly Gln Arg Ile Thr Phe Pro Gly Glu
225                 230                 235                 240

Ala Asp Glu Ala Pro Asp Thr Ile Thr Gly Asp Ile Val Phe Val Leu
                245                 250                 255

Gln Gln Lys Glu His Pro Lys Phe Lys Arg Lys Gly Asp Asp Leu Ile
            260                 265                 270

Val Asp His Thr Leu Ser Leu Thr Glu Ala Leu Cys Ala Ser Gln Phe
        275                 280                 285

Ile Leu Thr His Leu Asp Gly Asp Leu Leu Ile Lys Ser Gln Pro Gly
    290                 295                 300

Glu Val Val Lys Pro Asp Gln Phe Lys Ala Ile Asn Asp Glu Gly Met
305                 310                 315                 320

Pro Met Tyr Gln Arg Pro Phe Met Arg Gly Lys Leu Tyr Ile His Phe
                325                 330                 335
```

Ser Val Asp Phe Pro Asp Ser Leu Pro Pro Asp Gln Cys Lys Ala Leu
        340                 345                 350

Glu Ala Val Leu Pro Ser Arg Thr Ser Val Gln Leu Ser Asp Met Glu
        355                 360                 365

Leu Asp Glu Cys Glu Glu Thr Thr Leu His Asp Val Asn Phe Asp Glu
    370                 375                 380

Glu Met Arg Arg Lys Gln Gln Gln Ala Gln Glu Ala Tyr Asp Glu Asp
385                 390                 395                 400

Asp Asp Met His Gly Gly Gly Gln Arg Val Gln Cys Ala Gln Gln
                405                 410                 415

<210> SEQ ID NO 31
<211> LENGTH: 1260
<212> TYPE: DNA
<213> ORGANISM: Lycopersicum esculentum

<400> SEQUENCE: 31
atgtttggaa gagcaccgaa gaagagcgat aatacaaagt attatgagat cttaggagtt      60
cctaaggctg cttctcagga agatctcaaa aaggcttatc gtaaagctgc atcaaaaat     120
caccctgata agggaggcga tcctgagaag tttaaagagc ttgctcaagc ttatgaggtt     180
ctgagtgacc ggagaagcg tgagatatat gatcagtatg agaggatgc tctaaaggaa      240
ggaatgggtg gtggaggtgg tggacatgaa ccatttgata tatttcaatc attcttcggt     300
ggtggtggaa acccctttgg tggtggtgga agcagcagag tccgaagaca gagaaggaga     360
gaggatgtta ccacccgct caaggtttct ttagaggatc tttacaatgg acatcaaag      420
aagcttttcac tatctcgcaa tgtgttgtgc tcaaagtgca agggcaaagg ttccaagtca    480
ggtgcttcaa tgaaatgttc tggctgtcaa gggtctggaa tgaaagtttc tatcagacag     540
ctcggtccat ccatgatcca gcagatgcag caccttgca atgagtgcaa gggtactgga      600
gagacgatca gtgacaaaga taggtgccct cagtgcaagg gtgagaaggt tgtgcaggag     660
aagaaggtgt tggaagttca cgtggagaag ggtatgcaga tgggcaaaa gataacattt      720
ccaggcgagg cagatgaagc gccagatacc atcactggag acattgtttt tgtcttgcaa     780
caaaaggaac atcctaagtt caagcgaaag ggagatgatc tttttgttga gcacacattg     840
agccttgacg agtctctatg tggttttccag tttgttctga ctcacctaga caacagacag     900
ctgctcatta gtcccaacc tggcgaagtt gtcaagcctg atcagtttaa ggctatcaac      960
gatgaaggaa tgccgatgta ccaaaggccg ttcatgaagg gcaaaatgta cattcacttc    1020
actgttgatt cccccgagtc attacacgca gagcagtgca agaaccttga ggctgtgctg    1080
cctcccaaaa ccaaattgca gatatcagat atggaattgg acgagtggga ggagactact    1140
ttgcacgatg tcaacattga ggaggagatg cgaaggaagc agcaagctgc caagaggca    1200
caggacgaag atgacgatat gcctggtggt gcacagagag tccaatgtgc acagcagtaa    1260

<210> SEQ ID NO 32
<211> LENGTH: 419
<212> TYPE: PRT
<213> ORGANISM: Lycopersicum esculentum

<400> SEQUENCE: 32

Met Phe Gly Arg Ala Pro Lys Lys Ser Asp Asn Thr Lys Tyr Tyr Glu
1               5                   10                  15

Ile Leu Gly Val Pro Lys Ala Ala Ser Gln Glu Asp Leu Lys Lys Ala
            20                  25                  30

-continued

```
Tyr Arg Lys Ala Ala Ile Lys Asn His Pro Asp Lys Gly Asp Pro
             35                  40                  45
Glu Lys Phe Lys Glu Leu Ala Gln Ala Tyr Glu Val Leu Ser Asp Pro
 50                  55                  60
Glu Lys Arg Glu Ile Tyr Asp Gln Tyr Gly Glu Asp Ala Leu Lys Glu
 65                  70                  75                  80
Gly Met Gly Gly Gly Gly Gly His Glu Pro Phe Asp Ile Phe Gln
             85                  90                  95
Ser Phe Phe Gly Gly Gly Asn Pro Phe Gly Gly Gly Ser Ser
             100                 105                 110
Arg Val Arg Arg Gln Arg Gly Glu Asp Val Ile His Pro Leu Lys
             115                 120                 125
Val Ser Leu Glu Asp Leu Tyr Asn Gly Thr Ser Lys Lys Leu Ser Leu
     130                 135                 140
Ser Arg Asn Val Leu Cys Ser Lys Cys Lys Gly Lys Gly Ser Lys Ser
145                 150                 155                 160
Gly Ala Ser Met Lys Cys Ser Gly Cys Gln Gly Ser Gly Met Lys Val
                 165                 170                 175
Ser Ile Arg Gln Leu Gly Pro Ser Met Ile Gln Gln Met Gln His Pro
             180                 185                 190
Cys Asn Glu Cys Lys Gly Thr Gly Glu Thr Ile Ser Asp Lys Asp Arg
             195                 200                 205
Cys Pro Gln Cys Lys Gly Glu Lys Val Val Gln Glu Lys Lys Val Leu
     210                 215                 220
Glu Val His Val Glu Lys Gly Met Gln Asn Gly Gln Lys Ile Thr Phe
225                 230                 235                 240
Pro Gly Glu Ala Asp Glu Ala Pro Asp Thr Ile Thr Gly Asp Ile Val
                 245                 250                 255
Phe Val Leu Gln Gln Lys Glu His Pro Lys Phe Lys Arg Lys Gly Asp
             260                 265                 270
Asp Leu Phe Val Glu His Thr Leu Ser Leu Asp Glu Ser Leu Cys Gly
             275                 280                 285
Phe Gln Phe Val Leu Thr His Leu Asp Asn Arg Gln Leu Leu Ile Lys
     290                 295                 300
Ser Gln Pro Gly Glu Val Val Lys Pro Asp Gln Phe Lys Ala Ile Asn
305                 310                 315                 320
Asp Glu Gly Met Pro Met Tyr Gln Arg Pro Phe Met Lys Gly Lys Met
                 325                 330                 335
Tyr Ile His Phe Thr Val Asp Phe Pro Glu Ser Leu His Ala Glu Gln
             340                 345                 350
Cys Lys Asn Leu Glu Ala Val Leu Pro Pro Lys Thr Lys Leu Gln Ile
             355                 360                 365
Ser Asp Met Glu Leu Asp Glu Trp Glu Thr Thr Leu His Asp Val
     370                 375                 380
Asn Ile Glu Glu Glu Met Arg Arg Lys Gln Gln Ala Ala Gln Glu Ala
385                 390                 395                 400
Gln Asp Glu Asp Asp Met Pro Gly Gly Ala Gln Arg Val Gln Cys
                 405                 410                 415
Ala Gln Gln

<210> SEQ ID NO 33
<211> LENGTH: 1272
<212> TYPE: DNA
```

<213> ORGANISM: Medicago sativa

<400> SEQUENCE: 33

```
atgtttgggc gcggaccaac aaggaagagt gataacacca atattacga tattcttggt    60
gtttcaaaaa gtgctagtga agatgaaatc aagaaagcct atagaaaggc agcgatgaag   120
aaccatccag ataagggtgg ggatcctgag aagttcaagg agttgggcca agcatatgaa   180
gtgttgagcg atcctgaaaa gaaagaactg tatgatcaat atggtgaaga tgcccttaaa   240
gaaggaatgg ggggaggcgc aggaagctca tttcataatc cgtttgatat tttcgaatca   300
ttttttggtg caggctttgg tggtggtggt ccttcacgcg caagaagaca gaagcaagga   360
gaagatgtgg tgcattctat aaaggtttcc ttggaggatg tgtataacgg cactacaaag   420
aagctatcac tttctaggaa tgcactgtgc tcaaaatgta aagggaaagg ttcaaaaagt   480
ggaactgctg aaggtgtttt tggatgccag ggcacaggta tgaagattac agaaggcaa    540
attggactgg gcatgattca acaaatgcaa cacgtctgtc ctgactgcaa aggaacaggc   600
gaggtcatta gtgagagaga tagatgccct caatgcaagg aaacaagat tactcaagaa    660
aagaaggtgc tggaggtgca tgtggaaaag gggatgcagc agggtcacaa gattgtattc   720
gaaggacaag ctgatgaact ccctgataca atcacaggag acatagtttt tgtcttgcaa   780
gtaaagggac atccgaagtt tcggagggag cgtgatgacc ttcacattga acacaatttg   840
agcttaactg atgctctctg tggcttccag tttaatgtca cacatcttga tggaaggcaa   900
ctattggtca aatcgaaccc cggcgaagtc atcaagccag tcaacataa agctataaat    960
gatgagggaa tgccacaaca tggtaggccg ttcatgaagg gacgcctata catcaagttt  1020
agtgttgatt cccggattc gggttttctt tccccaagcc aaagcctgga attagaaaag  1080
atattacctc aaaagacaag caagaacttg tcccaaaagg aggtagatga ttgtgaggag  1140
accacccctgc atgatgtcaa tattgcagag gagatgagtc gaaagaagca acaataccgt  1200
gaggcatatg atgacgatga tgatgaagat gatgagcact cgcagcctcg ggtgcaatgc  1260
gctcaacagt ag                                                       1272
```

<210> SEQ ID NO 34
<211> LENGTH: 423
<212> TYPE: PRT
<213> ORGANISM: Medicago sativa

<400> SEQUENCE: 34

```
Met Phe Gly Arg Gly Pro Thr Arg Lys Ser Asp Asn Thr Lys Tyr Tyr
  1               5                  10                  15

Asp Ile Leu Gly Val Ser Lys Ser Ala Ser Glu Asp Glu Ile Lys Lys
             20                  25                  30

Ala Tyr Arg Lys Ala Ala Met Lys Asn His Pro Asp Lys Gly Gly Asp
         35                  40                  45

Pro Glu Lys Phe Lys Glu Leu Gly Gln Ala Tyr Glu Val Leu Ser Asp
     50                  55                  60

Pro Glu Lys Lys Glu Leu Tyr Asp Gln Tyr Gly Glu Asp Ala Leu Lys
 65                  70                  75                  80

Glu Gly Met Gly Gly Gly Ala Gly Ser Ser Phe His Asn Pro Phe Asp
                 85                  90                  95

Ile Phe Glu Ser Phe Phe Gly Ala Gly Phe Gly Gly Gly Gly Pro Ser
            100                 105                 110

Arg Ala Arg Arg Gln Lys Gln Gly Glu Asp Val Val His Ser Ile Lys
        115                 120                 125
```

Val Ser Leu Glu Asp Val Tyr Asn Gly Thr Thr Lys Lys Leu Ser Leu
        130                 135                 140

Ser Arg Asn Ala Leu Cys Ser Lys Cys Lys Gly Lys Gly Ser Lys Ser
145                 150                 155                 160

Gly Thr Ala Gly Arg Cys Phe Gly Cys Gln Gly Thr Gly Met Lys Ile
            165                 170                 175

Thr Arg Arg Gln Ile Gly Leu Gly Met Ile Gln Met Gln His Val
        180                 185                 190

Cys Pro Asp Cys Lys Gly Thr Gly Glu Val Ile Ser Glu Arg Asp Arg
        195                 200                 205

Cys Pro Gln Cys Lys Gly Asn Lys Ile Thr Gln Glu Lys Lys Val Leu
        210                 215                 220

Glu Val His Val Glu Lys Gly Met Gln Gln His Lys Ile Val Phe
225                 230                 235                 240

Glu Gly Gln Ala Asp Glu Leu Pro Asp Thr Ile Thr Gly Asp Ile Val
            245                 250                 255

Phe Val Leu Gln Val Lys Gly His Pro Lys Phe Arg Arg Glu Arg Asp
        260                 265                 270

Asp Leu His Ile Glu His Asn Leu Ser Leu Thr Asp Ala Leu Cys Gly
        275                 280                 285

Phe Gln Phe Asn Val Thr His Leu Asp Gly Arg Gln Leu Leu Val Lys
        290                 295                 300

Ser Asn Pro Gly Glu Val Ile Lys Pro Gly Gln His Lys Ala Ile Asn
305                 310                 315                 320

Asp Glu Gly Met Pro Gln His Gly Arg Pro Phe Met Lys Gly Arg Leu
            325                 330                 335

Tyr Ile Lys Phe Ser Val Asp Phe Pro Asp Ser Gly Phe Leu Ser Pro
        340                 345                 350

Ser Gln Ser Leu Glu Leu Glu Lys Ile Leu Pro Gln Lys Thr Ser Lys
        355                 360                 365

Asn Leu Ser Gln Lys Glu Val Asp Asp Cys Glu Glu Thr Thr Leu His
370                 375                 380

Asp Val Asn Ile Ala Glu Glu Met Ser Arg Lys Lys Gln Gln Tyr Arg
385                 390                 395                 400

Glu Ala Tyr Asp Asp Asp Asp Glu Asp Glu His Ser Gln Pro
            405                 410                 415

Arg Val Gln Cys Ala Gln Gln
            420

<210> SEQ ID NO 35
<211> LENGTH: 1257
<212> TYPE: DNA
<213> ORGANISM: Nicotiana tabacum

<400> SEQUENCE: 35
atgtttggga gaggaccaaa gaagagtgat aatacgaggt actatgaaat attgggtgtg      60
tcaaagaatg catcagatga tgaaatcaag aaagcttata gaaaagctgc tatgaagaat     120
caccctgata agggtggtga ccctgaaaag tttaaggagc ttgctcaagc ttatgaggtg     180
ttgagtgact cacagaagcg tgagatttat gatcagtatg agaagatgc attaaaagaa      240 ggaatgggtg gcggcggcgg aatgcatgat ccatttgaca tctttgaatc tttctttggt     300
ggcaatccat ttgaaggtgg tggtagcagc agaggaagaa gacagagaag ggtgaggat      360 gtagtgcatc cactgaaggt ctctctcgag gacctttaca gtgggataac caaaaaactc     420

```
tcccttttcgc gcaatgtcat ttgctccaag tgcagtggga aaggatcgaa gtctggtgct    480
tcaatgaagt gttctggttg taaaggtagt ggtatgaagg tttcaattag acaacttggc    540
ccttcaatga tccagcaaat gcagcacgct tgtaatgaat gcaagggtac tggagagact    600
attgacgata aggatcggtg ccctcggtgc aaaggtgaaa aagtggttca ggagaagaaa    660
gtccttgaag ttcatgttga aaaggcatg caaaatggac agaaaattac attccctgga     720
aaggctgatg aaaccoctga tgcaattact ggagatatag ttttgtgct ccagcagaaa     780 gacacccgag gttccaagag aaagggcgac gatctgtttg tagatcacac attgagtcta    840
actgaggctt tatgtggctt ccagttcata atgacacact tggatggcag acaactcctc    900
ataaaatcaa atctcgggga agttgttaaa cctgatcaat tcaaggcaat caatgatgag    960
ggaacgccaa tgtatcagag gccatttatg agggcaaat tgtacattcg tttcgtcgtt    1020
gaattcccag attcattgaa cacagaacag gtgaaggctc tggaggcaat cttaccacca    1080
agacctcagt cacagtacac agacatggaa ttggatgagt gtgaggagac ttctttacat    1140
gatgtgaata ttgaggagga aatgagaagg aaacaggcag ctcaacaaga ggcatatgat    1200
gaggatgatg agatgcatgg tggtggagga cagagagtac aatgtgcaca gcagtaa      1257
```

<210> SEQ ID NO 36
<211> LENGTH: 418
<212> TYPE: PRT
<213> ORGANISM: Nicotiana tabacum
<400> SEQUENCE: 36

```
Met Phe Gly Arg Gly Pro Lys Lys Ser Asp Asn Thr Arg Tyr Tyr Glu
1               5                   10                  15

Ile Leu Gly Val Ser Lys Asn Ala Ser Asp Asp Glu Ile Lys Lys Ala
            20                  25                  30

Tyr Arg Lys Ala Ala Met Lys Asn His Pro Asp Lys Gly Gly Asp Pro
        35                  40                  45

Glu Lys Phe Lys Glu Leu Ala Gln Ala Tyr Glu Val Leu Ser Asp Ser
    50                  55                  60

Gln Lys Arg Glu Ile Tyr Asp Gln Tyr Gly Glu Asp Ala Leu Lys Glu
65                  70                  75                  80

Gly Met Gly Gly Gly Gly Met His Asp Pro Phe Asp Ile Phe Glu
                85                  90                  95

Ser Phe Phe Gly Gly Asn Pro Phe Gly Gly Gly Gly Ser Ser Arg Gly
            100                 105                 110

Arg Arg Gln Arg Arg Gly Glu Asp Val Val His Pro Leu Lys Val Ser
        115                 120                 125

Leu Glu Asp Leu Tyr Ser Gly Ile Thr Lys Lys Leu Ser Leu Ser Arg
    130                 135                 140

Asn Val Ile Cys Ser Lys Cys Ser Gly Lys Gly Ser Lys Ser Gly Ala
145                 150                 155                 160

Ser Met Lys Cys Ser Gly Cys Lys Gly Ser Gly Met Lys Val Ser Ile
                165                 170                 175

Arg Gln Leu Gly Pro Ser Met Ile Gln Gln Met Gln His Ala Cys Asn
            180                 185                 190

Glu Cys Lys Gly Thr Gly Glu Thr Ile Asp Asp Lys Asp Arg Cys Pro
        195                 200                 205

Arg Cys Lys Gly Glu Lys Val Val Gln Glu Lys Lys Val Leu Glu Val
    210                 215                 220
```

-continued

```
His Val Glu Lys Gly Met Gln Asn Gly Gln Lys Ile Thr Phe Pro Gly
225                 230                 235                 240
Lys Ala Asp Glu Thr Pro Asp Ala Ile Thr Gly Asp Ile Val Phe Val
            245                 250                 255
Leu Gln Gln Lys Asp Thr Arg Gly Ser Lys Arg Lys Gly Asp Asp Leu
        260                 265                 270
Phe Val Asp His Thr Leu Ser Leu Thr Glu Ala Leu Cys Gly Phe Gln
    275                 280                 285
Phe Ile Met Thr His Leu Asp Gly Arg Gln Leu Leu Ile Lys Ser Asn
290                 295                 300
Leu Gly Glu Val Val Lys Pro Asp Gln Phe Lys Ala Ile Asn Asp Glu
305                 310                 315                 320
Gly Thr Pro Met Tyr Gln Arg Pro Phe Met Arg Gly Lys Leu Tyr Ile
            325                 330                 335
Arg Phe Val Val Glu Phe Pro Asp Ser Leu Asn Thr Glu Gln Val Lys
        340                 345                 350
Ala Leu Glu Ala Ile Leu Pro Pro Arg Pro Gln Ser Gln Tyr Thr Asp
    355                 360                 365
Met Glu Leu Asp Glu Cys Glu Glu Thr Ser Leu His Asp Val Asn Ile
370                 375                 380
Glu Glu Glu Met Arg Arg Lys Gln Ala Ala Gln Gln Glu Ala Tyr Asp
385                 390                 395                 400
Glu Asp Asp Glu Met His Gly Gly Gly Gly Gln Arg Val Gln Cys Ala
            405                 410                 415
Gln Gln

<210> SEQ ID NO 37
<211> LENGTH: 1272
<212> TYPE: DNA
<213> ORGANISM: Salix gilgiana

<400> SEQUENCE: 37
atgtttgggc gtgctccgag gaggagtgac aacaccaagt attatgaggt tttggctgtg      60
tcaaaaggtg caagtcaaga tgaactgaag aaggcttata agaaagctgc cataaagaat     120
catcctgata aggtggagat cctgaaaag ttcaaggagt gtctcaagc ttatgaagtc       180 cttagtgatc cagataaaag agaaatttat gatcaatatg gggaagatgc acttaaggag    240
gggatgggac ctggtggtgg tggggtggt cacaatccat ttgatatatt cgaatcattt      300
tttggtggag gtggttttgg tggtggtagc agctcaagag aagaaggca gaagcaaggt     360 gaagatgtag cgcaccctct gaaggtttcc ttagaggatt tgtacaatgg aacttcaaag    420
aaactctctc tttccagaaa cattttgtgt gccaaatgta agggaaagg ttcaaagagt      480 ggagcctttg gaaatgtcg tggctgccaa ggtactggaa tgaaagtttc aatccgacaa     540
attggattgg catgatgca acaaatgcaa catgtgtgtc ctgaatgcag gggctcaggt    600
gagctaatta gtgagaagga taatgccct cattgcagag gaacaaggt aacgcaggaa      660 aagagggtgc tggaagtgca tgttgaaagg ggaatgcagc atggccagaa gatagttttc    720
gaaggtcaag ctgatgaagc tcctgacaca attacagggg atgttgtttt tgtattgcaa    780
ctgaaaaagc actccaagtt tgaacggaaa atggatgatc tctttgtgga acactctctc    840
agtttaacag aggctctttg cgggtatcag tttgccctta cccatcttga tggtcggcag   900
cttcttatca aatcaaatcc ttacgagatt gtaaaacctg tcaatacaa agcaattaac    960 gatgaaggaa tgccacatca tcacaggccc ttcatgaggg gcaagctcta tatccatttt   1020
```

-continued

```
aatgtggtgt tccctgactc gggcactcta tccctgagc agtgccgtac tttagagact    1080
atactacccc caaggcaaag caaaaacttg tcagagatgg agattgataa ctgcgaagag    1140
acaattatgc atgatgtcaa tatggaggag gagaaaaggc ggaaacagca gcagcgccac    1200
cagcatgaag catatgatga ggatgaggag gaggaatcat ccatgccccg ggtgcagtgt    1260
gcccagcagt aa                                                        1272
```

<210> SEQ ID NO 38
<211> LENGTH: 423
<212> TYPE: PRT
<213> ORGANISM: Salix gilgiana

<400> SEQUENCE: 38

```
Met Phe Gly Arg Ala Pro Arg Arg Ser Asp Asn Thr Lys Tyr Tyr Glu
1               5                   10                  15

Val Leu Ala Val Ser Lys Gly Ala Ser Gln Asp Glu Leu Lys Lys Ala
            20                  25                  30

Tyr Lys Lys Ala Ala Ile Lys Asn His Pro Asp Lys Gly Gly Asp Pro
        35                  40                  45

Glu Lys Phe Lys Glu Leu Ser Gln Ala Tyr Glu Val Leu Ser Asp Pro
    50                  55                  60

Asp Lys Arg Glu Ile Tyr Asp Gln Tyr Gly Glu Asp Ala Leu Lys Glu
65                  70                  75                  80

Gly Met Gly Pro Gly Gly Gly Gly Gly His Asn Pro Phe Asp Ile
                85                  90                  95

Phe Glu Ser Phe Phe Gly Gly Gly Phe Gly Gly Ser Ser Ser
            100                 105                 110

Arg Gly Arg Arg Gln Lys Gln Gly Glu Asp Val Ala His Pro Leu Lys
        115                 120                 125

Val Ser Leu Glu Asp Leu Tyr Asn Gly Thr Ser Lys Lys Leu Ser Leu
    130                 135                 140

Ser Arg Asn Ile Leu Cys Ala Lys Cys Lys Gly Lys Gly Ser Lys Ser
145                 150                 155                 160

Gly Ala Phe Gly Lys Cys Arg Gly Cys Gln Gly Thr Gly Met Lys Val
                165                 170                 175

Ser Ile Arg Gln Ile Gly Leu Gly Met Met Gln Met Gln His Val
            180                 185                 190

Cys Pro Glu Cys Arg Gly Ser Gly Glu Leu Ile Ser Glu Lys Asp Lys
        195                 200                 205

Cys Pro His Cys Arg Gly Asn Lys Val Thr Gln Glu Lys Arg Val Leu
    210                 215                 220

Glu Val His Val Glu Arg Gly Met Gln His Gly Gln Lys Ile Val Phe
225                 230                 235                 240

Glu Gly Gln Ala Asp Glu Ala Pro Asp Thr Ile Thr Gly Asp Val Val
                245                 250                 255

Phe Val Leu Gln Leu Lys Lys His Ser Lys Phe Glu Arg Lys Met Asp
            260                 265                 270

Asp Leu Phe Val Glu His Ser Leu Ser Leu Thr Glu Ala Leu Cys Gly
        275                 280                 285

Tyr Gln Phe Ala Leu Thr His Leu Asp Gly Arg Gln Leu Leu Ile Lys
    290                 295                 300

Ser Asn Pro Tyr Glu Ile Val Lys Pro Gly Gln Tyr Lys Ala Ile Asn
305                 310                 315                 320
```

```
Asp Glu Gly Met Pro His His Arg Pro Phe Met Arg Gly Lys Leu
            325                 330                 335

Tyr Ile His Phe Asn Val Val Phe Pro Asp Ser Gly Thr Leu Ser Pro
            340                 345                 350

Glu Gln Cys Arg Thr Leu Glu Thr Ile Leu Pro Pro Arg Gln Ser Lys
            355                 360                 365

Asn Leu Ser Glu Met Glu Ile Asp Asn Cys Glu Glu Thr Ile Met His
            370                 375                 380

Asp Val Asn Met Glu Glu Glu Lys Arg Arg Lys Gln Gln Gln Arg His
385                 390                 395                 400

Gln His Glu Ala Tyr Asp Glu Asp Glu Glu Glu Ser Ser Met Pro
            405                 410                 415

Arg Val Gln Cys Ala Gln Gln
            420
```

<210> SEQ ID NO 39
<211> LENGTH: 1263
<212> TYPE: DNA
<213> ORGANISM: Salix gilgiana

<400> SEQUENCE: 39

```
atgtttggga gagcaccaaa gaaaagcgac aacaccaagt actatgaggt tcttggagtc      60
tcaaagagtg cttcacagga tgatctaaag aaggcttata ggaaagcagc tatcaagaac     120
catcctgata agggcggtga tcctgaaaag ttcaaggagt tggcgcaagc atatgaggtt     180
ctgagtgacc ctgagaagcg tgagatatat gatcagtatg agaggatgc cctcaaggaa      240
ggaatgggta gcggcggcag cggcgctcac gatccattcg atatcttcca atccttcttt     300
ggtggtggca atccattcgg tggtggaggt agcagcaggg gccgaaggca agaaggggc      360
gaggatgtga tccaccctct gaaagtttct tttgaagacc tttataatgg cacatccaag     420
aagctttctc tttcacgaaa tgtaatctgc tccaagtgca gggcaaagg ttccaaatcc      480
ggagcatcat caaaatgtgc tggttgccaa ggttctggaa tgaaggtctc cataagacac     540
ctcggtcctt ctatgatcca gcaaatgcag catgcctgca atgaatgcaa gggcactggc     600
gagacaatta acgataagga ccgatgccct caatgcaagg gtgagaaggt tgtccaggag     660
aagaaagtgt tggaagtagt tgttgagaag ggcatgcaaa atgggcagaa ggtaacattt     720
cctggagaag ctgatgaggc gcctgacact gttacagggg acatagtctt cgtcctgcag     780
caaaaggatc accctaagtt taagagaaag ggtgatgacc tatttgttga gcacacacta     840
tctcttactg aggcactatg tggcttccaa ttcgtcttga cccatttgga tggaaggcag     900
ctcctgataa aatctcaacc cggggaagta gtcaagcctg atcaattcaa ggctataaat     960
gatgaaggaa tgccgatgta ccaaaggcca tttatgagag ggaaactcta cattcatttc    1020
agtgttgaat cccagactc cctgtccct gatatgtgca aggcgttgga ggccgtgctt      1080
cctccgcgag cctctgttca gctgactgac atggagcttg atgaatgcga ggaaactact    1140
ttacatgatg tgaacatcga tgaggagatg aggaggaaac agcaacagca ggcccaagaa    1200
gcgtatgatg aagatgatga gatgcctggt ggtgcccaga gggtgcagtg tgctcagcaa    1260
taa                                                                  1263
```

<210> SEQ ID NO 40
<211> LENGTH: 420
<212> TYPE: PRT
<213> ORGANISM: Salix gilgiana

```
<400> SEQUENCE: 40

Met Phe Gly Arg Ala Pro Lys Lys Ser Asp Asn Thr Lys Tyr Tyr Glu
1               5                   10                  15

Val Leu Gly Val Ser Lys Ser Ala Ser Gln Asp Asp Leu Lys Lys Ala
            20                  25                  30

Tyr Arg Lys Ala Ala Ile Lys Asn His Pro Asp Lys Gly Gly Asp Pro
        35                  40                  45

Glu Lys Phe Lys Glu Leu Ala Gln Ala Tyr Glu Val Leu Ser Asp Pro
    50                  55                  60

Glu Lys Arg Glu Ile Tyr Asp Gln Tyr Gly Glu Asp Ala Leu Lys Glu
65              70                  75                  80

Gly Met Gly Ser Gly Gly Ser Gly Ala His Asp Pro Phe Asp Ile Phe
                85                  90                  95

Gln Ser Phe Phe Gly Gly Gly Asn Pro Phe Gly Gly Gly Gly Ser Ser
                100                 105                 110

Arg Gly Arg Arg Gln Arg Arg Gly Glu Asp Val Ile His Pro Leu Lys
            115                 120                 125

Val Ser Phe Glu Asp Leu Tyr Asn Gly Thr Ser Lys Lys Leu Ser Leu
    130                 135                 140

Ser Arg Asn Val Ile Cys Ser Lys Cys Lys Gly Lys Gly Ser Lys Ser
145                 150                 155                 160

Gly Ala Ser Ser Lys Cys Ala Gly Cys Gln Gly Ser Gly Met Lys Val
                165                 170                 175

Ser Ile Arg His Leu Gly Pro Ser Met Ile Gln Gln Met Gln His Ala
            180                 185                 190

Cys Asn Glu Cys Lys Gly Thr Gly Glu Thr Ile Asn Asp Lys Asp Arg
        195                 200                 205

Cys Pro Gln Cys Lys Gly Glu Lys Val Val Gln Glu Lys Lys Val Leu
    210                 215                 220

Glu Val Val Val Glu Lys Gly Met Gln Asn Gly Gln Lys Val Thr Phe
225                 230                 235                 240

Pro Gly Glu Ala Asp Glu Ala Pro Asp Thr Val Thr Gly Asp Ile Val
                245                 250                 255

Phe Val Leu Gln Gln Lys Asp His Pro Lys Phe Lys Arg Lys Gly Asp
            260                 265                 270

Asp Leu Phe Val Glu His Thr Leu Ser Leu Thr Glu Ala Leu Cys Gly
        275                 280                 285

Phe Gln Phe Val Leu Thr His Leu Asp Gly Arg Gln Leu Leu Ile Lys
    290                 295                 300

Ser Gln Pro Gly Glu Val Val Lys Pro Asp Gln Phe Lys Ala Ile Asn
305                 310                 315                 320

Asp Glu Gly Met Pro Met Tyr Gln Arg Pro Phe Met Arg Gly Lys Leu
                325                 330                 335

Tyr Ile His Phe Ser Val Glu Phe Pro Asp Ser Leu Ser Pro Asp Met
            340                 345                 350

Cys Lys Ala Leu Glu Ala Val Leu Pro Pro Arg Ala Ser Val Gln Leu
        355                 360                 365

Thr Asp Met Glu Leu Asp Glu Cys Glu Glu Thr Thr Leu His Asp Val
    370                 375                 380

Asn Ile Asp Glu Glu Met Arg Arg Lys Gln Gln Gln Ala Gln Glu
385                 390                 395                 400

Ala Tyr Asp Glu Asp Asp Glu Met Pro Gly Gly Ala Gln Arg Val Gln
                405                 410                 415
```

Cys Ala Gln Gln
        420

<210> SEQ ID NO 41
<211> LENGTH: 1260
<212> TYPE: DNA
<213> ORGANISM: Solanum tuberosum

<400> SEQUENCE: 41

| | | |
|---|---|---|
| atgtttggga gggcaccaga gaagagcgac aacacgaagt actatgagat cttaggtgtc | 60 |
| cctaagactg ctgcacagga agatctcaag aaagcttacc gtaaagctgc tattaagaat | 120 |
| catcctgata agggaggtga tcctgaaaag tttaaagagc ttgcacaagc ttatgaggtt | 180 |
| ctgagtgatc ccgagaagcg tgagatatat gatcagtatg gagaagatgc tctcaaggaa | 240 |
| ggaatgggtg gtggaggtgg tggacacgac ccatttgata tttctcatc tttctttggt | 300 |
| ggcagcccat tggtggaggt ggtggaagc agcagaggaa gagacaaag aagaggagag | 360 |
| gatgttgtcc atcctctcaa gtttctctg gaggatctgt acaatggaac atcaaagaag | 420 |
| ctgtcactat ctcgcaatgt attgtgctcg aagtgcaagg ggaaaggatc taaatcaggt | 480 |
| gcttcaatga agtgttctgg ctgtcaaggg tctgggatga agtcactat tagacaactt | 540 |
| ggcccatcca tgatccagca gatgcagcac ccttgcaacg agtgtaaggg tactggtgag | 600 |
| atgatcaatg ataaagatag gtgtgggcag tgtaaaggtg agaaagttgt gcaggagaag | 660 |
| aaggtgttgg aagttgttgt cgagaagggg atgcagaacg acagaagat aacattcccg | 720 |
| ggcgaagctg atgaagcacc tgataccgtc actggggaca tagttttgt cttgcaacag | 780 |
| aaggaacatc ccaagtttaa gcgaaaggga gatgatctct tgtagagca caccttgagc | 840 |
| ttaaccgagg ccctgtgtgg tttccagttc atcttgactc acctagataa taggcagctg | 900 |
| atcatcaagc cccaagccgg agaagttgtc aagcctgatc aatttaaagc cataaatgat | 960 |
| gaaggaatgc ctatgtacca aaggccattt atgagaggaa aactatacat tcactttact | 1020 |
| gtagaattcc ccgacacatt atccccgag caatgcaaga accttgaagc agtattgcca | 1080 |
| ccaaaaccga aaacacaaat gactgatatg gaattggacg agtgcgagga gaccacctta | 1140 |
| catgatgtta acatcgaaga ggagatgcgg aggaagcagc aacaggccca agaggcatat | 1200 |
| gacgaagatg atgaagacat gcatggaggt gcacagagag ttcagtgtgc acaacagtaa | 1260 |

<210> SEQ ID NO 42
<211> LENGTH: 419
<212> TYPE: PRT
<213> ORGANISM: Solanum tuberosum

<400> SEQUENCE: 42

Met Phe Gly Arg Ala Pro Glu Lys Ser Asp Asn Thr Lys Tyr Tyr Glu
1               5                   10                  15

Ile Leu Gly Val Pro Lys Thr Ala Ala Gln Glu Asp Leu Lys Lys Ala
            20                  25                  30

Tyr Arg Lys Ala Ala Ile Lys Asn His Pro Asp Lys Gly Gly Asp Pro
        35                  40                  45

Glu Lys Phe Lys Glu Leu Ala Gln Ala Tyr Glu Val Leu Ser Asp Pro
    50                  55                  60

Glu Lys Arg Glu Ile Tyr Asp Gln Tyr Gly Glu Asp Ala Leu Lys Glu
65                  70                  75                  80

Gly Met Gly Gly Gly Gly Gly His Asp Pro Phe Asp Ile Phe Ser
                85                  90                  95

-continued

Ser Phe Phe Gly Gly Ser Pro Phe Gly Gly Gly Gly Ser Ser Arg
            100                 105                 110

Gly Arg Arg Gln Arg Arg Gly Glu Asp Val Val His Pro Leu Lys Val
        115                 120                 125

Ser Leu Glu Asp Leu Tyr Asn Gly Thr Ser Lys Lys Leu Ser Leu Ser
    130                 135                 140

Arg Asn Val Leu Cys Ser Lys Cys Lys Gly Lys Gly Ser Lys Ser Gly
145                 150                 155                 160

Ala Ser Met Lys Cys Ser Gly Cys Gln Gly Ser Gly Met Lys Val Thr
                165                 170                 175

Ile Arg Gln Leu Gly Pro Ser Met Ile Gln Gln Met Gln His Pro Cys
            180                 185                 190

Asn Glu Cys Lys Gly Thr Gly Glu Met Ile Asn Asp Lys Asp Arg Cys
        195                 200                 205

Gly Gln Cys Lys Gly Glu Lys Val Val Gln Glu Lys Lys Val Leu Glu
    210                 215                 220

Val Val Val Glu Lys Gly Met Gln Asn Gly Gln Lys Ile Thr Phe Pro
225                 230                 235                 240

Gly Glu Ala Asp Glu Ala Pro Asp Thr Val Thr Gly Asp Ile Val Phe
                245                 250                 255

Val Leu Gln Gln Lys Glu His Pro Lys Phe Lys Arg Lys Gly Asp Asp
            260                 265                 270

Leu Phe Val Glu His Thr Leu Ser Leu Thr Glu Ala Leu Cys Gly Phe
        275                 280                 285

Gln Phe Ile Leu Thr His Leu Asp Asn Arg Gln Leu Ile Ile Lys Pro
    290                 295                 300

Gln Ala Gly Glu Val Val Lys Pro Asp Gln Phe Lys Ala Ile Asn Asp
305                 310                 315                 320

Glu Gly Met Pro Met Tyr Gln Arg Pro Phe Met Arg Gly Lys Leu Tyr
                325                 330                 335

Ile His Phe Thr Val Glu Phe Pro Asp Thr Leu Ser Pro Glu Gln Cys
            340                 345                 350

Lys Asn Leu Glu Ala Val Leu Pro Pro Lys Pro Lys Thr Gln Met Thr
        355                 360                 365

Asp Met Glu Leu Asp Glu Cys Glu Glu Thr Thr Leu His Asp Val Asn
    370                 375                 380

Ile Glu Glu Glu Met Arg Arg Lys Gln Gln Ala Gln Glu Ala Tyr
385                 390                 395                 400

Asp Glu Asp Asp Glu Asp Met His Gly Gly Ala Gln Arg Val Gln Cys
                405                 410                 415

Ala Gln Gln

<210> SEQ ID NO 43
<211> LENGTH: 1293
<212> TYPE: DNA
<213> ORGANISM: Oryza sativa

<400> SEQUENCE: 43
atggtcaagg acaccaaatt ctacgacacc ctcggctgcg cgcccgacgc taccgagtct    60
cagctcaaga ccgcataccg caagggcgcc ctcaagcacc accccgacaa gaacgcacac   120
tcgcccgaat ccgaggagaa gttcaaggag atctcacacg catacgaagt cctctcagac   180
ccccaaaagc gccaaatcta cgaccagtat ggtgaggagg gtctcgagca gggtggtgga   240

```
atgggcggcg gcggaggcat ggctgccgag gacttgttcg cacagttctt cggcggcggc    300
ggtggaggcg gaggcttcgg tggcatgggc ggcatgttcg gcggtcgcga gcccggcccc    360
aagaaggctc gcaccatcca ccacgttcac aaggtctctc tcgaggacat ctaccgcggc    420
aaggtttcca agcttgccct gcagaagagc gtcatctgct ccaagtgtga tggccgcggt    480
ggtaaggagg gtgctgtgaa gacttgccag gcctgccagg gccagggtat gaagaccatg    540
atgcgccaga tgggtcccat gatccagcga ttccagaccg tctgccccga ctgcaacggt    600
gaggggagc aggtccgcga aaggacaag tgcaagcagt gctccggaaa gaagaccatc      660
atcgagcgca aggtgctcca cgtccacgtc gacaagggtg tgcaaagcgg caccaagatc    720
gacttcagag gcgagggtga ccagatgcct ggcgttgagc ccggtgatgt gcagttcgag    780
atcgagcaga agcctcaccc tcgcttccag cgcaagggtg acgacctcta ctaccacgcc    840
gagatcgacc ttcttactgc gctcgccggc ggtgccatct acgttgagca ccttgacgag    900
cgctggttga ccgtcgagat cctgcccggc gaggttatcg caccaggcga ggtcaaggtc    960
atccgcggcc agggtatgcc ctcataccgc caccacgacc acggcaacct ttacatccag   1020
ttcgacgtca agttccccac atccatccaa ggccctgccg acaaggacgg ccagtccacc   1080
tccatgtccg cacaacagat caaggccctc gaatccgtcc ttcctcctcg caagccccaa   1140
tcgatccctc ctcccgatgc tatgaccgag gacttccagc tcgagcgcgt agaccccatg   1200
gagggctccc gctccaaggg cgcccacagc atggacgagg acgatgacga gatgggcggc   1260
ggtggcgagc gcgtgcagtg cgcgtcgcag taa                                1293
```

<210> SEQ ID NO 44
<211> LENGTH: 430
<212> TYPE: PRT
<213> ORGANISM: Oryza sativa

<400> SEQUENCE: 44

```
Met Val Lys Asp Thr Lys Phe Tyr Asp Thr Leu Gly Cys Ala Pro Asp
1               5                   10                  15

Ala Thr Glu Ser Gln Leu Lys Thr Ala Tyr Arg Lys Gly Ala Leu Lys
            20                  25                  30

His His Pro Asp Lys Asn Ala His Ser Pro Glu Ser Glu Glu Lys Phe
        35                  40                  45

Lys Glu Ile Ser His Ala Tyr Glu Val Leu Ser Asp Pro Gln Lys Arg
    50                  55                  60

Gln Ile Tyr Asp Gln Tyr Gly Glu Glu Leu Glu Gln Gly Gly Gly
65                  70                  75                  80

Met Gly Gly Gly Gly Met Ala Ala Glu Asp Leu Phe Ala Gln Phe
                85                  90                  95

Phe Gly Gly Gly Gly Gly Gly Phe Gly Gly Met Gly Gly Met
            100                 105                 110

Phe Gly Gly Arg Glu Pro Gly Lys Lys Ala Arg Thr Ile His His
        115                 120                 125

Val His Lys Val Ser Leu Glu Asp Ile Tyr Arg Gly Lys Val Ser Lys
    130                 135                 140

Leu Ala Leu Gln Lys Ser Val Ile Cys Ser Lys Cys Asp Gly Arg Gly
145                 150                 155                 160

Gly Lys Glu Gly Ala Val Lys Thr Cys Gln Gly Cys Gln Gly Gln Gly
                165                 170                 175

Met Lys Thr Met Met Arg Gln Met Gly Pro Met Ile Gln Arg Phe Gln
            180                 185                 190
```

```
Thr Val Cys Pro Asp Cys Asn Gly Glu Gly Glu Gln Val Arg Glu Lys
            195                 200                 205

Asp Lys Cys Lys Gln Cys Ser Gly Lys Lys Thr Ile Ile Glu Arg Lys
        210                 215                 220

Val Leu His Val His Val Asp Lys Gly Val Gln Ser Gly Thr Lys Ile
225                 230                 235                 240

Asp Phe Arg Gly Glu Gly Asp Gln Met Pro Gly Val Glu Pro Gly Asp
                245                 250                 255

Val Gln Phe Glu Ile Glu Gln Lys Pro His Pro Arg Phe Gln Arg Lys
            260                 265                 270

Gly Asp Leu Tyr Tyr His Ala Glu Ile Asp Leu Leu Thr Ala Leu
        275                 280                 285

Ala Gly Gly Ala Ile Tyr Val Glu His Leu Asp Glu Arg Trp Leu Thr
        290                 295                 300

Val Glu Ile Leu Pro Gly Glu Val Ile Ala Pro Gly Glu Val Lys Val
305                 310                 315                 320

Ile Arg Gly Gln Gly Met Pro Ser Tyr Arg His His Asp His Gly Asn
                325                 330                 335

Leu Tyr Ile Gln Phe Asp Val Lys Phe Pro Thr Ser Ile Gln Gly Pro
            340                 345                 350

Ala Asp Lys Asp Gly Gln Ser Thr Ser Met Ser Ala Gln Gln Ile Lys
        355                 360                 365

Ala Leu Glu Ser Val Leu Pro Pro Arg Lys Pro Gln Ser Ile Pro Pro
370                 375                 380

Pro Asp Ala Met Thr Glu Asp Phe Gln Leu Glu Arg Val Asp Pro Met
385                 390                 395                 400

Glu Gly Ser Arg Ser Lys Gly Ala His Ser Met Asp Glu Asp Asp
                405                 410                 415

Glu Met Gly Gly Gly Gly Glu Arg Val Gln Cys Ala Ser Gln
            420                 425                 430

<210> SEQ ID NO 45
<211> LENGTH: 1263
<212> TYPE: DNA
<213> ORGANISM: Triticum aestivum

<400> SEQUENCE: 45
atggtaaaag ataccaaact atatgatact ctgggtattt ccccgacctg tactgaagcc    60
gagttaaaaa aagcatacaa aatcggagca cttaaacacc atcctgataa aaacgcctca   120
aatccagccg ccgcagaaaa atttaaagaa atatcgcacg catatgaagt actatctgac   180
cctcaaaaaa gacacatata cgaccaatat ggcgaagagg gccttgaggg aggtggtggt   240
gctgcgggag ggatgaacgc agaagattta ttctctcaat tcttcagcgg tggctctgcc   300 ttcgaggtg gaggattggg tggcatgttc ggggagggc acagcaacg tggccccca    360 aaagcccgca ccattcatca cgttcacaag gtatctctag aagatatcta ccgcggtaaa   420
atctcaaaac tggcactaca aaagtcagtc atatgccaca gtgtgaggg acggggtggc   480 aaagatggtg cagtaaaaaa atgtgccggc tgtgatggac atggaatgaa acaatgatg   540 cgtcaaatgg gtcctatgat tcagcggttt caaactcact gccccgactg caatggtgag   600
ggagaagtca tccgagagaa agataaatgt aagacgtgta acggtaaaaa gaccaacgtg   660
gaacgcaaag tactccacgt tcatgtggac agaggtgttc gatcggggca ccggattgaa   720
tttaaaggtg aaggagacca aaccccccgga gttcaacctg gagatgttat ctttgaaatt   780
```

-continued

```
gagcagaaac cacatccaag attccaacga aaagacgatg accttattta ccacgcagag    840
atcgaccttg ttactgcctt agcgggcggg tcaatcttca ttgagcactt agacgaaaga    900
tggctgagtg tggagatact tcctggagag gttatctcac ctggatccgt taagatgata    960
cgcggtcagg gtatgccatc ccatcgtcac cacgactatg gaaatatgtt tgtacagttt   1020
gatgtcaaat tccccgaaag taactttgct gcaaattccg aggcatacgc agctctgaag   1080
agtattattc cgccgactgt ggtacctatc actccaccca ctgataccat gactgaaact   1140
gtatacttcg aagacattga ccctactcaa caagctcgtg cacagggtgc cacagcaatg   1200
gatgaagacg atgaagatgg ccatccagcc ggcgccgaac gggttcaatg tgcgtcacag   1260
taa                                                                 1263
```

<210> SEQ ID NO 46
<211> LENGTH: 420
<212> TYPE: PRT
<213> ORGANISM: Triticum aestivum

<400> SEQUENCE: 46

```
Met Val Lys Asp Thr Lys Leu Tyr Asp Thr Leu Gly Ile Ser Pro Thr
1               5                   10                  15

Cys Thr Glu Ala Glu Leu Lys Lys Ala Tyr Lys Ile Gly Ala Leu Lys
            20                  25                  30

His His Pro Asp Lys Asn Ala Ser Asn Pro Ala Ala Ala Glu Lys Phe
        35                  40                  45

Lys Glu Ile Ser His Ala Tyr Glu Val Leu Ser Asp Pro Gln Lys Arg
    50                  55                  60

His Ile Tyr Asp Gln Tyr Gly Glu Glu Gly Leu Glu Gly Gly Gly Gly
65                  70                  75                  80

Ala Ala Gly Gly Met Asn Ala Glu Asp Leu Phe Ser Gln Phe Phe Ser
                85                  90                  95

Gly Gly Ser Ala Phe Gly Gly Gly Leu Gly Gly Met Phe Gly Gly
            100                 105                 110

Gly Pro Gln Gln Arg Gly Pro Pro Lys Ala Arg Thr Ile His His Val
        115                 120                 125

His Lys Val Ser Leu Glu Asp Ile Tyr Arg Gly Lys Ile Ser Lys Leu
    130                 135                 140

Ala Leu Gln Lys Ser Val Ile Cys His Lys Cys Glu Gly Arg Gly Gly
145                 150                 155                 160

Lys Asp Gly Ala Val Lys Lys Cys Ala Gly Cys Asp Gly His Gly Met
                165                 170                 175

Lys Thr Met Met Arg Gln Met Gly Pro Met Ile Gln Arg Phe Gln Thr
            180                 185                 190

His Cys Pro Asp Cys Asn Gly Glu Gly Glu Val Ile Arg Glu Lys Asp
        195                 200                 205

Lys Cys Lys Thr Cys Asn Gly Lys Lys Thr Asn Val Glu Arg Lys Val
    210                 215                 220

Leu His Val His Val Asp Arg Gly Val Arg Ser Gly His Arg Ile Glu
225                 230                 235                 240

Phe Lys Gly Glu Gly Asp Gln Thr Pro Gly Val Gln Pro Gly Asp Val
                245                 250                 255

Ile Phe Glu Ile Glu Gln Lys Pro His Pro Arg Phe Gln Arg Lys Asp
            260                 265                 270

Asp Asp Leu Ile Tyr His Ala Glu Ile Asp Leu Val Thr Ala Leu Ala
```

```
                275                 280                 285
Gly Gly Ser Ile Phe Ile Glu His Leu Asp Glu Arg Trp Leu Ser Val
            290                 295                 300

Glu Ile Leu Pro Gly Glu Val Ile Ser Pro Gly Ser Val Lys Met Ile
305                 310                 315                 320

Arg Gly Gln Gly Met Pro Ser His Arg His His Asp Tyr Gly Asn Met
                325                 330                 335

Phe Val Gln Phe Asp Val Lys Phe Pro Glu Ser Asn Phe Ala Ala Asn
            340                 345                 350

Ser Glu Ala Tyr Ala Ala Leu Lys Ser Ile Ile Pro Pro Thr Val Val
            355                 360                 365

Pro Ile Thr Pro Pro Thr Asp Thr Met Thr Glu Thr Val Tyr Phe Glu
            370                 375                 380

Asp Ile Asp Pro Thr Gln Gln Ala Arg Ala Gln Gly Ala Thr Ala Met
385                 390                 395                 400

Asp Glu Asp Asp Glu Asp Gly His Pro Ala Gly Ala Glu Arg Val Gln
                405                 410                 415

Cys Ala Ser Gln
            420

<210> SEQ ID NO 47
<211> LENGTH: 1320
<212> TYPE: DNA
<213> ORGANISM: Caenorhabditis elegans

<400> SEQUENCE: 47
atgtttggag gtggaagtag tggtcccgtg acaccacttt atacacaac actcaatgtg      60
agaccagacg cttcgcaggc cgacattaag aaatcttact tcaaacttgc taaagaatac   120
catccagata aaaacccgga ccatggagat aaattcaaag agatcagttt tgcctatgaa   180
gttctttcga gccctgaaaa acgacgcttg tatgacgcca gaggtttgga aggagttcaa   240
ggaggaggag ctggtggtgg tggaggaggc tttcctggag gtctgttctc tcacttcttc   300
ggcggtgctg gcggtgatga cgatgacgac gatgatgata tgggtggtca tccatttggt   360
ggcttgttcg gtggaatggg tggaatggga cgaggtggcc cacgtcggcg gaaattccaa   420
gatactgttc atcccctcaa tgttacactc gaagagcttt acgtcggaaa acatcaaag   480
ctgaagcttt ccaaaaaggc actctgtaaa acttgcgaag ggtcaggtgg aaagaaggga   540
gaaaaatata gtgtgatgc atgccgtggt cgtggagtga agacgatcgt tcagcaaatt   600
ggccccggaa tgctccaaca aatgcaggtt cactgtgatg cttgtaaggg ttctggaggc   660
aaagttccag caggtgataa gtgcaaagga tgccatggag aaaagtacga aaacgtttcg   720
aaaatattgg aggttcacgt tcttcctggc atgaaacata cgataaaat tacattcaaa   780
ggagatggag accaatctga cccagatggt gagccaggag atgttgtcat tgttattcaa   840
cagaaagatc atgatatttt caagagagat ggagatgatc ttcacatgac caagaaacta   900
tcactgaatg aggcactttg cggctataat ttccttatca acatcttga tggccatcct   960
ttggttcttt ctagtaaaca aggagatgtt atcaagccag gagtcatcag aggagttctt  1020
ggaaaaggaa tgccaaataa gaaatacca gaactcaaag gaaacttgtt cgttgaattt  1080
gaagtcgaat ttccaaagga gcatttcctc gatgatgaaa aagcttatgc cgttctgaaa  1140
agctgcttcc ctacctcaaa agttgtcaat gtcaccccag ctgccgcaga agtttctctt  1200
atggaatatg acgagaagaa gtacagccga ggacgtggcg gagacgctta caatgaagat  1260
```
tcggacgaag aacaacacgg aggacatcac ggacaaggcg tcagatgcca acaccaatag    1320

<210> SEQ ID NO 48
<211> LENGTH: 439
<212> TYPE: PRT
<213> ORGANISM: Caenorhabditis elegans

<400> SEQUENCE: 48

Met Phe Gly Gly Gly Ser Ser Gly Pro Val Asp Thr Thr Leu Tyr Thr
1               5                   10                  15

Thr Leu Asn Val Arg Pro Asp Ala Ser Gln Ala Asp Ile Lys Lys Ser
            20                  25                  30

Tyr Phe Lys Leu Ala Lys Glu Tyr His Pro Asp Lys Asn Pro Asp His
        35                  40                  45

Gly Asp Lys Phe Lys Glu Ile Ser Phe Ala Tyr Glu Val Leu Ser Ser
    50                  55                  60

Pro Glu Lys Arg Arg Leu Tyr Asp Ala Arg Gly Leu Glu Gly Val Gln
65                  70                  75                  80

Gly Gly Gly Ala Gly Gly Gly Gly Phe Pro Gly Gly Leu Phe
                85                  90                  95

Ser His Phe Phe Gly Gly Ala Gly Gly Asp Asp Asp Asp Asp Asp
            100                 105                 110

Asp Met Gly Gly His Pro Phe Gly Leu Phe Gly Met Gly Gly
            115                 120                 125

Met Gly Arg Gly Gly Pro Arg Arg Lys Phe Gln Asp Thr Val His
            130                 135                 140

Pro Leu Asn Val Thr Leu Glu Glu Leu Tyr Val Gly Lys Thr Ser Lys
145                 150                 155                 160

Leu Lys Leu Ser Lys Lys Ala Leu Cys Lys Thr Cys Glu Gly Ser Gly
                165                 170                 175

Gly Lys Lys Gly Glu Lys Tyr Lys Cys Asp Ala Cys Arg Gly Arg Gly
            180                 185                 190

Val Lys Thr Ile Val Gln Gln Ile Gly Pro Gly Met Leu Gln Gln Met
        195                 200                 205

Gln Val His Cys Asp Ala Cys Lys Gly Ser Gly Gly Lys Val Pro Ala
    210                 215                 220

Gly Asp Lys Cys Lys Gly Cys His Gly Glu Lys Tyr Glu Asn Val Ser
225                 230                 235                 240

Lys Ile Leu Glu Val His Val Leu Pro Gly Met Lys His Asn Asp Lys
                245                 250                 255

Ile Thr Phe Lys Gly Asp Gly Asp Gln Ser Asp Pro Asp Gly Glu Pro
            260                 265                 270

Gly Asp Val Val Ile Val Gln Gln Lys Asp His Asp Ile Phe Lys
        275                 280                 285

Arg Asp Gly Asp Asp Leu His Met Thr Lys Lys Leu Ser Leu Asn Glu
    290                 295                 300

Ala Leu Cys Gly Tyr Asn Phe Leu Ile Lys His Leu Asp Gly His Pro
305                 310                 315                 320

Leu Val Leu Ser Ser Lys Gln Gly Asp Val Ile Lys Pro Gly Val Ile
                325                 330                 335

Arg Gly Val Leu Gly Lys Gly Met Pro Asn Lys Lys Tyr Pro Glu Leu
            340                 345                 350

Lys Gly Asn Leu Phe Val Glu Phe Glu Val Glu Phe Pro Lys Glu His
        355                 360                 365

```
Phe Leu Asp Asp Glu Lys Ala Tyr Ala Val Leu Lys Ser Cys Phe Pro
    370                 375                 380

Thr Ser Lys Val Val Asn Val Thr Pro Ala Ala Ala Glu Val Ser Leu
385                 390                 395                 400

Met Glu Tyr Asp Glu Lys Lys Tyr Ser Arg Gly Arg Gly Gly Asp Ala
                405                 410                 415

Tyr Asn Glu Asp Ser Asp Glu Glu Gln His Gly Gly His His Gly Gln
            420                 425                 430

Gly Val Arg Cys Gln His Gln
        435
```

<210> SEQ ID NO 49
<211> LENGTH: 1194
<212> TYPE: DNA
<213> ORGANISM: Homo sapiens

<400> SEQUENCE: 49

```
atggtgaaag aaacaactta ctacgatgtt ttggggtca aacccaatgc tactcaggaa      60
gaattgaaaa aggcttatag gaaactggcc ttgaagtacc atcctgataa gaacccaaat    120
gaaggagaga gtttaaaaca gatttctcaa gcttacgaag ttctctctga tgcaaagaaa    180
agggaattat atgacaaagg aggagaacag gcaattaaag agggtggagc aggtggcggt    240
tttggctccc ccatggacat ctttgatatg tttttttggag gaggaggaag gatgcagaga    300
gaaaggagag gtaaaaatgt tgtacatcag ctctcagtaa ccctagaaga cttatataat    360
ggtgcaacaa gaaaactggc tctgcaaaag aatgtgattt gtgacaaatg tgaaggtaga    420
ggaggtaaga aaggagcagt agagtgctgt cccaattgcc gaggtactgg aatgcaaata    480
agaattcatc agataggacc tggaatggtt cagcaaattc agtctgtgtg catggagtgc    540
cagggccatg gggagcggat cagtcctaaa gatagatgta aaagctgcaa cggaaggaag    600
atagttcgag agaaaaaaat tttagaagtt catattgaca aaggcatgaa agatggccag    660
aagataacat tccatggtga aggagaccaa gaaccaggac tggagccagg cgatattatc    720
attgtgttag atcagaagga ccatgctgtt tttactcgac gaggagaaga ccttttcatg    780
tgtatggaca tacagctcgt tgaagcactg tgtggcttcc acaagccaat atctactctt    840
gacaaccgaa ccatcgtcat cacctctcat ccaggtcaga ttgtcaagca tggagatatc    900
aagtgtgtac taaatgaagg catgccaatt tatcgtagac catatgaaaa gggtcgccta    960
atcatcgaat ttaaggtaaa ctttcctgag aatggctttc tctctcctga taaactgtct   1020
ttgctggaaa aactcctacc cgagaggaag gaagtggaag agactgatga gatggaccaa   1080
gtagaactgg tggactttga tccaaatcag gaaagacggc gccactacaa tggagaagca   1140
tatgaggatg atgaacatca tcccagaggt ggtgttcagt gtcagacctc ttaa          1194
```

<210> SEQ ID NO 50
<211> LENGTH: 397
<212> TYPE: PRT
<213> ORGANISM: Homo sapiens

<400> SEQUENCE: 50

```
Met Val Lys Glu Thr Thr Tyr Tyr Asp Val Leu Gly Val Lys Pro Asn
1               5                   10                  15

Ala Thr Gln Glu Glu Leu Lys Lys Ala Tyr Arg Lys Leu Ala Leu Lys
            20                  25                  30

Tyr His Pro Asp Lys Asn Pro Asn Glu Gly Glu Lys Phe Lys Gln Ile
        35                  40                  45
```

```
Ser Gln Ala Tyr Glu Val Leu Ser Asp Ala Lys Lys Arg Glu Leu Tyr
 50                  55                  60

Asp Lys Gly Gly Glu Gln Ala Ile Lys Glu Gly Ala Gly Gly Gly
 65                  70                  75                  80

Phe Gly Ser Pro Met Asp Ile Phe Asp Met Phe Gly Gly Gly
                 85                  90                  95

Arg Met Gln Arg Glu Arg Arg Gly Lys Asn Val Val His Gln Leu Ser
                100                 105                 110

Val Thr Leu Glu Asp Leu Tyr Asn Gly Ala Thr Arg Lys Leu Ala Leu
            115                 120                 125

Gln Lys Asn Val Ile Cys Asp Lys Cys Glu Gly Arg Gly Lys Lys
130                 135                 140

Gly Ala Val Glu Cys Cys Pro Asn Cys Arg Gly Thr Gly Met Gln Ile
145                 150                 155                 160

Arg Ile His Gln Ile Gly Pro Gly Met Val Gln Gln Ile Gln Ser Val
                165                 170                 175

Cys Met Glu Cys Gln Gly His Gly Glu Arg Ile Ser Pro Lys Asp Arg
                180                 185                 190

Cys Lys Ser Cys Asn Gly Arg Lys Ile Val Arg Glu Lys Lys Ile Leu
            195                 200                 205

Glu Val His Ile Asp Lys Gly Met Lys Asp Gly Gln Lys Ile Thr Phe
            210                 215                 220

His Gly Glu Gly Asp Gln Glu Pro Gly Leu Glu Pro Gly Asp Ile Ile
225                 230                 235                 240

Ile Val Leu Asp Gln Lys Asp His Ala Val Phe Thr Arg Arg Gly Glu
                245                 250                 255

Asp Leu Phe Met Cys Met Asp Ile Gln Leu Val Glu Ala Leu Cys Gly
                260                 265                 270

Phe Gln Lys Pro Ile Ser Thr Leu Asp Asn Arg Thr Ile Val Ile Thr
            275                 280                 285

Ser His Pro Gly Gln Ile Val Lys His Gly Asp Ile Lys Cys Val Leu
290                 295                 300

Asn Glu Gly Met Pro Ile Tyr Arg Arg Pro Tyr Glu Lys Gly Arg Leu
305                 310                 315                 320

Ile Ile Glu Phe Lys Val Asn Phe Pro Glu Asn Gly Phe Leu Ser Pro
                325                 330                 335

Asp Lys Leu Ser Leu Leu Glu Lys Leu Leu Pro Glu Arg Lys Glu Val
            340                 345                 350

Glu Glu Thr Asp Glu Met Asp Gln Val Glu Leu Val Asp Phe Asp Pro
            355                 360                 365

Asn Gln Glu Arg Arg Arg His Tyr Asn Gly Glu Ala Tyr Glu Asp Asp
        370                 375                 380

Glu His His Pro Arg Gly Gly Val Gln Cys Gln Thr Ser
385                 390                 395

<210> SEQ ID NO 51
<211> LENGTH: 1230
<212> TYPE: DNA
<213> ORGANISM: Sacharomyces cereviseae

<400> SEQUENCE: 51
atggttaaag aaactaagtt ttacgatatt ctaggtgttc cagtaactgc cactgatgtc      60
gaaattaaga aagcttatag aaaatgcgcc ttaaaatacc atccagataa gaatccaagt     120
```

-continued

```
gaggaagctg cagaaaagtt caaagaagct tcagcagcct atgaaatttt atcagatcct      180 gaaagagag  atatatatga ccaatttggt gaagatggtc taagtggtgc tggtggcgct      240
ggcggattcc caggtggtgg attcggtttt ggtgacgata tcttttccca attctttggt      300
gctggtggcg cacaaagacc aagaggtccc caaagaggta agatatcaa  gcatgaaatt      360 tctgcctcac ttgaagaatt ataagggt   aggacagcta agttagccct aacaaacag       420 atcctatgta aagaatgtga aggtcgtggt ggtaagaaag gcgccgtcaa gaagtgtacc      480
agctgtaatg gtcaaggtat aaatttgta  acaagacaaa tgggtccaat gatccaaaga      540
ttccaaacag agtgtgatgt ctgtcacggt actggtgata tcattgatcc taaggatcgt      600
tgtaaatctt gtaacggtaa gaaagttgaa acgaaagga  agatcctaga agtccatgtc      660
gaaccaggta tgaagatgg  tcaaagaatc gttttcaaag gtgaagctga ccaagcccca      720
gatgtcattc caggtgatgt tgtcttcata gtttctgaga gaccacacaa gagcttcaag      780
agagatggta tgatttagt  atatgaggct gaaattgatc tattgactgc tatcgctggt      840
ggtgaatttg cattggaaca tgtttctggt gattggttaa aggtcggtat tgttccaggt      900
gaagttattg ccccaggtat gcgtaaggtc atcgaaggta aggtatgcc  aattccaaaa      960 tacggtggct atggtaattt aatcatcaaa tttactatca agttcccaga aaaccatttc     1020
acatcagaag aaaacttgaa gaagttagaa gaaattttgc ctccaagaat tgtcccagcc     1080
attccaaaga aagctactgt ggacgaatgt gtactcgcag actttgaccc agccaaatac     1140
aacagaacac gggcctccag gggtggtgca aactatgatt ccgatgaaga agaacaaggt     1200
ggcgaaggtg ttcaatgtgc atctcaatga                                      1230
```

<210> SEQ ID NO 52
<211> LENGTH: 409
<212> TYPE: PRT
<213> ORGANISM: Sacharomyces cereviseae

<400> SEQUENCE: 52

```
Met Val Lys Glu Thr Lys Phe Tyr Asp Ile Leu Gly Val Pro Val Thr
1               5                   10                  15

Ala Thr Asp Val Glu Ile Lys Lys Ala Tyr Arg Lys Cys Ala Leu Lys
                20                  25                  30

Tyr His Pro Asp Lys Asn Pro Ser Glu Glu Ala Glu Lys Phe Lys
        35                  40                  45

Glu Ala Ser Ala Ala Tyr Glu Ile Leu Ser Asp Pro Glu Lys Arg Asp
    50                  55                  60

Ile Tyr Asp Gln Phe Gly Glu Asp Gly Leu Ser Gly Ala Gly Gly Ala
65                  70                  75                  80

Gly Gly Phe Pro Gly Gly Gly Phe Gly Phe Gly Asp Asp Ile Phe Ser
                85                  90                  95

Gln Phe Phe Gly Ala Gly Gly Ala Gln Arg Pro Arg Gly Pro Gln Arg
                100                 105                 110

Gly Lys Asp Ile Lys His Glu Ile Ser Ala Ser Leu Glu Glu Leu Tyr
        115                 120                 125

Lys Gly Arg Thr Ala Lys Leu Ala Leu Asn Lys Gln Ile Leu Cys Lys
    130                 135                 140

Glu Cys Glu Gly Arg Gly Gly Lys Lys Gly Ala Val Lys Lys Cys Thr
145                 150                 155                 160

Ser Cys Asn Gly Gln Gly Ile Lys Phe Val Thr Arg Gln Met Gly Pro
                165                 170                 175
```

```
Met Ile Gln Arg Phe Gln Thr Glu Cys Asp Val Cys His Gly Thr Gly
                180                 185                 190

Asp Ile Ile Asp Pro Lys Asp Arg Cys Lys Ser Cys Asn Gly Lys Lys
            195                 200                 205

Val Glu Asn Glu Arg Lys Ile Leu Glu Val His Val Glu Pro Gly Met
        210                 215                 220

Lys Asp Gly Gln Arg Ile Val Phe Lys Gly Glu Ala Asp Gln Ala Pro
225                 230                 235                 240

Asp Val Ile Pro Gly Asp Val Val Phe Ile Val Ser Glu Arg Pro His
                245                 250                 255

Lys Ser Phe Lys Arg Asp Gly Asp Asp Leu Val Tyr Glu Ala Glu Ile
            260                 265                 270

Asp Leu Leu Thr Ala Ile Ala Gly Gly Glu Phe Ala Leu Glu His Val
        275                 280                 285

Ser Gly Asp Trp Leu Lys Val Gly Ile Val Pro Gly Glu Val Ile Ala
290                 295                 300

Pro Gly Met Arg Lys Val Ile Glu Gly Lys Gly Met Pro Ile Pro Lys
305                 310                 315                 320

Tyr Gly Gly Tyr Gly Asn Leu Ile Ile Lys Phe Thr Ile Lys Phe Pro
                325                 330                 335

Glu Asn His Phe Thr Ser Glu Glu Asn Leu Lys Lys Leu Glu Glu Ile
            340                 345                 350

Leu Pro Pro Arg Ile Val Pro Ala Ile Pro Lys Lys Ala Thr Val Asp
        355                 360                 365

Glu Cys Val Leu Ala Asp Phe Asp Pro Ala Lys Tyr Asn Arg Thr Arg
        370                 375                 380

Ala Ser Arg Gly Gly Ala Asn Tyr Asp Ser Asp Glu Glu Glu Gln Gly
385                 390                 395                 400

Gly Glu Gly Val Gln Cys Ala Ser Gln
                405
```

<210> SEQ ID NO 53
<211> LENGTH: 1239
<212> TYPE: DNA
<213> ORGANISM: Homo sapiens

<400> SEQUENCE: 53

```
atggctaacg tggctgacac gaagctgtac gacatcctgg gcgtcccgcc cggcgccagc     60
gagaacgagc tgaagaaggc atacagaaag ttagccaagg aatatcatcc tgataagaat    120
ccaaatgcag gagacaaatt taagaaata agttttgcat atgaagtact atcaaatcct    180
gagaagcgtg agttatatga cagatacgga gagcaaggtc ttcgggaagg cagcggcgga    240
ggtggtggca tggatgatat tttctctcac attttttggtg ggggattgtt cggcttcatg    300
ggcaatcaga gtagaagtcg aaatggcaga agaagaggag aggacatgat gcatccactc    360
aaagtatctt tagaagatct gtataatggc aagacaacca aactacaact tagcaagaat    420
gtgctctgta gtgcatgcag tggccaaggc ggaaagtctg gagctgtcca aaagtgtagt    480
gcttgtcgag gtcgaggtgt gcgcatcatg atcagacagc tggctccagg gatggtacaa    540
cagatgcagt ctgtgtgctc tgattgtaat ggagaaggag aggtaattaa tgaaaaagac    600
cgctgtaaaa atgtgaaggg gagaaggtg attaagaag tcaagattct gaagtccac     660
gtagacaaag gcatgaaaca tggacagaga attacattca ctggggaagc agaccaggcc    720
ccaggagtgg aacccggaga cattgttctt ttgctacagg agaagaaca tgaggtattt    780
```

```
cagagagatg ggaatgattt gcacatgaca tataaaatag gacttgttga agctctatgt    840
ggatttcagt tcacatttaa gcaccttgat ggacgtcaga ttgtggtgaa ataccccct    900 ggcaaagtaa ttgaaccagg gtgtgttcgt gtagttcgag gtgaagggat gccgcagtat    960
cgtaatccct ttgaaaaagg tgatcttttac ataaagtttg atgtgcagtt tcctgaaaac   1020
aactggatca acccagacaa gctttctgaa ctagaagatc ttctgccatc tagaccggaa   1080
gttcctaaca taattggaga aacagaggag gtagagcttc aggaatttga tagcactcga   1140
ggctcaggag gtggtcagag gcgtgaagcc tataatgata gctctgatga agaaagcagc   1200
agccatcatg gacctggagt gcagtgtgcc catcagtaa                          1239
```

<210> SEQ ID NO 54
<211> LENGTH: 412
<212> TYPE: PRT
<213> ORGANISM: Homo sapiens

<400> SEQUENCE: 54

```
Met Ala Asn Val Ala Asp Thr Lys Leu Tyr Asp Ile Leu Gly Val Pro
  1               5                  10                  15

Pro Gly Ala Ser Glu Asn Glu Leu Lys Lys Ala Tyr Arg Lys Leu Ala
             20                  25                  30

Lys Glu Tyr His Pro Asp Lys Asn Pro Asn Ala Gly Asp Lys Phe Lys
         35                  40                  45

Glu Ile Ser Phe Ala Tyr Glu Val Leu Ser Asn Pro Glu Lys Arg Glu
     50                  55                  60

Leu Tyr Asp Arg Tyr Gly Glu Gln Gly Leu Arg Glu Gly Ser Gly Gly
 65                  70                  75                  80

Gly Gly Gly Met Asp Asp Ile Phe Ser His Ile Phe Gly Gly Gly Leu
                 85                  90                  95

Phe Gly Phe Met Gly Asn Gln Ser Arg Ser Arg Asn Gly Arg Arg Arg
            100                 105                 110

Gly Glu Asp Met Met His Pro Leu Lys Val Ser Leu Glu Asp Leu Tyr
        115                 120                 125

Asn Gly Lys Thr Thr Lys Leu Gln Leu Ser Lys Asn Val Leu Cys Ser
    130                 135                 140

Ala Cys Ser Gly Gln Gly Gly Lys Ser Gly Ala Val Gln Lys Cys Ser
145                 150                 155                 160

Ala Cys Arg Gly Arg Gly Val Arg Ile Met Ile Arg Gln Leu Ala Pro
                165                 170                 175

Gly Met Val Gln Gln Met Gln Ser Val Cys Ser Asp Cys Asn Gly Glu
            180                 185                 190

Gly Glu Val Ile Asn Glu Lys Asp Arg Cys Lys Lys Cys Glu Gly Lys
        195                 200                 205

Lys Val Ile Lys Glu Val Lys Ile Leu Glu Val His Val Asp Lys Gly
    210                 215                 220

Met Lys His Gly Gln Arg Ile Thr Phe Thr Gly Glu Ala Asp Gln Ala
225                 230                 235                 240

Pro Gly Val Glu Pro Gly Asp Ile Val Leu Leu Leu Gln Glu Lys Glu
                245                 250                 255

His Glu Val Phe Gln Arg Asp Gly Asn Asp Leu His Met Thr Tyr Lys
            260                 265                 270

Ile Gly Leu Val Glu Ala Leu Cys Gly Phe Gln Phe Thr Phe Lys His
        275                 280                 285

Leu Asp Gly Arg Gln Ile Val Val Lys Tyr Pro Pro Gly Lys Val Ile
```

```
                  290              295              300
Glu Pro Gly Cys Val Arg Val Arg Gly Gly Met Pro Gln Tyr
305              310              315              320

Arg Asn Pro Phe Glu Lys Gly Asp Leu Tyr Ile Lys Phe Asp Val Gln
                325                 330                 335

Phe Pro Glu Asn Asn Trp Ile Asn Pro Asp Lys Leu Ser Glu Leu Glu
                340                 345                 350

Asp Leu Leu Pro Ser Arg Pro Glu Val Pro Asn Ile Ile Gly Glu Thr
                355                 360                 365

Glu Glu Val Glu Leu Gln Glu Phe Asp Ser Thr Arg Gly Ser Gly Gly
        370                 375                 380

Gly Gln Arg Arg Glu Ala Tyr Asn Asp Ser Ser Asp Glu Glu Ser Ser
385                 390                 395                 400

Ser His His Gly Pro Gly Val Gln Cys Ala His Gln
                405                 410
```

```
<210> SEQ ID NO 55
<211> LENGTH: 1239
<212> TYPE: DNA
<213> ORGANISM: Mus musculus

<400> SEQUENCE: 55
atggcgaacg tggccgacac gaagctgtac gacatcctgg gcgtccctcc cggcgctagc      60
gagaacgagc tgaagaaggc ataccgaaag ttagccaaag aataccaccc tgataagaat     120
ccaaatgctg agacaaaatt taagaaaata agttttgcat atgaagtatt gtcaaatcca     180
gagaagcgag agctgtatga cagatatgga gaacaaggcc tacgggaagg cagcggcgga     240 ggcgtggca tggatgatat cttctcacat attttggtg gaggattgtt tggcttatg       300 ggcaatcaga gtagaagtcg aaatggcaga agaagaggcg aggacatgat gcatccacta     360
aaagtatctt tagaagacct gtacaatggc aagacaacca actacaact tagcaagaat      420 gtgctctgta gtgcatgcag tggccaaggt gggaagtctg agctgttca gaaatgcagc     480 gcttgtcggg tcgaggtgt gcgcattatg atcagacagc tggctccagg aatggtgcag     540
cagatgcagt ccgtgtgctc cgactgtaat ggagaagggg aggtcatcaa tgaaaaagac     600
cgctgtaaaa aatgtgaagg gaagaaggta atcaaagaag tcaagattct ggaagtccat     660
gtagacaaag gcatgaaaca tggacagagg attacgttca ctggggaagc agaccaggct     720
ccaggagtgg aacctggaga tattgttctt ttgctacagg aaaaagaaca tgaggtgttc     780
cagagagatg ggaatgattt gcatatgaca tataagatag gactcgttga agctttatgt     840
ggatttcagt tcacatttaa acatcttgat gctcgtcaga ttgtggtgaa ataccccct      900 ggcaaagtaa ttgaaccagg atgtgttcgt gttgttcgag gtgaaggaat gccacagtat     960
cgtaatccct tgaaaagggt gatctctac ataaagtttg atgtacagtt tcctgagaat    1020
aactggatca acccagacaa actttctgaa ttagaagatc tcctgccatc tagaccagaa    1080
gttcctaatg ttattggaga gacagaagaa gtggagcttc aggaatttga tagcactcga    1140
ggctctggcg gtggtcagag acgtgaagcc tataatgata gctctgatga agaaagtagc    1200
agccatcatg gacctggagt gcagtgtgcc catcagtaa                           1239

<210> SEQ ID NO 56
<211> LENGTH: 412
<212> TYPE: PRT
<213> ORGANISM: Mus musculus
```

<400> SEQUENCE: 56

```
Met Ala Asn Val Ala Asp Thr Lys Leu Tyr Asp Ile Leu Gly Val Pro
1               5                   10                  15

Pro Gly Ala Ser Glu Asn Glu Leu Lys Lys Ala Tyr Arg Lys Leu Ala
            20                  25                  30

Lys Glu Tyr His Pro Asp Lys Asn Pro Asn Ala Gly Asp Lys Phe Lys
        35                  40                  45

Glu Ile Ser Phe Ala Tyr Glu Val Leu Ser Asn Pro Glu Lys Arg Glu
    50                  55                  60

Leu Tyr Asp Arg Tyr Gly Glu Gln Gly Leu Arg Glu Gly Ser Gly Gly
65                  70                  75                  80

Gly Gly Gly Met Asp Asp Ile Phe Ser His Ile Phe Gly Gly Gly Leu
                85                  90                  95

Phe Gly Phe Met Gly Asn Gln Ser Arg Ser Arg Asn Gly Arg Arg Arg
            100                 105                 110

Gly Glu Asp Met Met His Pro Leu Lys Val Ser Leu Glu Asp Leu Tyr
            115                 120                 125

Asn Gly Lys Thr Thr Lys Leu Gln Leu Ser Lys Asn Val Leu Cys Ser
        130                 135                 140

Ala Cys Ser Gly Gln Gly Gly Lys Ser Gly Ala Val Gln Lys Cys Ser
145                 150                 155                 160

Ala Cys Arg Gly Arg Gly Val Arg Ile Met Ile Arg Gln Leu Ala Pro
            165                 170                 175

Gly Met Val Gln Gln Met Gln Ser Val Cys Ser Asp Cys Asn Gly Glu
            180                 185                 190

Gly Glu Val Ile Asn Glu Lys Asp Arg Cys Lys Lys Cys Glu Gly Lys
            195                 200                 205

Lys Val Ile Lys Glu Val Lys Ile Leu Glu Val His Val Asp Lys Gly
        210                 215                 220

Met Lys His Gly Gln Arg Ile Thr Phe Thr Gly Glu Ala Asp Gln Ala
225                 230                 235                 240

Pro Gly Val Glu Pro Gly Asp Ile Val Leu Leu Leu Gln Glu Lys Glu
            245                 250                 255

His Glu Val Phe Gln Arg Asp Gly Asn Asp Leu His Met Thr Tyr Lys
            260                 265                 270

Ile Gly Leu Val Glu Ala Leu Cys Gly Phe Gln Phe Thr Phe Lys His
        275                 280                 285

Leu Asp Ala Arg Gln Ile Val Lys Tyr Pro Pro Gly Lys Val Ile
    290                 295                 300

Glu Pro Gly Cys Val Arg Val Arg Gly Glu Gly Met Pro Gln Tyr
305                 310                 315                 320

Arg Asn Pro Phe Glu Lys Gly Asp Leu Tyr Ile Lys Phe Asp Val Gln
            325                 330                 335

Phe Pro Glu Asn Asn Trp Ile Asn Pro Asp Lys Leu Ser Glu Leu Glu
            340                 345                 350

Asp Leu Leu Pro Ser Arg Pro Glu Val Pro Asn Val Ile Gly Glu Thr
        355                 360                 365

Glu Glu Val Glu Leu Gln Glu Phe Asp Ser Thr Arg Gly Ser Gly Gly
    370                 375                 380

Gly Gln Arg Arg Glu Ala Tyr Asn Asp Ser Ser Asp Glu Glu Ser Ser
385                 390                 395                 400

Ser His His Gly Pro Gly Val Gln Cys Ala His Gln
            405                 410
```

<210> SEQ ID NO 57
<211> LENGTH: 654
<212> TYPE: DNA
<213> ORGANISM: Oryza sativa

<400> SEQUENCE: 57

```
cttctacatc ggcttaggtg tagcaacacg actttattat tattattatt attattatta      60
ttattttaca aaatatataaa atagatcagt ccctcaccac aagtagagca agttggtgag    120
ttattgtaaa gttctacaaa gctaatttaa aagttattgc attaacttat ttcatattac    180
aaacaagagt gtcaatggaa caatgaaaac catatgacat actataattt tgttttattt    240
attgaaatta tataattcaa agagaataaa tccacatagc cgtaaagttc tacatgtggt    300
gcattaccaa aatatatata gcttacaaaa catgacaagc ttagtttgaa aaattgcaat    360
ccttatcaca ttgacacata aagtgagtga tgagtcataa tattattttc tttgctaccc    420
atcatgtata tatgatagcc acaaagttac tttgatgatg atatcaaaga acattttag    480
gtgcacctaa cagaatatcc aaataatatg actcacttag atcataatag agcatcaagt    540
aaaactaaca ctctaaagca accgatggga aagcatctat aaatagacaa gcacaatgaa    600
aatcctcatc atccttcacc acaattcaaa tattatagtt gaagcatagt agta           654
```

<210> SEQ ID NO 58
<211> LENGTH: 51
<212> TYPE: DNA
<213> ORGANISM: Artificial sequence
<220> FEATURE:
<223> OTHER INFORMATION: primer: prm04266

<400> SEQUENCE: 58

```
ggggacaagt ttgtacaaaa aagcaggctt cacaatgtac ggacgcatgc c              51
```

<210> SEQ ID NO 59
<211> LENGTH: 50
<212> TYPE: DNA
<213> ORGANISM: Artificial sequence
<220> FEATURE:
<223> OTHER INFORMATION: primer: prm04267

<400> SEQUENCE: 59

```
ggggaccact ttgtacaaga aagctgggtg catcgaattg ttcttactgc                 50
```

<210> SEQ ID NO 60
<211> LENGTH: 427
<212> TYPE: PRT
<213> ORGANISM: Arabidopsis thaliana

<400> SEQUENCE: 60

```
Met Arg Arg Phe Asn Trp Val Leu Arg His Val Gln Ala Arg Arg Thr
1               5                   10                  15

Phe Asp Ser Ala Ile Gly Leu Arg Gln Gly Ser Gln Lys Pro Leu Phe
            20                  25                  30

Glu Arg Tyr Ile His Ala Thr Gly Ile Asn Asn Ser Ala Arg Asn
        35                  40                  45

Tyr Tyr Asp Val Leu Gly Val Ser Pro Lys Ala Thr Arg Glu Glu Ile
    50                  55                  60

Lys Lys Ser Phe His Glu Leu Ala Lys Lys Phe His Pro Asp Thr Asn
65                  70                  75                  80

Arg Asn Asn Pro Ser Ala Lys Arg Lys Phe Gln Glu Ile Arg Glu Ala
```

```
                85                  90                  95
Tyr Glu Thr Leu Gly Asn Ser Glu Arg Arg Glu Tyr Asp Lys Leu
            100                 105                 110

Gln Tyr Arg Asn Ser Asp Tyr Val Asn Asn Asp Gly Gly Asp Ser Glu
            115                 120                 125

Arg Phe Arg Arg Ala Tyr Gln Ser Asn Phe Ser Asp Thr Phe His Lys
            130                 135                 140

Ile Phe Ser Glu Ile Phe Glu Asn Asn Gln Ile Lys Pro Asp Ile Arg
145                 150                 155                 160

Val Glu Leu Ser Leu Ser Leu Ser Glu Ala Ala Glu Gly Cys Thr Lys
            165                 170                 175

Arg Leu Ser Phe Asp Ala Tyr Val Phe Cys Asp Ser Cys Asp Gly Leu
            180                 185                 190

Gly His Pro Ser Asp Ala Ala Met Ser Ile Cys Pro Thr Cys Arg Gly
            195                 200                 205

Val Gly Arg Val Thr Ile Pro Pro Phe Thr Ala Ser Cys Gln Thr Cys
            210                 215                 220

Lys Gly Thr Gly His Ile Ile Lys Glu Tyr Cys Met Ser Cys Arg Gly
225                 230                 235                 240

Ser Gly Ile Val Glu Gly Thr Lys Thr Ala Glu Leu Val Ile Pro Gly
            245                 250                 255

Gly Val Glu Ser Glu Ala Thr Ile Thr Ile Val Gly Ala Gly Asn Val
            260                 265                 270

Ser Ser Arg Thr Ser Gln Pro Gly Asn Leu Tyr Ile Lys Leu Lys Val
            275                 280                 285

Ala Asn Asp Ser Thr Phe Thr Arg Asp Gly Ser Asp Ile Tyr Val Asp
290                 295                 300

Ala Asn Ile Ser Phe Thr Gln Ala Ile Leu Gly Gly Lys Val Val Val
305                 310                 315                 320

Pro Thr Leu Ser Gly Lys Ile Gln Leu Asp Ile Pro Lys Gly Thr Gln
            325                 330                 335

Pro Asp Gln Leu Leu Val Leu Arg Gly Lys Gly Leu Pro Lys Gln Gly
            340                 345                 350

Phe Phe Val Asp His Gly Asp Gln Tyr Val Arg Phe Arg Val Asn Phe
            355                 360                 365

Pro Thr Glu Val Asn Glu Arg Gln Arg Ala Ile Leu Glu Glu Phe Ala
            370                 375                 380

Lys Glu Glu Ile Asn Asn Glu Leu Ser Asp Ser Ala Glu Gly Ser Trp
385                 390                 395                 400

Trp Asn Leu Thr Gly Pro Gln Ile Ile Arg Asp Phe Ser Leu Met Val
            405                 410                 415

Leu Leu Ala Leu Leu Leu Ser Arg Leu Met Gly
            420                 425

<210> SEQ ID NO 61
<211> LENGTH: 500
<212> TYPE: PRT
<213> ORGANISM: Arabidopsis thaliana

<400> SEQUENCE: 61

Met Ala Ala Leu Ala Ser Pro Ser Leu Ile Pro Ser Ser Leu Cys Phe
1               5                   10                  15

Ala Ala Ala Ala Asp Gly Pro Arg Ser Leu Ser Ser Asn Phe Ser Ala
            20                  25                  30
```

-continued

```
Phe Ser Asp Gly Gly Ser Asn Phe Arg Tyr His Lys Ser Phe Leu Ser
    35                  40                  45
Leu Ser Ser Ser Ser Ser Ser Thr Pro Tyr Arg Asn Arg Arg Gly
    50                  55                  60
Arg Ser Leu Val Val Phe Ala Thr Ser Gly Asp Tyr Tyr Ala Thr Leu
65                  70                  75                  80
Gly Val Ser Lys Ser Ala Asn Asn Lys Glu Ile Lys Ala Ala Tyr Arg
                85                  90                  95
Arg Leu Ala Arg Gln Tyr His Pro Asp Val Asn Lys Glu Pro Gly Ala
                100                 105                 110
Thr Glu Lys Phe Lys Glu Ile Ser Ala Ala Tyr Glu Val Leu Ser Asp
            115                 120                 125
Glu Gln Lys Arg Ala Leu Tyr Asp Gln Tyr Gly Glu Ala Gly Val Lys
            130                 135                 140
Ser Thr Val Gly Gly Ala Ser Gly Pro Tyr Thr Ser Asn Pro Phe Asp
145                 150                 155                 160
Leu Phe Glu Thr Phe Phe Gly Ala Ser Met Gly Gly Phe Pro Gly Met
                165                 170                 175
Asp Gln Ala Asp Phe Gly Arg Thr Arg Arg Ser Arg Val Thr Lys Gly
                180                 185                 190
Glu Asp Leu Arg Tyr Asp Ile Thr Leu Glu Leu Ser Glu Ala Ile Phe
            195                 200                 205
Gly Ser Glu Lys Glu Phe Asp Leu Thr His Leu Glu Thr Cys Glu Ala
            210                 215                 220
Cys Ala Gly Thr Gly Ala Lys Ala Gly Ser Lys Met Arg Ile Cys Ser
225                 230                 235                 240
Thr Cys Gly Gly Arg Gly Gln Val Met Arg Thr Glu Gln Thr Pro Phe
                245                 250                 255
Gly Met Phe Ser Gln Val Ser Ile Cys Pro Asn Cys Gly Gly Asp Gly
                260                 265                 270
Glu Val Ile Ser Glu Asn Cys Arg Lys Cys Ser Gly Glu Gly Arg Val
            275                 280                 285
Arg Ile Lys Lys Ser Ile Lys Val Lys Ile Pro Pro Gly Val Ser Ala
            290                 295                 300
Gly Ser Ile Leu Arg Val Ala Gly Glu Gly Asp Ser Gly Pro Arg Gly
305                 310                 315                 320
Gly Pro Pro Gly Asp Leu Tyr Val Tyr Leu Asp Val Glu Asp Val Arg
                325                 330                 335
Gly Ile Glu Arg Asp Gly Ile Asn Leu Leu Ser Thr Leu Ser Ile Ser
                340                 345                 350
Tyr Leu Asp Ala Ile Leu Gly Ala Val Val Lys Val Lys Thr Val Glu
            355                 360                 365
Gly Asp Thr Glu Leu Gln Ile Pro Pro Gly Thr Gln Pro Gly Asp Val
            370                 375                 380
Leu Val Leu Ala Lys Lys Gly Val Pro Lys Leu Asn Arg Pro Ser Ile
385                 390                 395                 400
Arg Gly Asp His Leu Phe Thr Val Lys Val Ser Val Pro Asn Gln Ile
                405                 410                 415
Ser Ala Gly Glu Arg Glu Leu Leu Glu Glu Leu Ala Ser Leu Lys Asp
                420                 425                 430
Thr Ser Ser Asn Arg Ser Arg Thr Arg Ala Lys Pro Gln Gln Pro Ser
            435                 440                 445
Thr Leu Ser Thr Ala Pro Ser Gly Ser Glu Asn Lys Lys Asp Glu Val
```

```
                450                 455                 460
Lys Glu Glu Asn Glu Pro Glu Gln Glu Asn Tyr Leu Trp Asn Asn
465                 470                 475                 480

Ile Lys Glu Phe Ala Gly Ser Val Ala Asn Gly Ala Leu Lys Trp Leu
                485                 490                 495

Arg Asp Asn Leu
            500

<210> SEQ ID NO 62
<211> LENGTH: 442
<212> TYPE: PRT
<213> ORGANISM: Arabidopsis thaliana

<400> SEQUENCE: 62

Met Ala Ile Ile Gln Leu Gly Ser Thr Cys Val Ala Gln Trp Ser Ile
1               5                   10                  15

Arg Pro Gln Phe Ala Val Arg Ala Tyr Tyr Pro Ser Arg Ile Glu Ser
                20                  25                  30

Thr Arg His Gln Asn Ser Ser Ser Gln Val Asn Cys Leu Gly Ala Ser
            35                  40                  45

Lys Ser Ser Met Phe Ser His Gly Ser Leu Pro Phe Leu Ser Met Thr
        50                  55                  60

Gly Met Ser Arg Asn Met His Pro Pro Arg Arg Gly Ser Arg Phe Thr
65                  70                  75                  80

Val Arg Ala Asp Ala Asp Tyr Tyr Ser Val Leu Gly Val Ser Lys Asn
                85                  90                  95

Ala Thr Lys Ala Glu Ile Lys Ser Ala Tyr Arg Lys Leu Ala Arg Asn
            100                 105                 110

Tyr His Pro Asp Val Asn Lys Asp Pro Gly Ala Glu Glu Lys Phe Lys
        115                 120                 125

Glu Ile Ser Asn Ala Tyr Glu Val Leu Ser Asp Asp Glu Lys Lys Ser
130                 135                 140

Leu Tyr Asp Arg Tyr Gly Glu Ala Gly Leu Lys Gly Ala Ala Gly Phe
145                 150                 155                 160

Gly Asn Gly Asp Phe Ser Asn Pro Phe Asp Leu Phe Asp Ser Leu Phe
                165                 170                 175

Glu Gly Phe Gly Gly Gly Met Gly Arg Gly Ser Arg Ser Arg Ala Val
            180                 185                 190

Asp Gly Gln Asp Glu Tyr Tyr Thr Leu Ile Leu Asn Phe Lys Glu Ala
        195                 200                 205

Val Phe Gly Met Glu Lys Glu Ile Glu Ile Ser Arg Leu Glu Ser Cys
210                 215                 220

Gly Thr Cys Glu Gly Ser Gly Ala Lys Pro Gly Thr Lys Pro Thr Lys
225                 230                 235                 240

Cys Thr Thr Cys Gly Gly Gln Gly Gln Val Ser Ala Ala Arg Thr
                245                 250                 255

Pro Leu Gly Val Phe Gln Gln Val Met Thr Cys Ser Ser Cys Asn Gly
            260                 265                 270

Thr Gly Glu Ile Ser Thr Pro Cys Gly Thr Cys Ser Gly Asp Gly Arg
        275                 280                 285

Val Arg Lys Thr Lys Arg Ile Ser Leu Lys Val Pro Ala Gly Val Asp
        290                 295                 300

Ser Gly Ser Arg Leu Arg Val Arg Gly Glu Gly Asn Ala Gly Lys Arg
305                 310                 315                 320
```

```
Gly Gly Ser Pro Gly Asp Leu Phe Val Ile Glu Val Ile Pro Asp
            325                 330                 335

Pro Ile Leu Lys Arg Asp Asp Thr Asn Ile Leu Tyr Thr Cys Lys Ile
            340                 345                 350

Ser Tyr Ile Asp Ala Ile Leu Gly Thr Thr Leu Lys Val Pro Thr Val
            355                 360                 365

Asp Gly Thr Val Asp Leu Lys Val Pro Ala Gly Thr Gln Pro Ser Thr
        370                 375                 380

Thr Leu Val Met Ala Lys Lys Gly Val Pro Val Leu Asn Lys Ser Asn
385                 390                 395                 400

Met Arg Gly Asp Gln Leu Val Arg Val Gln Val Glu Ile Pro Lys Arg
                405                 410                 415

Leu Ser Lys Glu Glu Lys Lys Leu Ile Glu Glu Leu Ala Asp Met Ser
            420                 425                 430

Lys Asn Lys Thr Ala Asn Ser Thr Ser Arg
            435                 440

<210> SEQ ID NO 63
<211> LENGTH: 517
<212> TYPE: PRT
<213> ORGANISM: Arabidopsis thaliana

<400> SEQUENCE: 63

Met Ala Ala Met Ala Arg Cys Ala Leu Ile Pro Ser Ile Asn Pro Ala
1               5                   10                  15

His Ser Phe Arg His Gln Phe Pro Gln Pro Asn Ala Ser Phe Tyr Leu
            20                  25                  30

Pro Pro Thr Leu Pro Ile Phe Ser Arg Val Arg Arg Phe Gly Ile Ser
        35                  40                  45

Gly Gly Tyr Arg Arg Arg Val Ile Thr Met Ala Ala Gly Thr Asp His
    50                  55                  60

Tyr Ser Thr Leu Asn Val Asn Arg Asn Ala Thr Leu Gln Glu Ile Lys
65                  70                  75                  80

Ser Ser Tyr Arg Lys Leu Ala Arg Lys Tyr His Pro Asp Met Asn Lys
                85                  90                  95

Asn Pro Gly Ala Glu Asp Lys Phe Lys Gln Ile Ser Ala Ala Tyr Glu
            100                 105                 110

Val Leu Ser Asp Glu Glu Lys Arg Ser Ala Tyr Asp Arg Phe Gly Glu
        115                 120                 125

Ala Gly Leu Glu Gly Asp Phe Asn Gly Ser Gln Asp Thr Ser Pro Gly
    130                 135                 140

Val Asp Pro Phe Asp Leu Tyr Ser Ala Phe Phe Gly Gly Ser Asp Gly
145                 150                 155                 160

Phe Phe Gly Gly Met Gly Glu Ser Gly Gly Met Gly Phe Asp Phe Met
                165                 170                 175

Asn Lys Arg Ser Leu Asp Leu Asp Ile Arg Tyr Asp Leu Arg Leu Ser
            180                 185                 190

Phe Glu Glu Ala Val Phe Gly Val Lys Arg Glu Ile Glu Val Ser Tyr
        195                 200                 205

Leu Glu Thr Cys Asp Gly Cys Gly Gly Thr Gly Ala Lys Ser Ser Asn
    210                 215                 220

Ser Ile Lys Gln Cys Ser Ser Cys Asp Gly Lys Gly Arg Val Met Asn
225                 230                 235                 240

Ser Gln Arg Thr Pro Phe Gly Ile Met Ser Gln Val Ser Thr Cys Ser
                245                 250                 255
```

```
Lys Cys Gly Gly Glu Gly Lys Thr Ile Thr Asp Lys Cys Arg Lys Cys
            260                 265                 270

Ile Gly Asn Gly Arg Leu Arg Ala Arg Lys Lys Met Asp Val Val
            275                 280                 285

Pro Pro Gly Val Ser Asp Arg Ala Thr Met Arg Ile Gln Gly Glu Gly
290                 295                 300

Asn Met Asp Lys Arg Ser Gly Arg Ala Gly Asp Leu Phe Ile Val Leu
305                 310                 315                 320

Gln Val Asp Glu Lys Arg Gly Ile Arg Arg Glu Gly Leu Asn Leu Tyr
                325                 330                 335

Ser Asn Ile Asn Ile Asp Phe Thr Asp Ala Ile Leu Gly Ala Thr Thr
            340                 345                 350

Lys Val Glu Thr Val Glu Gly Ser Met Asp Leu Arg Ile Pro Pro Gly
            355                 360                 365

Thr Gln Pro Gly Asp Thr Val Lys Leu Pro Arg Lys Gly Val Pro Asp
        370                 375                 380

Thr Asp Arg Pro Ser Ile Arg Gly Asp His Cys Phe Val Val Lys Ile
385                 390                 395                 400

Ser Ile Pro Lys Lys Leu Ser Glu Arg Glu Lys Leu Val Glu Glu
                405                 410                 415

Phe Ser Ser Leu Arg Arg Ser Ser Ser Thr Gly Pro Thr Glu Thr
                420                 425                 430

Arg Gln Glu Glu Gln Ser Phe Gly Ser Glu Pro Arg Lys Glu Pro Ser
                435                 440                 445

Leu Trp His Lys Met Lys Asn Phe Ile Arg Pro Glu Asp Ser Arg Thr
        450                 455                 460

Lys Phe Gly Thr Met Ser Leu Asn Pro Ser Leu Pro Leu Arg Arg Met
465                 470                 475                 480

Lys Val Ser Glu Thr Ser Ile Ala Phe Ser Val Leu Ala Leu Cys Val
                485                 490                 495

Ile Thr Ser Ala Val Ala Leu Val Gln Lys Lys Gly Asn Arg Leu Lys
                500                 505                 510

Gln Lys Lys Glu Thr
        515

<210> SEQ ID NO 64
<211> LENGTH: 447
<212> TYPE: PRT
<213> ORGANISM: Arabidopsis thaliana

<400> SEQUENCE: 64

Met Ala Leu Ile Gln Phe Gly Ser Ser Cys Val Ala Gln Trp Gly Ile
1               5                   10                  15

Leu Arg Pro Arg Phe Ala Val Lys Ala Phe Tyr Pro Ser Arg Leu Glu
            20                  25                  30

Ser His Gln Asp Asn Cys Ile Ser Gln Ile Asn Cys Leu Gly Ala Ser
        35                  40                  45

Arg Ser Ser Met Phe Ala Gln Gly Ser Leu Pro Phe Leu Ser Leu Thr
    50                  55                  60

Gly Val Ser Pro Asn Thr His Ser Arg Gly Ala Arg Phe Thr Val
65                  70                  75                  80

Arg Ala Asp Thr Asp Phe Tyr Ser Val Leu Gly Val Ser Lys Asn Ala
                85                  90                  95

Thr Lys Ala Glu Ile Lys Ser Ala Tyr Arg Lys Leu Ala Arg Ser Tyr
```

```
                100                 105                 110
His Pro Asp Val Asn Lys Asp Ala Gly Ala Glu Asp Lys Phe Lys Glu
            115                 120                 125

Ile Ser Asn Ala Tyr Glu Ile Leu Ser Asp Asp Glu Lys Arg Ser Leu
        130                 135                 140

Tyr Asp Arg Tyr Gly Glu Ala Val Lys Gly Ala Gly Met Gly Gly
145                 150                 155                 160

Met Gly Asp Tyr Ser Asn Pro Phe Asp Leu Phe Glu Ser Leu Phe Glu
                165                 170                 175

Gly Met Gly Gly Met Gly Gly Met Gly Gly Met Gly Ser Arg Gly
            180                 185                 190

Ser Arg Ser Arg Ala Ile Asp Gly Glu Asp Glu Tyr Tyr Ser Leu Ile
        195                 200                 205

Leu Asn Phe Lys Glu Ala Val Phe Gly Ile Glu Lys Glu Ile Glu Ile
        210                 215                 220

Ser Arg Leu Glu Ser Cys Gly Thr Cys Asn Gly Ser Gly Ala Lys Ala
225                 230                 235                 240

Gly Thr Lys Pro Thr Lys Cys Lys Thr Cys Gly Gly Gln Gly Gln Val
                245                 250                 255

Val Ala Ser Thr Arg Thr Pro Leu Gly Val Phe Gln Gln Val Met Thr
            260                 265                 270

Cys Ser Pro Cys Asn Gly Thr Gly Glu Ile Ser Lys Pro Cys Gly Ala
        275                 280                 285

Cys Ser Gly Asp Gly Arg Val Arg Arg Thr Lys Arg Ile Ser Leu Lys
        290                 295                 300

Val Pro Ala Gly Val Asp Ser Gly Ser Arg Leu Arg Val Arg Gly Glu
305                 310                 315                 320

Gly Asn Ala Gly Lys Arg Gly Gly Ser Pro Gly Asp Leu Phe Ala Val
                325                 330                 335

Ile Glu Val Ile Pro Asp Pro Val Leu Lys Arg Asp Asp Thr Asn Ile
            340                 345                 350

Leu Tyr Thr Cys Lys Ile Ser Tyr Val Asp Ala Ile Leu Gly Thr Thr
        355                 360                 365

Leu Lys Val Pro Thr Val Asp Gly Glu Val Asp Leu Lys Val Pro Ala
        370                 375                 380

Gly Thr Gln Pro Ser Thr Thr Leu Val Met Ala Lys Lys Gly Val Pro
385                 390                 395                 400

Val Leu Asn Lys Ser Lys Met Arg Gly Asp Gln Leu Val Arg Val Gln
                405                 410                 415

Val Glu Ile Pro Lys Arg Leu Ser Lys Glu Glu Lys Met Leu Val Glu
            420                 425                 430

Glu Leu Ala Asp Met Ser Lys Asn Lys Val Ala Asn Ser Arg Arg
        435                 440                 445

<210> SEQ ID NO 65
<211> LENGTH: 456
<212> TYPE: PRT
<213> ORGANISM: Arabidopsis thaliana

<400> SEQUENCE: 65

Met Val Pro Ser Asn Gly Ala Lys Val Leu Arg Leu Leu Ser Arg Arg
1               5                   10                  15

Cys Leu Ser Ser Ser Leu Ile Gln Asp Leu Ala Asn Gln Lys Leu Arg
            20                  25                  30
```

```
Gly Val Cys Ile Gly Ser Tyr Arg Arg Leu Asn Thr Ser Val Gly Asn
         35                  40                  45

His Ala Asn Val Ile Gly Asp Tyr Ala Ser Lys Ser Gly His Asp Arg
 50                  55                  60

Lys Trp Ile Asn Phe Gly Phe Asn Thr Asn Phe Gly Ser Thr Arg
 65                  70                  75                  80

Ser Phe His Gly Thr Gly Ser Ser Phe Met Ser Ala Lys Asp Tyr Tyr
                     85                  90                  95

Ser Val Leu Gly Val Ser Lys Asn Ala Gln Glu Gly Glu Ile Lys Lys
                100                 105                 110

Ala Tyr Tyr Gly Leu Ala Lys Lys Leu His Pro Asp Met Asn Lys Asp
         115                 120                 125

Asp Pro Glu Ala Glu Thr Lys Phe Gln Glu Val Ser Lys Ala Tyr Glu
 130                 135                 140

Ile Leu Lys Asp Lys Glu Lys Arg Asp Leu Tyr Asp Gln Val Gly His
145                 150                 155                 160

Glu Ala Phe Glu Gln Asn Ala Ser Gly Gly Phe Pro Asn Asp Gln Gly
                165                 170                 175

Phe Gly Gly Gly Gly Gly Gly Phe Asn Pro Phe Asp Ile Phe Gly
                180                 185                 190

Ser Phe Asn Gly Asp Ile Phe Asn Met Tyr Arg Gln Asp Ile Gly Gly
         195                 200                 205

Gln Asp Val Lys Val Leu Leu Asp Leu Ser Phe Met Glu Ala Val Gln
 210                 215                 220

Gly Cys Ser Lys Thr Val Thr Phe Gln Thr Glu Met Ala Cys Asn Thr
225                 230                 235                 240

Cys Gly Gly Gln Gly Val Pro Pro Gly Thr Lys Arg Glu Lys Cys Lys
                245                 250                 255

Ala Cys Asn Gly Ser Gly Met Thr Ser Leu Arg Arg Gly Met Leu Ser
         260                 265                 270

Ile Gln Thr Thr Cys Gln Lys Cys Gly Gly Ala Gly Gln Thr Phe Ser
 275                 280                 285

Ser Ile Cys Lys Ser Cys Arg Gly Ala Arg Val Val Arg Gly Gln Lys
         290                 295                 300

Ser Val Lys Val Thr Ile Asp Pro Gly Val Asp Asn Ser Asp Thr Leu
305                 310                 315                 320

Lys Val Ala Arg Val Gly Gly Ala Asp Pro Glu Gly Asp Gln Pro Gly
                325                 330                 335

Asp Leu Tyr Val Thr Leu Lys Val Arg Glu Asp Pro Val Phe Arg Arg
         340                 345                 350

Glu Gly Ser Asp Ile His Val Asp Ala Val Leu Ser Val Thr Gln Ala
             355                 360                 365

Ile Leu Gly Gly Thr Ile Gln Val Pro Thr Leu Thr Gly Asp Val Val
 370                 375                 380

Val Lys Val Arg Pro Gly Thr Gln Pro Gly His Lys Val Val Leu Arg
385                 390                 395                 400

Asn Lys Gly Ile Arg Ala Arg Lys Ser Thr Lys Phe Gly Asp Gln Tyr
                405                 410                 415

Val His Phe Asn Val Ser Ile Pro Ala Asn Ile Thr Gln Arg Gln Arg
         420                 425                 430

Glu Leu Leu Glu Glu Phe Ser Lys Ala Glu Gln Gly Glu Tyr Glu Gln
 435                 440                 445

Arg Thr Ala Thr Gly Ser Ser Gln
```

```
                    450             455

<210> SEQ ID NO 66
<211> LENGTH: 8
<212> TYPE: PRT
<213> ORGANISM: Artificial sequence
<220> FEATURE:
<223> OTHER INFORMATION: Conserved sequence for the zinc binding domain
<220> FEATURE:
<221> NAME/KEY: MISC_FEATURE
<222> LOCATION: (2)..(3)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is any amino acid

<400> SEQUENCE: 66

Cys Xaa Xaa Cys Xaa Gly Xaa Gly
1               5
```